US010788419B2

(12) United States Patent
Thompson

(10) Patent No.: US 10,788,419 B2
(45) Date of Patent: Sep. 29, 2020

(54) DEVICES, SYSTEMS, AND METHODS FOR AGROCHEMICAL DETECTION AND AGROCHEMICAL COMPOSITIONS

(71) Applicant: Spogen Biotech Inc., St. Louis, MO (US)

(72) Inventor: Brian M. Thompson, Creve Coeur, MO (US)

(73) Assignee: Spogen Biotech Inc., St. Louis, MO (US)

( * ) Notice: Subject to any disclaimer, the term of this patent is extended or adjusted under 35 U.S.C. 154(b) by 90 days.

(21) Appl. No.: 15/982,752

(22) Filed: May 17, 2018

(65) Prior Publication Data

US 2018/0364155 A1     Dec. 20, 2018

Related U.S. Application Data

(60) Provisional application No. 62/507,602, filed on May 17, 2017.

(51) Int. Cl.
*G01N 21/31*     (2006.01)
*G01N 21/05*     (2006.01)
(Continued)

(52) U.S. Cl.
CPC ............ *G01N 21/31* (2013.01); *G01J 3/0218* (2013.01); *G01N 21/01* (2013.01); *G01N 21/05* (2013.01); *G01N 21/255* (2013.01); *G01N 21/80* (2013.01); *G01N 21/3577* (2013.01); *G01N 21/78* (2013.01); *G01N 2021/0156* (2013.01); *G01N 2021/1746* (2013.01); *G01N 2021/6439* (2013.01); *G01N 2021/7786* (2013.01)

(58) Field of Classification Search
CPC .......... G01J 3/0218; G01N 2021/0156; G01N 2021/1746; G01N 2021/6439; G01N 2021/7786; G01N 21/01; G01N 21/05; G01N 21/255; G01N 21/31; G01N 21/3577; G01N 21/78; G01N 21/80
See application file for complete search history.

(56) References Cited

U.S. PATENT DOCUMENTS 5,442,437 A  8/1995  Davidson
5,900,944 A  5/1999  Mawby
(Continued)

OTHER PUBLICATIONS

Bill Johnson et al., Cleaning Field Sprayers to Avoid Crop Injury, MU Extension, University of Missouri-Columbia, dated 1999, pp. 6.
(Continued)

*Primary Examiner* — Hina F Ayub
(74) *Attorney, Agent, or Firm* — Stinson LLP

(57) ABSTRACT

Systems, devices, and methods for detecting agrochemicals in environments associated with agricultural equipment are described. Certain agrochemicals that are formulated for being detected using the systems, devices, and methods disclosed herein are also described. The devices, systems, and methods disclosed herein are generally configured to use spectral characteristics to detect agrochemicals in an environment associated with agricultural equipment. The spectral characteristics can be analyzed in various ways to provide different types of information about the agrochemicals and/or the environment.

60 Claims, 42 Drawing Sheets

(51) Int. Cl.
  *G01J 3/02*    (2006.01)
  *G01N 21/01*   (2006.01)
  *G01N 21/25*   (2006.01)
  *G01N 21/80*   (2006.01)
  *G01N 21/3577* (2014.01)
  *G01N 21/78*   (2006.01)
  *G01N 21/77*   (2006.01)
  *G01N 21/17*   (2006.01)
  *G01N 21/64*   (2006.01)

(56) References Cited

U.S. PATENT DOCUMENTS

| | | | |
|---|---|---|---|
| 5,901,264 A | 5/1999 | Camlibel et al. | |
| 6,888,636 B2* | 5/2005 | Martino | G01N 21/05 356/319 |
| 2002/0101586 A1* | 8/2002 | Kim | G01J 3/2803 356/319 |
| 2006/0219261 A1 | 10/2006 | Lin et al. | |
| 2011/0068940 A1* | 3/2011 | Kim | G01N 1/22 340/632 |
| 2012/0200855 A1 | 8/2012 | Bonyuet et al. | |
| 2013/0128267 A1* | 5/2013 | Kang | G01N 21/4795 356/326 |
| 2014/0264004 A1 | 9/2014 | Cooks et al. | |
| 2014/0358381 A1 | 12/2014 | Holland | |
| 2016/0054281 A1 | 2/2016 | Smeeton et al. | |
| 2017/0167679 A1 | 6/2017 | Yui et al. | |

OTHER PUBLICATIONS

Water quality affects herbicide efficacy, https://oregonstate.edu/dept/nursery-weeds/feature_articles/spray_tank/spray_tank.htm, dated 1994 and 1999, pp. 4.

Written Opinion and International Search Report, Application No. PCT/US18/33213, dated Sep. 27, 2018, pp. 14.

Behrens et al., Dicamba Resistance: Enlarging and Preserving Biotechnology-Based Weed Management Strategies, Faculty Publications from the Center for Plant Science Innovations, dated May 25, 2007, pp. 21.

Curran et al., Adjuvants for Enhancing Herbicide Performance, Penn State Cooperative Extension College of Agricultural Sciences, dated 2009, pp. 6.

Johnson, et al., 2,4-D- and Dicamba-tolerant Crops—Some Facts to Consider, Purdue University Cooperative Extension Service, dated Nov. 2012, pp. 7.

* cited by examiner

FIG. 28D

Alpha-Cypermethrin (Astound Duo)

*Bacillus thuringiensis* (1.55 × 10⁸ spores/mL) Amax 255 nm

- 1X
- 0.5X
- 0.25X
- 0.125X
- 0.0625X
- 0.0313X
- 0.0156X
- 0.0078X

DEVICES, SYSTEMS, AND METHODS FOR AGROCHEMICAL DETECTION AND AGROCHEMICAL COMPOSITIONS

CROSS-REFERENCE TO RELATED APPLICAITONS

This application claims priority to U.S. Provisional Patent Application No. 62/507,602, entitled "APPARATUS AND METHOD FOR MEASURING PESTICIDES AND PESTICIDE END PRODUCTS IN AN ENVIRONMENT" and filed on May 17, 2017, which is hereby incorporated by reference in its entirety.

JOINT RESEARCH AGREEMENT

The claimed invention was made by or on behalf of Elemental Enzymes Ag and Turf, LLC and Nufarm Americas Inc., parties to a joint research agreement in effect before the date of the claimed invention, and is a result of activities within the scope of the joint research agreement.

FIELD

The present invention relates generally to systems and methods for detecting agrochemicals.

BACKGROUND

Agrochemicals, including pesticides (e.g., insecticides, fungicides, herbicides, etc.) plant growth regulators, and fertilizers, are widely used to improve crop quality and yield. Pesticides are commonly used to control weeds, pests, insects, fungi, nematodes, and other diseases. Pesticides are commonly applied by spraying a pesticide-containing solution onto a crop. Fertilizers, which are used to promote plant growth, are applied in a similar manner. After an agrochemical solution has been applied, there is a residual amount of the agrochemical that remains in the spray equipment, such as the spray tank, the spray nozzle(s), and any fluid conduits between the spray tank and the nozzle(s). Proper care and cleaning procedures to remove agrochemical residues from the spray equipment after a spray application are important for the proper maintenance of equipment and safety to subsequent sensitive crops that are sprayed or treated. Additionally, there is a need to identify the amount of pesticides, plant health agents, and plant growth promoting products in a mixture.

It is also important to remove pesticide or other agrochemical residue from the spray equipment and any equipment used to apply, prepare, contain, or transport spray solutions, or that is used to manufacture or store active ingredients, or prepare formulations of the pesticides to prevent crop injury from unintentional carry-over or cross contamination of pesticides to crops that are sensitive to the pesticide residue. Residual contamination in the tank and/or other spray equipment can cause significant damage to plants even at extremely low pesticide application levels. This contamination can come from spray solutions, transport or storage vessels for pesticides, manufacturing cross contamination or pesticide precursor chemicals or formulations, or manufacturing waste streams. Injury due to not adequately cleaning the equipment is particularly problematic for growth regulator or auxin-like herbicides commonly used to control perennial and annual broadleaf weeds in which case even small amounts of herbicidal residue could result in significant damage to sensitive or non-target plants and crop plants. For example, the benzoic acid herbicides, such as dicamba are well known for their ability to produce crop injury when residues are applied to sensitive plants. Crop damage can also occur from other auxin-like herbicides including but are not limited to the phenoxyacetic acids (phenoxys), such as 2,4-D, 2,4-DB, 2,4-DP (dichloroprop or dichloroprop acid), 2,4,5-T, 2,4,5-TP, MCPA, MCPB, MCPB NA, MCPB acid, MCPP (mecoprop), (+)R-2-(4-chloro-2 methylphenoxy) Propionic acid (Mecoprop-P Technical acid), Dichlorprop-P Technical acid and Tropotox (MCPB+MCPA), Quinclorac, Quinmerac, and other 2,4-D amine or ester formulations, and the pyridine-carboxylic acids, such as Clopyralid, Picloram, Triclopyr, Aminopyralid, Aminocyclopyrachlor, Halauxifen-methyl, Florpyrauxifen-benzyl, Clacyfos, and their precursor chemistries or pesticide end-products.

In addition, there is a need to reduce or monitor pesticide levels in fruit wash areas, post-harvest dips, fertilizer and irrigation lines, trickle lines, pumps, chemigation systems, fertigation systems, and overhead sprinkler systems.

Agrochemicals are sometimes applied as seed coatings to crop seeds. A "seed treatment" refers to any substance that is used to coat a seed. For example, seed treatments may be an application of biological organisms, chemical ingredients, inoculants, herbicide safeners, micronutrients, plant growth regulators, seed coatings, etc. applied to a seed to suppress, control or repel plant pathogens, insects, or other pests that attack seeds, seedlings plant parts, or plants. In many cases seed treatments include application of a pesticide to the surface of a seed as a coating that is designed to reduce, control or repel disease organisms, insects, or other pests that attack seed or seedlings grown from treated seeds. Seed treatments are commonly applied by spraying or otherwise depositing a material containing the desired ingredient or combination of ingredients onto the seeds. The equipment used to apply the seed treatment to the seeds needs to be cleaned for reasons that are similar to the reasons the equipment used to apply a pesticide to a field needs to be cleaned, especially when the seed treatment includes one or more pesticides. Even if a seed treatment does not include a pesticide, however, it can be important to clean the equipment used to apply the seed coating to the seeds.

The same agricultural equipment is commonly used to apply more than one type of agrochemical in a series of different agrochemical applications. Similarly, seed treatment or other manufacturing equipment may be used in connection with different types of agrochemicals. In a typical process for cleaning application and/or manufacturing equipment, any unused pesticide product (e.g., spray or seed treatment material) is drained from the tank and all hoses nozzles and related equipment and disposed of in accord with federal, state, and local guidelines. The tank and fluid lines are rinsed with clean water. The tank can be filled with water and one or more cleaners added to the water to make a cleaning solution. The cleaning solution can be recirculated through the equipment with all spray nozzles closed by valves, which provides agitation to help the cleaning process. The cleaning solution can also be allowed to stand in the tank and related equipment. All strainers, screens, and filters are typically removed and soaked. The order of the steps can be varied. The steps are often repeated. It is commonly recommended that the process includes soaking the equipment in the cleaning solution overnight. The time required to complete this cleaning process is usually in the range of 4-36 hours. Thus, the equipment has significant downtime each time it needs to be cleaned.

Custom spray applications to crops, which are becoming common in agricultural practices, can employ the use of more than one pesticide at the same time, for example, applying a growth regulator herbicide, such as dicamba, combined with 2,4-D or a combination of herbicide mixes combined with a fungicide, or an insecticide. These combinations of agrochemicals can make equipment clean out procedures even more problematic. Commercial cleaners are currently available for the cleaning of spray tanks. Typically, the use of these cleaners requires the cleaning rinsate to remain in the spray tank overnight with additional water rinses that follow the cleaning process. This process is expensive from both a time and cost perspective to the user, farmer or grower. In addition, many commercially available cleaners are caustic which can be harmful to the operator with exposure and not considered to be environmentally safe or friendly.

The present inventors have made various improvements to systems and methods of determining a concentration and nature of an agrochemical, such as a pesticide or a pesticide end-product, in an environment, which are described in detail below.

SUMMARY

One aspect of the invention is an apparatus for detecting, measuring and quantifying the amount of at least one pesticide or pesticide end-product in an environment. The apparatus includes a light source and a spectrophotometric device comprising a detector positioned to receive light from the light source after the light has been transmitted through or reflected by the environment. The spectrophotometric device is configured to measure intensity of the received light as a function of wavelength to determine spectral characteristics of the received light. The apparatus includes a processor configured to measure a concentration of a pesticide or pesticide end-product using the spectral characteristics of the received light.

Another aspect of the invention is a system for analyzing the amount of a pesticide and/or a pesticide end-product in an environment. The system includes a processor having a data exchange interface. The processor's data exchange interface is configured for receiving information about a concentration of the pesticide or pesticide end-product in the environment from another data exchange interface. The information includes a series of measurements of the concentration of the pesticide or pesticide end-product. The processor is configured to use the information about the concentration of the pesticide or pesticide end-product to: predict at time t1 a first predicted rate-of-change of the concentration using a first set of filter parameters; calculate a predicted concentration of the pesticide or pesticide end-product at a time t2 based on the information and the predicted rate of change, wherein time t2 is after time t1; compare the predicted concentration of the pesticide or pesticide end-product at time t2 to a measurement of the concentration of the pesticide or pesticide end-product corresponding to time t2 to determine a difference between the predicted concentration at time t2 and the measured concentration at time t2; determine a second set of filter parameters different from the first set of filter parameters based on the difference between the predicted concentration at time t2 and the measured concentration at time t2; and calculate a predicted concentration of the pesticide or pesticide end-product at a time t3 using the second set of filter parameters, wherein time t3 is different from time t1 and different from time t2.

Another aspect of the invention is a method for detecting, measuring and quantifying the amount of at least one pesticide or pesticide end-product in an environment. The method includes receiving light from a light source after the light has been transmitted through or reflected by the environment. The intensity of the received light is measured as a function of wavelength to obtain spectral characteristics of the received light. A concentration of the pesticide or pesticide end-product is determined using the spectral characteristics of the received light.

Yet another aspect of the invention is an attachment for agricultural spray equipment. The attachment includes a conduit for containing a pesticide containing fluid. A pair of windows is installed generally on opposite sides of the conduit. The attachment also has a connector configured for attaching the conduit to at least one of an in-line filter and a spray boom.

Still another aspect of the invention is a nozzle for applying a pesticide. The nozzle has a nozzle body and a pair of windows installed on generally opposite sides of the nozzle body.

Another aspect of the invention is a tank for containing a pesticide containing solution. The tank includes a wall at least partially enclosing a space for holding the solution; and a system for determining an amount of pesticide in the solution. The system includes a light source and a spectrophotometric device including a detector positioned to receive light from the light source after the light has been transmitted through or reflected by the solution. The spectrophotometric device is configured to measure intensity of the received light as a function of wavelength to determine spectral characteristics of the received light. The system includes a processor configured to measure a concentration of the pesticide or pesticide end-product using the spectral characteristics of the received light. At least the light source and spectrophotometric device is built into the wall.

Another aspect of the invention is a kit for installing a system for determining an amount of pesticide or pesticide end-product in a solution contained in a piece of agricultural spray equipment on the agricultural spray equipment. The kit includes a light source and a photodetector device including a detector. The spectrophotometric device is configured to measure intensity of light received by the detector as a function of wavelength to determine spectral characteristics of the received light. The kit includes a processor configured to measure a concentration of the pesticide or pesticide end-product using the spectral characteristics of the received light. The kit also includes a conduit for flowing fluid in a space between the light source and the spectrophotometric device and a connector for connecting the conduit to the agricultural spray equipment so that fluid from the piece of agricultural spray equipment can flow through the conduit. The kit has instructions for connecting the connector to the piece agricultural spray equipment.

In another aspect, the invention includes a method of measuring a concentration of a substance in an environment. The method includes receiving light from a light source after the light has been transmitted through or reflected by the environment. The intensity of the received light is measured as a function of wavelength to obtain spectral characteristics of the received light. A concentration of the substance is determined using the spectral characteristics of the received light. The substance is selected from the group consisting of an adjuvant, a fertilizer, a growth regulator, a micronutrient, a biological control agent, a plant health agent, an inoculant, a surfactant, an osmoprotectant, a safener, a trace molecule, a buffering agent, a trace element, a water conditioning agent and a hard water solute.

Still another aspect of the invention is an apparatus for measuring a concentration of a substance in an environment. The apparatus includes a light source and a spectrophotometric device including a detector positioned to receive light from the light source after the light has been transmitted through or reflected by the environment. The spectrophotometric device is configured to measure intensity of the received light as a function of wavelength to determine spectral characteristics of the received light. The apparatus includes a processor configured to measure a concentration of the substance using the spectral characteristics of the received light. The substance is selected from the group consisting of an adjuvant, a fertilizer, a growth regulator, a micronutrient, a biological control agent, a plant health agent, an inoculant, a surfactant, an osmoprotectant, a safener, a trace molecule, and a hard water solute.

Another aspect of the invention is a method of evaluating the cleanliness of a returnable or reusable container. The method includes receiving light from a light source after the light has been transmitted through or reflected by a material on or flowing from the container. The intensity of the received light is measured as a function of wavelength to obtain spectral characteristics of the received light. A concentration of a pesticide or pesticide end-product is determined using the spectral characteristics of the received light.

In one aspect, an apparatus for detecting, measuring and quantifying the amount of at least one agrochemical in an environment comprises a light source. A spectrophotometric device comprises a detector positioned to receive light from the light source after the light has been transmitted through or reflected by said environment. The spectrophotometric device is configured to measure intensity of the received light as a function of wavelength to determine spectral characteristics of the received light. A processor is configured to measure a concentration of said agrochemical using the spectral characteristics of the received light.

In another aspect, a system for analyzing the amount of an agrochemical in an environment comprises a processor having a data exchange interface. The processor's data exchange interface is configured for receiving information about a concentration of the agrochemical in the environment from another data exchange interface. Said information includes a series of measurements of the concentration of the agrochemical. The processor is configured to use the information about the concentration of the agrochemical to: predict at time t1 a first predicted rate-of-change of said concentration using a first set of filter parameters; calculate a predicted concentration of said agrochemical at a time t2 based on said information and said predicted rate of change, wherein time t2 is after time t1; compare said predicted concentration of said agrochemical at time t2 to a measurement of said concentration of said agrochemical corresponding to time t2 to determine a difference between the predicted concentration at time t2 and the measured concentration at time t2; determine a second set of filter parameters different from the first set of filter parameters based on said difference between the predicted concentration at time t2 and the measured concentration at time t2; and calculate a predicted concentration of said agrochemical at a time t3 using said second set of filter parameters, wherein time t3 is different from time t1 and different from time t2.

In still another aspect, a method for detecting, measuring and quantifying the amount of at least one agrochemical in an environment comprises receiving light from a light source after the light has been transmitted through or reflected by said environment. Intensity of the received light is measured as a function of wavelength to obtain spectral characteristics of the received light. A concentration of said agrochemical is determined using the spectral characteristics of the received light.

In one or more embodiments of the method, one or more of the following steps is performed based on the determined concentration of the agrochemical in the environment: cleaning agricultural equipment defining the environment with a cleaning agent; ceasing cleaning agricultural equipment defining the environment; using agricultural equipment defining the environment with another agrochemical; refraining from using the agricultural equipment defining the environment with another agrochemical; disposing of rinsate in agricultural equipment defining the environment; adding cleaning agent to rinsate in agricultural equipment defining the environment; spraying another agrochemical from agricultural spray equipment defining the environment; refraining from or ceasing spraying an agrochemical solution having another agrochemical agent in agricultural spray equipment defining the environment; refraining from treating seeds with a seed treatment comprising another agrochemical agent using seed treatment equipment defining the environment; treating seeds with a seed treatment comprising another agrochemical agent using seed treatment equipment defining the environment; generating a dispatch alert indicating that a residue of the agrochemical is present in the environment when the environment is expected to be substantially free of the agrochemical; adding a detoxifying formulation to a solution in agricultural equipment defining the environment; generating a dispatch alert indicating that the concentration of the agrochemical in agricultural equipment defining the environment is at a safe zone concentration; determining compliance with crop loss insurance requirements; adjusting one of a crop loss insurance premium rate and a crop loss insurance deductible; advancing a production process for an agrochemical product to a subsequent processing step; delaying advancing a production process for an agrochemical product to a subsequent processing step; determining whether to clean a returned drum defining the environment; cleaning a returned drum defining the environment; and refraining from cleaning a returned drum defining the environment.

In another aspect, an attachment for agricultural spray equipment comprises a conduit for containing an agrochemical containing fluid and a pair of windows. At least one window is formed in the conduit. The at least one window is configured to transmit electromagnetic radiation through the window. A connector is configured for attaching the conduit to at least one of an in-line filter and a spray boom. A detector detects electromagnetic radiation transmitted through the window associated with the agrochemical containing fluid. The detector is configured to detect the agrochemical based on the electromagnetic radiation that is transmitted through the window.

In still another aspect, a nozzle for applying an agrochemical comprises a nozzle body defining an outlet opening through which an agrochemical containing fluid can be dispensed. A pair of windows is installed on generally opposite sides of the nozzle. A least one window is formed in the nozzle body. The at least one window is configured to transmit electromagnetic radiation through the window. A detector detects electromagnetic radiation transmitted through the window associated with the agrochemical containing fluid. The detector is configured to detect the agrochemical based on the electromagnetic radiation that is transmitted through the window.

In yet another aspect, a tank for containing an agrochemical containing solution comprises a wall at least partially enclosing a space for holding the solution. A system for determining an amount of an agrochemical in the solution comprises a light source. A spectrophotometric device comprises a detector positioned to receive light from the light source after the light has been transmitted through or reflected by said solution. The spectrophotometric device is configured to measure intensity of the received light as a function of wavelength to determine spectral characteristics of the received light. A processor is configured to measure a concentration of said agrochemical using the spectral characteristics of the received light. At least the light source and photometric device are built into the wall.

In another aspect a kit for installing a system for determining an amount of an agrochemical in a solution contained in a piece of agricultural spray equipment on the agricultural spray equipment comprises a light source. A spectrophotometric device comprises a detector. The spectrophotometric device is configured to measure intensity of light received by the detector as a function of wavelength to determine spectral characteristics of the received light. A processor is configured to measure a concentration of said agrochemical using the spectral characteristics of the received light. A conduit is configured for flowing fluid in a space between the light source and the spectrophotometric device. A connector connects the conduit to the agricultural spray equipment so that fluid from the piece of agricultural spray equipment can flow through the conduit. The kit comprises instructions for connecting the connector to the piece agricultural spray equipment.

In yet another aspect, a method for measuring a concentration of a substance in an environment comprises receiving light from a light source after the light has been transmitted through or reflected by said environment. Intensity of the received light is measured as a function of wavelength to obtain spectral characteristics of the received light. A concentration of the substance is measured using the spectral characteristics of the received light. The substance is selected from the group consisting of an adjuvant, a fertilizer, a growth regulator, a micronutrient, a biological control agent, a plant health agent, an inoculant, a surfactant, an osmoprotectant, a safener, a trace molecule, and a hard water solute.

In still another aspect, an apparatus for measuring a concentration of a substance in an environment comprises a light source. A spectrophotometric device comprises a detector positioned to receive light from the light source after the light has been transmitted through or reflected by said environment. The spectrophotometric device is configured to measure intensity of the received light as a function of wavelength to determine spectral characteristics of the received light. A processor is configured to measure a concentration of the substance using the spectral characteristics of the received light. The substance is selected from the group consisting of an adjuvant, a fertilizer, a growth regulator, a micronutrient, a biological control agent, a plant health agent, an inoculant, a surfactant, an osmoprotectant, a safener, a trace molecule, and a hard water solute.

In still another embodiment, a method of evaluating the cleanliness of a returnable or reusable container comprises receiving light from a light source after the light has been transmitted through or reflected by a material on or flowing from the container. Intensity of the received light is measured as a function of wavelength to obtain spectral characteristics of the received light. A concentration of an agrochemical is determined using the spectral characteristics of the received light.

In another aspect, a method for evaluating use of an agrochemical comprises providing a fluid that may include the agrochemical. Receiving light from a light source after the light has been transmitted through or reflected by at least a portion of the fluid. Intensity of the received light is measured as a function of wavelength to obtain spectral characteristics of the received light. A concentration of the agrochemical in the fluid is determined using the spectral characteristics of the received light.

In certain embodiments of the method, the method further comprises performing at least one of the following steps based on the determined concentration of the agrochemical in the fluid: cleaning agricultural equipment in which the fluid is received with a cleaning agent; ceasing cleaning agricultural equipment in which the fluid is received; using agricultural equipment in which the fluid is received with another agrochemical; refraining from using the agricultural equipment in which the fluid is received with another agrochemical; disposing of rinsate in agricultural equipment in which the fluid is received; adding cleaning agent to rinsate in agricultural equipment in which the fluid is received; spraying another agrochemical from agricultural spray equipment in which the fluid is received; refraining from or ceasing spraying an agrochemical solution having another agrochemical agent in agricultural spray equipment in which the fluid is received; refraining from treating seeds with a seed treatment comprising another agrochemical agent using seed treatment equipment in which the fluid is received; treating seeds with a seed treatment comprising another agrochemical agent using seed treatment equipment in which the fluid is received; generating a dispatch alert indicating that a residue of the agrochemical is present in the fluid when the fluid is expected to be substantially free of the agrochemical; adding a detoxifying formulation to the fluid; generating a dispatch alert indicating that the concentration of the agrochemical in the fluid is at a safe zone concentration; determining compliance with crop loss insurance requirements; adjusting one of a crop loss insurance premium rate and a crop loss insurance deductible; advancing a production process for an agrochemical product to a subsequent processing step; delaying advancing a production process for an agrochemical product to a subsequent processing step; determining whether to clean a returned drum in which the fluid is received; cleaning a returned drum in which the fluid is received; and refraining from cleaning a returned drum in which the fluid is received.

In another aspect, a composition is provided. The composition comprises an agrochemical and a tracer dye or a tracer pigment.

In still another aspect, a method for detecting the presence of an agrochemical in a liquid is provided. The method comprises obtaining an absorbance spectrum for the liquid. The liquid has contacted equipment previously exposed to a composition comprising the agrochemical and a tracer dye or a tracer pigment. The method further comprises comparing the absorbance spectrum to a reference absorbance spectrum for the tracer dye or the tracer pigment. The reference spectrum for the tracer dye or the tracer pigment having an absorbance maximum (Amax) at one or more wavelengths. The presence of an Amax in the absorbance spectrum for the liquid at the same wavelength or wavelengths indicates that the agrochemical is present in the liquid.

In yet another aspect, a method for detecting a counterfeit agricultural composition is provided. The method comprises obtaining an absorbance spectrum from a suspected counterfeit agricultural composition and comparing the absorbance spectrum obtained for the suspected counterfeit agricultural composition to a reference absorbance spectrum for a genuine agricultural composition. The genuine agricultural composition comprises an agrochemical and a tracer dye or a tracer pigment. The reference spectrum has an absorbance maximum (Amax) for the dye or the pigment at one or more wavelengths. The absence of an Amax in the absorbance spectrum for the suspected counterfeit agricultural composition at the same wavelength or wavelengths indicates that the suspected counterfeit agricultural composition is a counterfeit composition.

Other aspects will be in part apparent and in part pointed out hereinafter.

BRIEF DESCRIPTION OF THE DRAWINGS

FIG. 28D is a graph showing detected absorption in a defined wavelength range of samples of alpha-cypermethrin (ASTOUND® DUO);

FIG. 29 is a graph showing detected absorption in a defined wavelength range of samples of a microbial spore-based product, *Bacillus thuringiensis* (Bt), at different concentrations;

Figure 1:
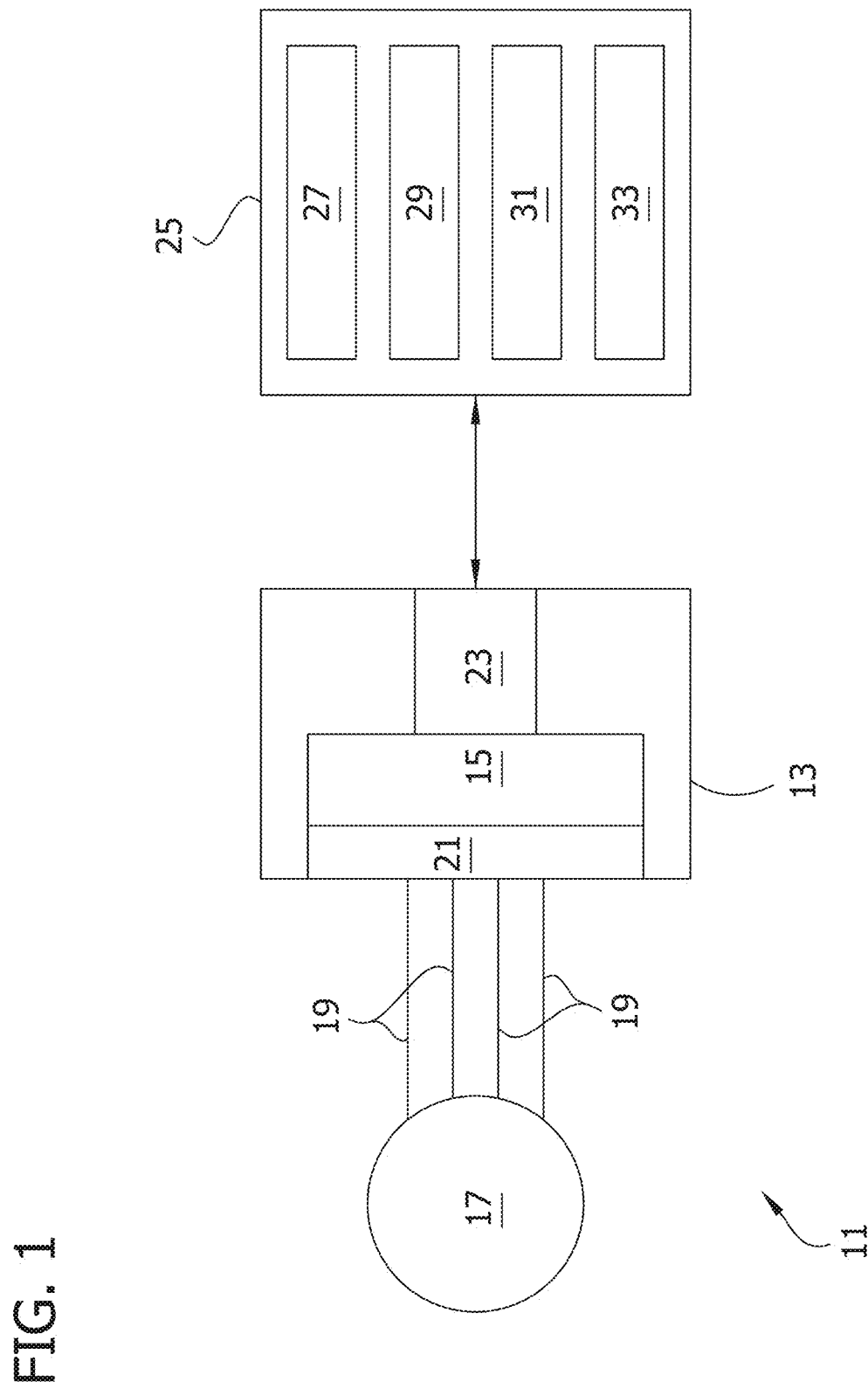
FIG. 1 is a schematic diagram illustrating one embodiment of an agrochemical detection system.

FIG. 30A is a graph showing detected absorption in a defined wavelength range of samples of dichlorosalicyclic acid (DCSA) at different concentrations;

FIG. 30B is a graph showing detected absorption in a defined wavelength range of samples of 2-chloroanisole at different concentrations;

FIG. 30C is a graph showing detected absorption in a defined wavelength range of samples of 3-chloroanisole at different concentrations;

FIG. 30D is a graph showing detected absorption in a defined wavelength range of samples of 2,5-dichloroanisole at different concentrations;

FIG. 31A is a graph showing detected absorption in a defined wavelength range of a sample of dicamba;

FIG. 31B is a graph showing detected absorption in a defined wavelength range of a sample of glufosinate contaminated with trace amounts of dicamba;

FIG. 31C is a graph showing detected absorption in a defined wavelength range of a sample of glufosinate;

FIG. 31D is a graph showing detected absorption in a defined wavelength range of a sample of glufosinate contaminated with trace amounts of imidacloprid;

FIG. 31E is a graph showing detected absorption in a defined wavelength range of a sample of imidacloprid;

FIG. 31F is a graph showing detected absorption in a defined wavelength range of a sample of azoxystrobin contaminated with trace amounts of imidacloprid;

FIGS. 32A-H provide illustrative UV-VIS spectra showing the spectral characteristics of formulated dicamba (CLASH™ Amax 230 nm, 280 nm; FIG. 32A); formulated 2,4-D (WEEDAR® 64; Amax 230 nm, 280 nm; FIG. 32B); a yellow tracer dye (Amax 425 nm; FIG. 32C); a red spectral tracer dye (Amax 530 nm; FIG. 32D); a mixture of the yellow tracer dye and the formulated dicamba (FIG. 32E); a mixture of the red tracer dye and the formulated 2,4-D (FIG. 32F); and mixtures containing 1:1 (FIG. 32G) or 2:1 (FIG. 32H) concentration ratios of the formulated dicamba mixed with the yellow tracer dye and the red tracer dye mixed with the formulated 2,4-D;

FIG. 33A provides illustrative UV-VIS spectra for a series of dilutions of dicamba formulated for volatility reduction (XTENDIMAX® VAPORGRIP®) mixed with an orange-red tracer dye (Amax approximately 625 nm), at various dilutions; and FIG. 33B provides a standard curve generated using the data provided in FIG. 33A correlating the average absorbance of the orange-red tracer dye to the dicamba concentration. The concentration of dicamba in solution was highly correlated to the absorbance of the spectral dye.

Corresponding reference characters indicate corresponding parts throughout the drawings.

DETAILED DESCRIPTION

The present disclosure describes systems, devices, and methods for detecting agrochemicals in environments associated with agricultural equipment. In addition, the present disclosure describes certain agrochemicals that are formulated for being detected using the systems, devices, and methods disclosed herein. As explained below, the devices, systems, and methods disclosed herein are generally configured to use spectral characteristics to detect agrochemicals in an environment associated with agricultural equipment. The spectral characteristics can be analyzed in various ways to provide different types of information about the agrochemicals and/or the environment.

Definitions

The following definitions are provided to aid understanding of the detailed description.

"2,4-Dichlorophenoxyacetic acid" also referred to as "2,4-D" is an organic compound that acts as a systemic herbicide which selectively kills most broadleaf weeds. 2,4-D is an herbicide that comes in several chemical forms, comprising salts, esters, and acid forms and it is often mixed with other herbicides. The toxicity of 2,4-D depends on its form.

"Agricultural equipment" includes "agricultural spray equipment," "manufacturing equipment," and other machines, passaging, devices, storage containers, and structures used in an agricultural setting that may come into contact with an agrochemical. In addition, agricultural equipment includes machines, passaging, devices, storage containers, and structures used in the manufacture of an agrochemical or other agricultural product.

"Agricultural spray equipment" includes, but is not necessarily limited to, a tank, a storage tank, a bulk tank, a spray tank, a nurse tank, a rinse tank, a tank drain, a seed treatment machinery, a boom, a boom sprayer, a lance sprayer, a spray rig, a container, a drum, a jug, a receptacle, a basin, a chamber, a nozzle, a nozzle screen, a nozzle filter, a nozzle fitting, a nozzle body, a screen, a strainer, a valve, a pipe, a pump, a wick wiper, a line, a tubing, a hose, a hose fitting and a spray affiliated with the equipment. Agricultural spray equipment also includes seed treatment systems, soil injection equipment, irrigation and chemigation systems, fertigation systems, overhead spray lines, solenoids, filters, pumps, transport, and storage equipment.

"Agrochemical" includes any chemical or biological agent used for agricultural purposes, used in the production of an agricultural product (e.g., a precursor), or any byproduct thereof (e.g., an end-product). Agrochemicals include any pesticide (e.g., herbicides, insecticides, fungicides, bactericides, nematicides, virucides, etc.) or pesticide end-product, biologics, adjuvants, fertilizers, inoculants, growth regulators, surfactants, osmoprotectants, safeners, and seed treatment agents.

The term "auxin herbicide" as used herein refers to any herbicide that is structurally similar to a naturally occurring auxin. Auxin herbicides typically exert their herbicidal activity by mimicking the natural plant hormone indole-3-acetic acid (IAA) or another naturally occurring auxin, producing rapid uncontrolled growth and killing the plant.

"Biofertilizers" as used herein references a subcategory of biostimulants that are useful to increase nutrient use efficiency and open new routes of nutrient acquisition by plants, for example, plant growth promoting microbes.

A "cross contaminant" as used herein refers to a harmful substance that passes unintentionally and indirectly from one surface material to another as may occur with spray or other forms of contamination in contact with a piece of agricultural equipment.

"Detoxify", "detoxifying" or "detoxification" as used herein refers to any modification to a pesticide product that reduces either the amount or the effect of the pesticide compound. A reduced pesticide effect includes any decrease in the amount of residual pesticide that remains on a surface material to be detoxified. The detoxification could be performed on any surface material, including the surfaces of agriculture equipment used in spray applications and surfaces of equipment used in pesticide production manufacturing.

"Dicamba" refers to 3,6-dichloro-o-anisic acid or 3,6-dichloro-2-methoxy benzoic acid and its related acids and salts. Dicamba salts comprise but are not limited to: isopropylamine, diglycoamine, dimethylamine, potassium and sodium. "Dicamba" can also refer to a "dicamba metabolite" or a "derivative of dicamba" which includes a substituted benzoic acid, and biologically acceptable salts thereof. The "dicamba metabolite" and "dicamba derivative" can have herbicidal activity.

"Drift" as used herein, refers to the physical movement of spray particles resulting from pesticide application by wind or inversion after the particles leave a sprayer and before they reach the intended target. Drift mainly occurs when spray applications occur in unfavorable weather conditions, but most commonly happens when windy conditions occur during application of a pesticide. The amount of drift can also be affected by characteristics such as the application technique and the physical characteristics of the equipment used, such as the size of a spray nozzle. In general, equipment that generates smaller droplets and application techniques that require the droplets to travel longer distances to reach the intended target both tend to increase the amount of drift.

"Fluid" means any substance that is flowable, such as a liquid, a gas, or a fluidizable solid such as granular material or powder.

A "growth regulator herbicide" as used herein is also referred to as an auxin-like herbicide. Growth regulator herbicides are generally formulated as amine salts or low-volatile esters and are found in the following groups: phenoxy herbicides, benzoic acid herbicides, pyridine herbicides, and quinoline herbicides and include different chemical classes such as phenoxycarboxylic acids, benzoic acids, pyridine-carboxylic acids, aromatic carboxymethyl derivatives and quinolinecarboxylic acids. Growth regulator herbicides shall also include auxin derivatives, including auxin, IAA, IBA, and other plant growth hormone and plant growth hormone derivatives.

A "hard water solute" as used herein refers to the minerals in "hard water". The mineral content in hard water generally consists of calcium and magnesium ions, however, in some geographical areas, iron, aluminum and manganese may also be present at elevated levels. A hard water solute(s) is formed when water percolates through deposits of limestone or chalk which are largely made up of calcium and magnesium carbonates, but may also include chlorides, bicarbonates (HCO3-), and carbonates (CO3-2) and other ions derived from carbon dioxide.

The term "insect growth regulator" (IGR) refers to a chemical substance that inhibits or modifies the life cycle of an insect, for example, compounds like benzoylurea pesticides. Insect growth regulators shall also include feeding inhibitors, deterrents, and other insecticidal actives.

"Manufacturing equipment" as used herein references any piece of equipment, apparatus (e.g., tanks, mixers, filling lines, packing equipment), or any attachment (e.g., hose, tubing) used in the production of a pesticide precursor, intermediate, or final product.

The term, "neonicotinoid" as used herein refers to a systemic agricultural insecticide resembling nicotine. Certain studies have found a link between the use of neonicotinoids and declining bee populations.

A "non-target plant" as used herein refers to a plant that is not intended to be treated with a particular pesticide or have that pesticide applied to it. A non-target plant may refer to a plant that is sensitive to injury by the pesticide and may also refer to a non-transgenic plant that is not resistant to one or more herbicides or other pesticides.

The term "osmolarity" or "osmotic concentration" as used herein refers to the measure of solute concentration, defined as the number of osmoles (osmol/Osm) of solute per liter (L) of solution (osmol/L or Osm/L).

The term "pesticide end-product" as used herein refers to one or more products that result due to a chemical breakdown reaction (conversion) of a pesticide. For example, a common end-product that results in the breakdown or degradation reactions for dicamba is 3,6-dichloro-2-hydroxybenzoic acid (3,6-DC SA).

The term "pH" as used herein is a measure of acidity or alkalinity of an aqueous solution. It is approximately the negative of the logarithm to base 10 of the molar concentration, measured in units of moles per liter, of hydrogen ions. A pH value is a number ranging from 0 to 14.

A "plant biostimulant" as used herein is any substance or microorganism applied to plants with the aim to enhance nutrition efficiency, abiotic stress tolerance, and/or crop quality traits, regardless of its nutrients content, for example, plant, seaweed or algal extracts.

The phrase a "plant part" as used herein refers to a part of a plant and may include a cell, a leaf, a stem, a flower, a floral organ, a fruit, pollen, a vegetable, a tuber, a bulb, a root ball, a root stock, a root, or a seed.

The phrase "precursor chemistry" as used herein refers to a chemical that is used to manufacture a pesticide, as well as impurities in a pesticide.

The term "rinsate" as used herein refers to the rinse water or cleaning solution that may contain diluted concentrations of pesticide(s), residual concentrations of one or more pesticides, precursor chemistries, or pesticide end-products that result from cleaning or detoxifying pesticide residues in or on agricultural or manufacturing equipment, for example, the solution that results from cleaning a tank, a storage tank, a bulk tank, a spray tank, a rinse tank or any combination thereof.

A "safe zone" is a concentration of a pesticides or pesticide end-products contained in the rinsate or remaining with the agricultural spray equipment that can be applied to a plant or an environment and not cause injury or harm to the plant or to the environment. The safe zone for a pesticide is a concentration that is low enough that during a spray or change out with another pesticide, the remaining low level of pesticide residue remaining in the tank, nozzles, lines, etc. will not cause injury to a plant, a non-target plant, a sensitive plant, a field of plants, a pollinator, a waterway or a natural environment that is at risk of being exposed to the pesticide, such as by cross contamination, drift, etc. In some cases, a safe zone may be determined with respect to single pesticide and/or pesticide end-product. In other cases, a safe zone may be determined in a manner that accounts for potential cumulative effects and/or interactions of multiple different pesticides and pesticide end-products.

A "seed treatment" refers to a substance that is used to coat a seed. For example, seed treatments may be an application of biological organisms, chemical ingredients, inoculants, herbicide safeners, micronutrients, plant growth regulators, germination enhancers or suppressors, seed coatings, etc., such as provided to a seed to promote growth of a seedling/plant and/or to suppress, control or repel plant pathogens, insects, or other pests that attack seeds, seedlings or plants. Specific use of "pesticide seed treatment" as used herein refers to an application of a pesticide to the surface of a seed as a coating that is designed to reduce, control or repel disease organisms, insects, or other pests that attack seed or seedlings grown from treated seed. The seed treatment that would require removal during the cleaning of pesticide seed treatment machinery refers to the removal of a pesticide or multiple pesticides.

"Seed treatment equipment" as used herein refers to apparatus for applying a seed treatment to a seed. Seed treatment equipment can include, but is not limited to: injection systems, sprayers or other dispensers, monitors for seed flow, pumps, seed belts, and a treatment, collection or mixing chamber, bin, basin, reservoir, or tank. Such equipment is used, for example, to deliver a single or multiple products contained in a slurry, a coating, or an encrusting to seeds in a continuous, one time application or simultaneously with multiple products.

The term "spectrophotometric device," "photodetector device," as used herein refers to an apparatus having the ability to measure the intensity of electromagnetic radiation in at least a portion of the electromagnetic radiation spectrum, e.g., as transmitted through, reflected by, or emitted by particular substances. For example, a "spectrophotometric device" may provide a quantitative measurement of the reflection or transmission properties of a material as a function of wavelength over at least a portion of the electromagnetic spectrum. The portion of the spectrum that a spectrophotometric device measures can include, for example, the visible, the fluorescence emitted, the ultraviolet, and/or the infrared portions of the spectrum. The spectrophotometric device may also include spectrophotometer, a photodiode or an array of photodiodes, a photosensor, a photodetector, and may also include a laser device that emits light through a process of optical amplification based on the simulated emission of electromagnetic radiation. The spectrophotometric device can also be a microelectromechanical system (MEMS) or nanoelectromechanical system (NEMS).

The phrases "sufficiently reduce", "sufficiently remove", "sufficiently detoxify" or "sufficiently clean", refer to processes in which the amount of a pesticide or the effect of the pesticide is reduced/decreased in rinsate remaining in pesticide application equipment or manufacturing equipment to a concentration that will not cause injury to a plant, a field of plants, a plant part, soil, a waterway or a natural environment.

The word "tank" refers to a container suitable for containing pesticide solutions and includes the following: a tank, a storage tank, a bulk tank, a spray tank, a nurse tank, a rinse tank, and a manufacturing vessel.

As used herein, the term "tracer dye" refers to any natural or synthetic chemical compound that when present in a solution, has one or more absorbance maxima (Amax) in the ultraviolet (UV) or visible range of the electromagnetic spectrum and can be detected using a spectrophotometric device. The term "tracer pigment" refers to any natural or synthetic chemical compound that when present in a suspension, has one or more absorbance maxima (Amax) in the ultraviolet (UV) or visible range of the electromagnetic spectrum and can be detected using a spectrophotometric device. When present in a liquid (e.g., when dissolved or suspended in a liquid), the tracer dyes and pigments can be used to detect and/or quantify the amount of another chemical compound (e.g., a pesticide or other agrochemical) also present in the liquid.

A "user's device" or "user device" refers to any device that a user may choose to use as an interface and includes, without limitation, a computer, an IPAD, an I-watch, a tablet, a phone, a data logger, a computer software, a computer hardware, a diagnostic receiver, a data mitigation system, a bidirectional exchange interface, a data portal, a data capture device, a cloud, a cable, a satellite system, a monitor, a data repository, a digital video browser, an app, a native app, a hybrid app, a web app, a web browser, a remote sensing device, a boom spray applicator control unit, and/or an industrial process control system.

"Volatility" refers to movement of a gaseous form of a pesticide after the pesticide has been deposited on an intended target as a typically a liquid. After deposition, the pesticide may change from a liquid to gaseous form and the gaseous form may move off the target with wind currents and inversion layers. A pesticide's volatility is influenced by many factors, including its vapor pressure, concentration, and rate of transport to the surface of the leaf or soil. Other factors that influence volatility include the temperature of the air, leaf, or soil; the water content of leaf or soil surface; and the velocity of air movement above the surface of the leaf or soil.

A "waterway" as used herein refers to any body of water and can include: streams, rivers, pools, ponds, lakes, irrigation ditches, canals, estuaries, dams, creeks and surface or ground water aquifers, water treatment plants, manufacture waste streams, drains, pipes, and holding tanks.

"Algorithm" as used herein describes a procedure or mathematical formula using a finite number of step for identifying, measuring and quantifying a pesticide or a pesticide end-product in solution. The algorithm may be a single algorithm, an adjusting algorithm, multiple algorithms, chemometric (learning) algorithms or combinations of these as described in the present invention and can be used for measuring at a single time point or simultaneously identifying and measuring the concentration of a pesticide or mixture of pesticides in real time.

"Window(s)" as used herein can be any transparent solid or material that allows for the transmittance of light.

Agrochemical Detection System

One embodiment of a system 11 of the present invention is illustrated in FIG. 1. The system 11 includes a photodetector device 13 including one or more detectors 15 positioned to detect light (broadly, electromagnetic radiation) after the light has interacted with an object or area that potentially has one or more agrochemicals associated therewith. For example, the light can be detected after it has been transmitted through, reflected by, or emitted by the object or substances in the area. In the example illustrated in FIG. 2, a series of detectors 15 are configured to receive light from a flow cell 17 that receives fluid that may contain an agrochemical, such as a spray solution to be applied to a seed or crop or a cleaning solution used to clean equipment of pesticide residue. The detectors 15 are thereby positioned to detect light that has been transmitted through and/or reflected by the material in the flow cell 17. The light can be natural ambient light. Alternatively, one or more light sources (not shown) may be positioned to direct light toward the object or area that potentially contains a pesticide or pesticide end-product. The detectors 15 are suitably spaced apart from one another (e.g., to form an array of detectors). For example, each detector 15 may be positioned at a different location to measure the concentration of a pesticide, pesticide precursor chemistry, or pesticide end-product at multiple different locations, such as various locations that may be of interest in equipment used to apply pesticides, store pesticides, manufacture pesticides, or to apply a seed treatment to seeds.

Agricultural Equipment

In one or more embodiments, the detection system 11 is used to detect an agrochemical in an environment associated with agricultural equipment. For example, the detection system 11 can be used to detect an agrochemical in an environment associated with field equipment (e.g., agricultural spray equipment) as described in further detail below. In addition, the detection system 11 can be used to detect an agrochemical in an environment associated with a processing facility at which an agrochemical or other agricultural product is manufactured.

Spray Equipment

Figure 2:
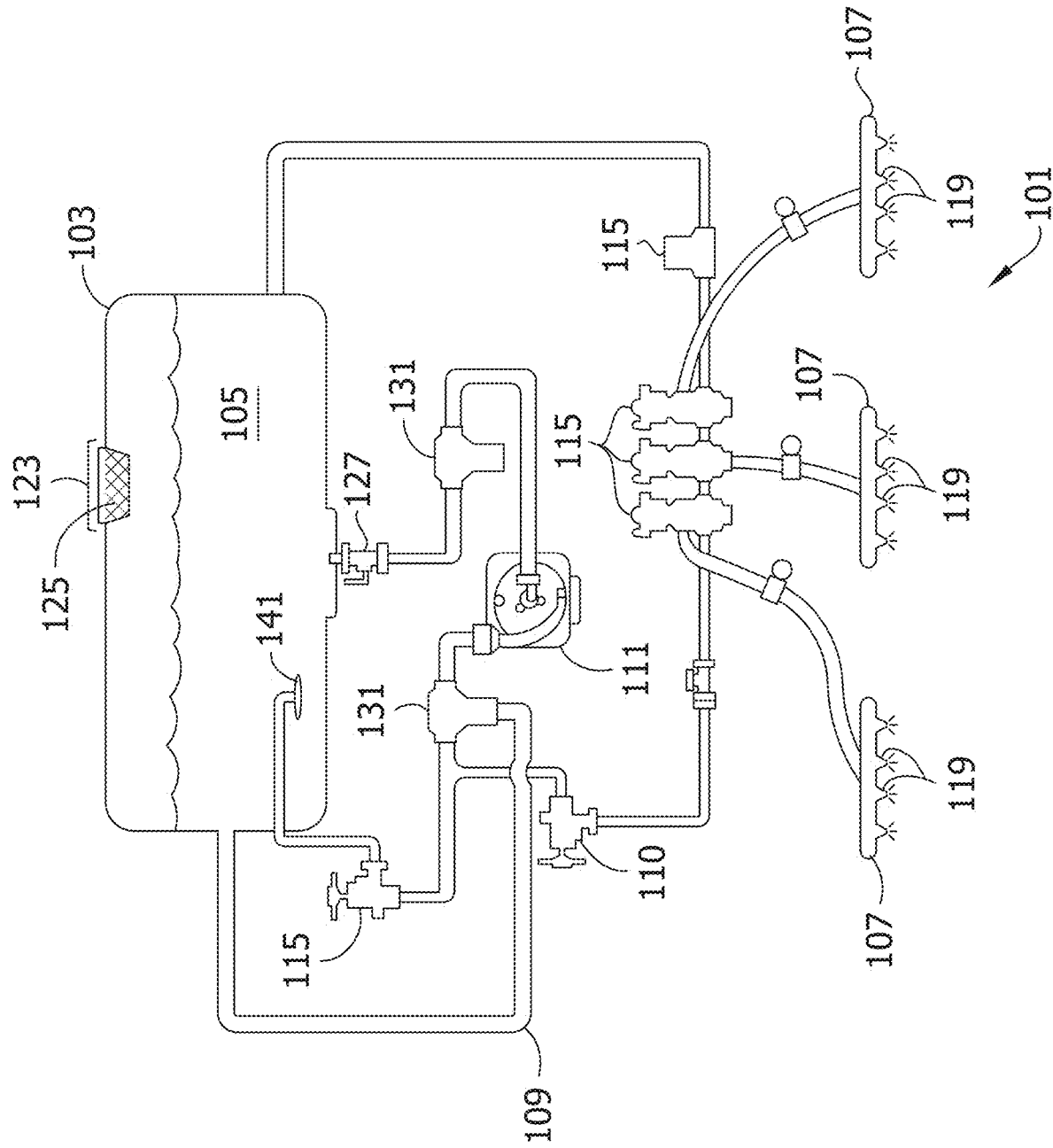
FIG. 2 is a schematic diagram illustrating one embodiment of agricultural equipment for spraying an agrochemical solution and to which the detection system can be operatively connected.

Referring to FIG. 2, one embodiment of agricultural spray equipment (broadly, agricultural equipment) with which the detection system 11 can be used is generally designated at reference number 101. The agricultural spray equipment 101 is generally configured, in one or more embodiments, for applying a solution containing one or more agrochemicals to a field or to crops growing in a field. The spray equipment 101, which can be referred to as a sprayer, a spraying system, or more generally as a system for applying pesticides or other chemicals, includes a tank 103 for receiving a solution 105 containing one or more pesticides or other agrochemicals, one or more spraying devices 107, a plumbing system 109 connecting the tank to the spraying devices, and a pump 111 operable to pump the solution through the plumbing system from the tank to the spraying devices. The spraying equipment 101 also includes a number of valves 115 in the plumbing system 109 operable to control flow of the pesticide solution 105 through the plumbing system. One or more screens 123, 131 are also included in the plumbing system 109 to filter out debris from the pesticide solution 105 or prevent debris from falling into the tank 103. The screens or other filters can be important because debris in the pesticide solution 105 can plug the nozzles 119 on the spraying devices 107 and thereby interfere with the ability of the spraying devices to produce the spray evenly, as is required to ensure even application of the pesticide solution on the target of the pesticide application.

Figure 3:
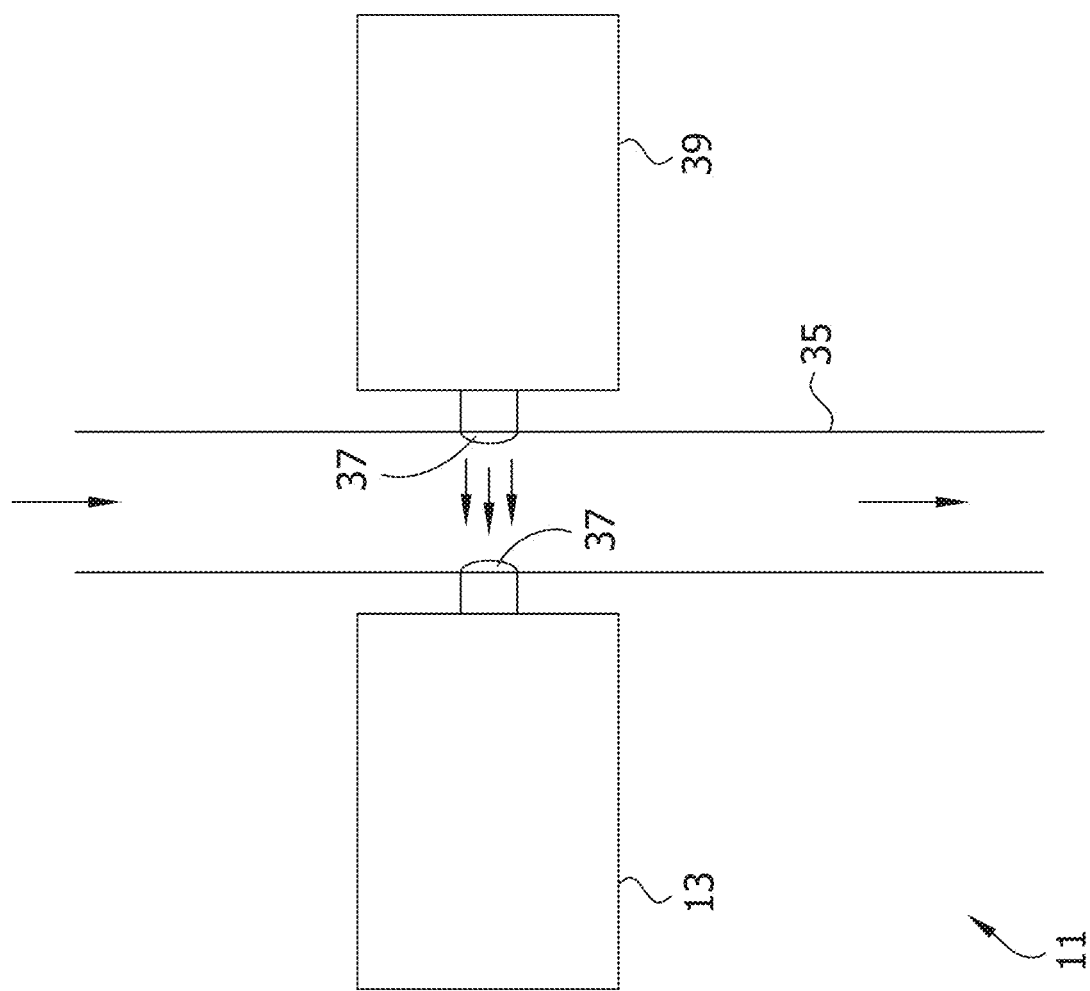
FIG. 3 is a schematic illustration of one arrangement of the detection system in which a photodetector device and a light source are arranged adjacent a fenestrated conduit.

The spraying system 101 illustrated in FIG. 3 is just one example of a spraying system with which the systems and methods of the present invention may be used. It is understood that the configuration of the spraying system can vary widely from what is illustrated in FIG. 3. For example, the spraying system could be a chemical induction system that uses the venturi effect to draw one or more pesticides and/or other chemicals into the spray stream at a location downstream from the pump. However, the system 101 illustrated in FIG. 3 will now be described in more detail to provide detailed examples of how the system 11 illustrated in FIG. 2 can be positioned in relation to the equipment. The tank 103 of the spraying system 101 can be any conventional spray tank. It suitably has a lid 123 covering an opening at the top of the tank 103 through which water or other materials used to make the pesticide solution 105 can be added to the tank. A screen 125 suitably covers the opening to limit the opportunity for debris to fall into the tank 103. A shut-off valve 127 at the bottom of the tank 103 controls drainage from the tank. The plumbing system 109 directs fluid from the shut-off valve 127 to the pump 111. As illustrated in FIG. 3, a screen 131 or other filter is installed in the plumbing system between the tank 103 and the pump 111 to prevent any debris in the tank from reaching the pump. It is understood that a similar screen could be installed in the tank 103 over the drain in addition to, or instead of, the screen 131.

Pesticides can settle to the bottom of the spray tank 103 and if left in the tank can dry and harden onto the walls of the tank, as well as in any attachments or fittings connected to the tank. Pesticide residues can also accumulate and sometimes absorb into or on hoses or other fluid lines in the plumbing system 109. Residues can also accumulate due to repeated coats of spray followed by drying on the spraying device(s) 107, pump 111, any of the valves 115, screens 117, inside the top of the spray tank (e.g., on the lid 123 or screen 125 at the top of the tank) and around any baffles that may be in the tank or on irregular surfaces inside tanks caused by baffles, plumbing fixtures, agitation units, checked or cracked hosing, etc. This residue can be a major source of contamination. The system 11 is configured to detect these types of residues.

The instrument 13 illustrated in FIG. 1 is suitably mounted directly on the agricultural spray equipment 101 or other agricultural equipment. For example, the flow cell 17 in FIG. 1 can be installed in one of the fluid lines of the plumbing system 109 or in the tank 103. Alternatively, the instrument 13 can be mounted on a hand-held device (not shown) and moved by a user to an environment of interest (e.g., the surface of a piece of the spray equipment 101 or an area adjacent the spray equipment) for assessment by the hand-held device of the amount of pesticide and/or pesticide end-product at that location. For example, the system 11 can include a cuvette (not shown) configured so it can be inserted by a user into the tank 103 for manual sampling of the tank contents to measure the amount of pesticide or pesticide end-product the pesticide solution or rinsate in the tank. More generally, the instrument 13 (or one of more of its detectors 15) can be mounted (substantially permanently or temporarily) in position to detect light after it has interacted with any of the following pieces of spray equipment: the tank 103 or its contents, the spraying devices 107, the plumbing system 109, the pump 111, any of the valves 115, 127, any of the screens 117 in the plumbing 109 or the screens 125, 131 in the tank, any of the nozzles 119, a spray exiting the nozzles 121, a lid 123 on the tank 103 or any other unlabeled components of the spray equipment.

Transmission of Spectral Data

In one or more embodiments, the system 11 can include one or more radiation guides, for example a light guide such as one or more optical fibers 19, which can be configured for conveying light or other radiation from the object or area of interest to one or more of the detectors 15. (Radiation guides can also be configured for conveying radiation from a source of radiation (e.g., a light source) to an object of interest or flow cell in certain embodiments). Optical fibers or other radiation guides may facilitate positioning the detectors 15 at a distance from the object or area of interest, for example in a more protected area or in an area that is more easily accessible. For example, it may be easier to position an optical fiber 19 in a tight space on the equipment 101 than it is to position the detector(s) 15 in that same space. In certain embodiments, the optical fibers 19 comprise solarization resistant optical fibers (SROF). Ultraviolet radiation, such as is present in sunlight, has a tendency to degrade optical fibers, resulting in increased light absorption in the fiber that occurs over time. Over time the gradual increase in absorption of light by the optical fiber changes the measured spectral characteristics of light transmitted through the fiber. Solarization resistant optical fibers are made of materials that resist this type of UV degradation. In one more embodiments, the instrument 13 includes one or more spectral filters 21 adapted to filter radiation in one or more spectral bandwidths. The spectral filter(s) 21 can be adapted to eliminate interference from sources of light or radiation that are not associated with the object or area of interest. The spectral filters 21 are suitably electronic filters that can be modified during use (e.g., in response to changing conditions) as will be described in more detail below.

In certain embodiments, the system 11 can comprise a spectral light interface (SLI) 23 configured to transmit filtered spectral data to a data exchange interface 25 for outputting data to another device, such as a personal computer, tablet computer, smartphone, or other mobile device. In the embodiment illustrated in FIG. 1, the data exchange interface 25 includes a wireless communication device 27, a data processing system 29, data storage 31, and a communications interface 33. The data exchange interface can have other configurations in other embodiments. The illustrated data exchange interface 25 suitably includes systems that can be used together or in the alternative to provide a user multiple options for linking the photodetector device 13 to the user's device(s). For example, the wireless communication device 27 provides the option to output data wirelessly to a remote PC or other computer, a tablet computer, a smartphone, a remote sensing device, or other mobile device. The data processing system 29 provides the option for the system 11 itself to perform various computing functions, which will be discussed in more detail below. It is understood however, that these computing functions could also or alternatively be performed in one or more external devices the user connects to the system 11. The data storage 31 provides the option to store data collected by the system in the data exchange interface 25 (e.g., for permanent storage and/or for download to a device at a later time). The communications interface 33 provides the option for a user to exchange information by plugging the user's device into the communications interface 33. For example, the communications interface can suitably be a USB port or other standard interface with ISOBUS compatible options (International Organization for Standardization, ISO). It is also understood that the system 11 could be implemented as a stand-alone system, in which case all of the processing would be performed within the system without communication with any outside devices.

Radiation Connections

The system 11 is configured to be operatively connected to agricultural equipment such as the agricultural spray equipment 101, seed treatment equipment, or pesticide manufacturing equipment so the spectrophotometric device 13 can detect light or other radiation after it has interacted with a material that has been received in the agricultural equipment that may contain an agrochemical. Several different arrangements that facilitate an operative connection between the system 11 and agricultural equipment will be described in detail below. However, it will be understood that an agrochemical detection system could be connected to a piece of agricultural equipment in other ways in other embodiments.

Fenestrated Fluid Passage

Referring to FIG. 3, in one or more embodiments, the detection device 13 is operatively connected to a piece of agricultural equipment by being positioned adjacent a fenestrated passage 35 (broadly, a fenestrated structure). For example, the passage 35 can comprise a pipe, a tube, a conduit, a cuvette, a nozzle, etc. for receiving a flowing fluid or a generally static fluid. The passage 35 comprises at least one window 37 that is transparent to radiation having a wavelength in a range of interest for detecting one or more agrochemicals in the fluid. Suitably, the detection device 13 is operatively aligned with the window 37 to detect spectral characteristics of the fluid based on the radiation transmitted through the window. In the illustrated embodiment, the passage 35 comprises a conduit having first and second windows 37 on diametrically opposite sides of the conduit. The windows 37 are in registration with one another to pass radiation from a source 39 external to the flow cell, through the fluid received in the flow cell, to the detection device 15. In the illustrated embodiment, the radiation source 39 comprises a powered light source such as one or more halogen bulbs, an LED, an array of LEDS, one or more deuterium bulbs, one or more xenon bulbs, combinations thereof, etc. In certain embodiments, the radiation source 39 can comprise ambient light. The illustrated light source 39 is mounted adjacent one of the windows 37 so the light from the light source passes through the window. The photodetector device 13 is mounted adjacent the opposite window so it can detect light exiting the space for containing the fluid. Thus, the photodetector device 13 is positioned so it can detect light from the light source after the light has interacted with materials in the conduit 35.

Transparent windows 37 as illustrated in FIG. 3 can be installed on opposite sides of various different fluid passages in agricultural spray equipment, seed treatment equipment, or pesticide manufacturing equipment to facilitate use of the system 11.

Connected by Fiber Optic Cables

Figure 4:
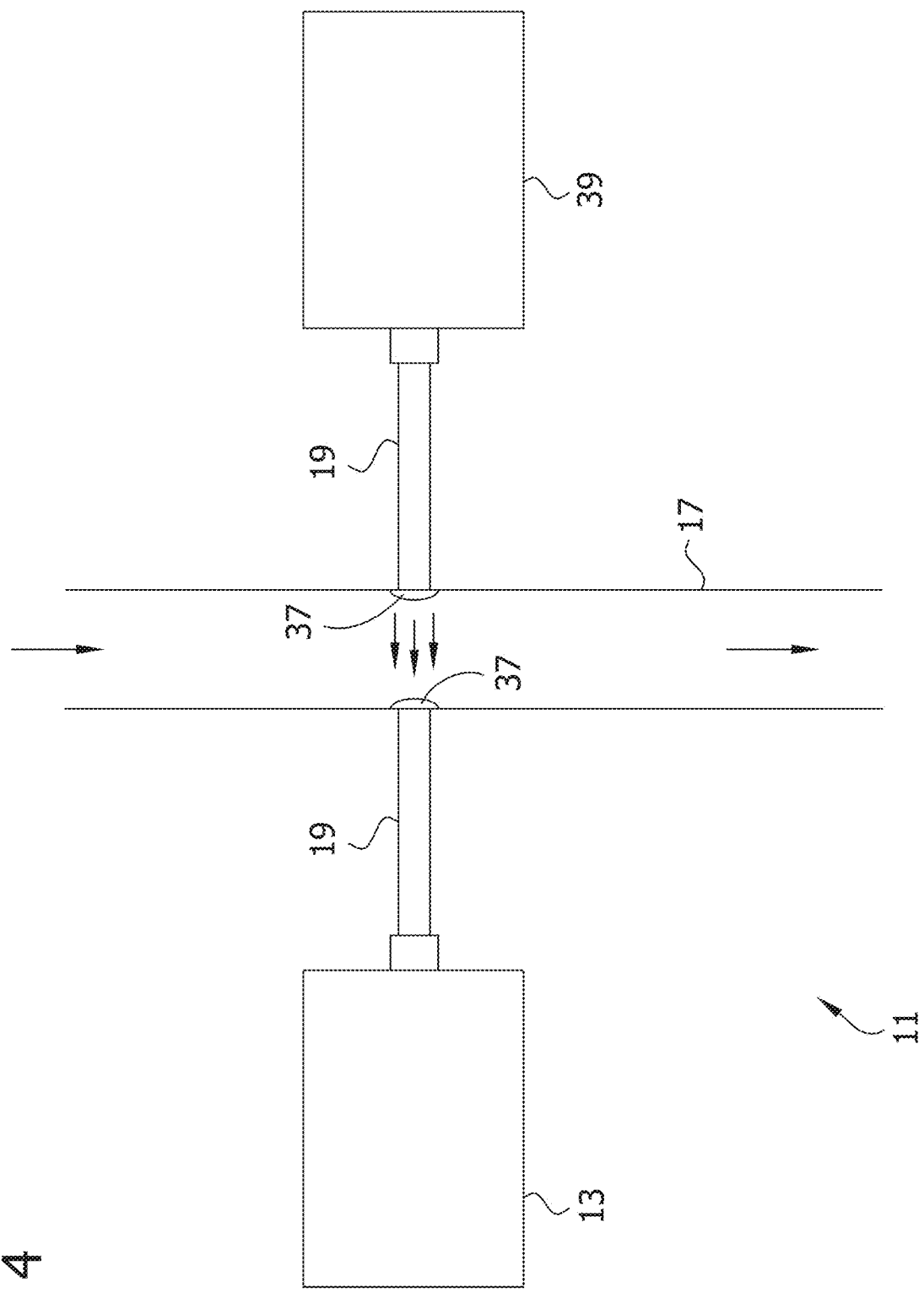
FIG. 4 is a schematic illustration of another arrangement of the detection system in which optical fibers operatively connect the photodetector device and the light source to the fenestrated conduit.

It is not necessary to mount either the light source 39 or the photodetector device 13 adjacent to any window. In some cases, it may be desirable to use one or more fiber optical cables (e.g., solarization resistant fiber optic cables) to convey light between a window and a remote location where it may be more desirable to mount the light source and/or detection device 13. Referring to FIG. 4, in one or more embodiments the light source 39 is positioned at a remote location and one or more optical fibers 19 (or other radiation guide) is positioned to convey light from the light source 39 to the window 37. In FIG. 4, the detection device 13 is also located at a remote location and one or more additional optical fibers 19 is positioned to convey light exiting the window 37 after it has interacted with the material in the conduit 35 to the photodetector device.

Flow Cell Spliced into Conduit

Figure 5:
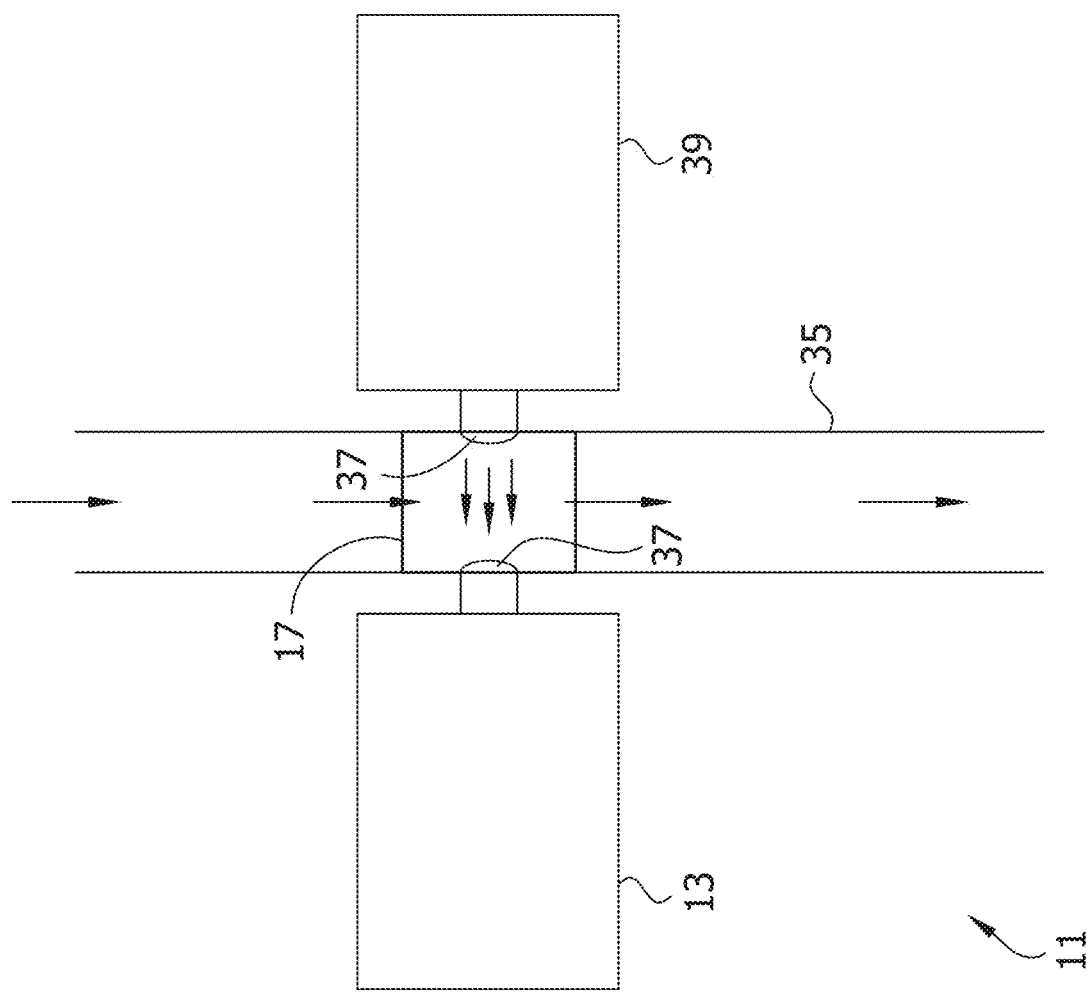
FIG. 5 is a schematic illustration of another arrangement of the detection system in which the photodetector device and the light source are operatively connected to a flow cell.

Referring to FIG. 5, in certain embodiments a substantially transparent flow cell 17 can be spliced into the passage 35. For example, in one or more embodiments, the passage 35 comprises a conduit of a piece of agricultural equipment and the flow cell 17 is spliced into the conduit such that fluid flowing through the agricultural equipment flows directly through the flow cell 17. The light source 39 is mounted adjacent to one of side of the flow cell 17 and the photodetector device 13 is mounted adjacent the opposite side of the flow cell 17. Thus, the light from the light source 39 can be detected by the photodetector device 13 after the light has interacted with material in the flow cell.

A flow cell as illustrated in FIG. 5 can be spliced into the various different fluid passages in agricultural spray equipment, seed treatment equipment, or agrochemical manufacturing equipment to facilitate use of the system 11.

Mounting of System on Agricultural Equipment

In certain embodiments, a portion of or the entire agrochemical detection system 11 can be mounted directly on the agricultural equipment. Certain components that may be used to facilitate mounting portions of the agrochemical detection system on a piece of agricultural equipment are described in further detail below. It will be understood that the agrochemical detection system can be mounted on a piece of agricultural equipment in other ways in other embodiments.

Protective Casing

Figure 6:
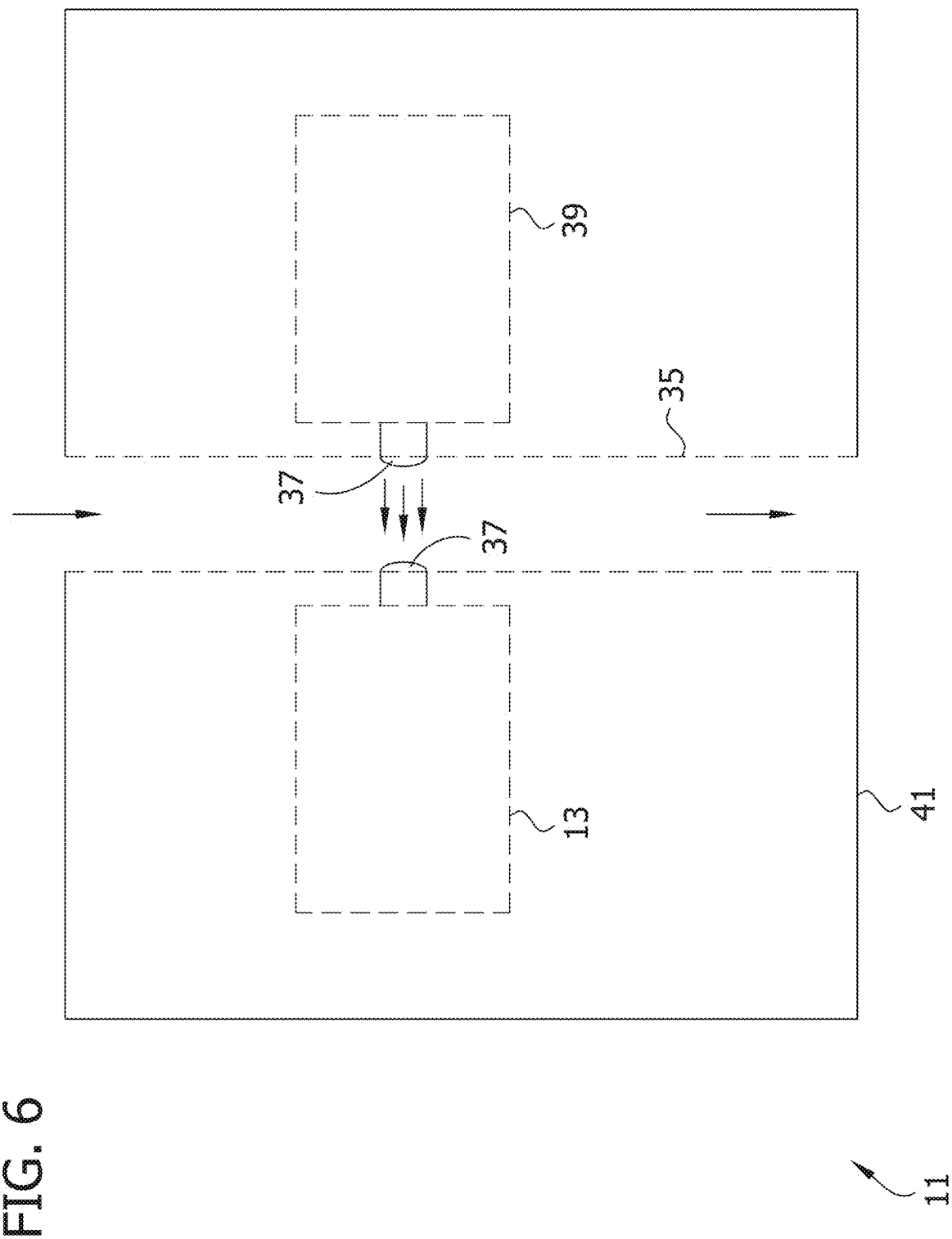
FIG. 6 is a schematic illustration of another arrangement of the detection system comprising a protective casing.
Figure 7:
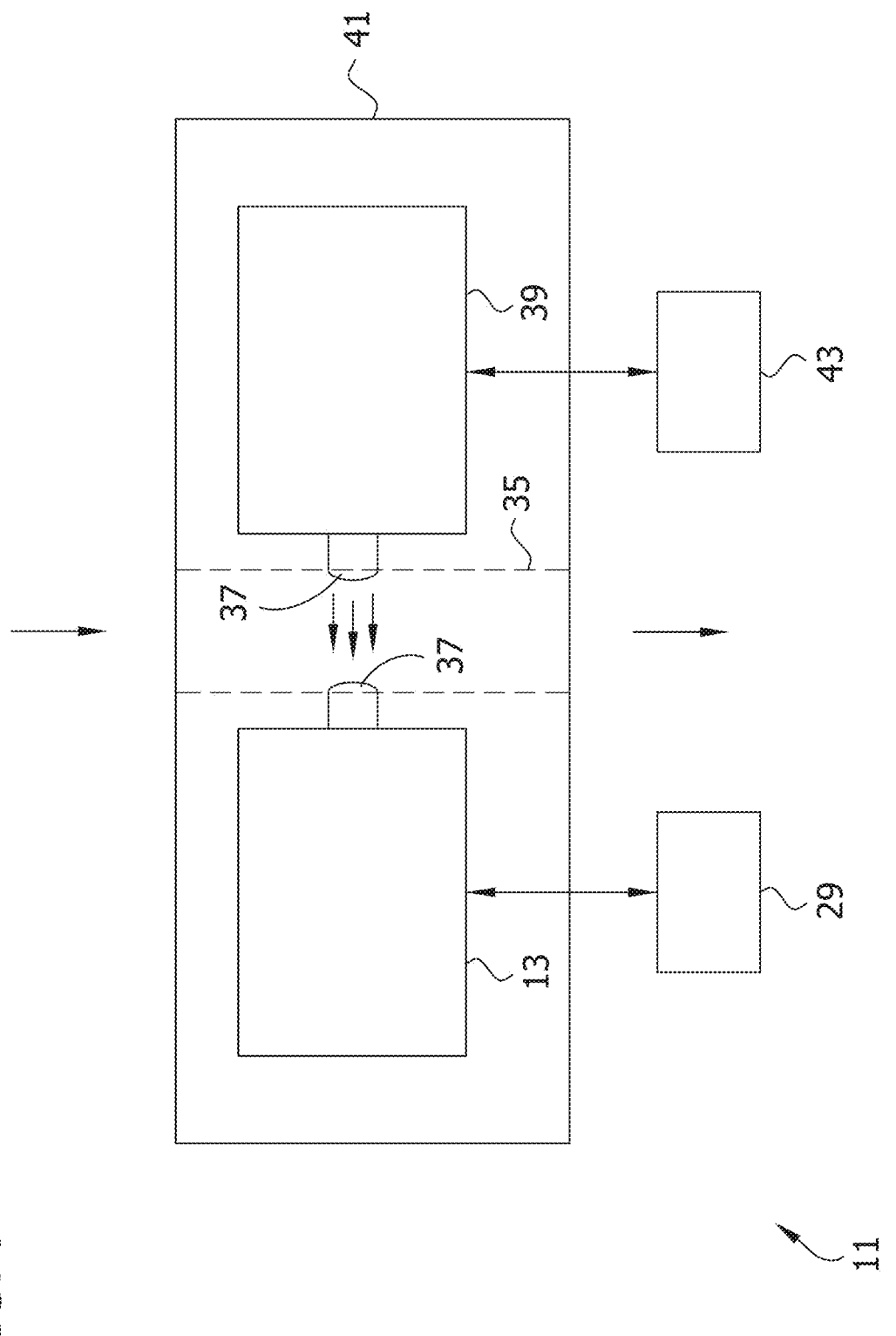
FIG. 7 is a schematic illustration of another arrangement of the detection system comprising a processor and a power supply.

Agricultural spraying equipment, seed treatment equipment, and agrochemical manufacturing equipment are commonly used in environments and/or have attributes that may damage sensitive optical and electronic equipment. Thus, when the photodetector device 13 or other electronic components of the agrochemical detection system are mounted directly on a piece of agricultural equipment, in some cases, it may be desirable to mount some or all of the components of the system inside a protective casing or cover 41. FIG. 6 illustrates one embodiment of a protective casing 41 that encloses a light source 39 and the photodetector device 13. There are various ways to arrange one or more components of the system 11 in a protective casing 41 while still allowing the photodetector device 13 to detect light after the light has interacted with a material that is to be analyzed. In FIG. 7, for example, a conduit 35 extends through the casing 41 between an inlet and an outlet on the casing to convey fluid to be analyzed through the casing. In the illustrated embodiment, the conduit 35 is straight and the inlet and outlet are on opposite sides of the casing. However, it is understood that the locations of the inlets and outlets could be different from what is illustrated if desired. The light source 39 and photodetector device 13 are mounted inside the casing 41 on opposite sides of the conduit 35. As illustrated, transparent windows 37 are installed in the conduit 35 and the light source 39 and photodetector device 13 are positioned adjacent the windows. Thus, the components inside the casing 41 in FIG. 6 correspond to the components of the agrochemical detection system 11 as illustrated in FIG. 3, but it is understood that the casing could enclose other arrangements of components in other embodiments.

The casing 41 is suitably water resistant, shock resistant, heat resistant, and/or chemical resistant. The casing 41 can be made water resistant by constructing the casing so it is sealed against ingress of water. The casing 41 can be made shock resistant by selecting a durable material to form the casing and/or by using vibration damping mounts to mount the spectrophotometric device 13, light source, and any other sensitive components of the system to the casing. The casing 41 can be made heat resistant by using a material that has a low thermal conductivity to form the casing and/or by adding thermal insulation to the casing. The casing 41 can be made chemical resistant by using a material selected for its inert chemical properties, such as a chemical resistant polymer. Those skilled in the art will be able to select suitable materials for chemical resistance to pesticides and related chemicals. In one or more embodiments, the casing 41 includes a bottom portion and a top portion (broadly, first and second portions) that are configured to be selectively closed and a seal that is configured to seal the interfaces between the bottom portion and the top portion to prevent the ingress of dirt, dust, or other contaminants into the casing.

Mounted with Additional Components

One or more additional components may be mounted on the agricultural equipment along with the photodetector device 13 and light source 28. For example, in FIG. 7, the system 11 includes a microprocessor 29 that is connected to the photodetector device 13 for analyzing signals therefrom (e.g., according to one or more of the algorithms described below). The microprocessor is suitably configured for collecting data from the photodetector device, and transmitting, processing, or processing and transmitting the data to end user or another intermediate device. The microprocessor 29 may also contain transmission hardware such as hardware for any of the following communications: wireless connection, Bluetooth, IR, cellular communication, LAN, USB, firewire, or other wired or unwired connection with ISOBUS compatible options (International Organization for Standardization, ISO). Also, a battery or other power supply 43 is suitably mounted on the equipment (e.g., to power the light source as in FIG. 8). The battery or other power supply 43 can be rechargeable, single use, or multiuse. The power can be direct or alternating current and may be conveyed from external power supplies, including optionally power from spray rigs and other agricultural equipment. Although the battery or power supply 43 is illustrated in FIG. 7 as providing power for the light source only, it is understood the battery or other power supply may supply power to any combination of the light source, spectrophotometric device, the microprocessor, and other components of the system 11 that may use power. Although the microprocessor 29 and the battery 43 are shown as being mounted externally to the protective casing 41, it will be understood that they could be received inside the protective casing with the photodetector device 13 in certain embodiments.

Figure 8:
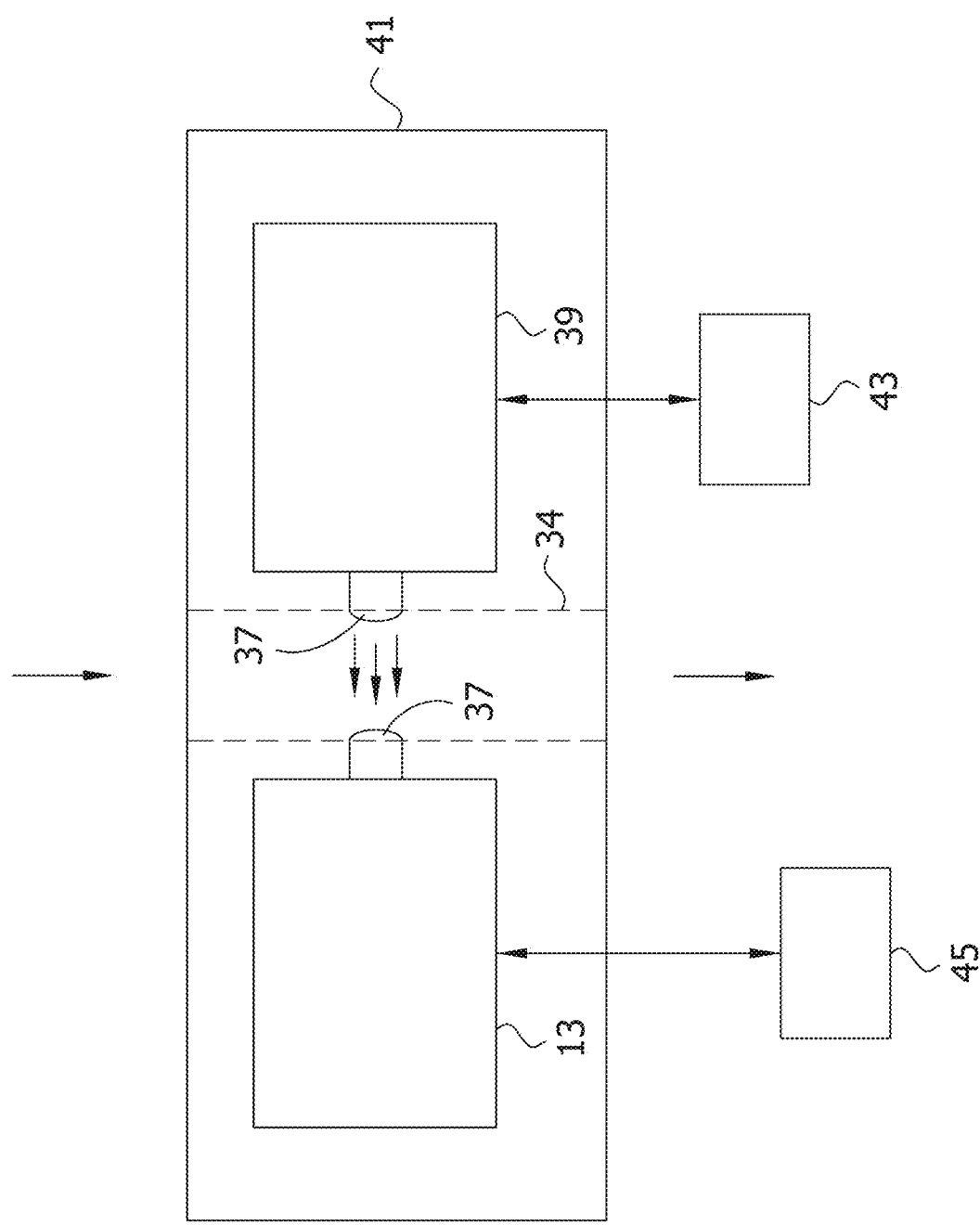
FIG. 8 is a schematic illustration of another arrangement of the detection system comprising a display.

FIG. 8 shows another example that is similar to FIG. 7, but in which a display 45 is mounted on the agricultural equipment along with the battery or other power source. The display 45 is suitably mounted on agricultural spray equipment, such as in the cab of a spray rig or mounted elsewhere externally or internally on a spray rig. The display 45 can be connected to other components of the system 11 via a hardwire connection or a wireless connection. The display 45 can optionally be or include the display of a tablet computer, phone, laptop, or other portable device configured to communicate with the system 11. In FIG. 8, a processor, such as the microprocessor 29 may also be mounted on the equipment or, if desired, a remote processor may be used (e.g., using wireless connection to the spectrophotometric device 13 and/or the display).

If desired the microprocessor 29, display 45, and/or battery 43 or other power supply may be enclosed, or at least partially enclosed, in the casing illustrated in FIG. 7.

Mounting Systems

Figure 9:
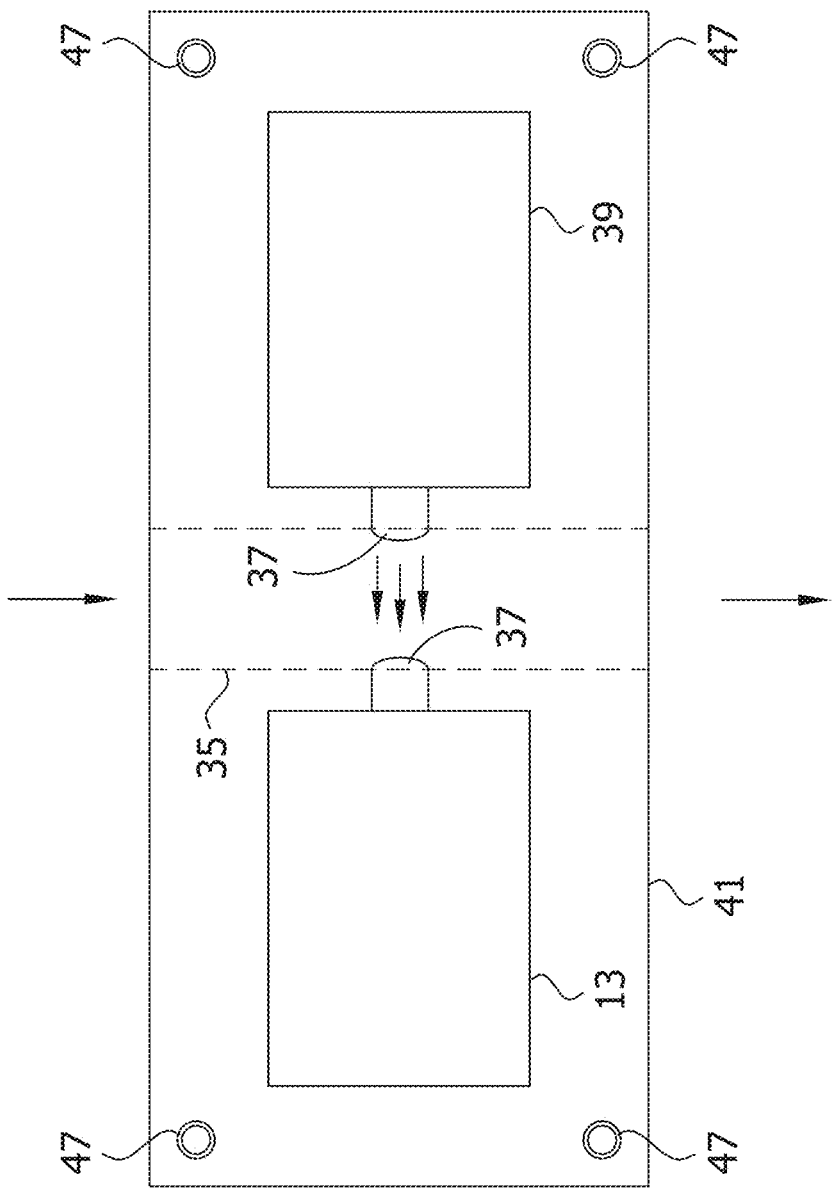
FIG. 9 is a schematic illustration of another arrangement of the detection system comprising mounting brackets.

The system 11 suitably includes a mounting system for mounting the components of the system on the agricultural equipment. Referring to FIG. 9, in one embodiment, the mounting system includes a set of brackets 47 or other suitable mounts having at least one of the following characteristics: the ability to insulate the mounted component(s) from vibrations; the ability to form a mechanical interface with a corresponding part of the equipment on which the system 11 or a component of the system is to be mounted; resistance to water; resistance to heat; chemical resistance to pesticides and pesticide end products; and combinations thereof. The mounting system may be sold separately from the system 11 as a mounting kit. For example, different mounting kits may be created for mounting the system 11 on different specific pieces of agricultural spray equipment, seed treatment equipment, or pesticide manufacturing equipment. Alternatively, the mounting system may be sold with the system 11. It is also understood that the system 11 can be sold without any mounting system without departing from the scope of the invention.

Fluid Connections

In certain embodiments, the agrochemical detection system 11 is directly fluidly connected to a piece of agricultural equipment. In one or more embodiments, the agrochemical detection system 11 is instead configured to receive a sample of fluid associated with the agricultural equipment that is separately delivered to the agrochemical detection system. The agrochemical detection system 11 can be fluidly coupled to the agricultural equipment in any suitable way. Certain embodiments of fluid connections between the system 11 and agricultural equipment are described below. It is understood that other ways of fluidly connecting the system to the agricultural equipment can be used in other embodiments.

Connection to Multiple Fluid Sources

Figure 10:
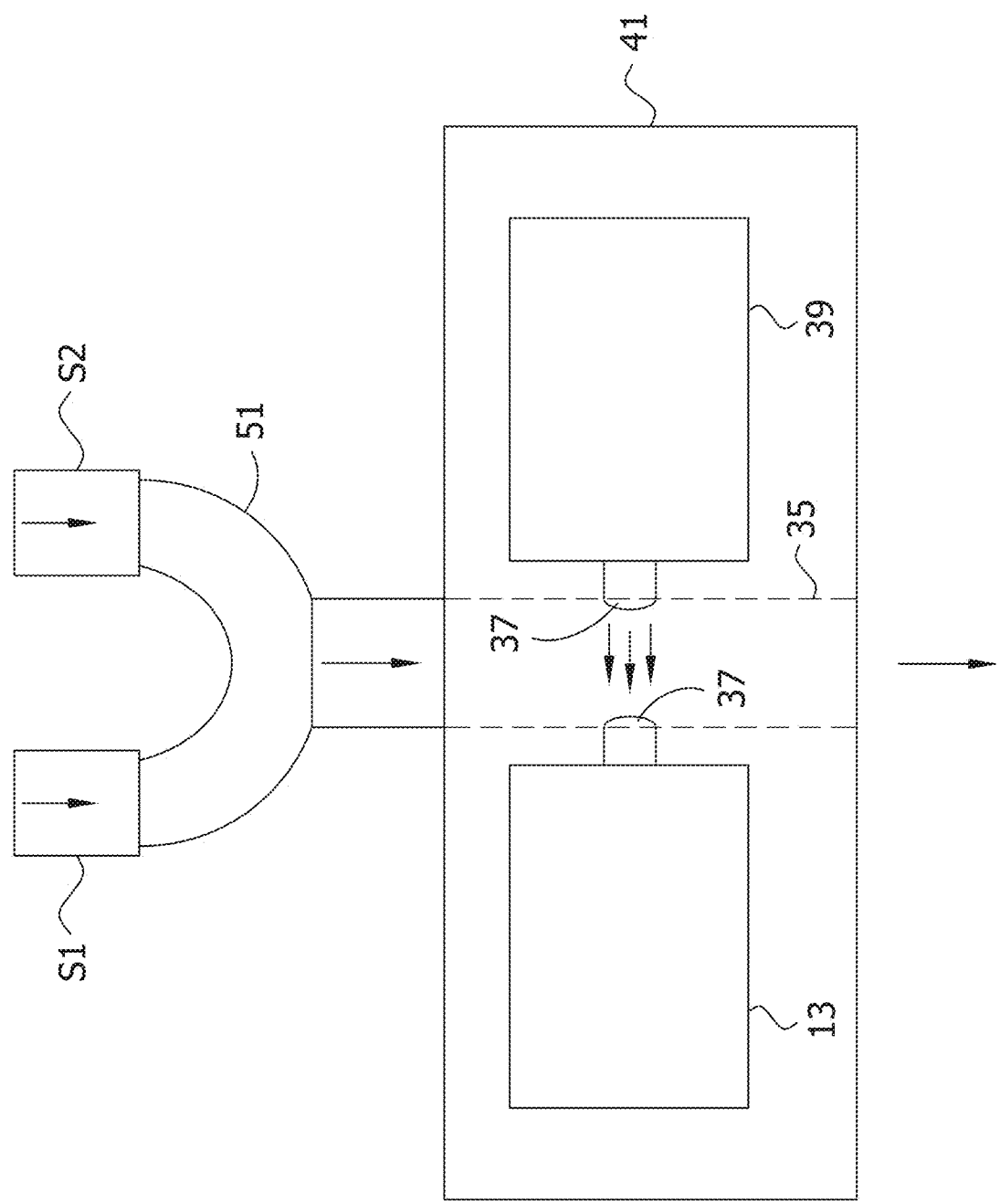
FIG. 10 is a schematic illustration of another arrangement of the detection system in which the fenestrated conduit can be fluidly connected to a plurality of sources of fluid.

In one or more embodiments, the system 11 is fluidly coupled to the agricultural equipment to receive fluids from multiple different sources (e.g., drains from multiple different tanks, etc.). Referring to FIG. 10, the system 11 is mounted in a fluidic system downstream from two or more different sources S1, S2. For example, a wye connection 51 may be used to fluidly couple the system 11 to two different sources S1, S2. Multiple wye connections 51 and/or a manifold may be used to fluidly couple the system to more than two different sources. If desired the wye connection(s) 51 or manifold may be replaced with a suitable valve or set of valves to prevent fluid flow between the sources. For example, the wye connection 51 in FIG. 10 can suitably be replaced with a multi-way valve (two or more), which may be a manual valve or controlled by an actuator, such as a solenoid for automated control of the valve (e.g., by the microprocessor).

In one application of FIG. 10, the first source S1 is a clean water tank and the second source S2 is a spray tank or other agrochemical-containing structure. This can be advantageous because the system 11 can be configured to periodically switch from the agrochemical source S2 to the clean water source S1 to obtain dark and/or blank measurements that may be beneficial for removing noise from the spectral measurements. Alternatively, the first source S1 can be the boom of a spray rig and the second source S2 can be the spray tank of the spray rig to allow comparative readings between fluid in the tank and fluid in the boom. Other fluid sources could also be connected to the agrochemical detection system 11 in other embodiments.

Filtered Connection

Figure 11:
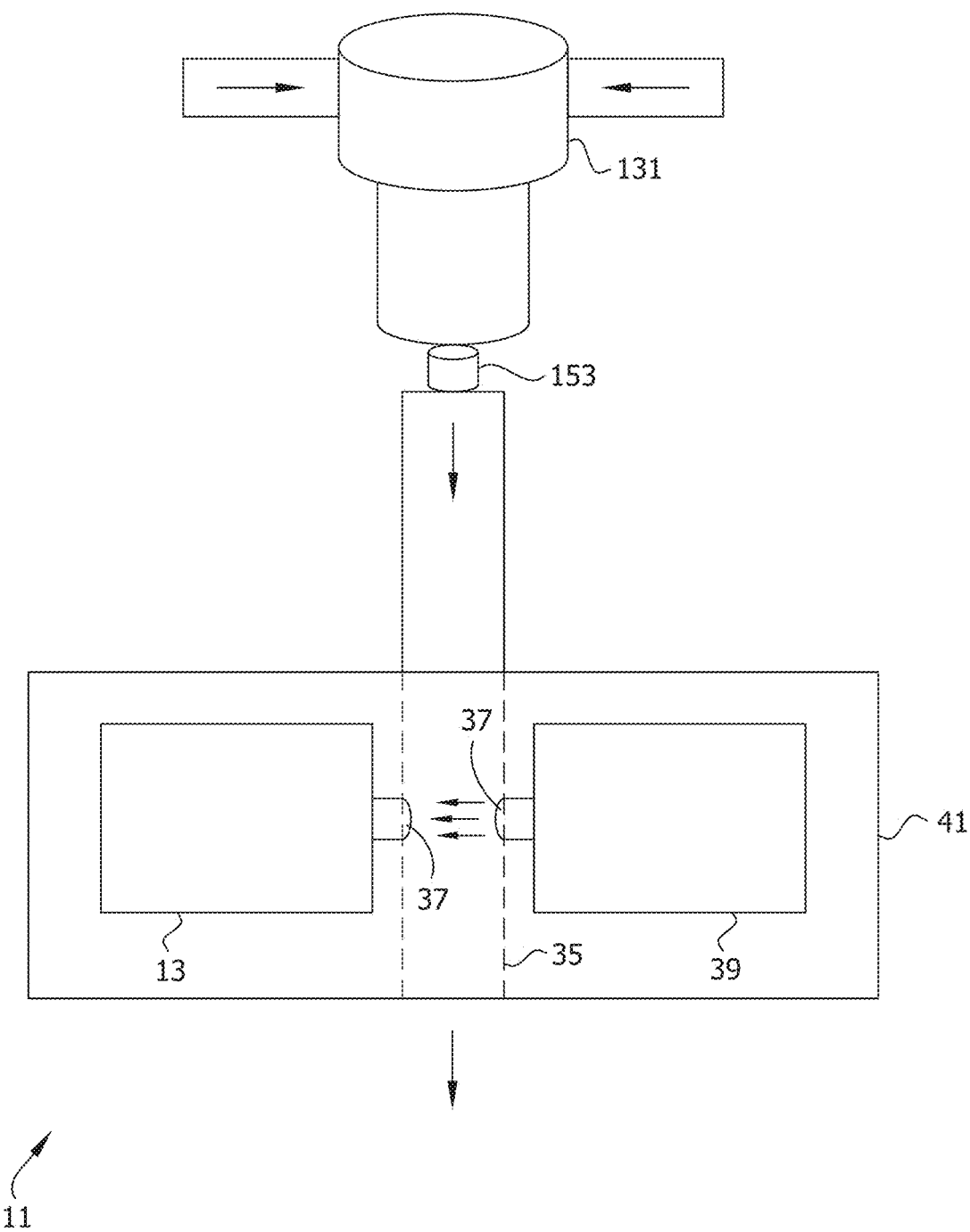
FIG. 11 is a schematic illustration of another arrangement of the detection system in which the fenestrated conduit is fluidly connected to a filter.

In one or more embodiments, the system 11 includes a connector for connecting the system to an inline a filter or strainer 131 in a passage of the agricultural equipment. Referring to FIG. 11, in certain embodiments, the system 11 includes a standard connector 153 that is attached or that may be attached to a filter/strainer or other similar in-line component of the agricultural equipment. The connector is suitably a standard hose connector for a line ranging in size from ¼ in to 2 in (about 0.6 cm to about 5 cm). In certain embodiments, the passage 35 of the agrochemical detection system 11 itself can include an inline strainer (not shown).

On or at End of Spray Boom

Figure 12:
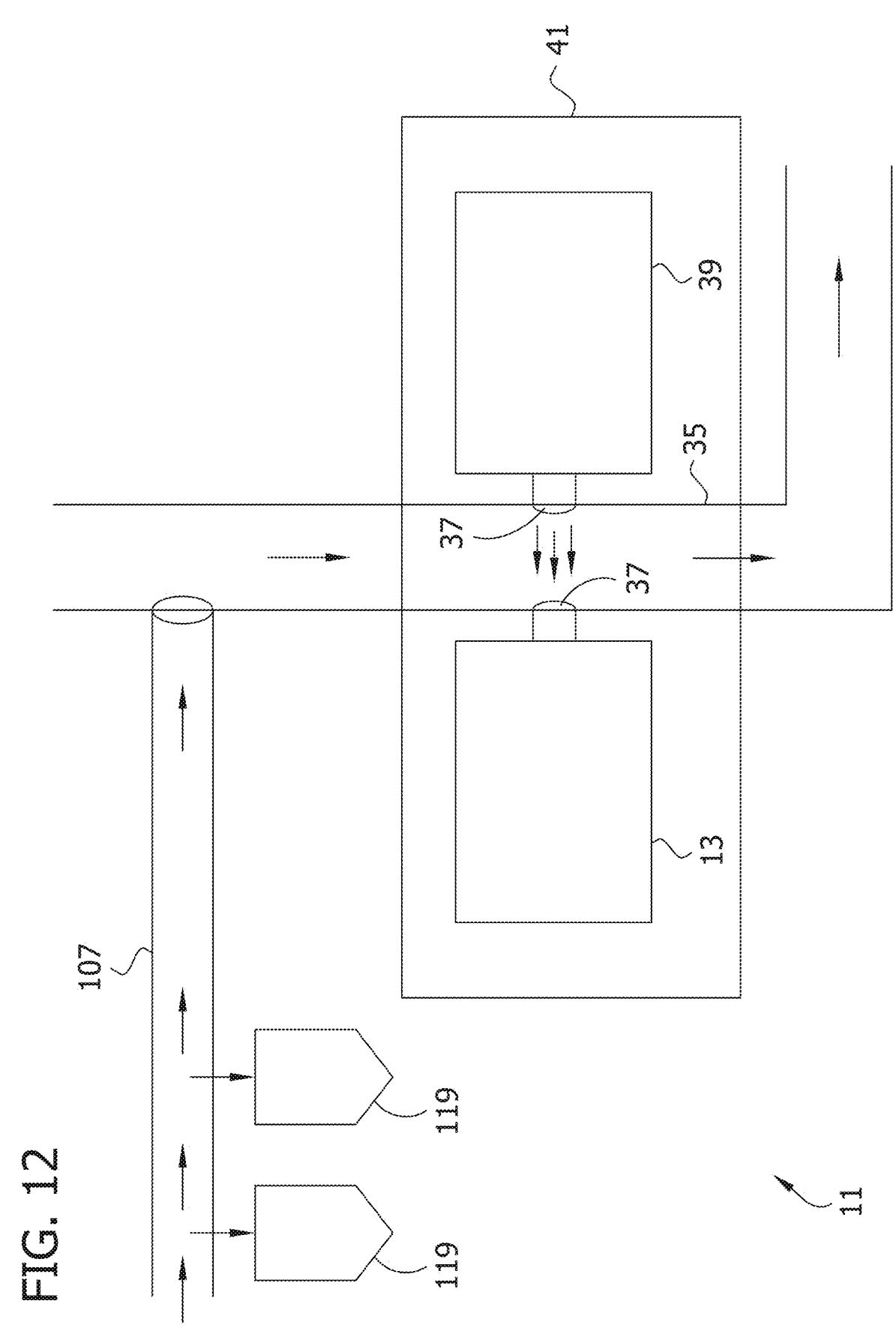
FIG. 12 is a schematic illustration of another arrangement of the detection system in which a fluid line extends from a spray boom to the detection system.
Figure 13:
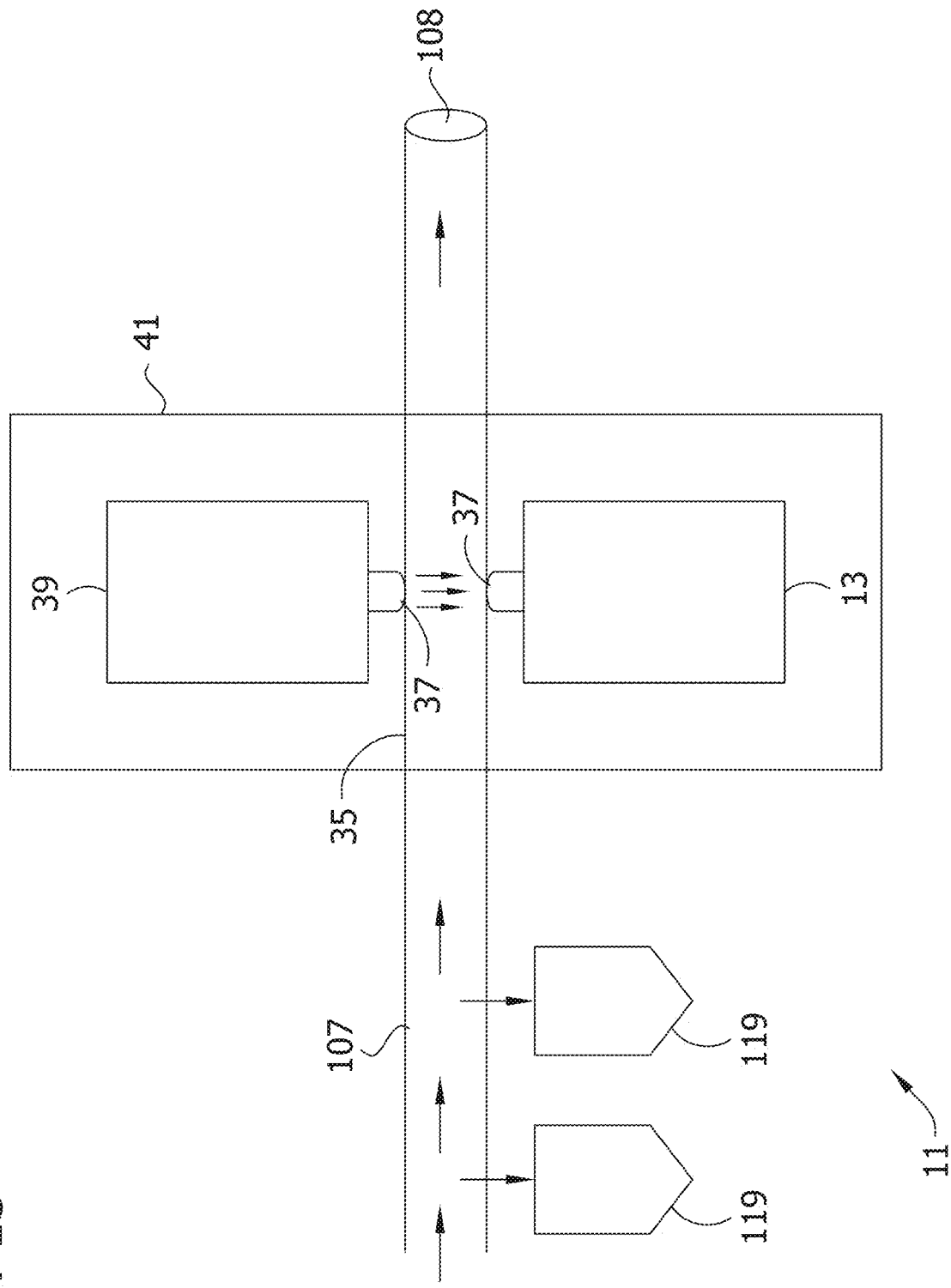
FIG. 13 is a schematic illustration of another arrangement of the detection system in which the detection system is mounted directly on the spay boom.
Figure 14:
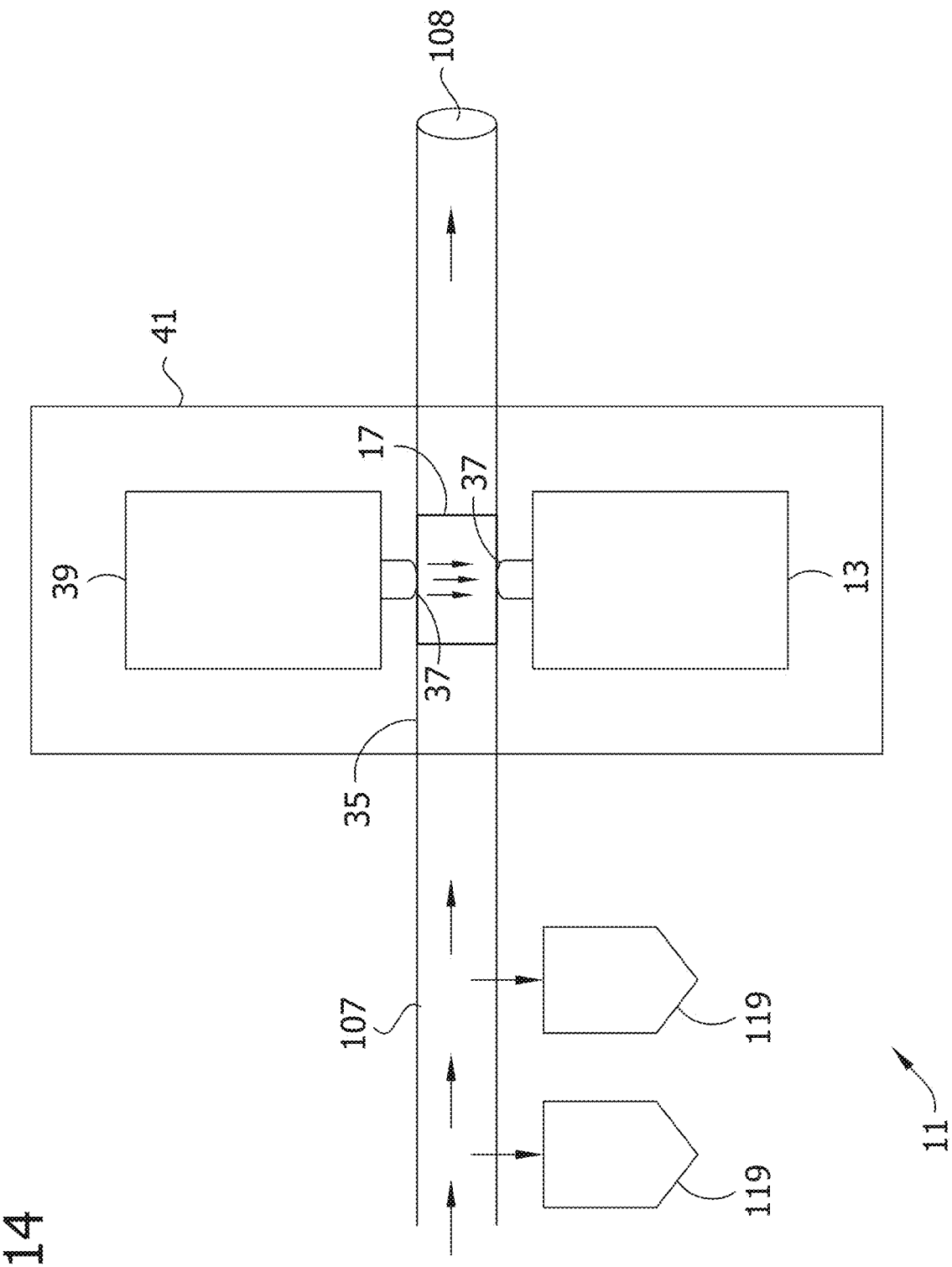
FIG. 14 is a schematic illustration of another arrangement of the detection system in which a flow cell spliced into the spray boom operatively connects the detection system to the spray boom.

Referring to FIGS. 12-14, in certain embodiments, the system 11 can be fluidly connected to agricultural spray equipment at a point of connection on or at the end of a spray boom. As is known to those skilled in the art, a spray boom can comprise a manifold (e.g., pipe) for simultaneously applying a pesticide or other chemical to a crop from multiple different spray nozzles, spray balls, or emitters distributed along the length of the manifold.

FIG. 12 illustrates one embodiment in which the system 11 is fluidly coupled to a downstream end of spray boom 107, for example, downstream from the spray nozzles 119. In other embodiments, the system 11 could be fluidly coupled to an upstream end of the spray boom or a middle segment of the spray boom without departing from the scope of the invention. In the embodiment shown in FIG. 12, however, a conduit 35 conveys fluid from the end of the spray boom to the system 11. In one or more embodiments, the conduit 35 has an outlet that is configured to discharge excess fluid from the spray boom after it flows through the agrochemical detection system. In certain embodiments, the outlet of the conduit 35 is configured to recirculate the fluid that passes through the system 11 back to a spray tank, a spray pump, or to a recirculation system used to prevent settling in the spray tank.

FIG. 13 shows an embodiment in which the system 11 is fluidly coupled to the spray boom 107 upstream of a downstream end cap 108 thereof. In the illustrated embodiment, the system 11 is fluidly coupled to the spray boom downstream of the downstream-most spray nozzle 119 (e.g., a spray ball, an emitter); but in other embodiments, the system is fluidly coupled to the spray boom at a point of connection upstream of one or more of the nozzles. In one or more embodiments, the system 11 is mechanically mounted directly on the spray boom 107, such that the windows 37 allow radiation such as light to be transmitted from inside the spray boom to the photodetector device 13.

FIG. 14 is similar to FIG. 13, except that in the arrangement shown in FIG. 14, a flow cell 17 has been spliced directly into the spray boom 107. The flow cell 17 fluidly couples the agrochemical detection system 11 to the boom 107, and in the illustrated embodiment, at least a portion of the system is supported directly on the spray boom. Again, although the system 11 is mounted between the last nozzle, spray ball, or emitter 119 and the end cap 108 in FIG. 14, it is understood the flow cell 17 and the rest of the system may be mounted anywhere along the length of the spray boom.

At Nozzle or Other Outlet

Figure 15:
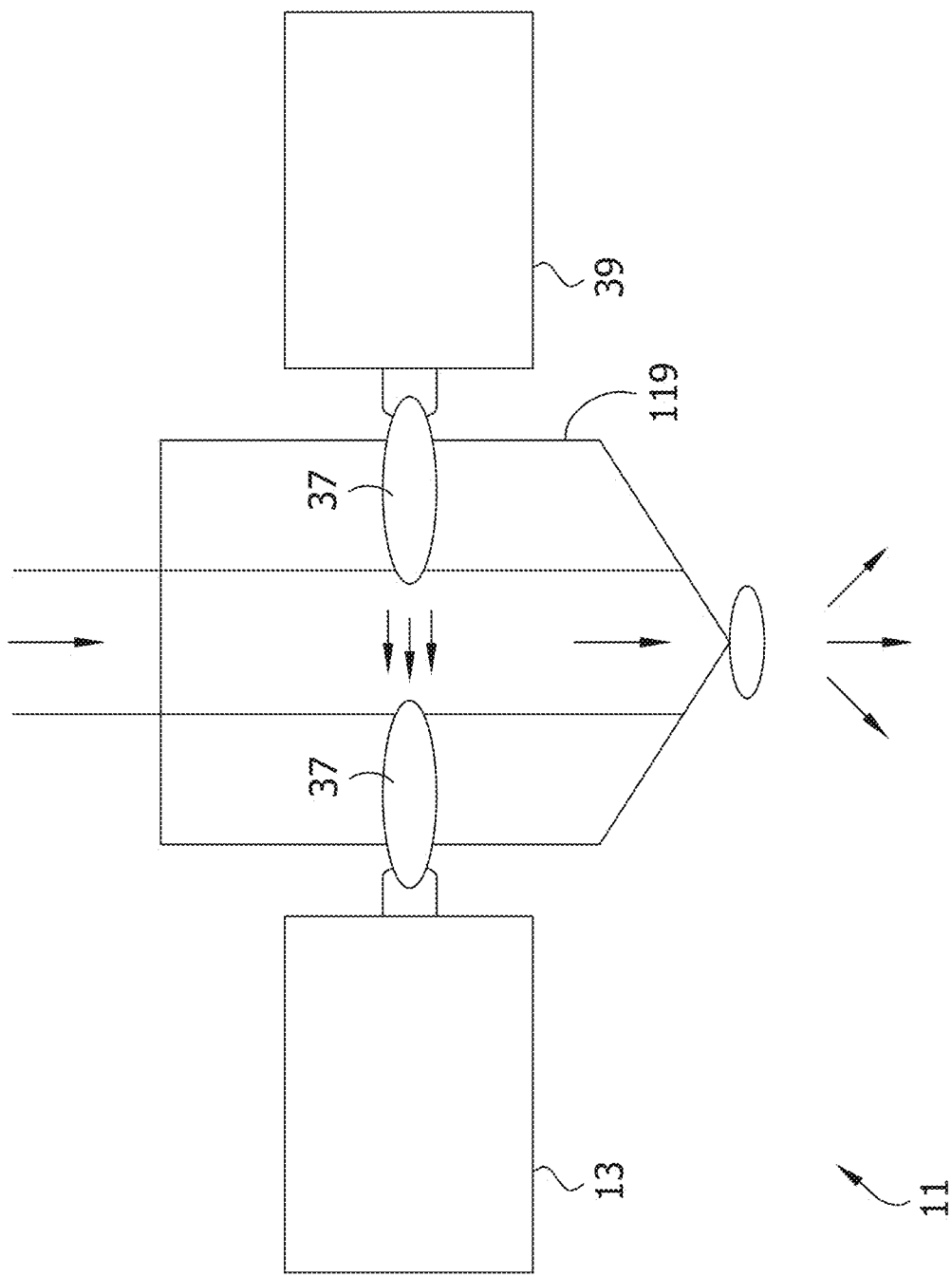
FIG. 15 is a schematic illustration of another arrangement of the detection system in which the detection system is mounted directly on a spray nozzle.

Referring to FIG. 15, in certain embodiments, the system 11 is fluidly coupled to agricultural spray equipment or other agricultural equipment at a point of connection at a spray nozzle 119 or other fluid outlet. The outlet could be a nozzle, spray ball, emitter, or other device configured to apply an agrochemical to crops, seeds, or other materials in a process facility. In the illustrated embodiment, at least a portion of the agrochemical detection system 11 is supported directly on the nozzle 119. For example, at least a portion of the agrochemical detection system could be formed integrally into the nozzle in certain embodiments. In other embodiments, a passage can divert fluid from the nozzle 119 to the system 11 supported at another location. In the illustrated embodiment, transparent windows 37 are positioned on opposite sides of the nozzle 37 upstream of and adjacent to the outlet(s). The light source 39 is positioned adjacent one of the windows 37 and the photodetector device 13 is positioned adjacent the opposite window so that the spectrophotometer device can detect light emitted by the source after it has interacted with any material between the windows. That is, the windows 37 allow radiation such as light to be transmitted from inside the nozzle 119 to the photodetector device 13.

Figure 16:
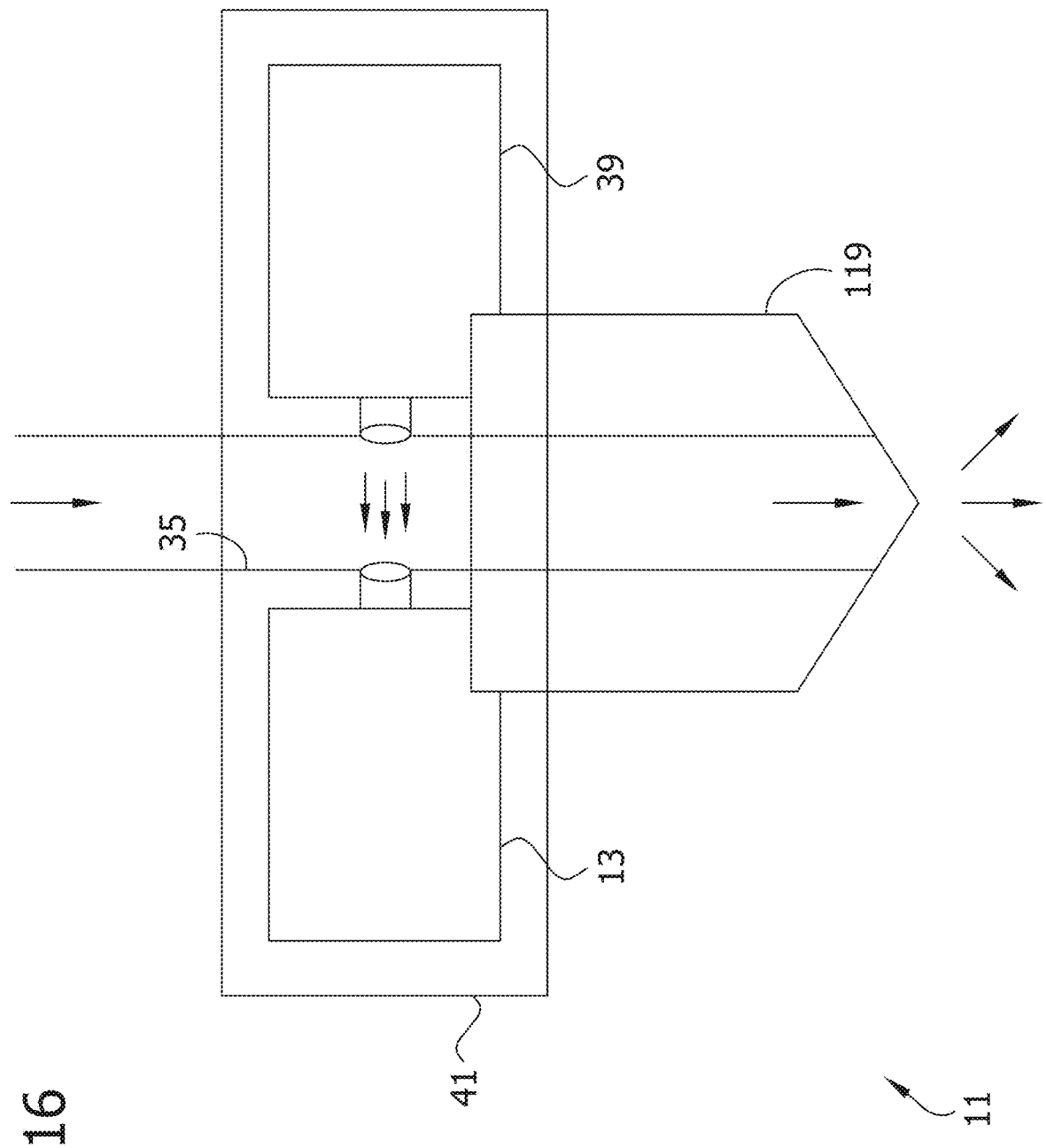
FIG. 16 is a schematic illustration of another arrangement of the detection system in which the detection system is operatively connected to a passage immediately upstream of the spray nozzle.

FIG. 16 illustrates an embodiment that is similar to FIG. 15 except that the system 11 is fluidly connected to the agricultural equipment at a point of connection that is located slightly upstream of the body forming the nozzle, spray ball, or emitter 119. For example, the system 11 is fluidly coupled to a passage that is fluidly coupled to the nozzle, spray ball, or emitter 119, such as a passage that extends between a spray boom and the nozzle, spray ball, or emitter. In the illustrated embodiment, at least a portion of the agrochemical detection system 11 is supported directly on the passage extending from the nozzle 119. In other embodiments, another passage can divert fluid to the system 11 supported at another location.

Figure 17:
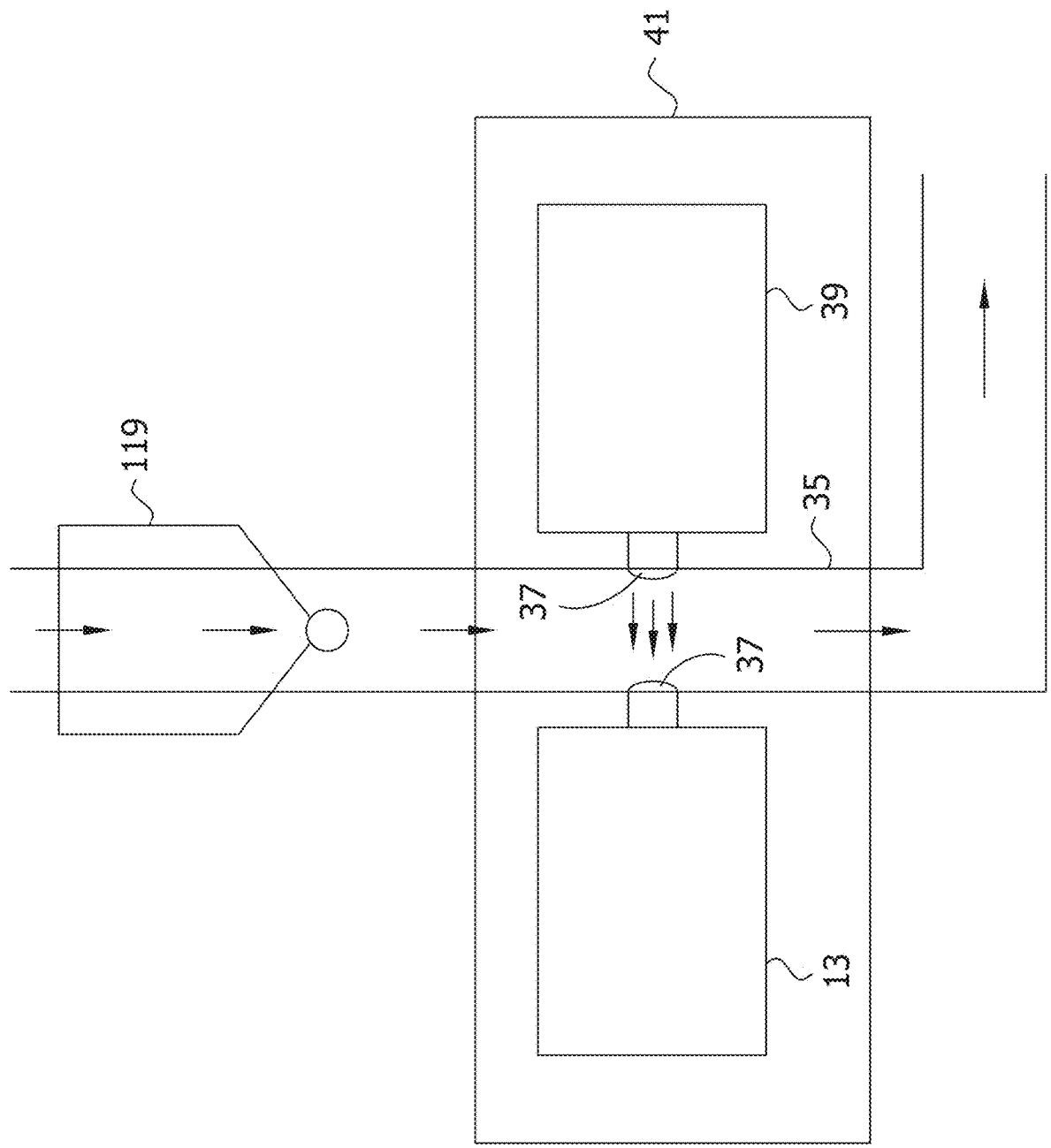
FIG. 17 is a schematic illustration of another arrangement of the detection system in which the detection system is operatively connected to a recirculation conduit downstream from the spray nozzle.

FIG. 17 illustrates another embodiment in which the system 11 is fluidly connected to the agricultural equipment at a point of connection that is downstream of an outlet of the nozzle 119. In this embodiment, the system 11 includes a discharge conduit 35 that is positioned to capture at least some of the material being dispensed from the spray nozzle, spray ball, emitter, or other agrochemical outlet 119. In the illustrated embodiment, at least a portion of the agrochemical detection system 11 is supported directly on the discharge conduit 35. In other embodiments, another passage can divert fluid to the system 11 supported at another location. The conduit 35 itself could have an outlet opening at a downstream end through which the agrochemical is configured to be discharged to a desired location. In certain embodiments, the conduit 35 is configured to deliver the fluid to a spray tank, a spray pump, or a recirculation system. In one or more embodiments, the spray nozzle, spray ball, emitter or other outlet 119 comprises a mock sprayer or mock outlet that does not actually apply agrochemical but is in all other respects the same as the devices that do apply the agrochemical. For example, a mock spray nozzle 119 may be installed on a spray boom 107 along with actual spray nozzles so the system 11 can gather data from the mock spray nozzle that is representative of what is being dispensed from the actual spray nozzles. Alternatively, the conduit 35 may be positioned to sample a small portion of the material applied by an actual spray nozzle, spray ball, emitter or other application device 119 (e.g., in the path of spray emitted from an actual spray nozzle or spray ball) to gather data from an actual pesticide application device.

In or on Tank

Figure 18:
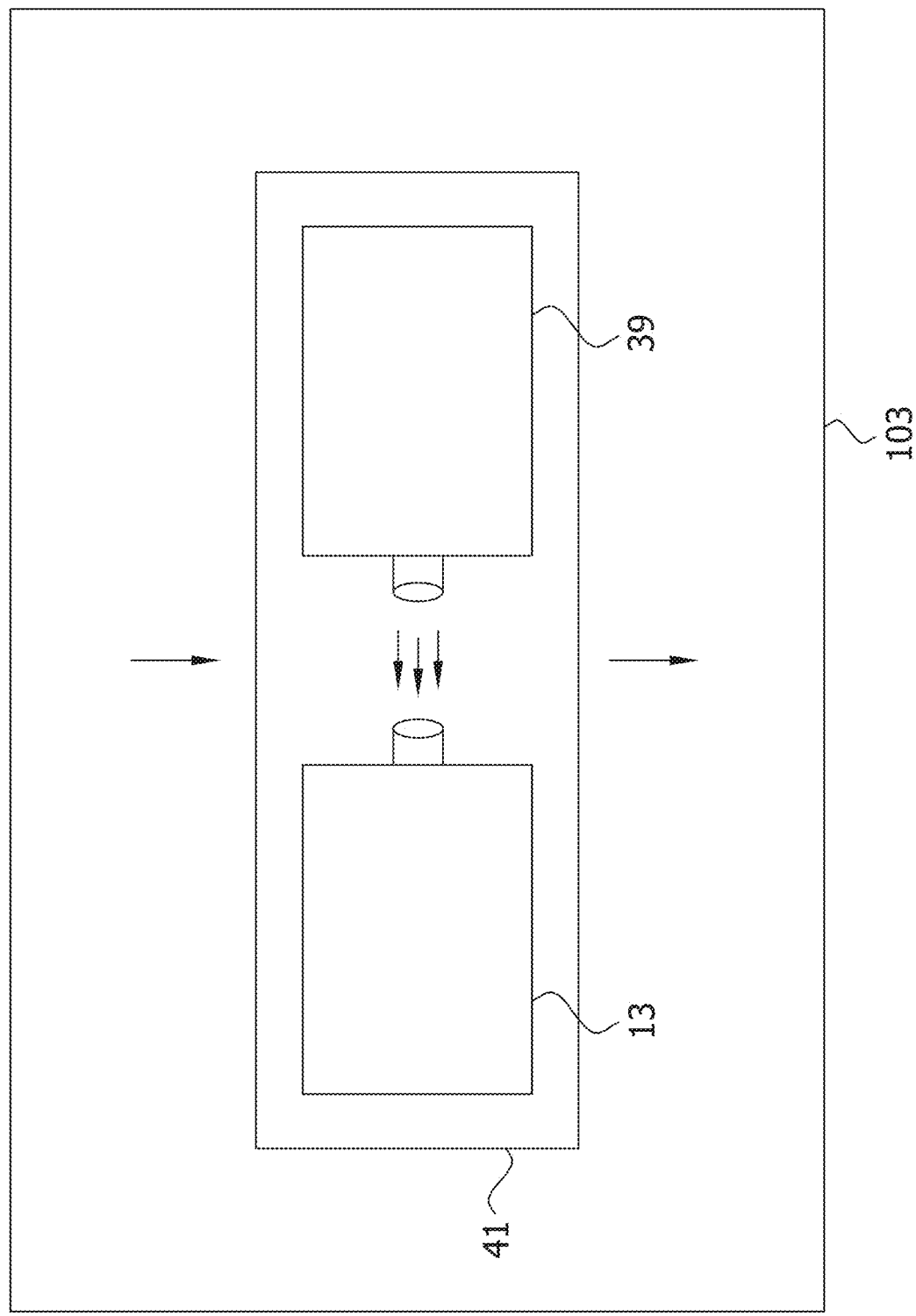
FIG. 18 is a schematic illustration of another arrangement of the detection system in which the detection system is received directly in a tank.

Referring to FIG. 18, in certain embodiments, the system can also be received in the interior of a tank 103 or other structure for containing or conveying a fluid. The tank 103 could be a spray tank or a storage or transport tank. If one or more components of the system 11 can be enclosed in a water-resistant or water-proof casing 41. In certain embodiments, at least a portion of the system 11 can be supported on a probe that can be inserted into the fluid stored in a tank or flowing through a passage. Alternatively, parts of the system 11 may be built into the wall of the tank or passage to protect them from the fluid contents. As another alternative, the system 11 may be mounted externally on the tank 103 and a conduit may be provided to convey fluid to the system so it can be analyzed. In one embodiment, the system 11 is included as part of a kit for mounting the system on a tank. Kits for mounting at least a portion of the system 11 at other locations of agricultural equipment and/or fluidly connecting the system to a source of agrochemical at other points of connection can also be used in other embodiments.

Example System

Figure 19:
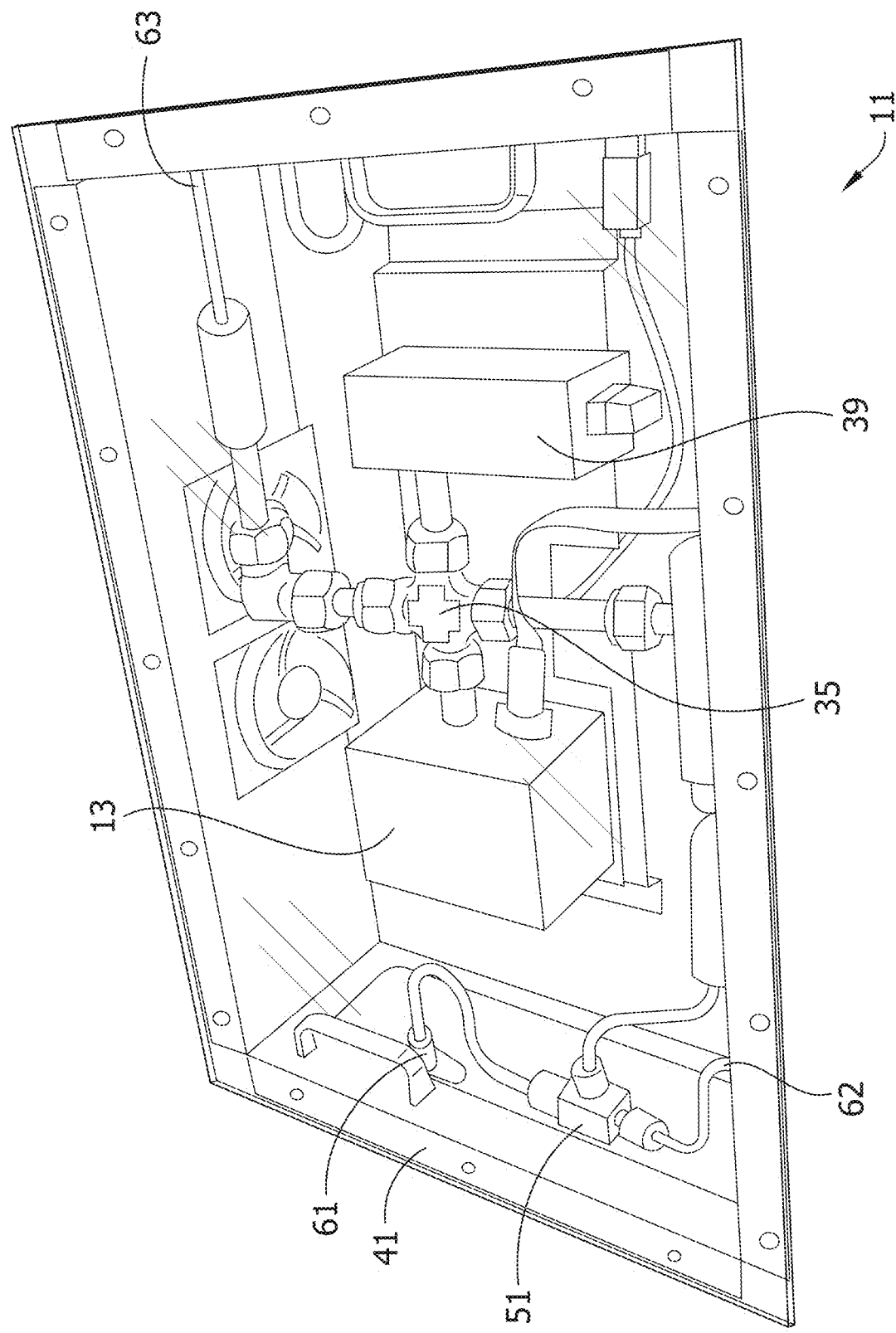
FIG. 19 is a perspective of one embodiment of the detection system.

Referring to FIG. 19, one embodiment of an agrochemical detection system is generally indicated at reference number 11. The illustrated components of the system 11 are received in a protective enclosure 41 that has a transparent cover so that the components are visible to a user. In other embodiments, the enclosure 41 is opaque. As explained above, the enclosure can comprise a protective (e.g., ruggedized casing) that is configured to protect the system from vibration, high/low temperatures, chemical hazards, and the like. In addition, as explained above, the enclosure 41 can be mounted directly on the agricultural equipment by way of brackets or the like.

The agrochemical detection system 11 includes passaging extending through the casing 41 from at least one fluid inlet 61, 62 to at least one fluid outlet 63. In the illustrated embodiment, the passaging comprises first and second fluid inlets 61, 62. The first fluid inlet 61 is configured to fluidly connect the passaging to an agrochemical source associated with agricultural equipment (e.g., a tank, a spray boom, a conduit, a nozzle, etc., as explained above). The second fluid inlet is configured to fluidly connect the system 11 to a clean water source. The passaging 11 includes at least one valve associated with a wye fitting 51 (e.g., a manifold) that is configured to selectively connect each of the inlets 61, 62 to a conduit 35 of the passaging that extends from the wye fitting to the outlet 63. A processor of the system 11 can be configured to control the valve associated with the wye fitting 51 in certain embodiments. The system 11 can selectively deliver clean water from the inlet 62 through the passaging when blank and dark spectral readings are desired and can selectively deliver a fluid that may contain agrochemical through the passaging when agrochemical detection is desired. Other embodiments can have other passaging configurations without departing from the scope of the invention.

The illustrated system 11 includes a photodetector 13 and a light source 39 (broadly, a radiation source) that are arranged on opposite sides of the conduit 35. The conduit 35 is configured so that the light source 39 delivers light (broadly, radiation; for example, visible light and ultraviolet light) through the conduit to the photodetector 13 and the photodetector receives the light after it has interacted with a substance in the conduit. For example, in certain embodiments, the conduit 35 comprises windows that are aligned with the light 39 and the photodetector 13 as explained above to allow passage of the light from the light source to the photodetector. In other embodiments, a flow cell is spliced into the conduit 35 at a location aligned with the light source 39 and the photodetector 13. The photodetector 13 is configured to detect spectral characteristics of the fluid after receiving the light from the conduit. As explained below, a processor (not shown) of the system 11 or another processor is configured to analyze the spectral data to detect the agrochemical.

The photodetector 13 can be combined with wireless, cellular, Bluetooth, wired, optical, or other connections to deliver raw or processed spectral data to a phone, tablet, display, computer, memory, or integrated systems monitor for display or records for the end user. In certain embodiments, analytical processes for evaluating the spectral data can be performed at the detector 13 or processor of the system 11 through built in programs. In one or more embodiments, raw or preprocessed data can be sent to a second device for processing of the data at a location remote from the system 11 and, in some embodiments, a location remote from the agricultural equipment. These processing devices can have their own built in displays, batteries, resistant cases, and connections (such as USB, firewire, ports) to enhance the ability of the device to be used in the field.

Detection Devices

As set forth above, the system 11 can utilize a photodetector device 13 comprising one or more photodetectors 15 to detect spectral characteristics of a substance in which agrochemical detection is desired. Any suitable type of photodetector device and photodetector may be used within the scope of the invention. For example, in one or more embodiments, the photodetector device 13 comprises a spectrometer that is configured to detect absorbance, reflectance, or transmission in at least the ultraviolet spectrum (UV) and the visible light spectrum (VIS). In certain embodiments, the photodetector is configured to detect spectral characteristics in other wavelength ranges (e.g., infrared, etc.). Other types of photodetectors may also be used as described in further detail below.

Microelectromechanical System Measurement Detector

In one or more embodiments, the photodetector device 13 comprises a microelectromechanical system (MEMS) with spectrophotometric capabilities. For example, a spectrophotometric MEMS 13 can be placed in line of (e.g., in fluid communication with) a flowing or static agrochemical-containing liquid to allow for detection of agrochemicals. The MEMS device(s) 13 can be a chip (MEMS-SPX, Knowles Electronics, LLC), a probe (DIP TIP™, World Precision Instruments) or other MEMs device for photodetection. In one embodiment, the MEMS device 13 received in a flow cell 17 (e.g., a stainless steel flow cell, such as a stainless steel flow cell having a 1-cm gap) and allows for the free movement of liquid through the flow cell. An MEMS device may be configured to detect spectral characteristics in UV, infrared, visible, or a combination of these light ranges to detect a wide range of agrochemicals.

The MEMS device 13 can be mounted on or fluidly connected to agricultural equipment in any of the configurations described above. In addition, the MEMS device 13 can be placed as a chip or probe, etc., inside any individual nozzle or multiple nozzles within agricultural equipment. The MEMS detector 13 can be utilized for various agricultural equipment, including nurse tanks, bulk tanks, handheld sprayers, spray rigs, tractors, nozzles, boom lines, overhead irrigation systems, in line irrigation systems, and crop-dusting aircraft. Moreover, the MEMS device can also be mounted on seed treatment equipment or pesticide manufacturing equipment.

Photodiodes

In one or more embodiments, the photodetectors 15 can comprise one or more photodiodes (broadly, semiconductors) (notably made of silicon, quartz, crystalline materials, any photovoltaic UV/VIS filtering glass to provide a broad spectral absorbance range). Suitably, each photodiode 15 is configured to convert light (or other electromagnetic radiation) to an electrical current generated when photons are absorbed in the photodiode. In certain embodiments, each photodiode 15 is provided with discrete color band separation or defined spectral bands with narrow selectivity. The photodiode 15 or photodiode array (two or more photodiodes) are placed within the apparatus 13 and may generate or transmit a signal (which may be augmented by an amplifier and a transistor(s) placed to provide increased output or amplification of the spectral signal) representing spectral characteristics in the range of ultra violet (UV), visible (VIS), and near infra-red (IR) wavelengths. Suitable photodiodes 15 include monochromatic and polychromatic photodiodes that have defined and customizable spectral wavelength bands. Positioning of a single or multiple set of photodiodes 15 can be used with narrow and/or broad band filters to filter out background light or noise providing for a high resolution customizable wavelength format. A photodiode array permits a broad wavelength spectral (nm) range to be simultaneously detected at discrete intervals and depends on the number of photodiodes as well as the discrete properties and the placement of the photodiodes. The photodiodes 15 may be connected to or fitted with optical filters, built in lenses, or other devices that enhance spectral transmission. The photodiodes 15 may vary in surface area. The photodiode device 13 may be used as a single device or as two or more devices in tandem to detect, measure, and quantify an agrochemical that has a spectral trace that is identifiable in UV, VIS, or other wavelength ranges. For example, the photodiode device 13 can convert the spectral characteristics of a substance that may contain an agrochemical to a measurable electrical output signal(s) (for example, spectral traces captured at 230 nm, 250 nm and 280 nm converted to electrical signals). The at least one photodiode, two to three photodiodes, or multiple photodiodes arranged in tandem are suitably configured to detect a unique agrochemical fingerprint or chemical signature.

The photodiode(s) 13 can be incorporated into a photodetector device 13 and then be mounted on agricultural equipment or fluidly connected to agricultural equipment in any suitable manner, such as any manner described above in reference to FIGS. 3-19. The photodiode 13 can be used as a single element in which the photodiode could be operated independently or in an array format comprising two or more photodiodes. The quality of the spectral trace data produced by one or more photodiodes (or other detectors) can, in certain embodiments, be enhanced using lenses or other optics that can collect an optimal amount of optical energy. In certain embodiments, the photodiodes (or other detectors) utilize band width filters that supply complete separation of spectral band width(s) to distinguish between the signature absorbance or spectral fingerprint for each diagnostic compound or chemistry. A general photodiode array in any of FIGS. 4-19 can include an amplifier that amplifies an output signal including the spectral characteristic data. Modulation of the amplified output signal can be performed using a transistor. Furthermore, the output of the amplified signal can be captured and displayed for real-time rapid detection or transferred remotely. Band shaping of the photodiode detector is performed using filtering materials such as colored filter glass, interference filters or dichroic filters. Combinations of the aforementioned filtering techniques can be combined in order to band-shape the radiation impinging on the photodiode surface, such as using a long pass edge filter or dichroic mirror to separate visible and infrared light. Light having wavelengths less than 700 nm are reflected 90 degrees to that of the incident light and NIR light having wavelengths greater than 700 nm pass through the filter.

Additional trimming of the photodiode output signals can be achieved using narrow band interference filters or color glass placed in front of the photodetectors that use a beam splitter to split the incident light into two different components. Here, the incident light is split into multiple equal beams, directed toward detectors having filters (FIG. 1). Light directionality received by the photodiode or photodiode array as described in FIGS. 3-19 is not limited and may be illuminated either from the top, bottom or at any incident angle provided to the photodiode or photodetector device. The photodiodes or photodiodes placed in an array in the apparatus can be segregated by a doped or depletion zone (p-type, n-type), a layer to distinguish the electrical impulses that acts as a spacer and used to isolate each photodiode from one another or un-doped format (PIN diode).

In certain embodiments, photodiodes that can be used as a singular photodiode or a multi-sensor array of photodiodes (two or more) and selected for discrete and defined measurement of color band selectivity have both narrow band and broad band measurement capabilities. Discrete optics are provided to filter out background wavelengths, which may have customizable wavelength boundaries. Other suitable photodiodes include monochromatic or polychromatic diodes, with absorbance color (nm) ranges in the Cyan, Red, Magenta, Green, Yellow and Blue spectra. The multicolor photodiode can detect the light wavelengths ranges from as low as near UV (200 nm) to wavelengths over 1700 nm. Spectral absorbance ranges may be broad 200-700 nm; 400-700 nm; 700-1200 nm, to shortwave infrared (1700 nm), or discrete wavelength absorbance spectral characteristics for: 230 nm, 250 nm, 280 nm, 425 nm 435 nm, 455 nm, 465 nm, 485 nm, 515 nm, 525 nm, 535 nm, 555 nm, 558 nm, 575 nm, 610 nm, 615 nm, 660 nm, 661 nm, 675 nm, 720 nm, 810 nm, 835 nm, 850 nm providing high band width resolution over a broad spectral range (200-1700 nm) with a band filter width of less than or approximately equal to +/−5 nm.

Processing and Analysis of Spectral Characteristics

The system 11 is suitably associated with a processor that analyzes the spectral data to detect, and in some embodiments, measure and quantify the amount of an agrochemical in the flow cell 17 or other environment from which the detectors 15 receive light. Referring to FIG. 1, in one embodiment, the processor can reside in the data exchange interface 25. In certain embodiments, the processor can be another processor that is internal to the system 11. In some embodiments, the processor can be located in a device(s) that is remote from the system 11, such as a mobile device (e.g., a phone, a tablet, etc.) or a computer (e.g., a laptop or a desktop). More than one processor in one or more locations (e.g., internal to the system 11 and external to the system) can also be used in certain embodiments.

Any suitable way of analyzing the spectral characteristics detected by the photodetector 15 to detect and/or measure an agrochemical may be used. For example, in one or more embodiments, the processor is configured to use a ratio of absorbance of radiation at two wavelengths by the object or area of interest to assess the concentration of one or more agrochemicals.

In one or more embodiments, the processor is configured to analyze the spectral data to measure and quantify the amount of multiple agrochemicals simultaneously. For example, different detectors 15 can have different filters 21 to isolate bandwidths that are pertinent for various different agrochemicals.

In some cases, a single absorbance reading can be sufficient for analysis of a substance. One example in which a single absorbance reading would be sufficient is if the overall absorbance at a set wavelength is below a minimal threshold indicating no detectable pesticide is present or that a safe zone has already been achieved. Additionally, a single absorbance spectra can be sufficient in some cases if calibrated against a non-absorbing background wavelength and predictive software.

In other cases, a comparison of the spectrum obtained using more than one wavelength can be utilized to identify an agrochemical. Ratios of absorbance at key wavelengths, such as the 276-nm-to-230-nm and 285-nm-to-230-nm, can be used identify an agrochemical or determine an agrochemical concentration in certain embodiments. More sophisticated algorithms (e.g., learning algorithms) or spectra recognition software can also be utilized to identify pesticides and other agrochemicals.

One embodiment of a method of detecting a concentration of an agrochemical will now be described.

Using a Standard Curve to Evaluate Agrochemical Concentration

Figure 20:
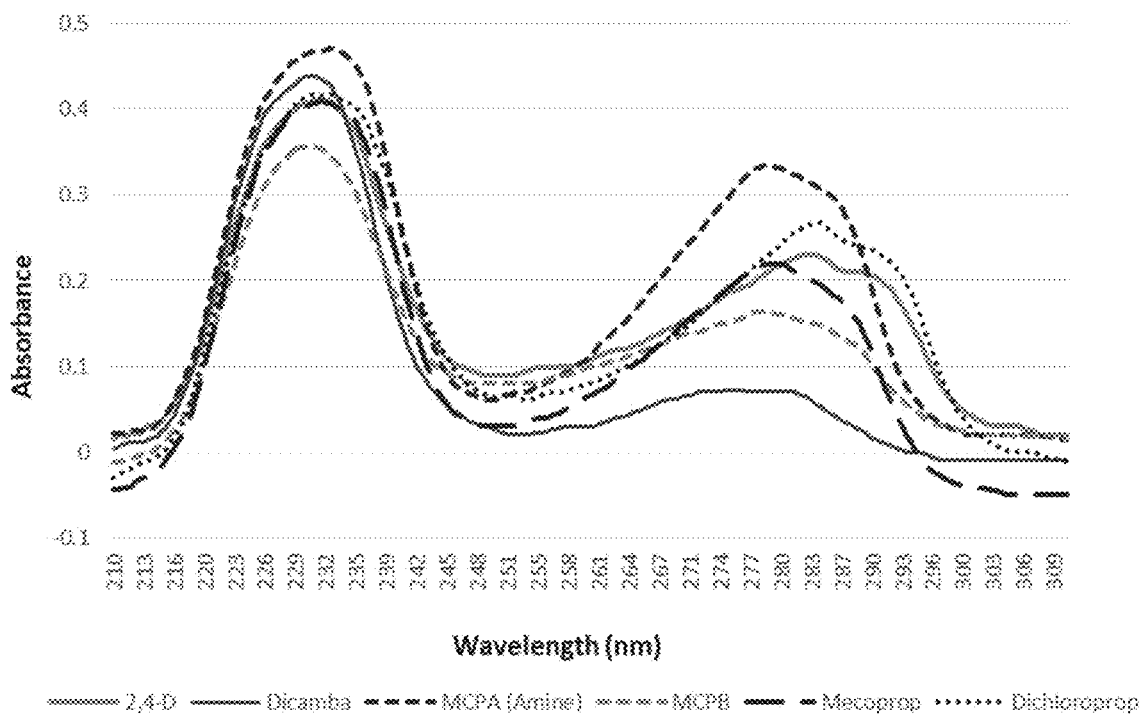
FIG. 20 is a graph showing detected absorption in a defined wavelength range of samples of 2,4-D, dicamba, MCPA (amine), MCPB, mecoprop, and dichloroprop.

In this embodiment, a standard curve for a particular agrochemical is obtained relating the concentration of the agrochemical to spectral data. For example, a standard curve can be obtained relating the concentration of agrochemical to a ratio of the absorbance of two different wavelengths. Referring to FIG. 20, which shows example absorption spectrum for several different pesticides, it can be seen that these pesticides exhibit two peaks in the absorption spectrum—one around 216-245 nm generally centered around 230 nm and another around 270-295 nm and generally centered around 280 nm.

Figure 21:
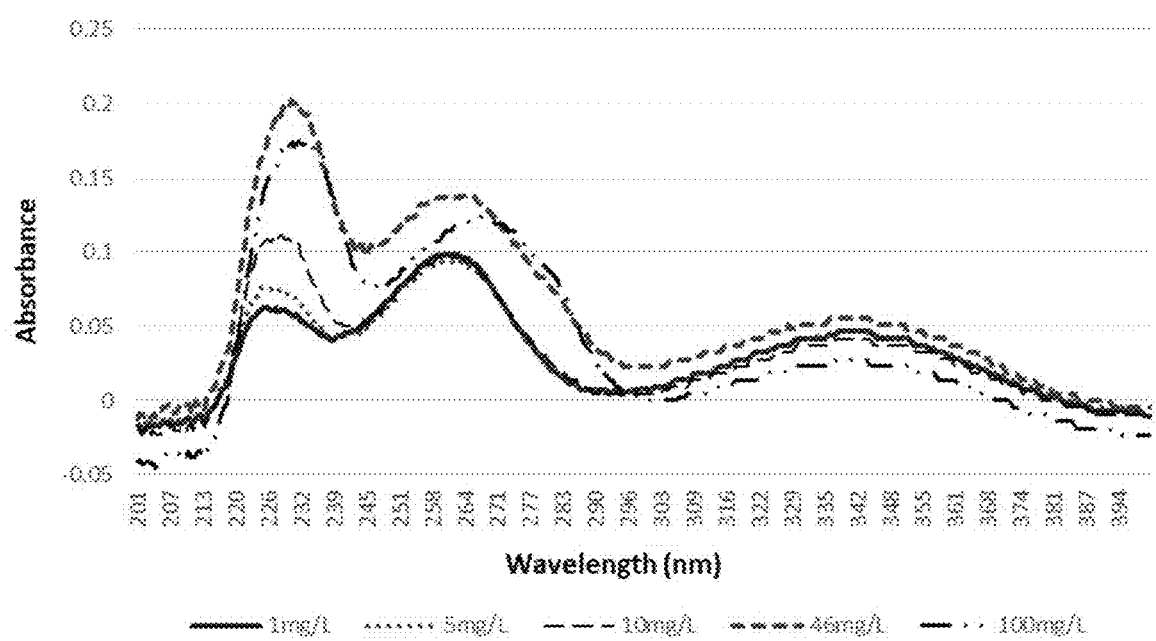
FIG. 21 is a graph showing detected absorption in a defined wavelength range of samples of dicamba at different concentrations.
Figure 22:
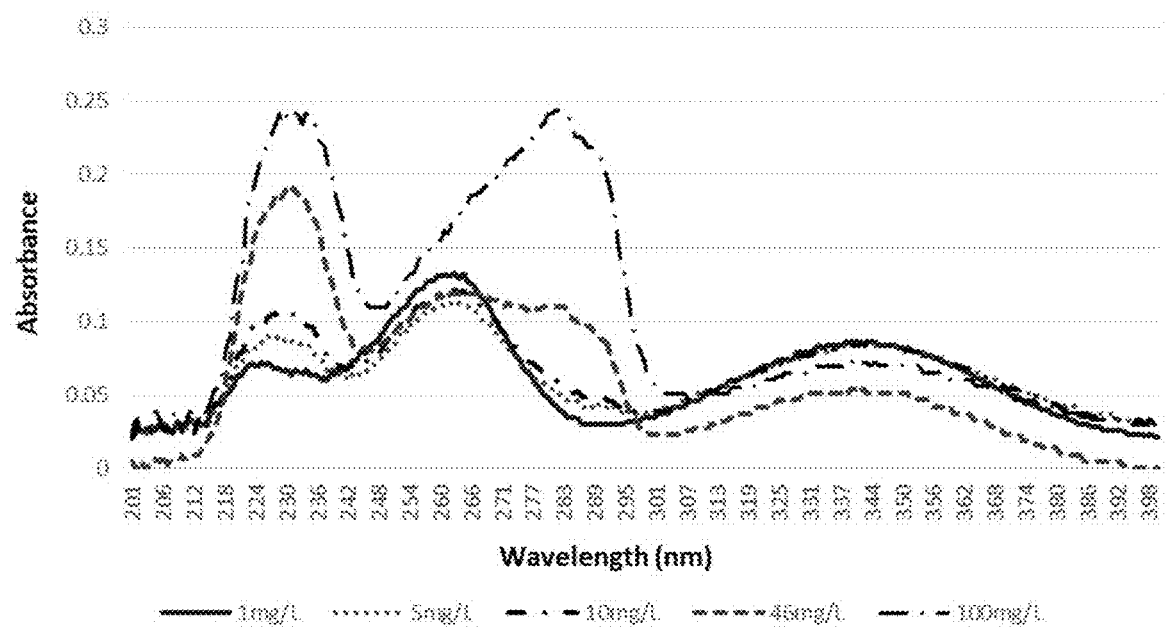
FIG. 22 is a graph showing detected absorption in a defined wavelength range of samples of 2,4-D at different concentrations.

The peaks in the absorption spectrum provide good candidates for setting up a ratio that may correlate with the concentration of the particular pesticide. FIGS. 21 and 22 show the spectral characteristics of a pesticide-containing solution at different concentrations of the pesticide. FIG. 21 shows the spectral absorbance of five different concentrations of dicamba, and FIG. 22 shows the spectral absorbance of 2,4-D. An equation can be determined describing the standard curve correlating the spectral characteristics with the pesticide concentration. Then field measurements taken by the system 11 can be plugged into the equation to determine the concentration.

This standard curve or the equation may be generated by empirical data using the system 11. Alternatively, the standard curve, the equation, or related information may be obtained from a manufacturer or other supplier of data concerning the particular pesticide or pesticide of interest. The standard curve or related information may be stored in the data exchange interface 25.

Specific examples of this algorithm's implementation will be provided in the paragraphs that follow, first by reference to dicamba and then by reference to 2,4-D. It is understood that the methods described in the two examples can be adapted for use with other agrochemicals.

Spectral Analysis Example 1

Generation of a Standard Curve for Dicamba

Figure 23:
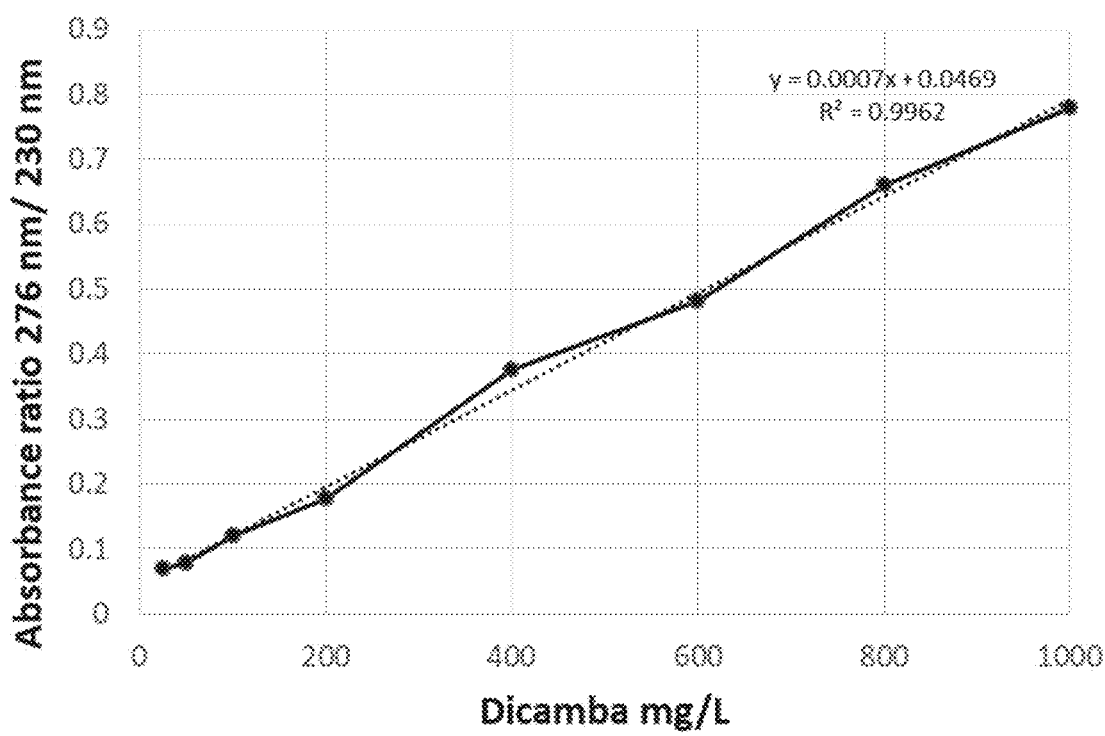
FIG. 23 is a graph illustrating one embodiment of a standard curve relating concentration of dicamba to spectral characteristics of the type that can be measured by the detection system.

A commercial formulation of dicamba (CLASH™) was used to generate a standard curve based on spectral absorbance data for the dicamba at concentrations in a range of from 1 mg/L to 1000 mg/L. Empirical data showing spectral characteristics at the various concentrations is illustrated in FIG. 21 (Amax 230, Amax 276). The dicamba solution samples were pipetted (200 µL) each into a UV-Star® microplate (GEINER BIO-ONE). Spectral traces in a wavelength range of from 200 nm to 400 nm (+/−3 nm) were collected for each of the dicamba solution samples at the varying concentration using a BioTek SYNERGY HTX (BioTek Instrument Inc.) plate reader. The results are shown in FIG. 21. FIG. 23 shows the determined standard curve for dicamba. To generate the standard curve, an empirically derived ratio of absorbance (276 nm:230 nm) was plotted as a function of the varying concentrations of dicamba. Data for known concentrations of dicamba were used to make the standard curve, plotting concentration on the x-axis and the ratio of absorbance at wavelengths of 276 nm:230 nm and on the y-axis. As the value of the 276 nm:230 nm absorbance ratio increases, the concentration of dicamba in solution increases. The initial concentration of dicamba in the tank and subsequent concentration measurements throughout the detoxification and/or cleaning procedure can be calculated using the predictive equation generated by the standard curve 'y=0.0007x+0.0469' where y is the absorbance ratio for 276 nm:230 nm, 0.0007 is the correction factor or the slope of the line of best fit, 0.0469 is a general correction factor or y-intercept (where the line touches the y-axis), and x as solved from the equation provides a measure of dicamba concentration. The linear regression value of $R^2=0.9962$ is the predicted measure of the correlation or relationship between the peak absorbance ratio (y-axis) and the concentration of dicamba (x-axis).

Spectral Analysis Example 2

Generation of Standard Curve for 2-4D

Figure 24:
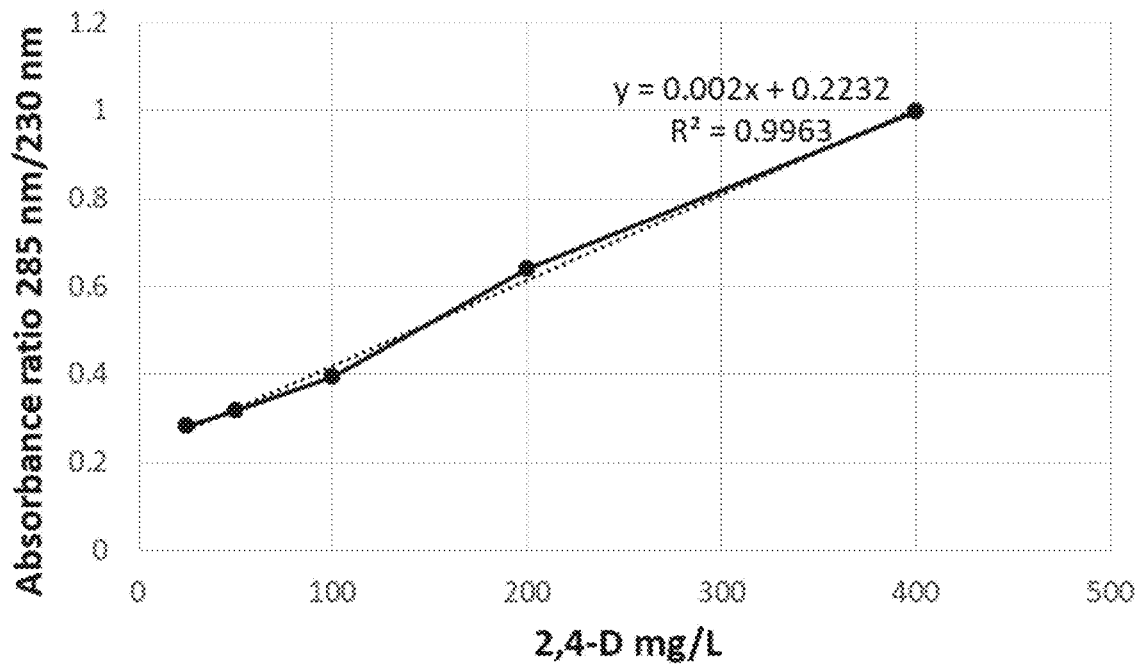
FIG. 24 is a graph illustrating one embodiment of a standard curve relating concentration of 2,4-D to spectral characteristics of the type that can be measured by the detection system.

A commercial formulation of 2,4-D (WEEDAR® 64) was used to generate a standard curve based on spectral absorbance data for 2,4-D at concentrations in a range of from 25 mg/L to 400 mg/L. The empirical data showing spectral characteristics at the various concentrations is illustrated in FIG. 22 (Amax 230, Amax 285). The 2,4-D solutions were pipetted (200 µL) each into a UV-Star® microplate (GEINER BIO-ONE). Spectral traces in a wavelength range of from 200 nm to 400 nm (+/−3 nm) were collected for each of the 2,4-D solutions at the varying concentration using a BioTek SYNERGY HTX (BioTek Instrument Inc.) plate reader. FIG. 24 shows a standard curve for 2,4-D that was plotted from the results of test. In the illustrated standard curve, a ratio of absorbance (285 nm:230 nm) is plotted as a function of the concentrations of 2,4-D. Empirical data for several known concentrations of 2,4-D were used to make the standard curve, plotting concentration of 2,4-D on the x-axis, and the ratio of absorbance (285 nm:230 nm) on the y-axis. As the value of the 285 nm:230 nm absorbance ratio increases, the concentration of 2,4-D also increases. The initial concentration of 2,4-D in the tank and subsequent concentration measurements throughout the detoxification and/or cleaning procedure can be calculated by the predictive equation generated by the standard curve 'y=0.002x+ 0.2232' where y is a measure of peak absorbance ratio (285 nm: 230 nm), 0.002 is the correction factor or the slope of the line of best fit, 0.2232 is provided as a general correction factor or y-intercept (where the line touches the y-axis), and x as solved from the equation provides a predictive measure of 2,4-D concentration. The linear regression value of $R^2=0.9963$ is the predicted measure of the correlation or relationship between the peak absorbance ratio (y-axis) and the concentration of 2,4-D (x-axis). In an absolute correlated relationship, the R2 valve is equal to 1.0, so again the regression value for this example indicates a strong correlation.

Noise-Reducing Filters

One or more filters can be used to reduce spectral noise effects. The noise-reducing filter(s) is suitably a data processing algorithm, such as a computer program that is executed by the processor. A noise-reducing filter can have either a linear or a non-linear input-output relationship. The selection of filter parameters is suitably performed in real time, with the coefficients of the filter being determined using a current input sample. Alternatively, the selection of filter parameters can be performed using a previously stored input signal sample. Adjustment of the parameters of a filter is suitably based on an assessment of the quality of the input signals to the filter. For example, the filter is suitably a linear filter. For a linear filter, the filter can have either a finite or an infinite impulse response. Alternatively, the filter may be a non-linear filter. The selection of filter parameters is suitably performed in real time, with the filter parameters being determined using current input samples. Alternatively, the filter parameters can be calculated using a buffer of recent input samples. Additionally, the selection of filter parameters may be based on more than one signal quality indicator. Furthermore, the selection of the filter parameters may be based on the output of an algorithm that combines several signal quality indicators. The noise-reducing filter(s) of the present invention can be used to receive input signals corresponding to sensed optical energies from a plurality of wavelengths. The filter(s) can be used in combination to determine the concentration of pesticides when signals received correspond to sensed optical energies from a plurality of wavelengths. The filter(s) are suitably configured to reduce background noise. For example, a dark measurement may be taken (e.g., with the light source turned off) to evaluate a current level of background noise. Alternatively, or additionally, a valve may be actuated (e.g., by the processor) periodically to cause pure water to flow through the system 11 to evaluate a current level of background noise.

Monitoring and Dispatching Alerts

The system 11 is suitably configured to quantify concentrations of one or more agrochemicals periodically or substantially continuously (e.g., during a predetermined monitoring period or during a cleaning process). Thus, the system 11 is suitably configured to monitor the concentration of one or more agrochemicals over time. The system 11 is also suitably configured to compare current concentrations of the agrochemicals to stored data (e.g., data stored in the data exchange interface 25 to determine when one or more events of interest has occurred. For example, the processor is suitably configured to determine one or more of the following:

(a) when a desired concentration of the agrochemical(s) has been reached in an environment (e.g., in a tank);

(b) whether an agrochemical formulation still meets the requirements for shelf-life (e.g., a sufficient portion of the pesticide has not yet decayed to a pesticide end-product);

(c) the amount of an agrochemical such as pesticide or pesticide end-product that remains in equipment after a spray or treatment application has been performed on a crop;

(d) the amount of agrochemical such as a pesticide or pesticide end-product that remains in equipment that has been used to apply a seed treatment to seeds;

(e) the amount of agrochemical such as a pesticide or pesticide end-product that remains in equipment after it has been used to manufacture a agrochemical;

(f) whether or not an agrochemical such as a pesticide has been sufficiently detoxified or removed from agricultural equipment and/or associated attachments;

(g) whether or not an agrochemical such as a pesticide has been sufficiently detoxified or removed from seed treatment equipment and/or associated attachments;

(h) whether or not an agrochemical such as a pesticide has been sufficiently detoxified or removed from pesticide manufacturing equipment and/or associated attachments and/or (i) whether or not an agrochemical such as a pesticide has been sufficiently removed from a rinsate and levels remaining in a rinsate are considered in the safe zone or in a non-injury causing zone to plants or the environment;

(j) whether or not an agrochemical such as a pesticide has been mixed correctly or used at the correct concentration, or the uniformity of a solution;

(k) the amount of an agrochemical such as a pesticide or pesticide end-product that remains in pesticide storage containers or equipment;

(l) the amount of pesticide precursor chemistry during manufacture, or that is contained in the finished pesticide product; or (m) a combination thereof.

The system 11 is suitably configured to provide dispatch alerts or alarms to a user (e.g., using the data exchange interface 25 to communicate with any of the user's devices) at any predetermined time to report the concentration of an agrochemical such as a pesticide(s) or pesticide end-product(s) in the environment (equipment). These alerts can be provided by the system 11 at any time interval or as a real-time continuous readout. These dispatch alerts provide the user with information about the concentration of pesticide or pesticide residue in or on agricultural equipment or other equipment. This can be particularly useful during the production manufacture of an agrochemical such as a pesticide, during application of a seed treatment to seeds, or during cleaning of any type of equipment involving pesticides, such as during the detoxification or clean out of an agrochemical such as a pesticide from agricultural equipment, for example tanks and booms associated with spray rigs. The dispatch alert may be in the form of a warning to the user during clean out procedures that the equipment contains levels of agrochemical (e.g., pesticide) that is not safe to plants, the environment, or for other uses. Thus, the system 11 can help reduce or prevent harmful effects that occur by applying a not sufficiently low enough amount of pesticide or other agrochemical to a plant, a non-target plant, or a field of plants, such as would occur if the rinsate has not yet reached the "safe zone" or a suitably low level of agrochemical that will not cause injury.

In certain embodiments, the concentration data can be correlated with flow rate data for an agrochemical such that the system is configured to determine an application rate of the agrochemical in real time. For example, it may be desirable to provide a real time indication of the application rate of one or more fertilizers, pesticides, or other agrochemicals as it is being sprayed or seeds, plants, or a field, or dispensed in a processing facility. The application rate can be determined as a function of the measured flow rate of a fluid containing the agrochemical and a determined concentration of the agrochemical(s) in the fluid. Alerts can be dispatched if the determined application rate deviates from an expected or desired application rate.

Predictive Abilities and Estimates

In one or more embodiments, the system 11 can be configured to perform predictive analytics. For example, the system 11 can be configured to provide an estimate of a time remaining before a specified event occurs. In one embodiment, one or more agrochemicals such as pesticides or pesticide end-products that remain in a spray tank, boom, lines, nozzles or other attachments associated with a spray rig or other agricultural equipment can be identified and the processor can use that information to estimate a time required for reduction of the amount of agrochemical in the equipment to safe or otherwise desired levels. Likewise, to provide another example, the system 11 can be configured to use information about the amount of agrochemical in the agricultural equipment to estimate when a level of agrochemical reduction (e.g., via a cleaning solution) will have been achieved in a rinsate such that it is safe to dispose of the rinsate. The system 11 is suitably configured to provide any estimates determined by the system to the user in the form of dispatch alerts (e.g., using the data exchange interface 25 to communicate with any of the user's devices).

This system 11 is suitably configured to estimate future and/or past agrochemical concentrations based on predictions calculated using an estimation algorithm. Information related to the removal rate, decay, or generation of one or more agrochemicals can be stored (e.g., in the data exchange interface 25). This information can be generated from empirical data and/or provided by a supplier, such as a manufacturer or other source of information. The information may include information about natural decay and/or generation rates as well as information about any pertinent chemical or biological processes (e.g., cleaning agents) that may be involved. The pertinent information for various different pesticides and/or pesticide end-products can vary from one chemical or combination of chemicals to the next. Also, the pertinent models (e.g., exponential decay, linear generation, or other more complex models) describing the process(es) that produce the change(s) in the concentration level(s) may vary depending on the chemicals, biological agents, and/or process(es) involved. The algorithm used by the system 11 can be adjusted based on the pesticide(s) or pesticide end-product(s) that are being measured, as well as any other pertinent facts or circumstances, to improve accuracy of predictions using the algorithm.

In some cases, the time required for a pesticide to turn into a pesticide end-product and/or for a cleaning solution to reduce the concentration of a pesticide or pesticide end-product may vary depending on various conditions. The system 11 suitably includes one or more additional detectors (not shown) configured to measure a variable that impacts the change in a pesticide or pesticide end-product over time. For example, the additional detectors are suitably configured to measure one or more of the following: a temperature, a pH, an osmolarity, and/or a concentration of another substance such as an adjuvant, a fertilizer, a growth regulator, a micronutrient, a biological control agent, a plant health agent, an inoculant, a trace molecule, a surfactant, and/or a hard water solute. The data from any such additional detectors can be used to improve the predictions concerning future and/or past concentration level(s) of any pesticide(s) and/or pesticide end-product(s) or other agrochemicals. The data from any such additional detectors can also be used to improve the accuracy of the measurement of the current concentration level(s) in cases in which the parameter monitored by the additional sensor(s) affects the spectral characteristics of the light detected by the system 11.

Accordingly, the system 11 is suitably configured to perform at least one of the following:

(a) estimate an agrochemical such as a pesticide or pesticide end-product concentration at a time t2 based on at least one measurement of the concentration of said pesticide or pesticide end-product taken at time t1, wherein t1 does not equal t2;

(b) estimate an agrochemical concentration such as a pesticide concentration at a time t3 based on at least two measurements of the concentration of said pesticide taken at time t1 and time t2, wherein t2>t1 and the change in the concentration from time t1 to time t2 represents a reduction of the pesticide in the environment;

(c) estimate a pesticide end-product concentration at a time t3 based on at least two measurements of the concentration of said pesticide end-product taken at time t1 and time t2, wherein t2>t1 and the change in the concentration from time t1 to time t2 represents an accumulation of pesticide end product in the environment;

(d) estimate an agrochemical concentration such as a pesticide concentration based on at least two measurements of the pesticide concentration taken at time t1 and time t2, wherein t2>t1 and the change in the concentration from time t1 to time t2 represents an accumulation of the pesticide in the environment;

(e) estimate a pesticide end-product concentration based on at least two measurements of the pesticide end-product concentration taken at time t1 and time t2, wherein t2>t1 and the change in the concentration from time t1 to time t2 represents a reduction of the pesticide or pesticide end product in the environment;

(f) estimate an agrochemical concentration such as a pesticide or pesticide end-product concentration based on a predetermined standard curve or library;

(g) estimate an agrochemical concentration such as a pesticide or pesticide end-product concentration based on a comparison to a background absorbance value of a different wavelength than the wavelength(s) used to identify the pesticide or pesticide end-product;

(h) estimate an agrochemical concentration such as a pesticide or pesticide end-product concentration based on a ratio of absorbances obtained;

(i) determine the agrochemical composition and/or identify agrochemicals end-products in a sample;

(j) estimate no agrochemical or type of agrochemical is present in a given sample; and (k) combinations thereof.

In one example of an algorithm the system 11 can use to predict concentration levels, the prediction algorithm is initialized with two initial concentration measurements to estimate either a dosage generation or a dosage decay rate. The dosage generation rate as part of the algorithm can be applied to a process to manufacture agrochemicals in a tank or a vessel and achieve a desired end concentration of the agrochemical and/or confirm a shelf life requirement for the concentration range of the agrochemical for quality assurance. The dosage decay rate as part of the algorithm can be applied to a process to detoxify or remove agrochemical from agricultural or other equipment used in the manufacture, transport or storage of agrochemicals. A logic block in the algorithm receives initial first and second concentration measurements from two different times and estimates the generation or decay rate of the agrochemical.

Once the initial concentration level of the agrochemical is determined, a predictive rate of the generation or decay rate for the agrochemical concentration is determined for subsequent measurements. Thus, predictive concentrations of the agrochemicals are based on estimates of the generation or decay rates of the concentrations in the environment at the first initial measurement at time (t1) compared to the second initial measurement at time (t2) and subsequent measurement times (t3+tn). That is the predictive rate of the generation or decay rate is suitably updated and refined after the initial prediction with additional data provided by the concentration measurements taken at the subsequent measurement times (t3+tn). The measured concentration and the predicted concentration of the agrochemicals for subsequent measurement times (t3+tn) are compared in order to determine discrepancies between the measurements made by the detector(s) and then adjustments are made in the system to adjust for changes in environmental parameters and measurement errors. The system 11 suitably includes a filter that is supplied with initial information, including the measurement error covariance, and estimates of the initial parameters and associated errors. This information is used to calculate a filter gain matrix. The system 11 suitably substantially continuously adjusts the light parameters or attributes to minimize (or eliminate) the errors due to uncertainties in the system and errors of the measurements. This can be through "dark" measurements without supplied light, or a clean water blank measurement to eliminate noise or background in a sample. In this manner, the algorithm(s) predict(s) concentrations for a next subsequent measurement and either the accumulated or reduced concentration of the agrochemical by adding up the concentration for each time increment in order that the total concentration at the end of the measurement time is predicted and may be compared with the predetermined final desired concentration level.

For example, using the magnitude of the discrepancy between the estimated and the measured concentrations, the system 11 further adjusts the light parameters or attributes, to increase accuracy of the subsequent predictions of the concentration of the agrochemical in the environment. After each adjustment, the system predicts the next measured concentration. The error between the concentration estimates and the measured data is determined and multiplied by the filter gain matrix to update the estimate and estimated error. Several measurements are taken and the system 11 calculates an estimate of the error in the measurement, calculates an estimate of the error in the environment, and then, using the filter and a filter gain, adjusts the filtering time constant as a function of the errors, for estimation of the generation or decay rate of pesticide in the environment. By calculating the generation or decay rate in the environment, the system 11 performs the next projected integrations of agrochemical concentration over a predetermined period of time, and knowing the thresholds associated with high and low ends of agrochemical detection, the system advises whether the pesticide concentration has sufficiently reached the predetermined concentration target in an environment.

Detection of agrochemical identity and concentration can be performed using a single algorithm, an adjusting algorithm, multiple algorithms, chemometric (learning) algorithms or combinations of these. The wavelength(s) utilized can be adjusted based on the agrochemical and light parameters. Additionally, single or selective light sources or filters can be used to eliminate noise or background and increase resolution.

The updated error and parameters are used as input to a model to predict the projected error and other parameters at the next time instance. As confidence in the accuracy of the parameters grows with each iteration, the filter gain matrix values decrease, causing the influence of the measurement data in updating the parameters and associated error to lessen. The filter is used to remove error and to improve the prediction of the concentration of the agrochemical at a certain time instance and the total dosage at the end of the measurement period. The predicted next concentrations are cumulatively added to obtain an accumulated concentration average. The system 11 additionally predicts the total concentration at the end of the measurement period.

The spectral bandwidth transmitted by the detector(s) 15, the percentage of transmission through or by the object or area of interest, and the logarithmic range of the sample absorption and alternatively a percentage of reflectance measurement are suitably used collectively to develop the algorithm. Spectrophotometric methods were developed to measure the transmittance or reflectance of pesticides in solutions at varying ranges of concentration and used to develop the algorithm of the invention. The diffusivity of agrochemical peak absorbance from 200-2500 nm can be used to detect any agrochemical as described in the embodiments of the invention. Specific pesticides and classes of pesticides were used to develop the algorithm. They were detected and quantified using various control standards and calibration parameters to identify the wavelengths for peak absorbance of the photometric determination.

In another example of an algorithm the system 11 can use, the algorithm determines from a single absorbance reading whether or not there is any detectable algorithm present and/or whether or not a safe zone has been achieved by comparing overall absorbance at a set wavelength to a threshold level or using predictions based on a calibration of the single absorbance reading against a non-absorbing background wavelength.

A single algorithm, an adjusting algorithm, multiple algorithms, chemometric (learning) algorithms or combinations of these can be used for simultaneously measuring the concentrations of one or more agrochemicals and one or more inert tracer dyes (discussed below) used in combinations with agrochemicals.

An algorithm for sensing multiple mixtures of pesticides using pattern recognition combined with chemometric approaches is described. A chemometric approach applies pattern recognition techniques and can be used to provide a real time spectral traces that provide a spectral signature or unique agrochemical fingerprint. In certain embodiments, chemometric algorithms are applied with a method for simultaneously identifying and measuring the concentration of multiple agrochemicals in an aqueous sample. Continuous and simultaneous measurements are taken and used to quantify the concentrations of multiple agrochemical-containing mixtures by determining the absorbance or emission spectrum of the agrochemical components in an aqueous solution(s) over a spectral range and then applying the chemometric algorithm(s) to analyze features in the spectral traces. The chemometric algorithm analysis allows for qualitative and quantitative spectral features that are specific to the individual agrochemical traces, thus allowing for both the identification as well as a quantitative determination of the concentration of the agrochemical(s) in a mixture. Applying chemometric algorithms are useful for measuring more than one or multiple agrochemicals in an aqueous solution in the wavelength range of 200-800 nm (or other higher wavelength ranges) and include multiple sampling and calibration measurements using pattern recognition based approaches. Narrow band spectra can be assigned for collection in discrete wavelength bandwidths to distinguish between the different signatures associated with an individual agrochemical. Calibrated standards are used initially in the development of the algorithm to minimize out any effect from background interference contributed from other constituents that are not agrochemicals in the sample mixture.

Accordingly, the system 11 is suitably configured to use the algorithms described herein to accurately estimate the amount of agrochemical residue that is currently in a tank at the initial time of measurement (t0). This is useful for confirming the concentration of an agrochemical during a manufacture process to determine if the correct or target final concentration has been achieved or to determine the estimated shelf life of an agrochemical solution. This is also useful for determining the pesticide concentration remaining in the tank at the initiation of the detoxification or removal process (t1) and at (t2) when the removal process has been completed.

Agrochemicals and Other Parameters that System can Detect

The system 11 described above can be used to detect, measure, and quantify any of the agrochemicals described herein, including: an herbicide, a fungicide, an insecticide, an insect growth regulator, a biocontrol agent, a bactericide, a nematicide, an acaricide and a virucide, a fertilizer, or any combination thereof Herbicides For example, the system 11 can be used to determine the amount of an herbicide(s) that exists in agricultural equipment or remaining on surfaces contaminated with residual herbicides. A list of herbicides that can be detected and monitored by the system 11 includes but is not limited to: acetochlor, acifluorfen and its sodium salt, aclonifen, acrolein (2-propenal), alachlor, alloxydim, ametryn, amicarbazone, amidosulfuron, aminopyralid, aminocyclopyrachlor, amitrole, ammonium sulfamate, anilofos, asulam, atrazine and s-metoachlor atrazine, azimsulfuron, beflubutamid, benazolin, benazolin-ethyl, bencarbazone, benfluralin, benfuresate, bensulfuron-methyl, bensulide, bentazone, benzobicyclon, benzoienap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, 4-(4-chloro-2-methylphenoxy) butyric acid, cafenstrole, carbetamide, carfentrazone, carfentrazone-ethyl, catechin, chlomethoxyfen, chloramben, chlorbromuron, chlorflurenol-methyl, chloridazon, chlorimuron-ethyl, chlorotoluron, chlorpropham, 2-chlorophenoxy acetic acid, chlorsulfuron, chlorthal-dimethyl, chlorthiamid, cinidon-ethyl, cinmethylin, cinosulfuron, clethodim, clodinafop-propargyl, clomazone, clomeprop, clopyralid, clorpyralid-acid, clopyralid-olamine, cloransulam-methyl, CUH-35 (2-methoxyethyl 2-'"4-chloro-2-fluoro-5-'(1-methyl-2-propynyl)oxy'phenyl'(3-fluorobenzoyl)amino'carbonyl'-1-cyclohexene-1-carboxylate)'", clopyralid, cumyluron, cyanazine, cycloate, cyclosulfamuron, cycloxydim, cyhalofop-butyl, 2,4-D, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dicamba, dichlorophenoxyacetic acid, dimethyl amine salt of 2,4-dochlorophenoxyacetic acid, 2,4-dichlorophenol, dichlobenil, dichlorprop acid, dichlorprop-P, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylamine salt (CMPP-P DMA), dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, flurochloridone, fluroxypyr, fluroxypyr 1-methyleptylester, flurtamone, fluthiacet-methyl, fomesafen, fomesafen sodium salt, foramsulfuron, fosamine-ammonium, guizalop, glufosinate, glufosinate-ammonium, glyphosate and its salts such as ammonium, isopropylammonium, potassium, sodium (including sesquisodium) and trimesium (alternatively named sulfosate, halosulfuron, halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-'(tetrahydro-2-pyranylmethyl-4H-1,2,4-triazole-4-carboxamide), 2-hydroxyphenoxy acetic acid, 4-hydroxyphenoxy acetic acid, imazamethabenz-methyl, imazamox, imazapic, imazapyr, imazaquin, imazaquin-ammonium, imazethapyr, imazethapyr-ammonium, imazosulfuron, indanofan, iodosulfuron, iodosulfuron-methyl, ioxynil, ioxynil octanoate, ioxynil-sodium, isoproturon, isouron, isoxaben, isoxaflutole, pyrasulfotole, lactofen, lenacil, linuron, maleic hydrazide, MCPA and its salts (for example, MCPA-dimethylammonium, MCPA-potassium and MCPA-sodium, esters (for example, MCPA-2-ethylhexyl, MCPA-butotyl) and thioesters (for example, MCPA-thioethyl), MCPB and its salts (for example, MCPB-sodium) and esters (for example, MCPB-ethyl), MCPB acids, MCPB+MCPA (trropotox), mecoprop, mecoprop-P, mefenacet, mefluidide, mesosulfuron-methyl, mesotrione, metam-sodium, metamifop, metamitron, metribuzin, metazachlor, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron, metsulfuron-methyl, micosulfuron, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron, primisulfuron-methyl, primisulfuron-prosulfuron, prodiamine, profoxydim, prometon, prometryn, propachlor, propanil, propaquizafop, propazine, propham, propisochlor, propoxycarbazone, (R)-2(-4-chloro-2-methoxyphenol) propionic acid, propyzamide, prosulfocarb, prosulfuron, protoporphyringogen oxidase (PPO), pyraclonil, pyraflufen-ethyl, pyroxasulfone, pyrasulfotole, pyrazogyl, pyrazolynate, pyrazoxyfen, pyrazosulfuron-ethyl, pyroxasulfone, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quizalofop-ethyl, quizalofop-P-ethyl, quizalofop-P-tefuryl, rimsulfuron, safluenacil, sethoxydim, siduron, simazine, simetryn, sulcotrione, sulfentrazone, sulfosulfuron, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, tribenuron, triberunon-methyl, thifensulfuron, triasulfuron, triaziflam, triclopyr, triclopyr-butotyl, triclopyr-triethylammonium, tridiphane, trietazine, trifloxysulfuron, trifluralin, triflusulfuron-methyl, tritosulfuron and vernolate.

The system 11 described herein can be used to selectively determine the amount of any herbicide in the broad classes of herbicides identified in Table 1.

TABLE 1

Classes of Commonly Used Herbicides

| Broad Classes | Example Pest Control Herbicides |
|---|---|
| Anilides/Anilines | acetochlor |
| | alachlor |
| | asulam |
| | benfluralin |
| | butachlor |
| | diethatyl |
| | diflufenican |
| | dimethenamid |
| | flamprop metazachlor |
| | metolachlor |
| | pendimethalin |
| | pretilachlor |
| | propachlor |
| | propanil |
| | trifluralin |
| Aromatic acids | aminopyralid |
| | chloramben |
| | clopyralid |
| | dicamba |
| | picloram |
| | pyrithiobac |
| | quinclorac |
| | quinmerac |
| Arsenicals | cacodylic acid |
| | copper arsenate |
| | DSMA |
| | MSMA |
| Organophosphorus | bensulide |
| | bialaphos |
| | ethephon |
| | fosamine |
| | glufosinate |
| | glyphosate |
| | piperophos |
| Phenoxy | 2,4-D |
| | 2,4-DB |
| | dichlorprop |
| | dichlorprop-p |
| | mecoprop-r |
| | mecoprop-p |
| | clomeprop |
| | fenoprop |
| | MCPA |
| | MCPB |
| | 2,4,5-T |
| Pyridines | dithiopyr |
| | fluroxypyr |
| | imazapyr |
| | thiazopyr |
| | triclopyr |
| | halauxifen methyl |
| | florpyrauxifen-benzyl |
| Quaternary | diquat |
| | MPP |
| | Paraquat |
| Triazines | ametryn |
| | atrazine |
| | cyanazine |
| | hexazinone |
| | prometon |
| | prometryn |
| | propazine |
| | simazine |
| | simetryn |
| | terbuthylazine |
| | terbutryn |
| Ureas | chlortoluron |
| | DCMU |
| | metsulfuron-methyl |

TABLE 1-continued

Classes of Commonly Used Herbicides

| Broad Classes | Example Pest Control Herbicides |
|---|---|
| Others | monolinuron |
| | tebuthiuron |
| | 3-AT |
| | aminocyclopyrachlor |
| | bromoxynil |
| | clomazone |
| | DCBN |
| | dinoseb |
| | juglone |
| | mesotrione |
| | methazole |
| | metam sodium |
| | metamitron |
| | metribuzin |
| | flucarbazone |
| | sulfentrazone |

In other applications, the system 11 described herein can be used to determine the amount of a growth regulator herbicide that exists in agricultural equipment or remaining on surfaces contaminated with residues from a growth regulator herbicide. Growth regulator herbicides, also referred to as auxin-like herbicides are generally formulated as amine salts or low-volatile esters. Detoxifying formulations can be used to detoxify any of the growth regulator herbicides in the following groups: phenoxy herbicides, benzoic acid herbicides, pyridine herbicides, and quinoline herbicides. Growth regulator or growth regulator herbicides, which include different chemical classes, such as phenoxy-carboxylic acids, benzoic acids, pyridine-carboxylic acids, aromatic carboxymethyl derivatives and quinolinecarboxylic acids, wherein the essential structural requirement for their activity is a strong negative charge on the carboxyl group of the dissociated molecule. Auxin-like herbicides are widely used herbicides in turf, crop, fallow, grass management, especially for home and golf course use, forest management, brush management in non-cropland sites and for controlling aquatic weeds. General categories of representative synthetic auxin, auxin-like or growth regulator herbicides include but are not limited to the phenoxyacetic acids (phenoxys), such as 2,4-D, 2,4-DB, 2,4-DP (dichlorprop or dichlorprop acid), 2,4,5-T, 2,4,5-TP, MCPA, MCPB, MCPB NA, MCPB acid, MCPP (mecoprop), (+)R-2-(4-chloro-2-methylphenoxy) Propionic acid (Mecoprop-P Technical acid), Dichlorprop-P Technical acid and Tropotox (MCPB+MCPA) and other 2,4-D amine or ester formulations, the benzoic acids, such as dicamba and the pyridine-carboxylic acids, such as Clopyralid, Picloram, Triclopyr, Aminopyralid, and Aminocyclopyrachlor, Such herbicide compositions and a list of commercially available herbicides that contain the growth regulator herbicides, dicamba and 2,4-D and can be detected, measured and quantified using the apparatus of the present invention are provided in Table 2.

TABLE 2

Dicamba and 2,4-D containing herbicide compositions
that are currently commercially available
Active Ingredients Dicamba
2,4-D
2,4-D, dimethylamine salt; Dicamba, dimethylamine salt
Dicamba, dimethylamine salt
Atrazine; Dicamba, potassium salt
2,4-D, glyphosate
Dicamba, glyphosate
2,4-D, 2-ethylhexyl ester; 2,4-DP-p, 2-ethylhexyl ester; Dicamba
Dicamba, sodium salt; Diflufenzopyr-sodium; Nicosulfuron
Dicamba, diglycolamine salt
Dicamba; MCPA, 2-ethylhexyl ester; Triclopyr, butoxyethyl ester
Dicamba, sodium salt; Diflufenzopyr-sodium
Dicamba, dimethylamine salt; MCPA, dimethylamine salt; Triclopyr, trimethylamine Salt
2,4-D; Dicamba
Dicamba, sodium salt; Primisulfuron-methyl
2,4-D, 2-ethylhexyl ester; Dicamba
Carfentrazone-ethyl; Dicamba; MCPA, 2-ethylhexyl ester; MCPP-p acid
2,4-D, dimethylamine salt; Dicamba; MCPP, dimethylamine salt
Dicamba, diglycolamine salt; Fluroxypyr,1-methylheptyl ester
2,4-D, dimethylamine salt; Dicamba, dimethylamine salt; Quinclorac; Sulfentrazone
Dicamba, sodium salt; Rimsulfron
2,4-D, 2-ethylhexyl ester; Carfentrazone-ethyl; Dicamba'; MCPP-p acid
2,4-D, dimethylamine salt; Dicamba, dimethylamine salt; MCPP-p, dimethylamine salt; Sulfentrazone
2,4-D, dimethylamine salt; Dicamba, dimethylamine salt; MCPP-p, dimethylamine salt;
2,4-D, dimethylamine salt; Dicamba, dimethylamine salt; MCPP-p, dimethylamine salt; MSMA
2,4-D, triisopropanolamine salt; Dicamba; Picloram, triisopropanolamine salt
Dicamba, sodium salt; Halosulfuron-methyl
Aminocyclopyrachlor The system 11 described herein is useful for detecting, measuring and quantifying auxin-like herbicides. Exemplary auxin herbicides include 2,4-dichlorophenoxyacetic acid (2,4-D), 4-(2,4-dichlorophenoxy) butanoic acid (2,4-DB), dichloroprop, dichloroprop-p, (4-chloro-2-methylphenoxy) acetic acid (MCPA), 4-(4-chloro-2-methylphenoxy) butanoic acid (MCPB), mecoprop, mecoprop-p, dicamba, picloram, fluroxypyr, chloramben, clopyralid, aminopyralid, triclopyr, quinmerac, and quinclorac, agriculturally acceptable salts, acids, or esters of any of these herbicides, and mixtures thereof.

Insecticides

In still other applications, the system 11 described can be used to determine the amount of an insecticide in an environment. For example, the system 11 is suitably for detecting, measuring and quantifying an insecticide or a combination of insecticides, which include but are not limited to: abamectin, acephate, acetamiprid, amidoflumet, avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim, flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen, spirotetramat, sulfoxaflor, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron.

Fungicides

Fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoximmethyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neoasozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pyrazophos, pyrifenox, pyrimethanil, pyrifenox, pyrolnitrine, pyroquilon, quincunazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents or biologically active compounds.

In other applications, the system 11 described herein can be used to determine the amount of a neonicotinoid class of insecticides in an environment, including: neonicotinoid, pyriproxyfen or diamide insecticides. Neonicotinoids comprise specifically a class of systemic agricultural insecticides that are neuro-active or selectively neurotoxic chemicals similar to nicotine. The neonicotinoid family includes acetamiprid, clothianidin, imidacloprid, nitenpyram, nithiazine, thiacloprid and thiamethoxam. The use of neonicotinoid insecticides has grown recently as they are selected for use over many organophosphate and carbamate insecticides. The neonicotinoid family includes acetamiprid, clothianidin, imidacloprid, nitenpyram, nithiazine, thiacloprid and thiamethoxam.

In still further applications, the system 11 described herein can be used to determine the amount of an insect growth regulator (IGR), such as: benzoylurea, hilmilin, diflubenzuron and triflumuron, which can inhibit development at varying stages of the mosquito lifecycle.

In other practical applications, the system 11 described herein can be used to determine the amount of an biologically active compound or biological control agent that can be used as insecticides, such as: abamectin, acephate, acetamiprid, amidoflumet, avermectin, azadirachtin, azinphosmethyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim, flufenoxuron, fonophos, halofenozide, hexaflumuron, imidacloprid, indoxacarb, isofenphos, luienuron, malathion, metaldehyde, methamidophos, methidathion, methomyl, methoprene, methoxychlor, monocrotophos, methoxyfenozide, nithiazin, novaluron, noviflumuron, oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin, sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (5)-3,5-dichloro-N-(3-chloro-1-ethyl-1-methyl-2-oxopropyl)-4-methylbenzamide, diclocymet, diclomezine, dicloran, difenoconazole, (5)-3,5-dihydro-5-methyl-2-(methylthio)-5-phenyl-3-(phenylamino)-4H-imidazol-4-one, dimethomorph, dimoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fentin hydroxide, fluazinam, fludioxonil, flumetover, flumorfflumorlin, fluoxastrobin, fluquinconazole, flusilazole, flutolanil, flutriafol, folpet, fosetyl-aluminum, furalaxyl, furametapyr, hexaconazole, ipconazole, iprobenfos, iprodione, isoprothiolane, kasugamycin, kresoximmethyl, mancozeb, maneb, mefenoxam, mepronil, metalaxyl, metconazole, metominostrobin/fenominostrobin, metrafenone, myclobutanil, neo-asozin (ferric methane-arsonate), nicobifen, orysastrobin, oxadixyl, penconazole, pencycuron, probenazole, prochloraz, propamocarb, propiconazole, proquinazid, prothioconazole, pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematicides such as aldicarb, oxamyl and fenamiphos; bactericides such as streptomycin.

Bactericides or Bacteriocides

Further, the system 11 described herein is suitable for detecting, measuring, and quantifying a bactericide or bacteriocide. Commonly used bactericides are disinfectants, antiseptics, or antibiotics, such as 8-hydroxyquinoline sulfate, bronopol, copper hydroxide, cresol, dichlorophen, dipyrithione, dodicin, fenaminosulf, formaldehyde, hexachlorophene, kasugarmycin, nitrapyrin, octhilinone, oxytetracycline, probenazole, streptomycin, tecloftalam, and thiomersal.

Nematicides

The system 11 described herein is also suitably configured to detect, measure and quantify nematicides, such as broad-spectrum nematicide toxicants that act systemically and possess high volatility or other properties promoting migration through the soil. Commonly used nematicides are classified generally into broad classes of: avermectin, botanical, carbamate, oxime carbamate, fumigant, organophosphorus, organothiophosphate, phosphonothioate nematicides. Unclassified nematicides refers to acetoprole, benclothiaz, chloropicrin, dazomet, DBCP, DCIP, fluazaindolizine, fluensulfone, furfural, metam, methyl isothiocyanate, tioxazafen, and xylenols.

Virucides

The system 11 described herein is also suitable for determining the amount of virucides in an environment, such as surface disinfectants or detergents, especially detoxifying disinfectants containing iodophors or phenolic-based compounds. Other virucides that can be detected, measured, and quantified by the system 11 include: Cyanovirin-N, Griffithsin, Scytovirin, NVC-422, Virkon Disinfectant/Cleaner P.W.S. Virucide (For veterinary use), Zidovudine, Zonrox bleach, other bleaches, lysol, wetting agents, alcohols, and solvents.

Acaricides

In still other applications, the system 11 is configured for determining the amount of acaricides, such as: permethrin, antibiotic miticides, carbamate miticides, formamidine miticides, dicofol, and a variety of commercially available systemic and non-systemic miticides: abamectin, acequinocyl, bifenazate, bifenazate, chlorfenapyr, clofentezine, cyflumetofen, cypermethrin, dicofol, etoxazole, fenazaquin, fenpyroximate, hexythiazox, imidacloprid, pyridaben, spiromesifen, and spirotetramat.

Biologics

In still other applications, the system 11 is configured to detect bacterial, viral, or fungal organisms for use in or with plant growth promotion, pesticides, or biopesticides. In addition, biological products can also be detected and quantified. Examples include: MBI-005 non-viable *Streptomyces acidiscabies* RL-110, MBI-010 systemic herbicide, autographa California nucleopolyhedrovirus strain FV11, *Spodoptera littoralis* nucleopolyhedrovirus, MBI-601 *Muscador albus* strain SA-13, MBI-011 *Sarmetine piper longum* extract, MBI-206 *Burkholderia* spp. strain A396, *S. Frugiperda* baculovirus, *Brevibacillus parabrevis* strain B50, *Acyl-homoserine lactone, Bacillus pumilus, Bacillus thuringiensis, Chromobacterium subtsugae* strain PRAA4-1T, Oxalic acid dihydrate, *Trichoderma* spp., *Natamycin, Beauvaria bassiana* strain PPRI 5339 or ANT-03, *Stringolactones, Aureobasidium pullalans* strains 14940 or 14941, *Clonostachys rosea* strain ACM941, *Malaleuca alternifolia, Bacillus amyloliquefacians, Bacillus firmus, Bacillus subtilis, Pasteuria nishiwazae* Pn1, Knotweed extract, *Bacillus* spp. F727, *Flavobacterium* spp., strain H492, metamiron, or *Epichloe* fungi.

Pesticide End-Products

The system 11 can further be configured to detect, measure and quantify a pesticide end-product that is produced when the pesticide or herbicide is detoxified or degraded to its less-toxic end products (e.g., in cases in which chemicals break down into reactants due to natural processes or interaction with cleaning or detoxifying products). Peak absorbance of the break down or end-products can be applied to the algorithms described herein to determine when a pesticide, for example, an herbicide has reached the desired concentration. Generally, speaking, the concentration(s) (measured and predicted) for the pesticide end-product(s) are inversely related to the concentration(s) of the pesticide(s) and can alternatively be used to determine when a pesticide has been sufficiently removed or detoxified to levels that are considered in the safe zone and will not pose injury to a plant, a field of plants, a plant part, a waterway or a natural environment.

Comparisons of dicamba concentrations and dicamba end-product generation or accumulation were analyzed using the system 11 in parallel with samples analyzed using liquid chromatography coupled with mass spectroscopy (LC/MS/MS) to determine the dicamba breakdown or end-product concentration with time. Liquid Chromatography (LC) combined with Mass Spectroscopy (MS) analyses showed a removal of the dicamba molecule, a commonly used systemic herbicide ($C_8H_6Cl_2O_3$) also characterized as 3,6-dichloro-2-methoxybenzoic acid accompanied by an increase in its end-product, DCSA or 3,6 dichlorosalicylic acid; 3,6-dichloro-2-hydroxybenzoic acid.

This is just one example of a specific combination of a pesticide and a pesticide end-product. It is understood that other pesticides and pesticide end products will have similar relationships and that detection by the system of a change in concentration of one or more pesticide end-product(s) may be used as a proxy for an inverse change in the corresponding pesticide.

Other Agricultural Parameters

In addition to determining the amount of pesticides or pesticide end-products in an environment, the system 11 described herein can include additional detectors (as described above in connection with the system in FIG. 2) configured to measure a plurality of other parameters in the environment. For example, the system 11 can be used to measure parameters including: a temperature, a pH, an osmolarity, hard water components, water conditioning agents or pH modifiers, and/or a concentration of an adjuvant, a fertilizer, a growth regulator, a micronutrient, a biological control agent, a plant health agent, an inoculant, a trace molecule, a surfactant, an osmoprotectant, a safener, diesel, oils, viscosity modifiers, and/or a hard water solute.

Adjuvants

For example, the system 11 is suitably configured to determine the amount of one or more adjuvants or agriculturally acceptable carriers that are included in a spray application and may be applied along with or without a pesticide. Adjuvants can also include agriculturally acceptable carriers. The agriculturally acceptable carrier can be any carrier suitable for agricultural use. For example, suitable agriculturally acceptable carriers include, but are not limited to dispersants, surfactants, additives, water, thickeners, anti-caking agents, residue breakdown, composting formulations, granular applications, diatomaceous earth, oils, coloring agents, stabilizers, preservatives, polymers, coatings, and combinations thereof. The additive can comprise an oil, a gum, a resin, a clay, a polyoxyethyleneglycol, a terpene, a viscid organic, a fatty acid ester, a sulfated alcohol, an alkyl sulfonate, a petroleum sulfonate, an alcohol sulfate, a sodium alkyl butane diamate, a polyester of sodiumthiobutane dioate, a benzene acetonitrile derivative, a proteinaceous material (e.g., a milk product, wheat flour, soybean meal, blood, albumin, gelatin, or a combination thereof), or a combination thereof. The thickener can include, but is not limited to, a long chain alkylsulfonate of polyethyleneglycol, a polyoxyethylene oleate, or a combination thereof. The surfactant can be a heavy petroleum oil, a heavy petroleumdistillate, a polyol fatty acid ester, a polyethoxylated fatty acid ester, an aryl alkylpolyoxyethylene glycol, an alkyl amine acetate, an alkyl aryl sulfonate, a polyhydric alcohol, analkyl phosphate, or a combination thereof. The anti-caking agent can be a sodium salt, a calcium carbonate diatomaceous earth, or a combination thereof. For example, the sodium salt can include a sodium salt of monomethyl naphthalene sulfonate, a sodium salt of dimethyl naphthalenesulfonate, a sodium sulfite, a sodium sulfate, or a combination thereof. Suitable agriculturally acceptable carriers include vermiculite, charcoal, sugar factory carbonation press mud, rice husk, carboxymethyl cellulose, peat, perlite, fine sand, calcium carbonate, flour, alum, a starch, talc, polyvinyl pyrrolidone, peanut husk or a combination thereof.

Fertilizers and Inoculants

Additionally, the system 11 described herein can be configured to determine the concentration of a fertilizer in an environment that is used in applications either with or without a pesticide. The system 11 can be used to detect a "fertilizer" (e.g., a liquid fertilizer), a "micronutrient fertilizer material" (e.g., boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof), an insecticide (e.g., an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof), a herbicide (e.g., a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivatives, oxadiazolinone, a phosphate, a phthalate, a picolinic acid compound, a triazine, a triazole, a uracil, a urea derivative, endothall, sodium chlorate, or a combination thereof), a fungicide (e.g., a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof), a molluscicide, an algicide, a plant growth amendment, a bacterial inoculant (e.g., a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus *Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof), a fungal inoculant (for example, a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof), or combinations thereof. The fertilizer can include, but is not limited to, ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, urea ammonium sulfate, sulfur-coated urea, polymer-coated urea, isobutylidene diurea, K2SO4—2MgSO4, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, humic acid, or a combination thereof. The fertilizer or plant biostimulant may also include plant, seaweed and algal extracts.

Growth Regulators

The system 11 described herein can be configured to determine the amounts of a growth regulator(s) or a plant growth stimulating compound(s) that are included in a spray application and may be applied along with or without a pesticide. Plant growth regulators include, but are not limited to: a cytokinin or acytokinin derivative, the cytokinin or the cytokinin derivative can comprise kinetin, cis-zeatin, trans-zeatin, 6-benzylaminopurine, dihydroxyzeatin, N6-(D2-isopentenyl) adenine, ribosylzeatin, N6-(D2-isopentenyl) adenosine, 2-methylthio-cis-ribosylzeatin, cis-ribosylzeatin,trans-ribosylzeatin, 2-methylthio-trans-ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, meta-methyltopolin, or a combination thereof. Where the plant growth stimulating compound comprises an auxin or an auxin derivative, the auxin or the auxin derivative can comprise an active auxin, an inactive auxin, a conjugated auxin, a naturally occurring auxin, or a synthetic auxin, or combinations thereof. Where the plant growth stimulating compound includes an auxin or an auxin derivative, the auxin or auxin derivative can include indole-3-acetic acid, indole-3-pyruvic acid, indole-3-acetaldoxime, indole-3-acetamide, indole-3-acetonitrile, indole-3-ethanol, indole-3-pyruvate, indole-3-acetaldoxime, indole-3-butyric acid, a phenylacetic acid, 4-chloroindole-3-acetic acid, polyglutarmic acid, trinexpac, a glucose-conjugated auxin, or combinations thereof.

Surfactants

The system 11 described can also be configured to detect and measure concentrations of one or more surfactants. Surfactants are usually organic compounds that are amphiphilic, meaning they contain both hydrophobic groups (their tails) and hydrophilic groups (their heads). Therefore, a surfactant contains both a water-insoluble (or oil-soluble) component and a water-soluble component. Fluorosurfactants have fluorocarbon chains. Siloxane surfactants have siloxane chains. Many important surfactants include a polyether chain terminating in a highly polar anionic group. The polyether groups often comprise ethoxylated (polyethylene oxide-like) sequences inserted to increase the hydrophilic character of a surfactant. Polypropylene oxides conversely, may be inserted to increase the lipophilic character of a surfactant. Most commonly, surfactants are classified according to polar head group as: nonionic, anionic, cationic, or amphoteric. A non-ionic surfactant has no charged groups in its head. The head of an ionic surfactant carries a net positive, or negative charge. If the charge is negative, the surfactant is more specifically called anionic; if the charge is positive, it is called cationic. If a surfactant contains a head with two oppositely charged groups, it is termed zwitterionic. Commonly used carboxylate surfactants, which are the most common surfactants include: the alkyl carboxylates (soaps), such as sodium stearate. More specialized species include sodium lauryl sarcosinate and carboxylate-based fluorosurfactants such as perfluorononanoate, perfluorooctanoate (PFOA or PFO). Commonly used anionic surfactants contain anionic functional groups at their head, such as sulfate, sulfonate, phosphate, and carboxylates. Prominent alkyl sulfates include ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), and sodium myreth sulfate. Others include: docusate (dioctyl sodium sulfosuccinate), perfluorooctanesulfonate (PFOS), perfluorobutanesulfonate, alkyl-aryl ether phosphates and alkyl ether phosphates. Commonly used cationic surfactants include: octenidine dihydrochloride, and other permanently charged quaternary ammonium salts: cetrimonium bromide (CTAB), cetylpyridinium chloride (CPC), benzalkonium chloride (BAC), benzethonium chloride (BZT), dimethyldioctadecylammonium chloride, dioctadecyldimethylammonium bromide (DODAB). Zwitterionic (amphoteric) surfactants are also commonly used and both cationic and anionic centers attached to the same molecule. The cationic part is based on primary, secondary, or tertiary amines or quaternary ammonium cations. The anionic part can be more variable and include sulfonates, as in the sultaines CHAPS (3-'(3-Cholamidopropyl)dimethylammonio'-1-propanesulfonate) and cocamidopropyl hydroxysultaine. Betaines such as cocamidopropyl betaine have a carboxylate with the ammonium. The most common biological zwitterionic surfactants have a phosphate anion with an amine or ammonium, such as the phospholipids phosphatidylserine, phosphatidylethanolamine, phosphatidylcholine, and sphingomyelins. Non-ionic surfactants, many which contain long chain alcohols. Prominent among these are the fatty alcohols, cetyl alcohol, stearyl alcohol, and cetostearyl alcohol (consisting predominantly of cetyl and stearyl alcohols), and oleyl alcohol. Commonly used nonionic surfactants include: trisloxanes, polyethylene glycol ($C_{2n}H_{4n+2}O_{n+1}$), diethylene glycol ($C_4H_{10}O_3$), polyoxyethylene glycol alkyl ethers (Brij): $CH_3-(CH_2)_{10-16}(O-C_2H_4)_{1-25}-OH$, octaethylene glycol monododecyl ether, pentaethylene glycol monododecyl ether, polyoxypropylene glycol alkyl ethers: $CH_3-(CH_2)_{10-16}-(O-C_3H_6)_{1-25}-OH$, glucoside alkyl ethers: $CH_3-(CH_2)_{10-16}(O-Glucoside)_{1-3}-OH$, decyl glucoside, lauryl glucoside, octyl glucoside, polyoxyethylene glycol octylphenol ethers: $C_8H_{17}-(C_6H_4)-(O-C_2H_4)_{1-25}-OH$, Triton X-100, polyoxyethylene glycol alkylphenol ethers: $C_9H_{19}-(C_6H_4)-(O-C_2H_4)_{1-25}-OH$, nonoxynol-9, glycerol alkyl esters, glyceryl laurate, polyoxyethylene glycol sorbitan alkyl esters: polysorbate, sorbitan alkyl esters: spans, cocamide MEA, cocamide DEA, dodecyldimethylamine oxide, block copolymers of polyethylene glycol and polypropylene glycol: poloxamers, polyethoxylated tallow amine (POEA). In addition, in ionic surfactants, the counter-ion can be: monatomic/inorganic: cations: metals: alkali metal, alkaline earth metal, transition metal, anions: halides: chloride (Cl—), bromide (Br—), iodide (I—), polyatomic/organic cations: ammonium, pyridinium, triethanolamine (TEA), anions: tosyls, trifluoromethanesulfonates, and methyl sulfate.

Osmoprotectants

The system 11 described herein can also be configured to measure one or more osmoprotectants. Osmoprotectants include a variety of compound classes, such as sugars (sucrose and trehalose), amino acids: glutamine, proline and alanine, charged amino acids, such as glutamate, B-glutamate, glutamate betaine, polyols (glycerol, arabitol and inositol) and heterosides (glucosylglycerol and mannosucrose). They include a variety of compound classes: sugars and derivatives, amino acids and derivatives and polyols and derivatives. They include solutes, such as betaine or ectoine. Glycine betaine or trimethylglycine is a preferred osmoprotectant. Among the common sugar osmoprotectants, sucrose and trehalose are accumulated by microorganisms as a response to salt stress. Some of the unusual osmoprotectant sugars include gentiobiose, melibiose, maltose, turanose, raffinose, stachyose, verbascose, altrose, palatinose and cellobiose, which are frequently reported in plants. These can also be catabolized to enhance the accumulation of other osmoprotectants. Some of the sugar alcohols (polyols) include glycerol, inositol, mannitol, sorbitol, arabitol and maltitol. Osmoprotection pathways have potential applications in transferring halotolerance to commercially important crops. Commonly used osmoprotectants also include: glucosylglycerol, dimethyl sulfoniopropionate, glutamine, glutamine amides, proline, N-acetylated diaminoacids, ectoines, and glycine betaine.

Safeners

The system 11 described herein can be configured to provide amounts and predictions for safener concentrations. Common safeners are summarized and are selected from the list of: 1,8-Naphthalic anhydride, Naphthalene-1,8-dicarboxylic anhydride, Dichlormid N,N-diallyl-2,2-dichloroacetamide, Cloquintocet, Cyometrinil (Z)-cyanomethoxyimino-(phenyl)acetonitrile, Oxabetrinil (Z)-1,3-dioxolan-2-ylmethoxyimino-(phenyl)acetonitrile, Fenchlorazole, Flurazole Benzyl-2-chloro-4-trifluoromethyl-1,3-thiazole-5-carboxylate, Fenclorim 4,6-Dichloro-2-phenylpyrimidine, Benoxacor (RS)-4-dichloroacetyl-3,4-dihydro-3-methyl-2H-1,4-benzoxazine, and Fluxofenim 4-Chloro-2,2,2-trifluoroacetophenone O-1,3-dioxolan-2-ylmethyloxime. A formulation comprising safeners can be applied to crops (for example, cereal crops such maize, rice, wheat and sorghum) against preemergence thiocarbamate and chloroacetanilide herbicides or for post-emergence herbicides in broadleaved crops. Additional safeners comprise: 1,8-Naphthalic anhydride, Naphthalene-1,8-dicarboxylic anhydride, Dichlormid N,N-diallyl-2,2-dichloroacetamide, Cyometrinil (Z)-cyanomethoxy-imino(phenyl)acetonitrile, Oxabetrinil (Z)-1,3-dioxolan-2-ylmethoxyimino-(phenyl)acetonitrile, Flurazole Benzyl-2-chloro-4-trifluoromethyl-1,3-thiazole-5-carboxylate, Fenclorim 4,6-Dichloro-2-phenylpyrimidine, Benoxacor (RS)-4-dichloroacetyl-3,4-dihydro-3-methyl-2H-1,4-benzoxazine, Fluxofenim 4-Chloro-2,2,2-trifluoroacetophenone O-1,3-dioxolan-2-ylmethyloxime, and Mefenpyr, MG-191.

Hard Water Solutes

The system 11 can also be configured to measure the composition and percentage of hard water solutes. Hard water contains high levels of calcium (Ca), magnesium (Mg), sodium (Na), and/or iron (Fe), aluminum (Al) and zinc (Zn). The hard water solutes comprising Al, Ca, Mg, Na, Fe, and Zn cations (positively charged ions) attach to negatively charged herbicide molecules. Often, the association between herbicides and these cations renders the herbicide ineffective. Hard water also affects glyphosate. Al, Ca, Mg, Fe, Na, or Zn could form a complex with the glyphosate adversely affecting its activity to bind the target enzyme in the plant. If glyphosate cannot bind to the enzyme, it will not provide proper activity needed for weed control. The mineral content in water generally consists of calcium and magnesium ions, however, in some geographical areas, iron, aluminum and manganese may also be present at elevated levels. Hard water solutes are formed when water percolates through deposits of limestone and chalk which are largely made up of calcium and magnesium carbonates, but may also include chlorides, bicarbonates (HCO3-), and carbonates (CO3-2) and other ions derived from carbon dioxide. Thus, the benefit of being able to determine the hard water solutes using the system 11 prior to applying a pesticide application and adjusting the amount of pesticide for effective control is a key benefit that may be obtained by using the system 11.

Methods of Using the Agrochemical Detection System

One embodiment of a method of the present invention includes using the system 11 described above to monitor the concentration(s) of one or more pesticides or pesticide end-products (broadly, agrochemicals) during a process of cleaning, preparing a solution, or detoxifying equipment used for processes involving pesticides, such as the agricultural equipment 101 described in detail above, other agricultural equipment, seed treatment equipment, or pesticide manufacturing equipment.

For example, the detector(s) 15 and/or optical fiber(s) 19 are operatively connected to the equipment to receive light from an object or area of interest. The light received by the detector(s) is filtered by the spectral filter(s) 21. The spectral characteristics of the light are analyzed by the system 11 to determine the concentration(s) of one or more pesticides, pesticide end-products, or other agricultural parameters, such as those described above. For example, a ratio of the spectral intensity at peaks in absorbance corresponding to a pesticide, pesticide end-product, or other chemical of interest is suitably used to determine the concentration level. Information about the measured concentration level(s) is suitably output (e.g., to a user's device), such as by using the data exchange interface 25 to connect the system 11 to the user's device and transmit the information to the user's device.

For example, the step of connecting the detector(s) 15 to the agricultural equipment can include the step of mounting the detector(s) or the optical fiber (17) on the equipment adjacent the object(s) or area(s) on the equipment that are of interest. In certain embodiments, the step of connecting the detector(s) to the agricultural equipment includes the step of moving a hand-held detector to a location that is of interest, such as by manually dipping the hand-held unit into a solution contained in the tank 103. In one or more embodiments, the step of connecting the detector(s) to the agricultural equipment comprises fluidly connecting the system 11 to the agricultural equipment such that fluid from the agricultural equipment flows through a conduit or flow cell of the system from which the detector(s) are configured to receive electromagnetic radiation.

In one embodiment, the method includes taking a single measurement of the concentration level(S) of one or more pesticides, pesticide end-products, or other agrochemicals described herein at a specified point in time. In another embodiment, the method includes monitoring the concentration levels of one or more pesticides, pesticide end-products, or other agrochemical described herein over multiple time points, in a substantially continuous or a non-continuous (e.g., periodic or intermittent) mode.

The method optionally includes the step of using the system 11 described above to estimate or predict the concentration of a pesticide, pesticide end-product, or other agrochemical of interest at a future time using a first measurement at time t1 and a second measurement at time t2. Alternatively, or additionally the method optionally includes the step of estimating an amount of time remaining until a specified event relating to the measured concentration level(s) occurs. For example, the method suitably includes estimating a time remaining before the level of one or more agrochemicals have been sufficiently reduced below a threshold level defining a safe zone. This may be determined by measuring the level of the agrochemical directly or by monitoring the level of an end-product of the agrochemical and using an inverse relationship between the pesticide level and the pesticide end-product level.

The method optionally includes dispatching one or more alerts to a user or a user's device. For example, the data exchange interface 25 suitably dispatches an alert when (a) the predicted accumulated concentration of one or more agrochemicals is equal to or approximates the predetermined dosage threshold or (b) the predicted reduced concentration of one or more agrochemicals equals or falls below a predetermined dosage threshold corresponding to a safe zone.

In one embodiment, the method includes cleaning the agricultural or other equipment by rinsing it with water. Alternatively, or additionally the method optionally includes adding one or more cleaning or detoxifying agents to facilitate the cleaning process. For example, an agricultural detoxifying formulation can be used individually or combined with one or more cleaning agents to facilitate reducing the concentration of at least one growth regulator herbicide selected from the group comprising: a phenoxy herbicide, a benzoic acid herbicide, a pyridine herbicide, a quinoline herbicide class, or any combination thereof. Alternatively, or additionally, the method also optionally includes using an agricultural detoxifying formulation individually or combined with one or more cleaning agents for reducing the concentration of at least one herbicide comprising: dicamba, 2,4-D, dichlorprop, dichlorprop-p, mecoprop, mecoprop-p, MCPB, MCPA, or any combination thereof.

The method optionally includes determining how much of an agricultural detoxifying formulation is required to sufficiently remove an agrochemical or an agrochemical residue remaining in agricultural equipment. For example, the system 11 suitably makes a recommendation to a user on an amount of formulation (e.g., in the form of an aqueous solution, a spray adjuvant, a diluent, a powder, a resin, a coating, a dust, a lubricant, a slurry, a water dispersible gel, a medium, a granule or a tablet) to add to sufficiently detoxify or clean: a tank, a storage tank, a bulk tank, a spray tank, a nurse tank, a rinse tank, a seed treatment machinery, a boom, a boom sprayer, a spray rig, a spray ball, an emitter, a container, a drum, a jug, a receptacle, a basin, a chamber, a nozzle, a valve, a solenoid, a filter, a pipe, a line, a tubing, a hose, a hose fitting and a spray affiliated with the equipment based on an initial measurement before the cleaning process begins.

The method optionally includes testing post-harvest dips, post-harvest treatment water, batch equipment, and other agricultural finished product equipment that may come in contact with pesticides, for which it would be advantageous to detect the identity, presence, and levels of pesticides that may be present.

Having described the method in broad terms, several specific examples of applications of the methods and, more generally, the system 11 will now be described.

Application Example 1

Agricultural Equipment Clean-Out

In one embodiment, the system 11 and the methods described herein can be applied to cleaning agricultural equipment. The procedure needed to properly clean agricultural equipment, for example, a spray tank, depend on several factors, including the composition of the spray tank, pesticides used and the sensitivity of a crop to which solution from the tank will be applied to following a tank cleaning.

Referring to FIG. 2, the standard clean-out begins with draining any pesticide solution from the tank 103 after pesticide application is complete. The tank 103 is typically filled and flushed with clean water. A commercial or other cleaner is added to the tank 103 to form a cleaning solution. The cleaning solution is recirculated through passaging with the spray nozzles 119 closed. The cleaning solution is allowed to stand in the tank 103 (e.g., overnight). At various points, an agitator 141 may be activated to agitate the contents of the tank 103. All strainers, screens and filters 123, 131 are removed and soaked in a cleaning solution (e.g., overnight). The rinsate containing the cleaning solution is drained from the tank 103 and disposed according to any applicable regulations. The tank 103 is again flushed with clean water, which is recirculated through the equipment. The resulting rinsate is drained. Various steps are repeated as may be necessary.

According to the methods of the present invention, the system 11 described above is used to detect, measure, and/or quantify the amount of one or more pesticides, pesticide end-products, or other chemicals involved in the cleaning process at one or more points during the process. For example, any of the steps may be repeated until the system 11 indicates a threshold for moving on to the next step in the cleaning process has been achieved. The system 11 may be also used at the end of the cleaning process to verify that the equipment is sufficiently clean. At any time during the process, the system 11 can be used to determine the level(s) of the pesticides, pesticide end products, or other chemicals to assess how the clean-out is progressing and make any adjustment that may be needed, such as adding more cleaning agent, repeating one or more cleaning steps, or moving on to the next step in the process. Dispatch alerts are optionally sent to a user's device to advise when key steps are completed or when intervention may be desired.

Commercial tank cleaners are available and recommended on many product labels. They fall into several major categories that help to remove water and oil-soluble pesticides. They can also be categorized as surfactants, sequestering agents and solubilizers. Suitable cleaning agents include: ammonia plus water, ammonia plus detergent, ammonia plus detergent and water, ammonia or commercial tank cleaner plus water, sodium hydroxide, sodium tripolyphosphate, kerosene or diesel fuel followed by ammonia and water, alkaline detergents and other detergent plus water, sodium hypochlorite (chlorine bleach), fuel oil or kerosene, hydrogen peroxide plus metallic ions, sulfonylurea salt and ethanolamine, washing soda plus kerosene plus liquid detergent, liquid detergent, water or any mixtures thereof and further described in Table 3. Any one of or combination of the cleaning agents may be used in one or more embodiments of a method of tank cleanout.

TABLE 3

| Commonly Used Tank Cleaning Agents Tank Cleaning Agents |
| --- |
| ammonia + water |
| ammonia or commercial tank cleaner + water |
| ammonia + detergent |
| ammonia + detergent + water |
| sodium hydroxide |
| sodium tripolyphosphate |
| alkaline detergent |
| kerosene or diesel fuel followed by ammonia + water |
| detergent (tri-sodium phosphate detergent) + water |
| chlorine bleach (sodium hypochlorite) |
| fuel oil or kerosene |
| hydrogen peroxide and metallic ions |
| sulfonylurea water soluble salt and ethanolamine |
| washing soda + kerosene + liquid detergent |
| liquid detergent |
| surfactants |
| Water |

Typically, the detoxification of many herbicides from spray equipment requires the use of ammonia or approved tank cleaners. Table 4 provides recommended cleaning solutions and cleaner procedures depending on the choice of pesticide for use in spray tanks.

TABLE 4

Cleaning solutions and cleaning procedures to use with different pesticide formulations in a spray tank

| Pesticide Formulation | Cleaning solution | Directions |
| --- | --- | --- |
| 2,4-D amine, Dicamba | Ammonia + detergent | Agitate, flush and let set over night, flush and rinse. |
| 2,4-D ester | Washing soda + kerosene + liquid detergent | Rinse inside of tank and flush the sprayer. Let sit for 2 hours, flush and rinse. |

TABLE 4-continued

Cleaning solutions and cleaning procedures to use with different pesticide formulations in a spray tank

| Pesticide Formulation | Cleaning solution | Directions |
| --- | --- | --- |
| Sulfonylurea, Chlorine, Sulphonamides, Imidazolinones, Triazolopyrimidines, Sulfonylamino-carbonyl triazolinones | Ammonia + detergent + water | Agitate and let set over night, flush and rinse |
| Other Herbicides, Insecticides Fungicides | Liquid detergent | Agitate, flush and rinse |

Although methods of tank clean out have been described in this section as being used for tanks containing a pesticide, it will be understood that the methods can also be used with tanks containing other agrochemicals.

Application Example 2

Cleaning Seed Treatment Equipment

In one or more embodiments, the systems and methods described herein can be applied to cleaning seed treatment equipment. Agrochemical seed treatments such as pesticides, inoculants, herbicide safeners, micronutrients, plant growth regulators, seed coatings, and colorants, are commonly applied to seeds using treatment machinery (broadly, agricultural equipment).

In certain embodiments, the system 11 is used to determine pesticide concentrations in substances received in or on seed treatment equipment when the seed treatment equipment is being cleaned. Commercial seed treaters (broadly, seed treatment equipment) are designed to apply accurately measured quantities of pesticides to a given weight of seed. There are three main types of commercial seed treaters: market-dust treater, slurry treater and direct treater (includes misting treater). Volumetric seed treatment equipment is commonly used to treat canola, cotton, soybean, sugar beet, sunflower, vegetable, and wheat seed. Commonly treated seed also include: corn sorghum, oats, rye, barley, millet, pine tree and most vegetable seed. Pesticides applied as seed treatments generally include fungicides and insecticides. Seed treatment materials are usually applied to a seed as a dust, a slurry, a powder, or a liquid. Common equipment used for seed treatment can include but are not necessarily limited to a drum treater, a commercial batch treater, a downstream drum treater, a continuous batch treating system, a supply tank, and/or various other tanks. The seed treatment equipment can also comprise: a tank agitator, a dosing pump, a drain plug, a drain plug valve, a valve assembly, etc. Seed treatments are generally provided to the seed with additional agents such as pesticide carriers, binders, stickers that can make the removal of seed treatments from equipment problematic and cumbersome.

The detector(s) 15 and/or optical fibers 17 of the system 11 are suitably mounted or held in one or more locations such that the detectors can receive light from an object or area of interest. The system 11 can be used during clean-out of seed treatment equipment in substantially similar ways to the way it is used to facilitate clean-out of agricultural equipment. The systems and methods can reduce the time needed to maintain and clean the equipment between seed treatment applications, thus reducing the time that the equipment is idle. The methods also help eliminate cross contamination that may occur between batches of different seed types that may require different seed treatments. If the seed treatment equipment has been idle for any period of time, sediment in the bottom of the equipment may be particularly difficult to clean-out and may present a heightened risk of cross-contamination. Thus, in certain embodiments, one or more of the detectors 15 and/or optical fibers 17 is suitably positioned to receive light from the bottom of a tank, drum treater, or other equipment in which sediment may have accumulated. The methods as described provide for a safe, compliant, efficient, and time effective means for the sufficient removal of a seed treatment from seed treatment machinery and any other associated application equipment used to treat seeds.

Although the methods of seed treatment equipment cleanout have been described in this section as being used for pesticide detection, it will be understood that the methods can also be used for other agrochemicals.

Application Example 3

Reducing Crop Injury

In one or more embodiments, the agrochemical detection system 11 can be applied to reducing the risk of crop injury. When a pesticide composition is sprayed from a tank or other vessel, a residual amount of the active pesticide agent typically remains in the tank or agricultural vessel. This pesticide residue, if left untreated, can pose a significant problem for farmers, growers, or custom operators by unintentionally damaging crops and other desirable plants located near the sprayed fields or growing on regions bordering a sprayed field. As a result, special precautions must be taken to prepare spray tanks (nurse tanks, etc.) and vessels for subsequent use following the application of pesticides. This problem is particularly acute for growth regulator or auxin-like herbicides, such as dicamba, where even small amounts of herbicidal residue could result in significant damage to sensitive crop plants.

Unintentional injuries to crops, particularly to non-target crop species can occur if the spray tanks used in pesticide applications have not been cleaned properly. In particular, injury can occur if pesticide residues build up and/or become crystalized in application equipment (tanks, lines, booms and nozzles) before applying subsequent pesticides (herbicides, etc.) to a crop. Injury from sprayer contamination can occur up to several months after using the sprayer if it has not been cleaned properly before applying pesticides (dicamba, etc.). Spray sumps and pumps, surfaces of the spray tank, inside the top of the spray tank and around baffles, plumbing fixtures, agitation units, hoses, screens and strainers should also be cleaned or replaced frequently as they can be a major source of contamination.

Dicamba, a benzoic acid herbicide can be applied to the leaves or to the soil and is used to control annual and perennial broadleaf weeds in grain crops and grasslands, and is also used to control brush and bracken in pastures. It is commonly used to eradicate broadleaf weeds before and after they sprout. Dicamba is also used in combination with a phenoxyalkanoic acid or other herbicides to control weeds in pastures, range land, and non-crop areas (fence-rows, roadways and wastage). Dicamba is typically formulated as a solution, suspension or wettable granules and can be applied by ground equipment, such as a spray rig with a boom or spray tank or by air. Dicamba, for example, causes significant damage to plants even at extremely low application levels. The levels of dicamba remaining in a tank drain have been reported to be approximately 5% with percentages exceeding 5% in the nozzles of the total concentration used for the spray application. Most dicotyledonous plants are sensitive to treatment with dicamba. For example, sensitive plants can show herbicide damage with symptoms pronounced after spraying dicamba even at the low level of 0.017 kg/ha with severity of symptoms increasing at 0.28 kg/ha and 0.56 kg/ha, the application levels normally used for weed control in agriculture. However, sensitive dicot plants like tobacco can display distinct injury symptoms even at levels of dicamba treatment as low as 0.001 to 0.01 g/ha. Soybeans will be sensitive to dicamba concentrations as low as 10 mg/L. Many farmers will dispose of the dicamba remaining in a tank or the dicamba rinsate after cleaning a tank in the field. Dicamba release in the environment by disposing of a dicamba containing rinsate can be found in soil and surface water (waterways), which can pose a concern for terrestrial and aquatic plant life.

Phenoxy acetic acids can also cause crop injury. Specific examples for use of phenoxy acetic acids as an herbicide application are 2,4-D for small grains, corn, grass pastures, MCPA for small grains and grass establishment, and 2,4-DB for alfalfa and soybean. Injury from phenoxy acetic acids can vary depending on the crop and concentration of herbicide that remains in the equipment. For example, all phenoxy acetic acids can produce similar symptomology in sugar beet. Sugar beet leaves will be flat on the ground within a few hours after exposure to phenoxy acetic acid herbicides. Leaf petioles exhibit symptoms of epinasty or leaf twisting, Sugar beet exposed to phenoxy acetic acids in the cotyledon or at an early stage of developmental growth may develop fused petioles, which is referred to as "stalking" or "trumpeting". New leaf growth after exposure often will be malformed with crinkled leaf margins, parallel veins, or leaf strapping. Thus, overall yields and root growth may be severely impacted.

Benzoic acids are another class of pesticide that can cause crop injury. Specific examples for use of benzoic acids (for example, dicamba) are used for corn, wheat, oats, sorghum, pastures, and other areas that include non-croplands. Application of dicamba that has left over residue that remains in the soil for example, after using pre-plant burn down procedures may significantly reduce crop emergence. Residual dicamba residue in the soil at the early stage growth can cause the "trumpeting" symptom (fused petioles). Similar injury symptoms of dicamba injury can occur if dicamba residue is not properly cleaned from a tank used for subsequent spray applications on different crops or using different applications of herbicides. Classic injury symptoms can include twisting and cupping of leaves, and the development of the first true leaves may be inhibited. Burning on leaves is also symptomatic of dicamba injury.

Pyridines form another class of pesticide capable of producing crop injury. Pyridines such as clopyralid for use as herbicide applications for small grains, sugar beet, corn and grass pastures, picloram for non-cropland, and grass pastures and triclopyr for non-cropland and grass pasture are widely used in agricultural practices. Pyridine injury symptoms occur readily accompanied by a warm, moist environment that favors phytotoxicity. The leaves may collapse or become flat and the petioles may exhibit epinasty. Also, leaves may become more strap-shaped. However, certain members in this class of herbicides may cause leaves to roll upward from the edges. Leaf rolling is caused to a greater extent by clopyralid. Pyridines also typically are persistent for longer periods of time in soils and can bind to other forms of organic matter, which can cause injury to plants as well as impact the compositional makeup of the natural microbial flora and fauna that exist in the soil environment.

Glyphosate is used as a post-emergent herbicide to control the growth of a wide variety of annual and perennial grass and broadleaf weed species in cultivated crop lands, including cotton production. Glyphosate herbicide mixes can contain ammonium salts, which can be used as an additional fertilizer treatment. Ammonium salts (NH4+) appear to be the active component of these fertilizer solutions and have improved the performance of certain herbicide consistency on some weeds. Herbicides that appear to benefit from the addition of ammonium are the relatively polar, weak acid herbicides such as the sulfonylureas, and the imidazolinones. Glyphosate mixes containing ammonium salts when added to a tank in a spray mix may solubilize any crystalized dicamba residue that remains in the tank, lines, nozzles or attachments. Therefore, glyphosate following a dicamba application can cause unintentional injury to non-target plant/crop. As a precautionary measure, any dicamba residue remaining in a tank should be detoxified and/or reduced prior to conducting any subsequent applications using glyphosate.

A method of limiting or preventing any of the crop injuries described above includes using the methods described herein (e.g., Application Example 1, supra) to ensure agricultural equipment (e.g., a spray tank) is sufficiently cleaned between pesticide applications. This reduces or eliminates cross-over contamination and crop injury that may result from insufficiently cleaned equipment.

Moreover, in one or more embodiments, the method comprises using the system to monitor concentration levels of a cross-contaminant pesticide (e.g., a different pesticide from the one being intentionally applied) during a pesticide application process. If the system 11 detects a sudden spike in the concentration of the cross contaminant, the system suitably generates a dispatch alert or alarm to alert that evidence of cross cross-contaminant has been detected, alerting the user of a possible pesticide (e.g., herbicide) residue crystal that had dried on the inner surface of a line or in a nozzle or fitting breaking free and then going into solution at one time point, thus resulting in an immediate rise in the concentration level of the cross-contaminant pesticide. This can also help reduce or eliminate crop injury.

Although the methods of reducing crop injury in this section are described as being used with pesticides, it will be understood that the methods can also be used with other agrochemicals.

Application Example 4

Cleaning Equipment That Has Not Drained Completely

In one embodiment, the system 11 and methods described herein can be applied to cleaning agricultural equipment, such as a tank, that is configured so that it is impossible or otherwise undesirable to fully drain the equipment of fluid after use. In other words, the system can be used in a method of cleaning agricultural equipment in which the agricultural equipment is never fully drained of fluid. Thus, in one or more embodiments, a method in the scope of this disclosure comprises the step of cleaning agricultural equipment without fully draining the agricultural equipment of fluid. When fluid in the agricultural equipment is not fully drained, the effectiveness of the cleaning agents may be greatly reduced and may even not be effective for removing the pesticide residue remaining in the tank or in other agricultural equipment. The method(s) as described herein provide a substantial benefit in this context. Spectral characteristics of the fluid can be monitored throughout the cleaning process to determine when the agrochemical of interest has been sufficiently removed from the equipment. As needed the cleaning process can be adjusted based on the information provided by the system 11 to add one or more detoxifying formulations directly to the solution remaining in the tank or in other equipment. This may provide a more effective detoxification and or removal process of the agrochemical for the user (farmer, grower, custom operator, etc.).

Application Example 5

Estimate and Provide Predictions for Safe Zone Requirements

In one or more embodiments, the agrochemical detection system 11 and methods described herein can be applied in a method of predicting (1) absolute concentration of the pesticide at a predetermined time point or over multiple time points or (2) a safe zone concentration when the pesticide concentration is low enough that during a spray or change out with another pesticide the level remaining in equipment will not cause injury to a plant (target or non-target plant), a field of plants, a plant part, a waterway or a natural environment. If desired, predictions can be rendered with as little as two or three measurements. Thus, the systems and methods suitably predict when it will be safe to use agricultural equipment for subsequent applications or dispose of rinsate in a safe manner after clean-out procedures have been performed. Moreover, the system 11 and method described herein can suitably confirm that safe zone requirements have been met using measurement data at the end of a cleaning process. The system 11 and methods described herein can also output dispatches to users in the form of safe zone recommendations, which are based on information provided by the user and/or stored in the system concerning the types of pesticides used and the types of crops to which they are applied to reduce the variability of outcomes related to risk from injury from pesticide contaminants on plants, fields of plants, plant parts, waterways, and other natural environments.

Safe zone levels when reached are suitably output to the user as dispatch alerts. For example, a first dispatch alert may be sent to the user when a first safe zone for a first type of crop having a higher tolerance for cross-contamination with the pesticide(s) involved has been achieved and a second dispatch may be sent to the user when a second safe zone for a second type of crop having a lower tolerance for cross contamination has been achieved.

Dicamba and 2,4-D concentrations which met the safe zone requirements developed for tank cleaning procedures after applications using dicamba and 2,4-D are recommended at equal to or below 15 mg/mL. Moderate injury has been noted to occur on soybean and cotton plants at approximately 15 mg/L to 50 mg/L concentration of dicamba or 2,4-D remaining. Concentrations in this range are considered to be in the warning zone. Concentrations of dicamba and 2,4-D above 50 mg/L are considered in the danger zone where the remaining herbicidal residue or rinsate containing the residue can be expected to cause injury to a plant, field of plants, a plant part, a waterway or a natural environment. In one or more embodiments, respective dispatch alerts are generated when one or more of these concentration levels are detected by the system 11.

The systems and methods described herein are also advantageous when used in the context of pre-plant burndown procedures followed by subsequent pesticide applications to plants or fields of plants. Pre-plant burndown is commonly used in many regions (particularly in the U.S.) to prepare fields for planting. The advantages of using pre-plant burndown methods include: improved control of problem weeds, seedbed cleaning at the time of planting, better stand establishment of the desired crops and rotational freedom with short pre-plant intervals. Commonly used commercial herbicides that are recommended for pre-plant burn down procedures for use prior to planting soybean include: acetochlor, 2,4-D, 2,4-D amine, chlorimuron+flumioxazin+pyroxasulfone, chlorimuron+tribenuron, metribuzin+chlorimuron, dimethenamid, imazethapyr+glyphosate, glyphosate, metribuzin, paraquat, metribuzin+chlorimuron, paraquat+metribuzin, thifensulfuron+tribenuron, imazethapyr, safluenacil, flumioxazin, chlorimuron and pyroxasulfone. While common herbicides for pre-plant burndown prior to planting corn include: 2,4-D, dicamba, atrazine, iodosulfuron, s-metoachlor atrazine+glyphosate, paraquat, thifensulfuron+tribenuron, flumetsulam+clopyralid, metribuzin, saflufenacil, flumioxazin and acetochlor. Common herbicides used for pre-plant burndown prior to planting no-till wheat include: glyphosate, dicamba, paraquat, saflufenacil. metsulufuron, chlorsulfuron, and carfentrazone.

Once burndown herbicides have been applied, the agricultural equipment should be thoroughly cleaned and the residual herbicides in the equipment sufficiently reduced to the predicted safe zone levels for that particular herbicide or herbicide mixtures. In any of the above scenarios, the systems and method described herein facilitate and expedite sufficient detoxification of the agricultural equipment. For example, after a pre-plant burndown application has been performed, the user can detoxify or reduce the pesticide in the agricultural equipment in less time providing the availability of the equipment with a faster turnaround for use on another application. Alternatively, the initial herbicide residue concentration can be determined by the system before application of the burn down herbicide to confirm the initial herbicide concentration levels are consistent with the requirements for burn down herbicide applications and then post use to determine when the safe zone levels during equipment cleaning procedures are met.

Although the prediction methods in this section are described as being used for pesticides (e.g., herbicides), it will be understood that the methods can also be used for other agrochemicals.

Application Example 6

Managing Risks of Crop Loss

In one or more embodiments, the systems 11 and methods described herein can also be applied to managing risk of crop loss. Increased risk of injury from herbicide applications on non-target or sensitive plants may occur as more herbicides are used and new technologies are brought to the field. The development of new herbicide technologies, such as the production of herbicide resistant crops, for example, soybean, cotton, wheat, and alfalfa increase the likelihood that current and new herbicides will be used in crop management practices. In addition, new pesticide, fungicide and fertilizer technologies are continuing to evolve and risk factors associated with these technologies continue to change.

The Risk Management Agency, which is associated with the U.S. Department of Agriculture, may approve one or more endorsements (for example, Best Management Practices—BMP Endorsement) for crop insurance products based on preferential detoxification/cleaning procedures recommended for sprayer application equipment that are used to apply agricultural pesticides.

An insurance product may include a crop risk insurance policy and an endorsement assembly associated with the crop insurance policy. The crop risk insurance policy component may insure against risk of loss due to pesticide residue contamination remaining in the equipment after an application and may be selective depending on the pesticide, as well as the target or non-target crops that are used with the application. Ancillary terms and conditions of the crop insurance policy may require the insured (farmer, grower, custom operator) to establish or have BMP guidelines in place that and have a compliance plan for cleaning and maintaining agricultural equipment that is used for spray applications of pesticides on crops.

The systems and methods described herein can be used to verify and ensure that a user has achieved compliance with any BMP guidelines or other ancillary requirements of the insurance policy related to reducing the risk of pesticide injury. The systems and methods described herein can be used to accurately measure the concentration of the pesticide or a pesticide end-product that is currently in or on the equipment so that base BMP or other ancillary requirements based on the recommended concentrations required to achieve effective detoxification and/or cleaning measures that ensure reduced risks to plants, fields of plants, plant parts, nearby waterways, or other natural environments can be developed. Additionally, the systems and methods described herein can also provide a date and time stamped record to provide verification that adequate cleaning of equipment has been achieved to meet safe zone levels. Additionally, or alternatively, reduced insurance premiums and/or other benefits under the policy can be made contingent on verification of BMP or other ancillary requirements through use of the systems and methods described herein. Thus, using the recommendations provided by the system may result in both a reduced cost for the deductible, as well as in a reduction in the premium rates for crop commodity insurance. Therefore, the method(s) of the present invention can be used to achieve lower mean premiums for crop insurance associated with a higher probability of indemnity payments if losses should occur. The increase in indemnity payments for crop insurance is proportionally related to an increase in the percentage of total liability (maximum indemnity), which further implies a higher premium subsidy rate.

The systems and methods described herein can minimize (1) the amount of liability insurance required by the user to carry with a crop insurance policy and (2) the amount of payment from a liability insurance policy provided by the insurance company to reduce the risk of injury on a crop resulting in reduced crop loss (for example, loss of revenue related to crop loss or reduction in yield of a crop). The systems and methods described herein can also provide savings on crop commodity insurance and reduce risk of loss for crops as designated in various risk categories, such crops include but are not limited to: corn, soybeans, wheat, small grains (oats, rye, barley), forages (alfalfa, corn silage, silage), fruits, vegetables and flowers for commodity usage.

The systems and methods described herein can also minimize the amount of liability insurance required to cover safety risks associated with tank clean out operations. The systems and methods described herein also facilitate safer and more environmentally friendly solutions for detoxifying or removing a pesticide or pesticide residue from equipment compared to the commercially available cleaners.

The systems and methods described herein can also reduce or eliminate the risk of damage caused by disposal of rinsate on a plant, a field of plants, a plant part, a waterway, or a natural environment.

Application Example 7

Production Manufacturing and Equipment

In one or more embodiments, the systems and methods described herein can be applied to manufacturing or developing a pesticide or pesticide-based product. The principal steps of manufacturing a pesticide are (a) preparation of process intermediates; (b) introduction of functional groups; (c) coupling and esterification; (d) separation processes, such as washing and stripping; and (e) purification of the final product. In pesticide manufacturing, an active pesticide ingredient is first synthesized in a chemical factory or laboratory. Next, a formulator for example, mixes the active ingredient with a carrier (for liquid pesticides) or with inert powders or dry fertilizers (for dust pesticides). Active ingredients and carriers are added to the formulation such as in the manufacture of a pesticide provided in a liquid formulation or active ingredients and inert powders such in the manufacture of a pesticide provided in a dust formulation. Each of these steps may include a monitoring step performed by the system 11 in which the concentration of the pesticide-related precursor(s), intermediate(s) or final product(s) to be measured either at a single time point or using continuous monitoring. This multi-step process can involve multiple pieces of equipment, such as those used in pesticide synthesis, scale up batch production and formulation to the final liquid, dust, slurry, granule, etc. containing the pesticide. Within this multi-step process many different manufacturing pieces of equipment can be included in the production and can include but are not limited to tanks, mixers, grating devices, powdering devices, adaptors, hoses, etc. for synthesizing, manufacturing, formulating, diluting, dispensing and packaging of the pesticide for delivery as a product supplied but not limited to a farmer or grower for use in agriculture.

The systems and methods described herein can be can be used during any of the steps in the pesticide manufacturing process to determine the concentration of the pesticide precursor, intermediate, or final product in order to ensure that the desired or accurate concentration is delivered during manufacture. The systems and methods described herein can also be used at any step of the process to determine if any of the equipment involved has been adequately cleaned and/or maintained after the manufacture is complete. The systems and methods described herein can also be used for monitoring the concentration of a pesticide in any of the equipment that is used in the processes from manufacture through packing.

Although the manufacturing and development methods in this section are described as being used for pesticides (e.g., herbicides), it will be understood that the methods can also be used for other agrochemicals.

Application Example 8

Checking Returnable/Reusable Containers

Agrochemicals such as pesticides and pesticide related products (e.g., pesticide precursors or other chemicals involved in pesticide manufacturing) are often transported and stored in drums or other containers. Moreover, it is often the case that the drums or other containers may be returned to the vender for reuse or reused once their contents have been exhausted. The drums commonly include one or more valves or couplers (e.g., from Micro Matic) that can be used to pump material from the container. The drums and any fittings, couplers, and/or valves thereon should be cleaned before they are returned and/or reused. Failure to clean the containers can lead to formation of crystals or dried solids that can affect the functionality of the couplers, valves, or other fittings and that can lead to deterioration of seals associated therewith.

Thus, in one or more embodiments, the system 11 can be used to check the cleanliness of returnable or reusable drums and any fittings thereon at any point before, during, or after cleaning. For example, a drum can be checked before cleaning to identify any agrochemical on or in the drum. This information can be used to determine how the drum will be cleaned (e.g., which type of cleansers or other chemicals to use). The drum can be checked during cleaning to monitor progress. The drum can be checked after cleaning to confirm the drum has been cleaned adequately. Likewise, a vendor who accepts return of containers that are supposed to have been cleaned may use the system 11 to check the containers after they have been received to confirm the customer did an adequate job of cleaning.

Concept Testing Example 1

Agrochemical Detection System Proof of Concept Testing

In this section, procedures used to validate the concept of the systems 11 and methods disclosed above are described.

In one testing procedure, a spectrophotometer 13 with UV VIS capabilities was operatively connected to a stainless steel flow cell 17 having a 1 cm gap using solarization resistant optical fibers 19. One of two different light sources 39 were connected by a second solarization resistant fiber optic cable 19 to the opposite side of the flow cell 17. The light sources 39 delivered light through the optical fibers 19 and the flow cell 17, and the spectrophotometer 13 detected the light after it had interacted with the substance received in the flow cell. It was found that the optimal light source can vary depending on the conditions and the objectives. For example, light in the UV range between 220 nm and 290 nm allows for good visibility of the absorbance of phenoxy (auxin-like) herbicides. The light sources 39 used for testing included a DH-2000 light source, comprising both a halogen light source and a deuterium light source, and a PV200 UV VIS light source, comprising a pulse xenon bulb. Both tested light sources 39 transmitted both UV and VIS into the flow cell 17. The flow cell was equipped with two transparent windows 37 that allow for the free transmittance of both UV and VIS through the windows.

To facilitate the concept testing, a recirculation test system with certain features corresponding conventional agricultural spray equipment was assembled. The recirculation test system included a pump 111 configured to recirculate fluid from a 100 L recirculating spray tank 103. The pump 111 was configured to circulate liquid from the tank 103 through a series of three boom lines 107 made of different material (stainless steel, carbon fiber, and rubber). At least one spray nozzle 119 was connected to each boom 107. The recirculation test system included a return line configured to carry fluid sprayed from each nozzle 119 back into the tank 103. This completed a recirculation loop through the spray lines, the spray boom line 107, and the spray nozzles 119, back to the main tank 103.

Several different arrangements of the detection system 11 were tested on the recirculation test system described above. In a first arrangement, the system 11 was fluidly coupled to the recirculation test system at the return line downstream of a nozzle 119. More specifically, the return line from the nozzle 119 to the tank 103 was modified to pass through the flow cell 17 of the system 11. In a second arrangement, a sampling line provided fluid communication between an end of the boom line and the flow cell 17. In a third arrangement, a sampling line provided fluid communication between the tank and the flow cell 17. In a fourth arrangement, cuvette samples were taken from the tank by way of a spigot and placed in a cuvette holder configured to hold 2 mL of sample. The cuvette holder was operatively arranged between the light 39 and the spectrophotometer 13 so that the spectrophotometer could receive light from the light source after it had interacted with the sample in the cuvette holder. Several other arrangements of the system were also tested. Testing demonstrated that useful spectral data for a fluid could be obtained at any of the arrangements described herein.

The same testing procedure was used in each of the four arrangements of the system 11 specifically enumerated above: Initially, the spectrophotometer 13 was turned on, and a dark measurement was made without any light from the light source 39. Twenty liters of tap water was then delivered to the recirculation test system. The light source 39 was then turned on and a blank measurement was made. Dicamba was then added to the recirculation test system to obtain a calibrated dicamba concentration of 6 g/L in the recirculation test system. After recirculation of the dicamba for ten minutes, the spectrophotometer 13 was used to obtain spectral traces including spectral data in the 220-240 nm range and the 250-280 nm range. In each of the four testing arrangements enumerated above, a minimum of three samples of spectral data from the dicamba solution were obtained using the spectrophotometer 13. The data from each sample were transferred by wireless connection to a laptop and processed, based on data from readings from the dark and blank measurements, to isolate spectral data relevant to the dicamba in the solution. The processed data for each sample was shown on the display of the laptop. Some of the processed data was analyzed using two methods of analysis described below.

In a first method of analysis, ratios of the peak absorbance of the spectra at certain wavelengths were computed and compared to corresponding reference ratios for auxin-like herbicides. It was found that at least certain herbicides could be positively identified based on absorbance ratios at least at the following wavelengths: 276 nm:230 nm; 285 nm:230 nm; 259 nm:230 nm; 237 nm:230 nm; 252 nm:230 nm; 252 nm:285 nm. These ratios have been found to be useful for identifying and distinguishing various auxin-like herbicides. For example, when an absorbance ratio of a substance at 276 nm:230 nm is higher than the absorbance ratio at 285 nm:230 nm, the spectral characteristics suggest that the substance more likely contains a dicamba herbicide than a 2,4-D amine herbicide. It is believed that agrochemicals could be identified using spectral characteristics at other wavelengths in other embodiments.

In a second method of analysis, peak values of absorbance of the acquired spectra were compared to predetermined standards to quantify a concentration of herbicide in the sample. The second method of analysis can be performed after identifying a particular herbicide using the first method of analysis discussed above or as an independent method of analysis. In one example of the second method of analysis, absorbance at a spectral peak (e.g., a known spectral peak for an herbicide or class of herbicides) can be used to determine a concentration of herbicide in a substance. For example, the peak absorbance at a wavelength in a range of from 220 nm to 240 nm or a range of from 250 nm to 280 nm, or alternatively, a ratio of peak absorbance at two wavelengths can be identified and compared to an empirically derived standard (e.g., a standard curve) that compares absorbance at the respective wavelength or the respective absorbance ratio to concentration of an herbicide of interest. This comparison was found to provide useful estimates of the concentration of herbicide in a sample during testing. Matching the detected peak absorbance or absorbance ratio to the predetermined standards (e.g., standard curves) allows for quantification of the auxin-like herbicides or other agrochemicals. It was also found that concentration can be estimated based on a comparison (e.g., a ratio) of an absorbance at a spectral peak with a non-peak (e.g., background) level of absorbance at a defined wavelength, such as the absorption at a wavelength of 200 nm.

Additionally, based on the testing conducted, it is believed that obtaining spectral measurements at different points in time can allow for extrapolation and prediction of herbicide changes (e.g., concentration changes) during a cleaning process. Using absorbance readings at two or more points in time, a projection line or curve can be generated that models herbicide concentration (or other herbicide characteristic) versus time. The slope of the projection line can be an estimate of the rate at which the concentration of herbicide is changing. Using this determined rate, an extrapolation for the time at which the herbicide concentration will reach zero or a predetermined desired level can be predicted.

Using the arrangements of the systems and the second method of analysis described above, the dicamba concentration in a recirculation test system was tested during a triple rinse treatment procedure. A triple rinse treatment procedure is an industry standard procedure for removing herbicides from spray equipment. This triple rinse treatment that was conducted entailed flushing the lines and tank of the recirculation test system three times. After each flushing was completed, 10 L of fresh water was added to the recirculation test system and circulated for a period of ten minutes. After each recirculation step, the system 11 was used to determine the herbicide concentration in a sample from the recirculation test system. The results are shown in the Table 5.

TABLE 5

Dicamba remaining in a tank after cleaning rinses

| Step | Peak Absorbance at 280 nm | Dicamba Concentration |
| --- | --- | --- |
| Initial Addition of Dicamba | 4.2 | 6.0 g/L |
| End of 1$^{st}$ Rinse | 3.0 | 1.5 g/L |
| End of 2$^{nd}$ Rinse | 0.4 | 220 mg/L |
| End of 3$^{rd}$ Rinse | 0.2 | 35 mg/L |

The results of this experiment show the system 11 described above can effectively detect and measure the amount (e.g., concentration) of agrochemical in agricultural equipment.

Although the testing described in this section was conducted using herbicides, it is thought that the system 11 and methods would function in the same manner for other types of agrochemicals Concept Testing Example 2

Agrochemical Spectral Signatures

As explained above, the system 11 can be used for detecting, measuring, analyzing, and monitoring one or more agrochemicals such as pesticides, pesticide end-products, fertilizers or mixtures of fertilizers and pesticides. More specifically, the system 11 can be used to detect a distinct spectral signature or marker associated with one or more agrochemicals or agrochemical concentrations. The spectral signature can then be used to identify the agrochemical or concentration of agrochemical in various methods as described above. This section describes testing that was performed to show that agrochemicals of various types have discernible spectral signatures that are useful for this type of analysis.

As described in further detail below, a testing procedure was used to obtain spectral data for various agrochemical solutions. Table 6 shows a ratio of peak absorbance at wavelengths of the 230 nm and 280 nm for certain pesticides that were tested. In addition, the spectral traces for various agrochemicals are shown in FIGS. 25A-31F. As indicated in Table 6, the ratio of absorbance at wavelengths of 230 nm and 280 nm differs among pesticides. Thus, in one or more embodiments, this ratio can be used as a signature for identifying a pesticide when using the systems and methods described above. As indicated in FIGS. 25A-31F, the spectral trace for each of the different agrochemicals is unique and thus provides a signature that distinguishes the agrochemical from all the others. It will be appreciated, therefore, that the systems and methods described herein can be used to detect and identify agrochemicals at least in part on the basis of their spectral signature (e.g., spectral trace, ratio of absorbance at certain wavelengths).

To generate the spectral data referenced in Table 6 and FIGS. 25A-31F, the following test procedure or a functionally equivalent procedure was used. Samples of the respective agrochemicals were measured using a UV-VIS BioTek SYNERGY HTX (BioTek Instrument Inc.) high throughput plate reader. A solution of each of the agrochemicals was made at a concentration of 1X and then recirculated through a 100 L spray tank for a period of 10 min before being sampled. For certain agrochemicals, the 1X pesticide solutions were further diluted as shown FIGS. 26-29 (in the figures, the number preceding 'X' indicates the multiple of dilution of the original 1X solution). Solutions were pipetted using a multi-channel pipettor (200 each) into a UV-Star® microplate (GREINER BIO-ONE). Serial dilutions of some of the samples were prepared by the addition of MilliQ water to each sample to bring the final volume up to 200 μL. Absorbance of the samples was measured in a wavelength range from at least 200 nm to a maximum of 800 nm. For many of the samples, absorbance at wavelengths of 230 nm and 280 nm wavelengths were recorded (as explained below, certain classes of pesticides were found to have absorbance peaks adjacent these wavelengths). Absorbance at a wavelength of about 250 nm was also recorded for several of the samples and used as a spectral control to distinguish between the 230 nm and 280 nm wavelength regions.

Figure 25A:
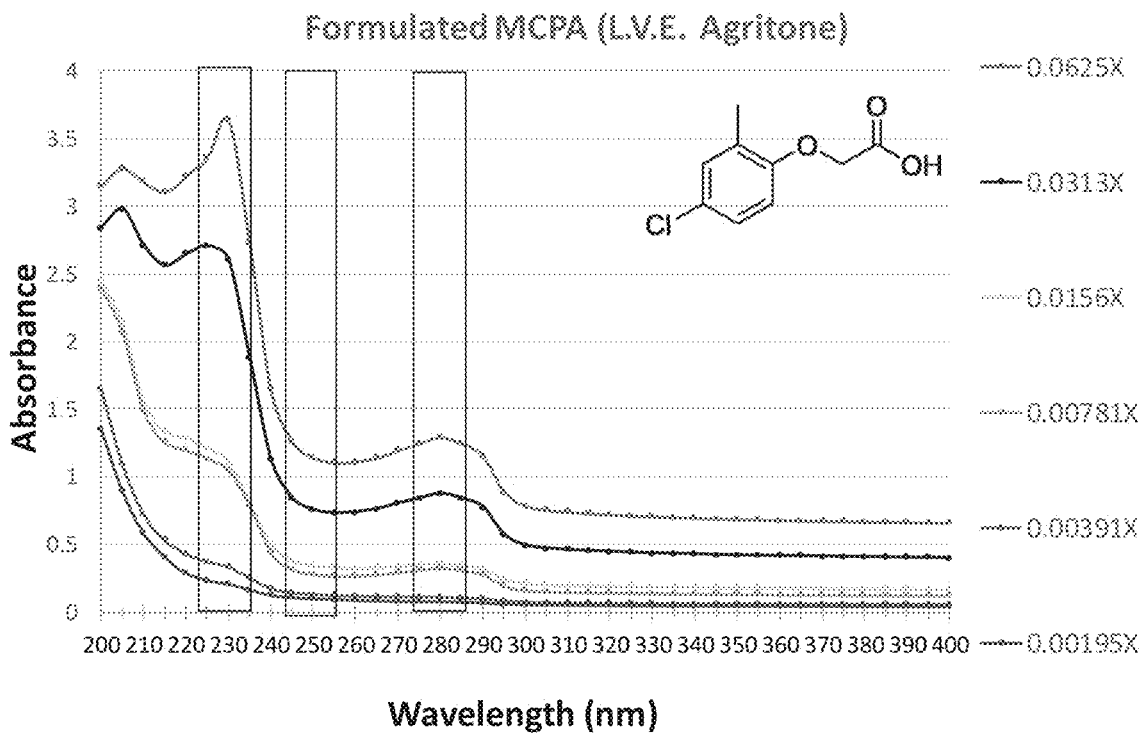
FIG. 25A is a graph showing detected absorption in a defined wavelength range of samples of formulated MCPA (ARGITONE®) at different concentrations
Figure 25B:
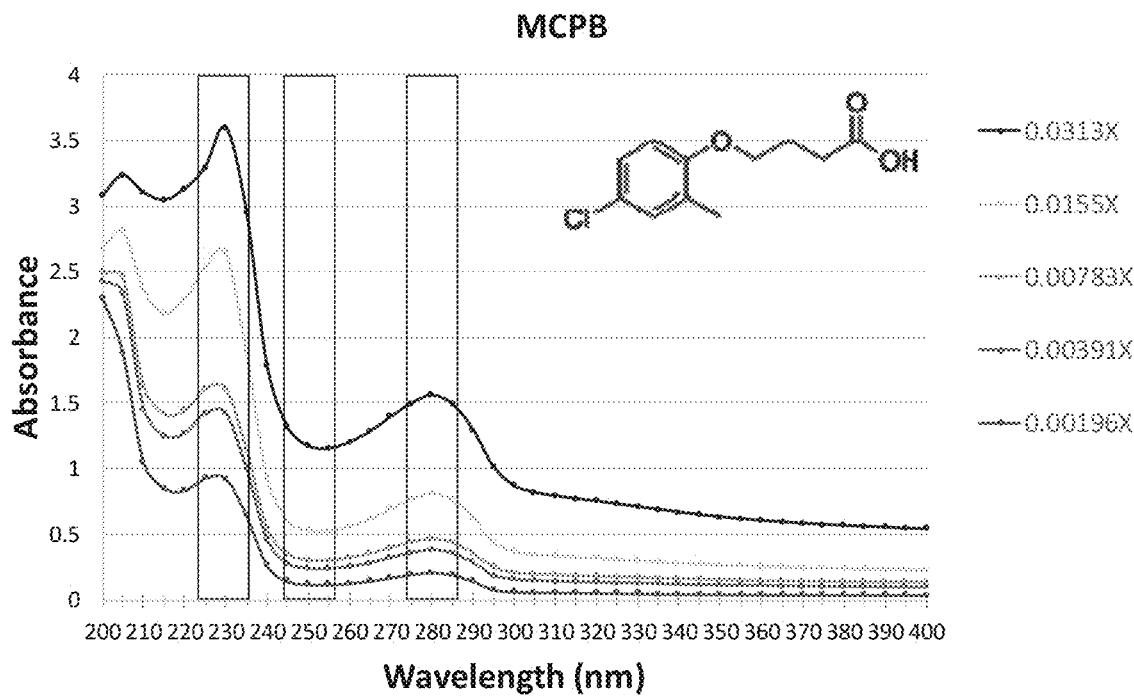
FIG. 25B is a graph showing detected absorption in a defined wavelength range of samples of MCPB at different concentrations.
Figure 25C:
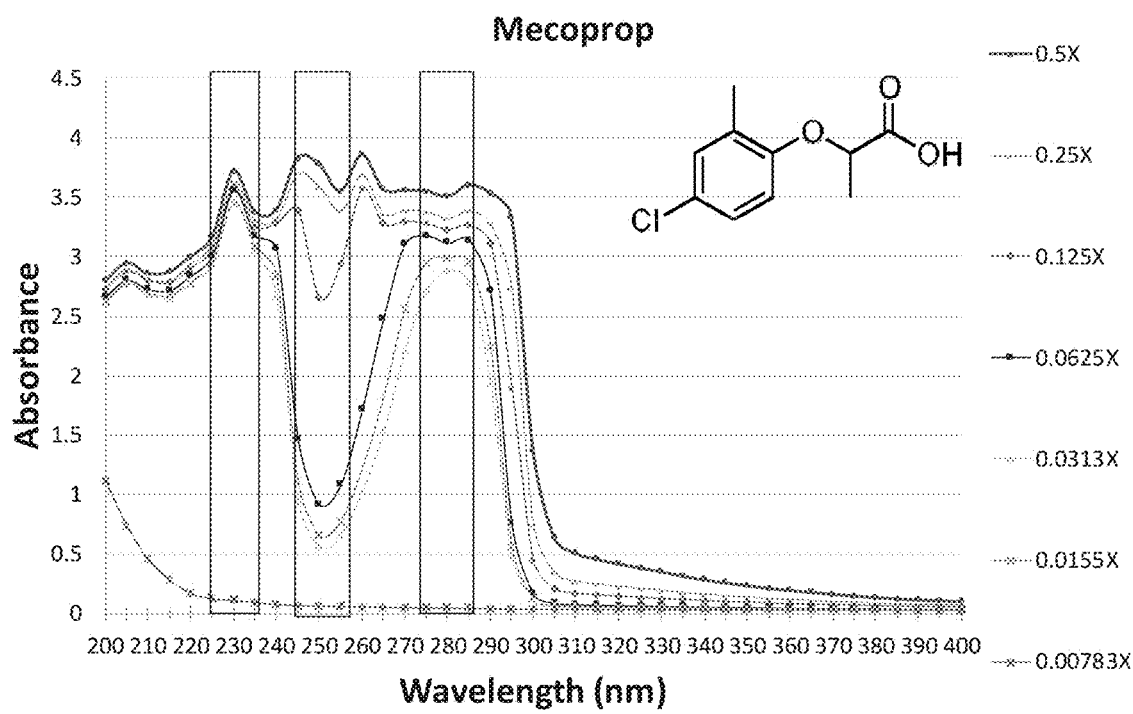
FIG. 25C is a graph showing detected absorption in a defined wavelength range of samples of mecoprop at different concentrations.
Figure 25D:
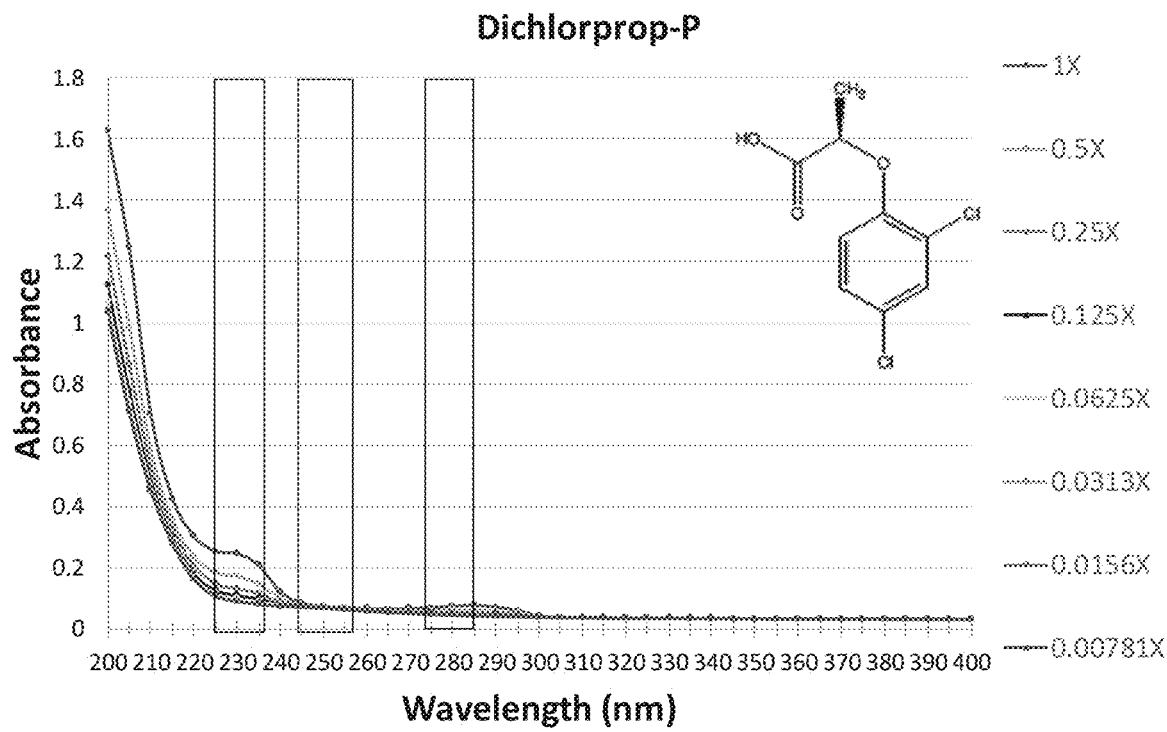
FIG. 25D is a graph showing detected absorption in a defined wavelength range of samples of dichlorprop-P at different concentrations.
Figure 25E:
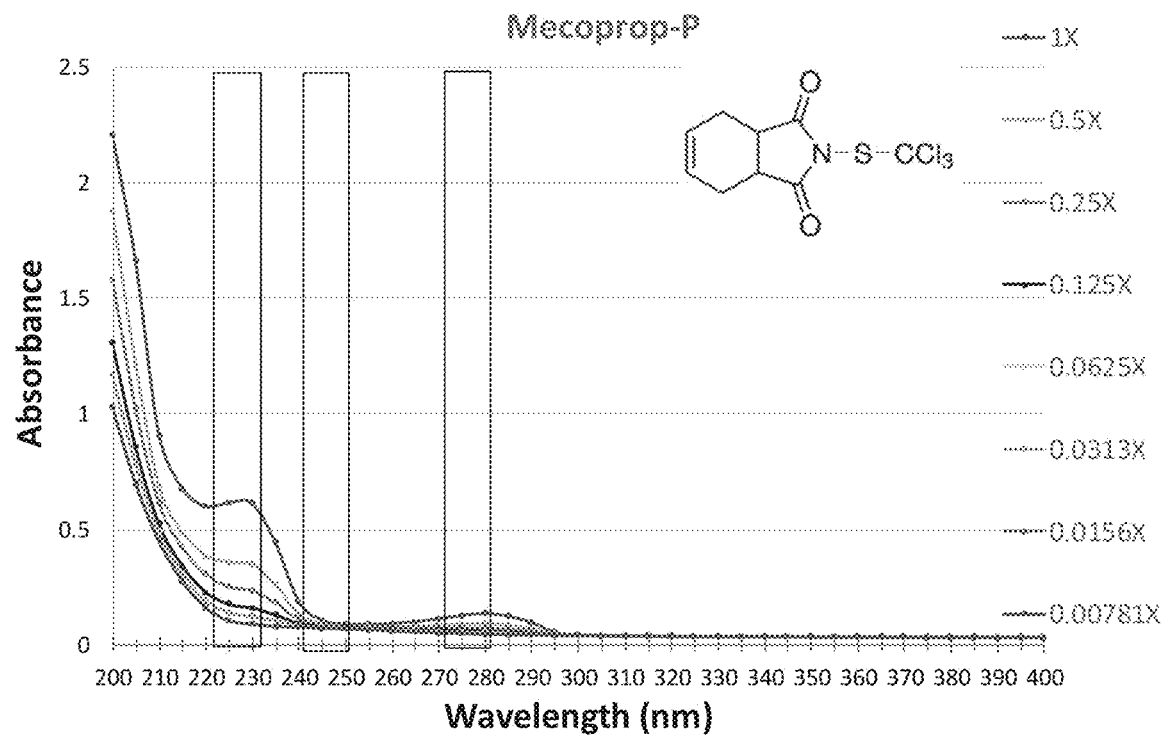
FIG. 25 E is a graph showing detected absorption in a defined wavelength range of samples of mecoprop-P at different concentrations.
FIG. 25F is a graph showing detected absorption in a defined wavelength range of samples of dichlorprop at different concentrations.
Figure 25F:
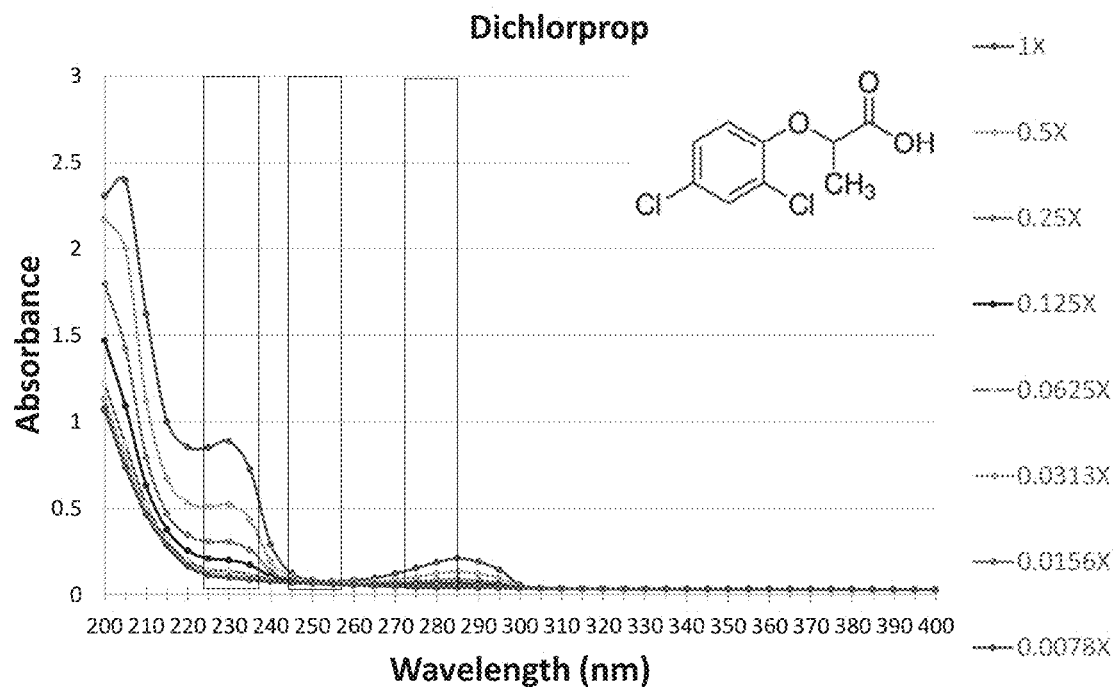

FIGS. 25A-25F show the detected absorbance spectra in a wavelength range of from 200 nm to 400 nm of various concentrations of formulated MCPA (L.V.E. ARGITONE®) (FIG. 25A), MCPB (FIG. 25B), mecoprop (methylchlorophenoxypropionic acid, MCCP) (FIG. 25C), dichloroprop-P (FIG. 25D), mcoprop-P (FIG. 25E), and dichloroprop (FIG. 25F). The sample X-concentrations listed in the right-hand margin of each of FIGS. 26A-26F are multiples of the 1X concentrations listed in table 6. As can be seen, the spectra of each sample are unique. The charts in FIGS. 25A-25F include superimposed vertical bars at wavelengths of 230±5 nm, 250±5 nm, and 280±5 nm. As can be seen, each pesticide has a local absorbance peak adjacent each of the 230±5 nm and 280±5 nm bars. A ratio of the absorbance at about 230 nm and 280 nm differs for each agrochemical tested as shown in table 6. Moreover, the peak absorbance at 230 nm and 280 nm decreased with the concentration for each of the pesticides in FIGS. 25A-25F.

Figure 26A:
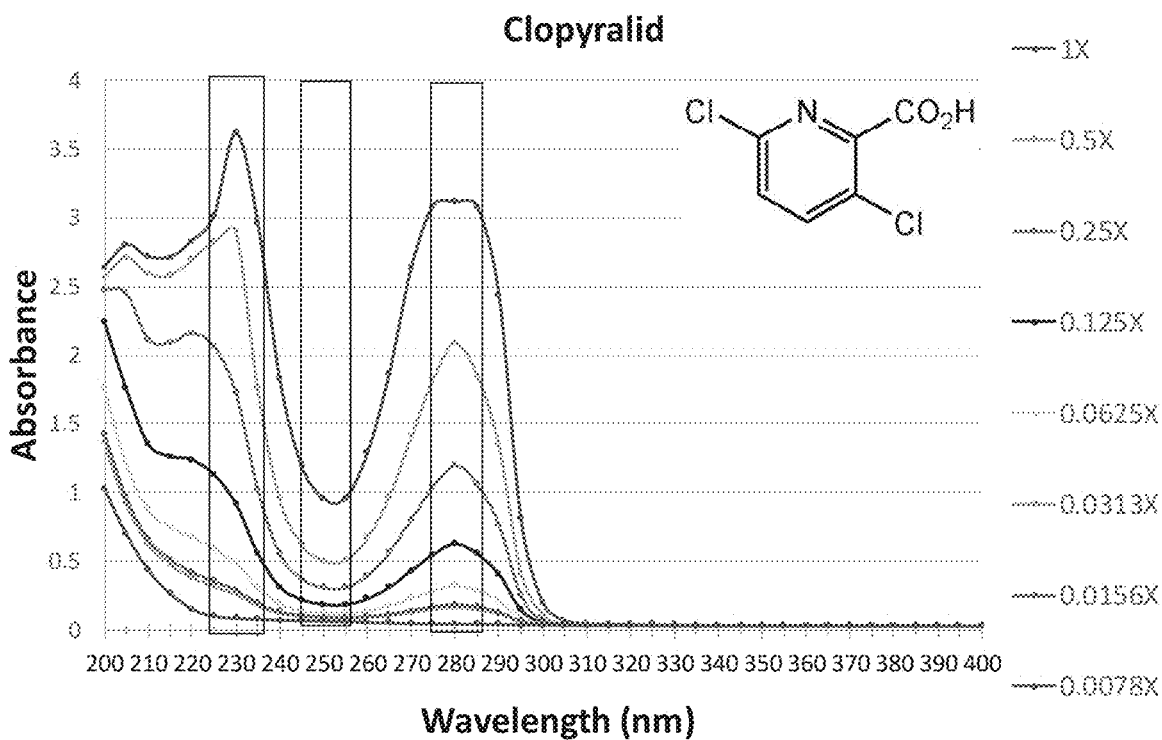
FIG. 26A is a graph showing detected absorption in a defined wavelength range of samples of clopyralid at different concentrations.
Figure 26B:
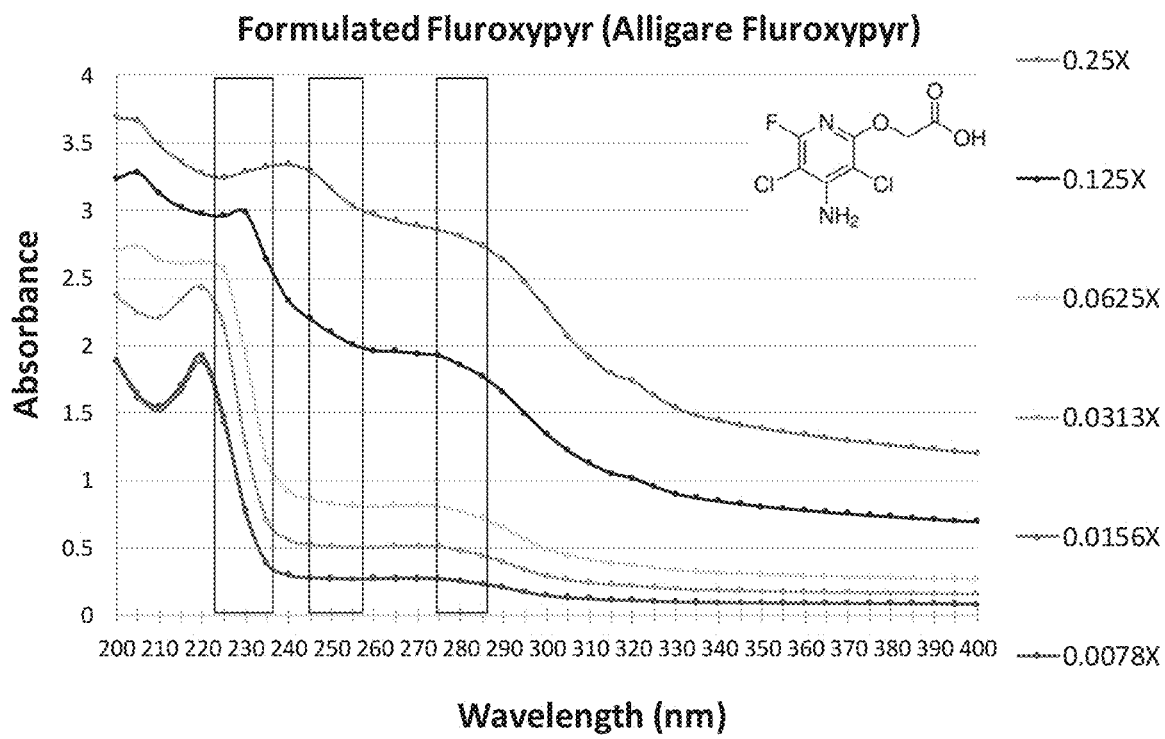
FIG. 26B is a graph showing detected absorption in a defined wavelength range of samples of formulated fluroxypyr (ALLIGARE fluroxypyr) at different concentrations.
Figure 26C:
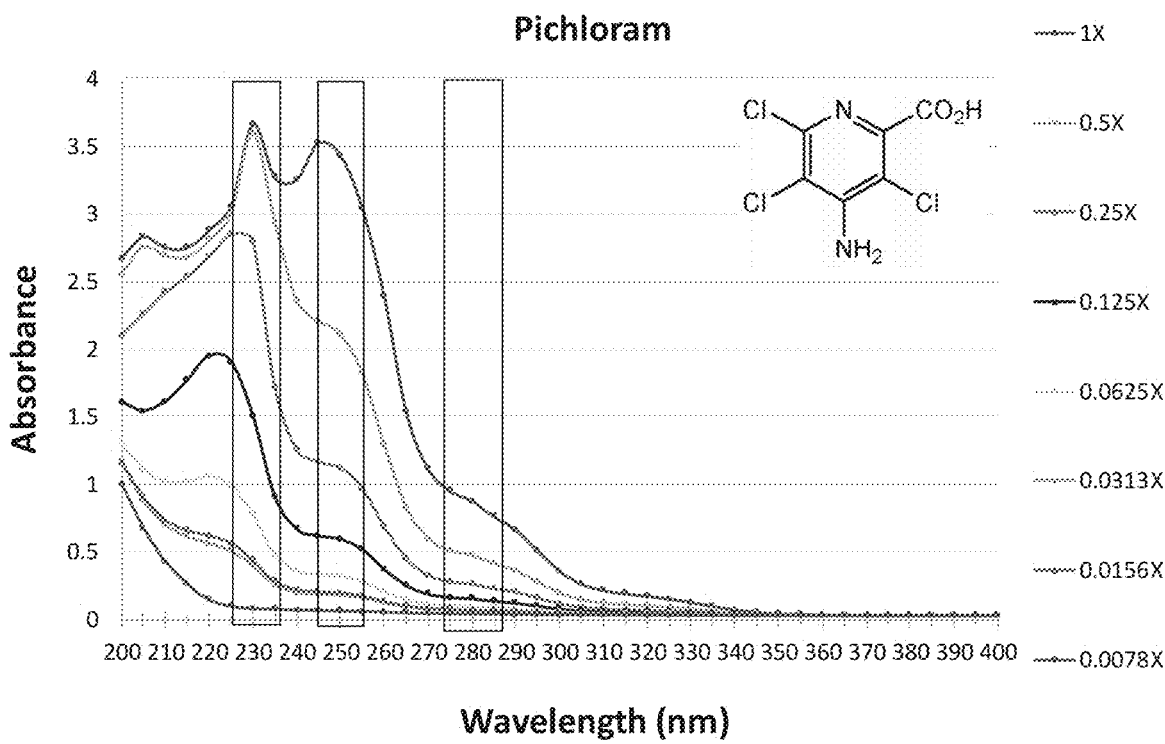
FIG. 26C is graph showing detected absorption in a defined wavelength range of samples of picloram at different concentrations.
Figure 26D:
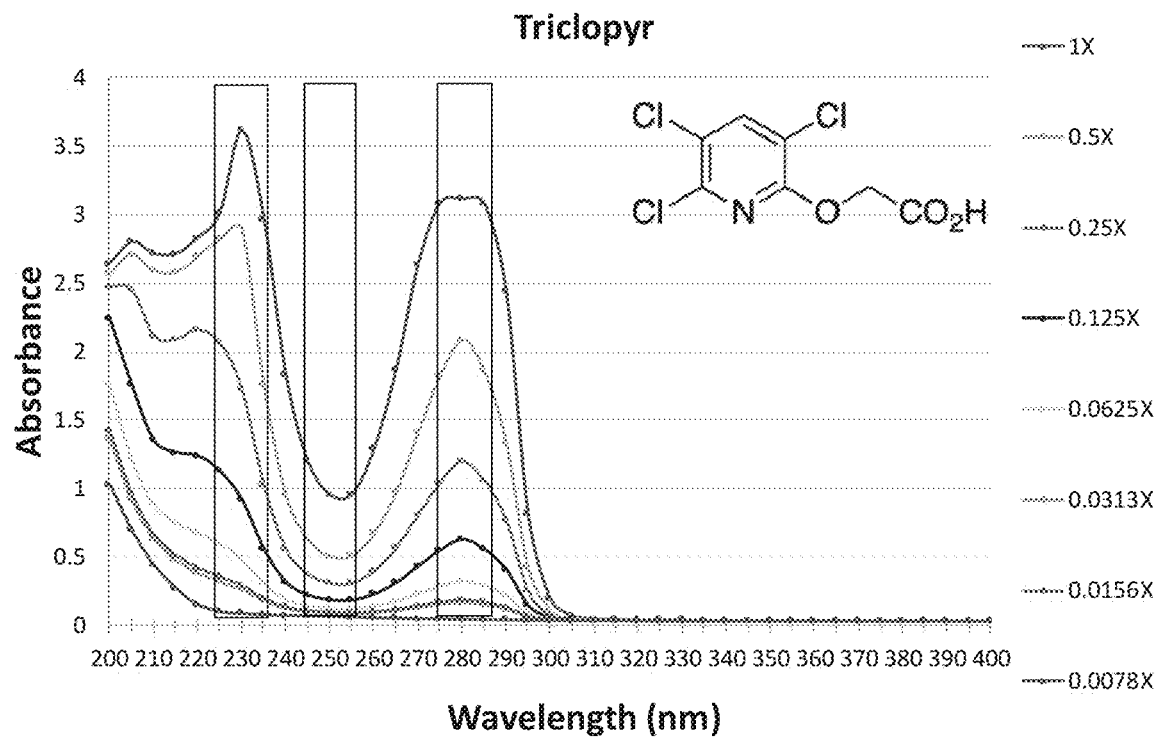
FIG. 26D is a graph showing detected absorption in a defined wavelength range of samples of triclopyr at different concentrations.

FIGS. 26A-26D show the detected absorbance spectra in a wavelength range of from 200 nm to 400 nm of various concentrations of clopyralid (FIG. 26A), formulated fluroxypyr (ALIIGARE fluroxypyr) (FIG. 26B), pichoram (FIG. 26C), and triclopyr (FIG. 26D). The X-sample X-concentrations listed in the right-hand margin of each of FIGS. 26A-26D are multiples of the 1X concentrations listed in table 6. As can be seen, the spectra of each sample are unique. The charts in FIGS. 26A-26D include superimposed vertical bars at wavelengths of 230±5 nm, 250±5 nm, and 280±5 nm. A ratio of the absorbance at wavelengths of about 230 nm and 280 nm differs for each agrochemical tested as shown in table 6. In addition, for each agrochemical, the absorbance at 230 nm, 250 nm, and 280 nm decreased with the concentration of each of the pesticides in FIGS. 26A-26D.

Figure 27A:
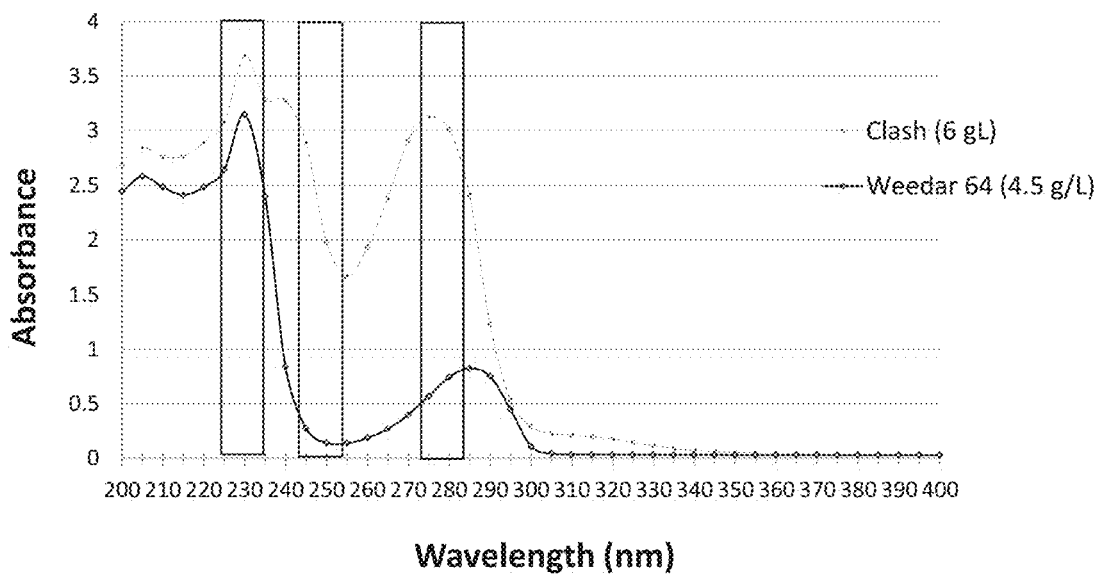
FIG. 27A is a graph showing detected absorption in a defined wavelength range of samples of formulated dicamba (CLASH™) and 2,4-D (WEEDAR®)
Figure 27B:
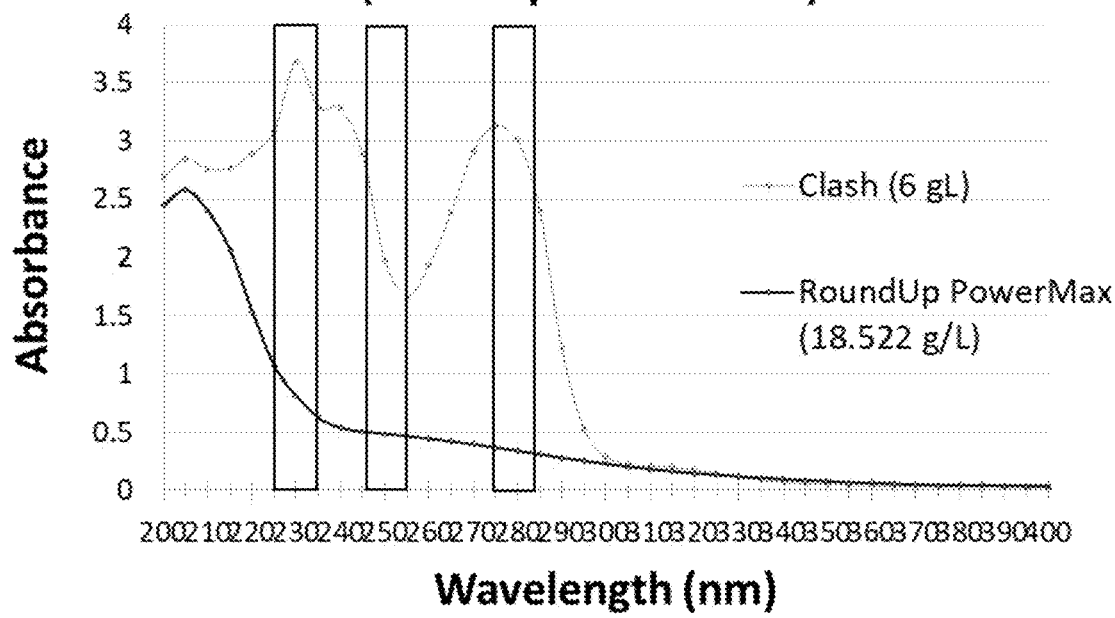
FIG. 27B is a graph showing detected absorption in a defined wavelength range of samples of formulated dicamba (CLASH™) and glyphosate (ROUNDUP POWERMAX®)
Figure 27C:
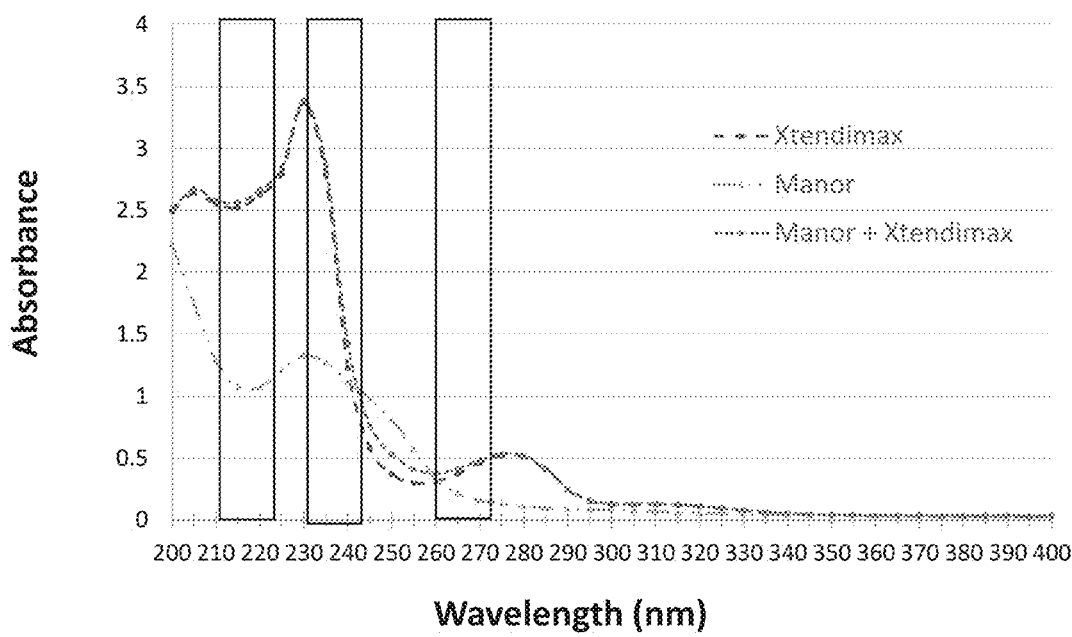
FIG. 27C is a graph showing detected absorption in a defined wavelength range of samples of formulated dicamba (XTENDIMAX® VAPORGRIP®), metsulfuron methyl (MANOR) and a combination thereof.
Figure 27D:
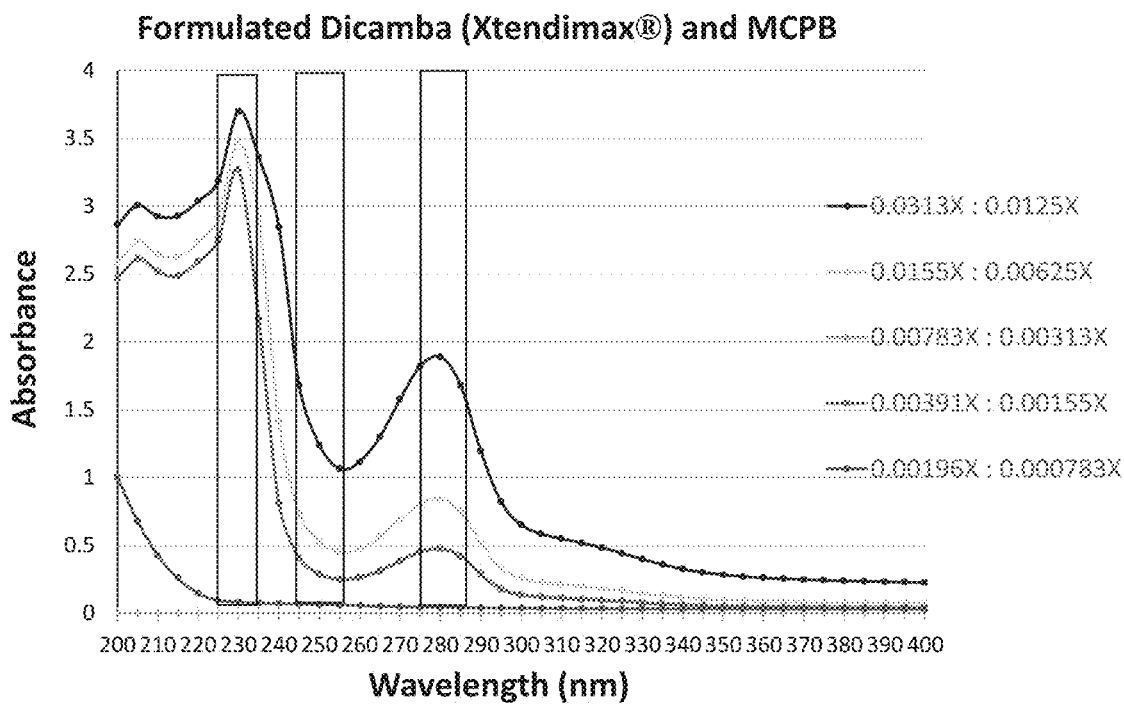
FIG. 27D is a graph showing detected absorption in a defined wavelength range of samples of a combination of formulated dicamba (XTENDIMAX® VAPORGRIP®) and MCPB at different concentrations.
Figure 27E:
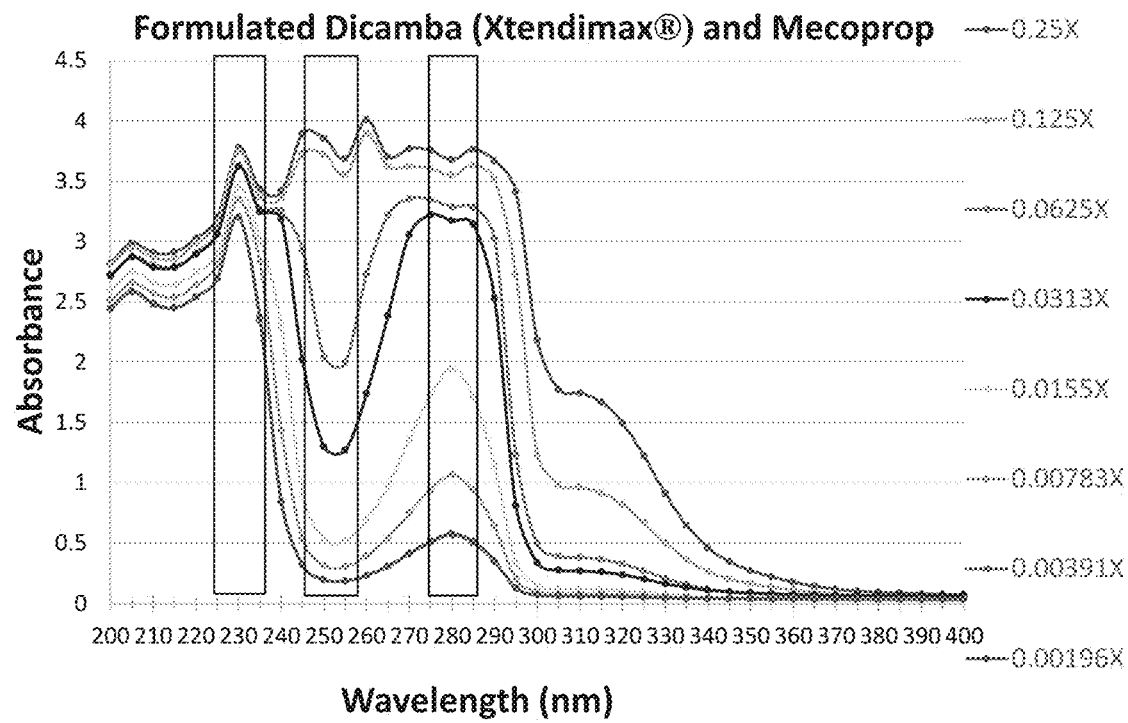
FIG. 27E is a graph showing detected absorption in a defined wavelength range of samples of a combination of formulated dicamba (XTENDIMAX® VAPORGRIP®) and mecoprop at different concentrations.
Figure 27F:
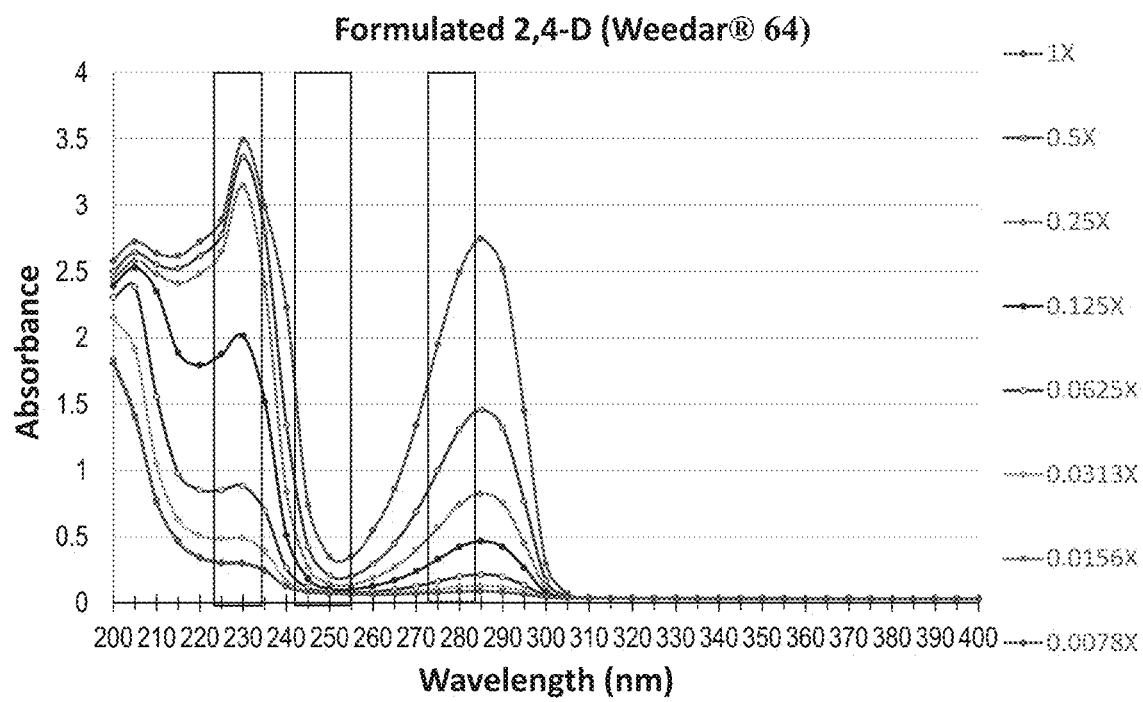
FIG. 27F is a graph showing detected absorption in a defined wavelength range of samples of formulated 2,4-D (WEEDAR® 64) at different concentrations.
Figure 28A:
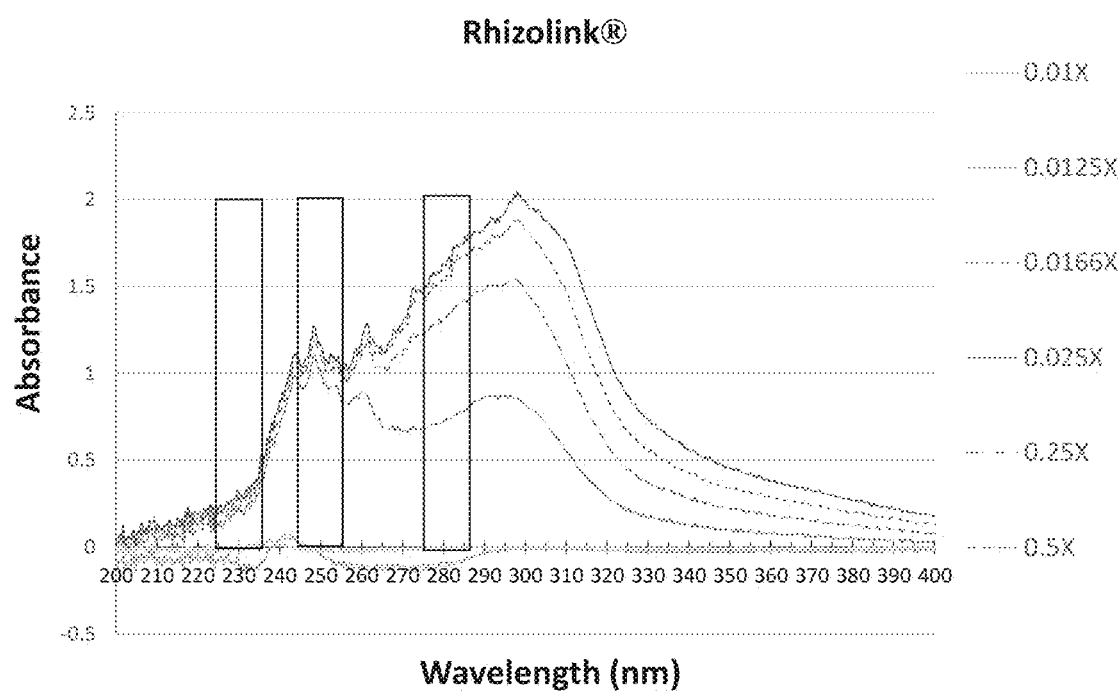
FIG. 28A is a graph showing detected absorption in a defined wavelength range of samples of RHIZONLINK® at different concentrations.

FIGS. 27A-27F show the detected absorbance spectra in a wavelength range of from 200 nm to 400 nm of various agrochemicals including a of formulated dicamba (CLASH™) and 2,4-D (WEEDAR®) (FIG. 27A); formulated dicamba (CLASH™) and glyphosate (ROUNDUP POWERMAX®) (FIG. 27B); formulated dicamba (XTENDIMAX® VAPORGRIP®), metsulfuron methyl (MANOR®), and a combination thereof (FIG. 27C); a combination of formulated dicamba (XTENDIMAX® VAPORGRIP®) and MCPB (FIG. 27D); a combination of formulated dicamba (XTENDIMAX® VAPORGRIP®) and mecoprop (FIG. 27E), and formulated 2,4-D (WEEDAR® 64) (FIG. 27F). The sample X-concentrations listed in the right-hand margin of each of FIGS. 27A-27F are multiples of the 1X concentrations listed in table 6 for the respective chemical. As can be seen, the spectra of each sample are unique. The charts in FIGS. 27A-27F include superimposed vertical bars at wavelengths of 230±5 nm, 250±5 nm, and 280±5 nm. A ratio of the absorbance at wavelengths of about 230 nm and 280 nm differs for each agrochemical or combination of agrochemical tested as shown in table 6. Moreover, the peak absorbance at 230 nm and 280 nm decreased with the concentration for each of the pesticides or pesticide combinations in FIGS. 27A-27F. p Although the above examples pertain to herbicides, other pesticides tested have also been shown to have identifiable spectral signatures. FIGS. 28C-28D show the detected absorbance spectra in a wavelength range of from 200 nm to 400 nm of various concentrations of the fungicide Captan (FIG. 28C) and the insecticide alpha-cypermethrin (ASTOUND DUO) (FIG. 28D). The sample X-concentrations listed in the right-hand margin of each of FIGS. 8C-28D are multiples of the 1X concentrations listed in table 6. As can be seen, the spectra of each sample are unique. The charts in FIGS. 25A-25F include superimposed vertical bars at wavelengths of 230±5 nm, 250±5 nm, and 280±5 nm. As can be seen, a ratio of the absorbance at about 230 nm and 280 nm differs for each agrochemical tested as shown in table 6. Moreover, the peak absorbance at 230 nm and 280 nm decreased with the concentration for each of the pesticides in FIGS. 25A-25F.

TABLE 6

Pesticides for detection, measurement and quantification

| Composition | Chemical Description | Active Ingredient (1X solution) | Amax. λ 230/280 nm Spectral Abs. Ratio (R): 230/280 | Figure Number & Panel Letter |
|---|---|---|---|---|
| Formulated MCPA (L.V.E Argritone ®) | Herbicide | 13.11 g/L | 3.639/1.293 R: 2.81 | 25A |
| MCPB | Herbicide | 18.2 g/L | 3.598/1.588 R: 2.27 | 25B |
| Mecoprop | Herbicide | 14.16 g/L | 3.562/3.503 R: 1.01 | 25C |
| Dichlorprop-P | Herbicide | 0.01 g/L | 0.245/0.073 R: 3.35 | 25D |
| Mecoprop-P | Herbicide | 0.01 g/L | 0.611/0.134 R: 4.56 | 25E |
| Dichloprop | Herbicide | 0.01 g/L | 0.888/0.189 R: 4.70 | 25F |
| Clopyralid | Herbicide | 0.050 g/L | 3.613/3.111 R: 1.16 | 26A |
| Formulated Fluroxypyr | Herbicide | 0.67 g/L | 3.291/2.809 R: 1.17 | 26B |
| Pichloram | Herbicide | 0.01 g/L | 3.598/0.879 | 26C |
| Triclopyr | Herbicide | 0.02 g/L | 3.613/3.111 R: 1.16 | 26D |
| Formulated Dicamba (CLASH ™) | Herbicide | 6.0 g/L | 3.684/3.010 R: 1.22 | 27A, 27B |
| 2,4-D (WEEDAR ® 64) | Herbicide | 4.5 g/L | 3.148/0.744 R: 4.23 | 27A, 27F |
| Glyphosate (Roundup PowerMax ®) | Herbicide | 18.52 g/L | 0.814/0.342 R: 2.380 | 27B |
| Formulated Dicamba (Xtendimax ®) | Herbicide | 12.03 g/L | 3.385/0.519 R: 6.52 | 27C, 27D, 27E |
| Metusulfuron Methyl (Manor ®) | Herbicide | 0.37 g/L | 1.234/0.114 R: 10.82 | 27C |
| Captan | Fungicide | 6.2 mL/L | 3.561/1.592 R: 2.24 | 28C |
| Alpha-Cypermethrin (Astound ® Duo) | Insecticide | 2.5 g/L | 3.474/1.707 R: 2.04 | 28D |

Although the above examples pertain to pesticides, other agrochemicals tested have also been shown to have identifiable spectral signatures. FIG. 28A shows the detected absorbance spectra in a wavelength range of from 200 nm to 400 nm of various concentrations of the fertilizer, RHIZO-LINK®, at a 9-15-3 (nitrogen-to-phosphorus-to-potassium) ratio, which has a 1X concentration 100 mL/L. As can be seen, the spectra for the RHIZO-LINK® samples are unique when compared with the spectra for the other agrochemicals shown in FIGS. 25A-31F. FIG. 28A includes superimposed vertical bars at wavelengths of 230±5 nm, 250±5 nm, and 280±5 nm. As can be seen, a ratio of the absorbance at about 230 nm and 280 nm differs from the other agrochemicals tested. Moreover, the peak absorbance at 230 nm and 280 nm decreased with the concentration of the fertilizer in the sample.

Table 7 provides a non-exhaustive list of certain other fertilizers that (based on the successful identification of spectral signatures of other agrochemicals described herein) are believed to have an identifiable spectral signature.

TABLE 7

Other commonly used water-soluble fertilizers available to plants for detection and measurement

| Fertilizer Description | General Percent of Active Ingredient |
| --- | --- |
| Urea | 46% nitrogen |
| Ammonium nitrate | 33% nitrogen |
| Ammonium sulfate | 21% nitrogen |
| Calcium nitrate | Variable |
| Diammonium phosphate | 18% nitrogen |
| Monoammonium phosphate | Equal to or less than 11% nitrogen; 48% phosphate |
| Triple super phosphate | variable |
| Potassium nitrate | 44% potassium |
| Potassium chloride | 60-62% potassium |

Figure 28B:
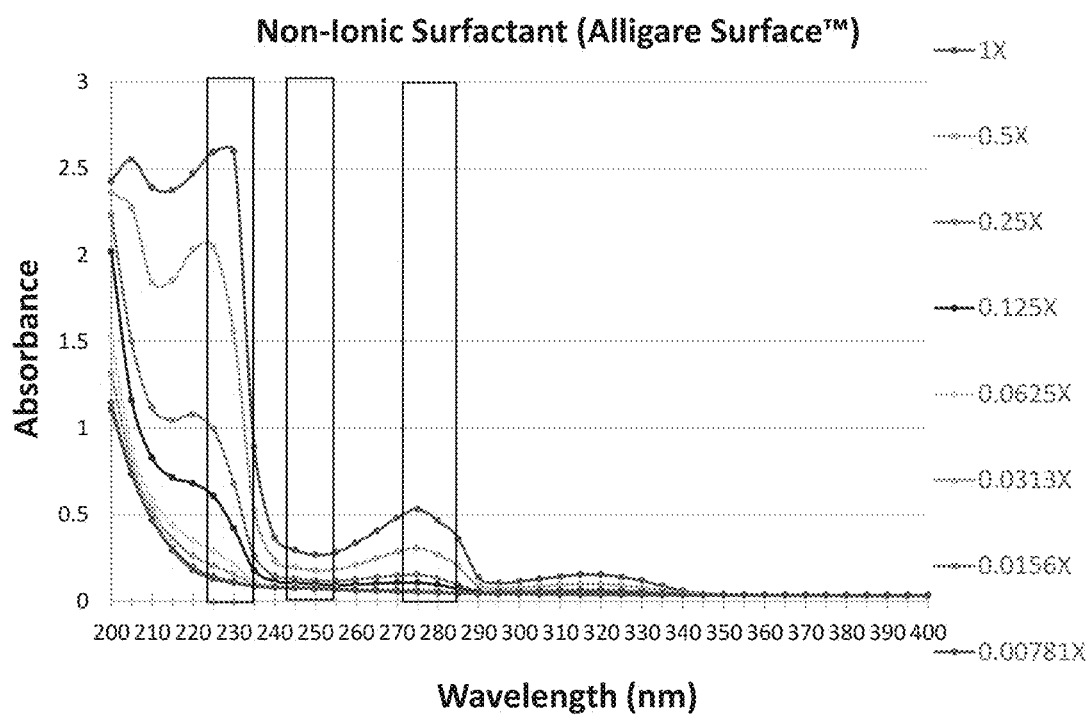
FIG. 28B is a graph showing detected absorption in a defined wavelength range of samples of a non-ionic surfactant (ALLIGARE SURFACE™) at different concentrations.
Figure 28C:
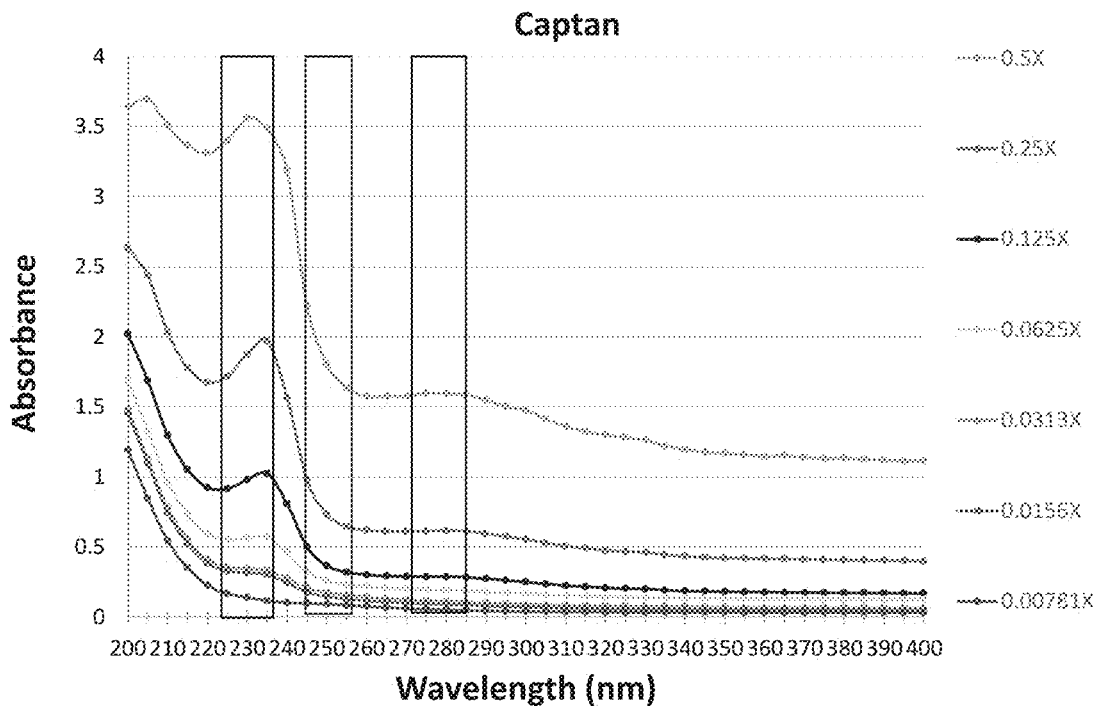
FIG. 28C is a graph showing detected absorption in a defined wavelength range of samples of CAPTAN® fungicide at different concentrations.

FIG. 28B shows the detected absorbance spectra in a wavelength range of from 200 nm to 400 nm of various concentrations of the non-ionic surfactant, ALLIGARE SURFACE™, which has a 1X concentration of 0.625 mL/L. As can be seen, the spectra for the ALLIGARE SURFACE™ samples are unique when compared with the spectra for the other agrochemicals shown in FIGS. 25A-31F. FIG. 28B includes superimposed vertical bars at wavelengths of 230±5 nm, 250±5 nm, and 280±5 nm. As can be seen, a ratio of the absorbance at about 230 nm and 280 nm differs from the other agrochemicals tested. Moreover, the peak absorbance at 230 nm and 280 nm decreased with the concentration of the surfactant in the sample.

FIG. 29 shows the absorbance spectra in a wavelength range of from 150 nm to 750 nm of various concentrations of an inoculant, *bacillus* thuingiensis having an optical density of 5.84, which has a 1X concentration of $1.55 \times 10^8$ spores/mL. As can be seen, the spectra for the inoculant samples are unique when compared with the spectra for the other agrochemicals shown in FIGS. 25A-31F. The inoculant exhibited an absorbance peak at wavelength of about 255 nm. Combination products containing an inoculant with a pesticide can also be distinguished due to the segregation of their absorbance peaks. For example, a combination product may exhibit an absorbance peak at a wavelength of 230 nm+/−5 nm due to the pesticide component as described above and another absorbance peak at a wavelength of 255 nm+/−5 nm as shown in FIG. 29.

Figure 30A:
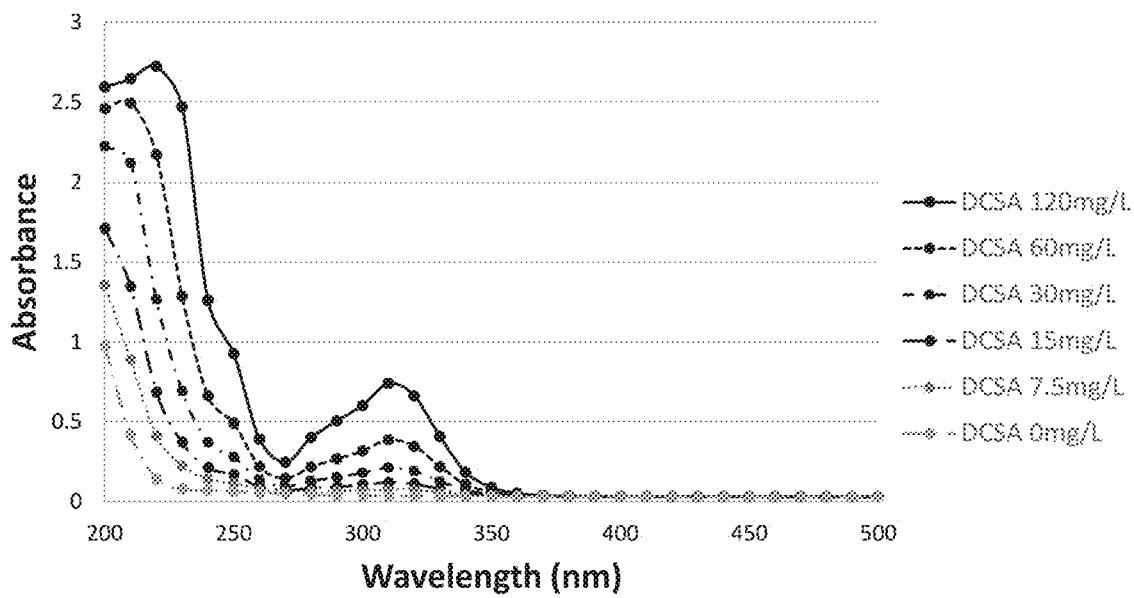
Figure 30B:
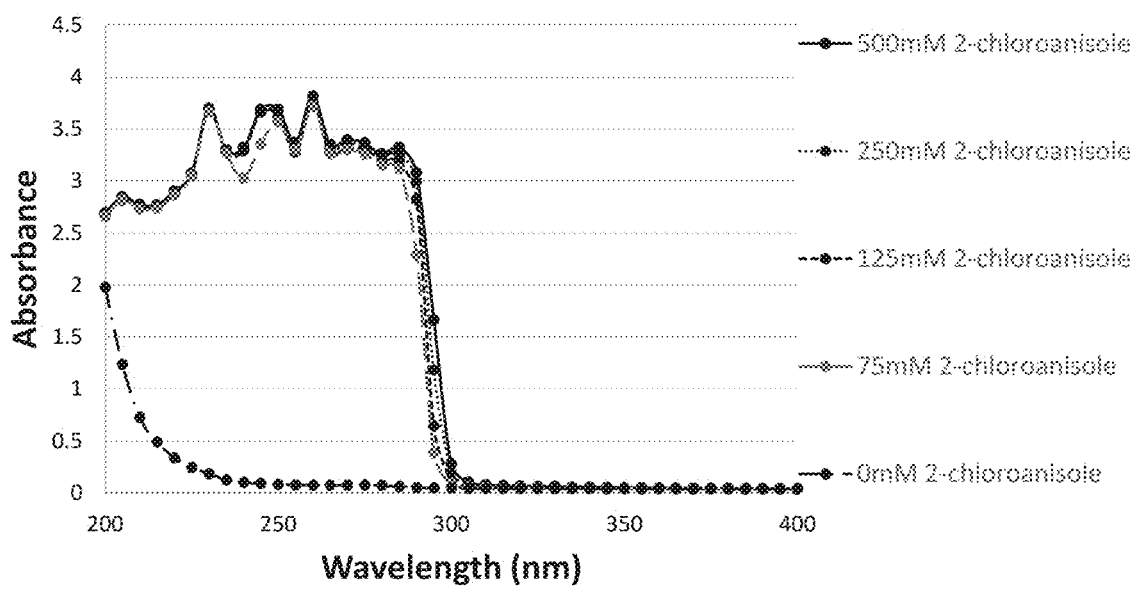
Figure 30C:
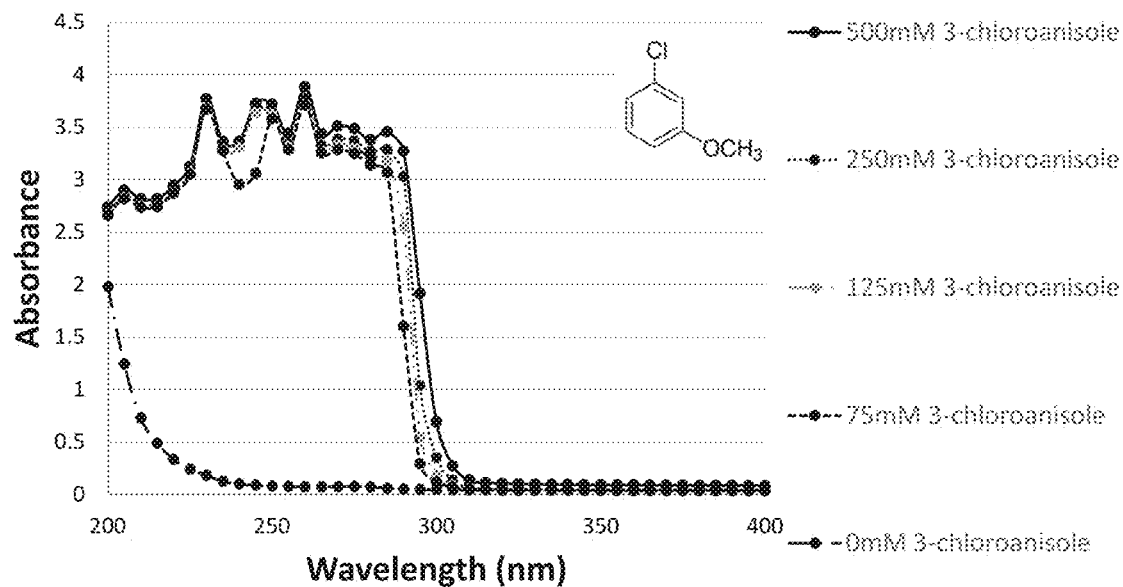
Figure 30D:
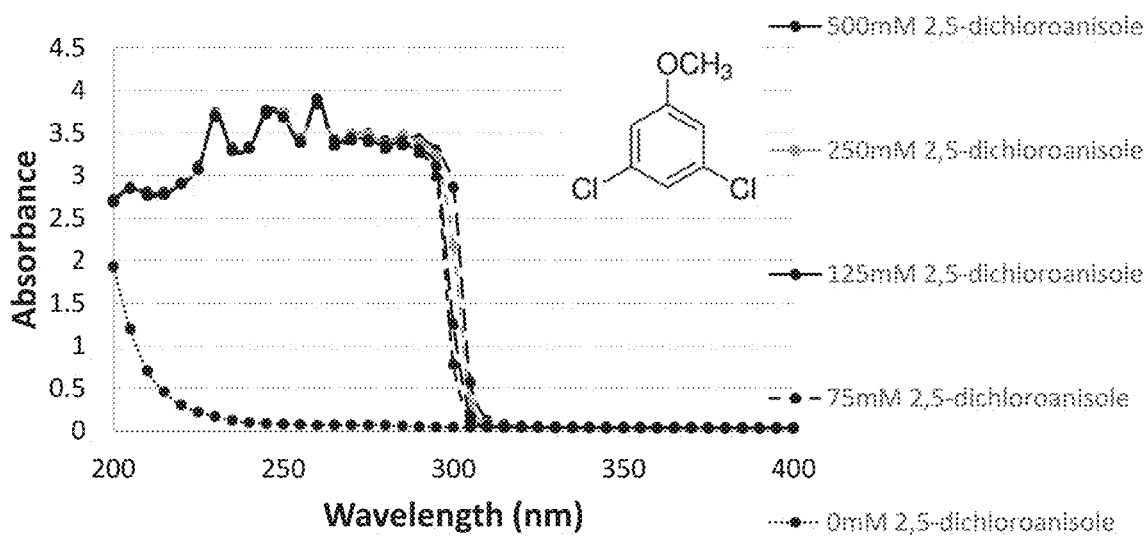

FIGS. 30A-30D show the detected absorbance spectra of different pesticide end-products. For example, FIG. 30A shows the detected absorbance spectra in a wavelength range of from 200 nm to 500 nm for dichlorosalicyclic acid (DCSA), an end-product of dicamba, at various concentrations indicated at right. FIGS. 30B-30D respectively show the detected absorbance spectra in a wavelength range of from 200 nm to 400 nm for 2-chloroanisole, 3-chloroanisole, and 2,5-chloroanisole, each an end product of dicamba, at various concentrations listed at right. DSCA is shown in FIG. 30A to have an absorbance peak at around 310 nm, and the absorbance at the 310-nm peak is shown to decrease with concentration. The spectra for each of the chloroanisole end-products exhibited discrete spectral peaks at about 230 nm, 250 nm and 260 nm (FIGS. 30B-30D), and the absorbance at the peaks tends to decrease with concentration. Thus, FIGS. 30A-30D show that certain pesticide end-products have identifiable spectral fingerprints that can be detected and analyzed using the systems and methods described above.

Figure 31A:
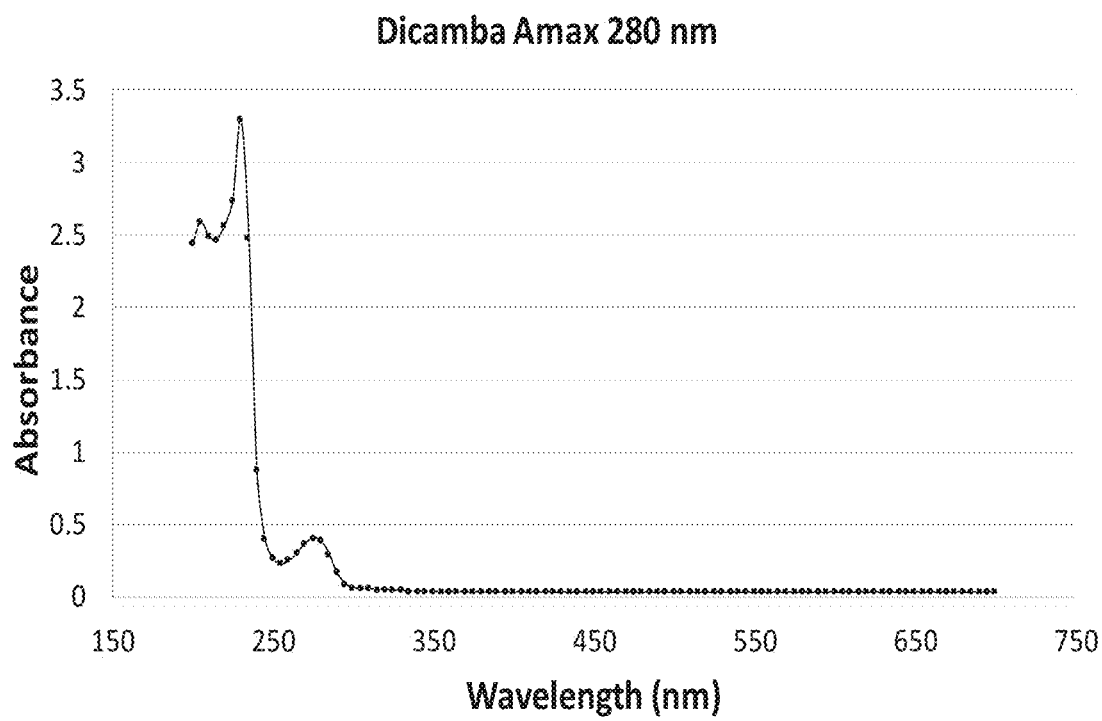
Figure 31B:
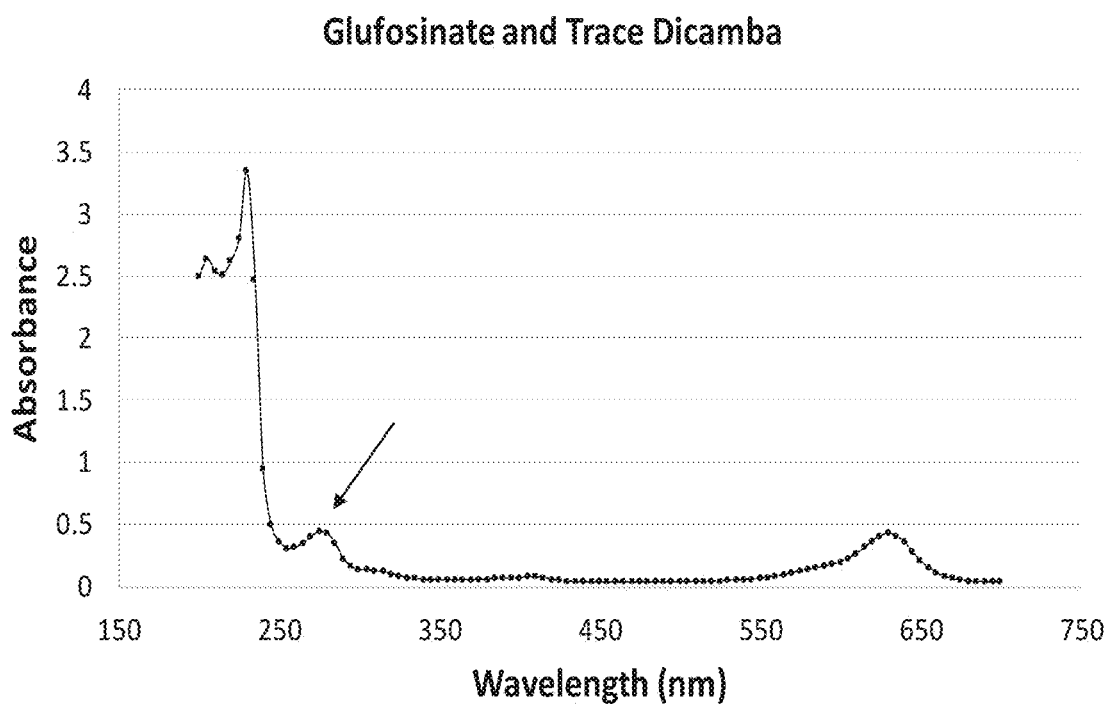
Figure 31C:
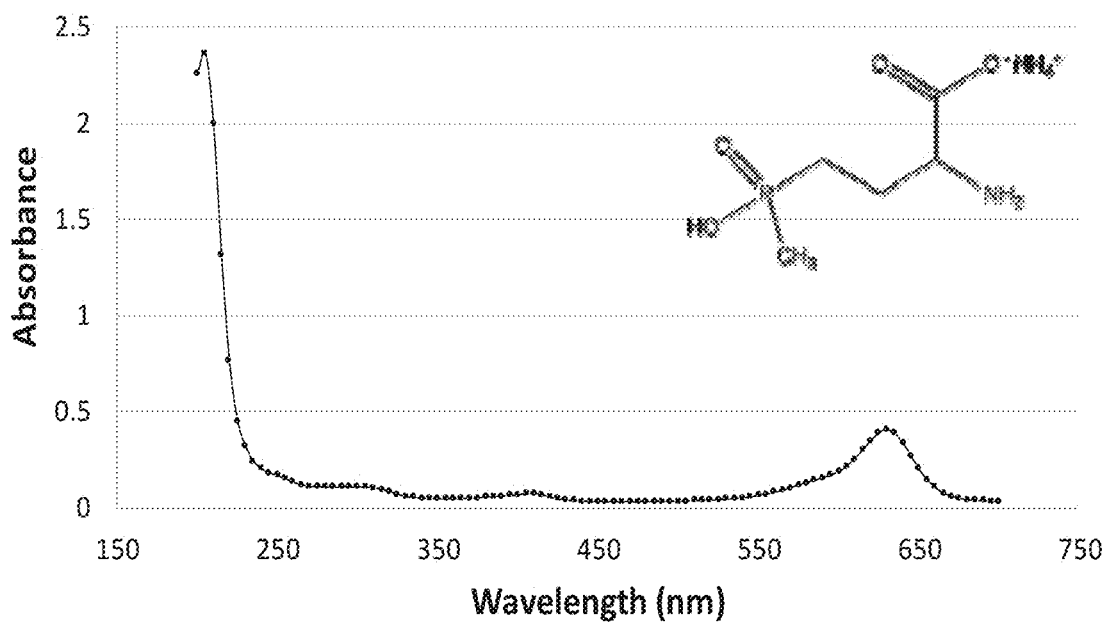

As explained above, the apparatus is particularly useful for the detection of a contaminating pesticide or a trace pesticide contaminant that can remain as a residue in agricultural equipment subsequently used for or with another agrochemical. FIGS. 31A-31F show detected spectral data that illustrate the feasibility of this technique. FIG. 31A shows spectral data for a dicamba solution, which has a pronounced absorbance peak at 280 nm. FIG. 31C shows spectral data for a substantially pure glufosinate solution, and FIG. 31B shows spectral data for a glufosinate solution that is contaminated by trace dicamba. As can be seen, the contaminated sample exhibits a minor absorbance peak at about 280 nm, caused by the trace dicamba. The systems and methods described above can be configured to dispatch an alert indicating detection of trace dicamba when a minor absorbance peak for trace dicamba is exhibited.

Figure 31D:
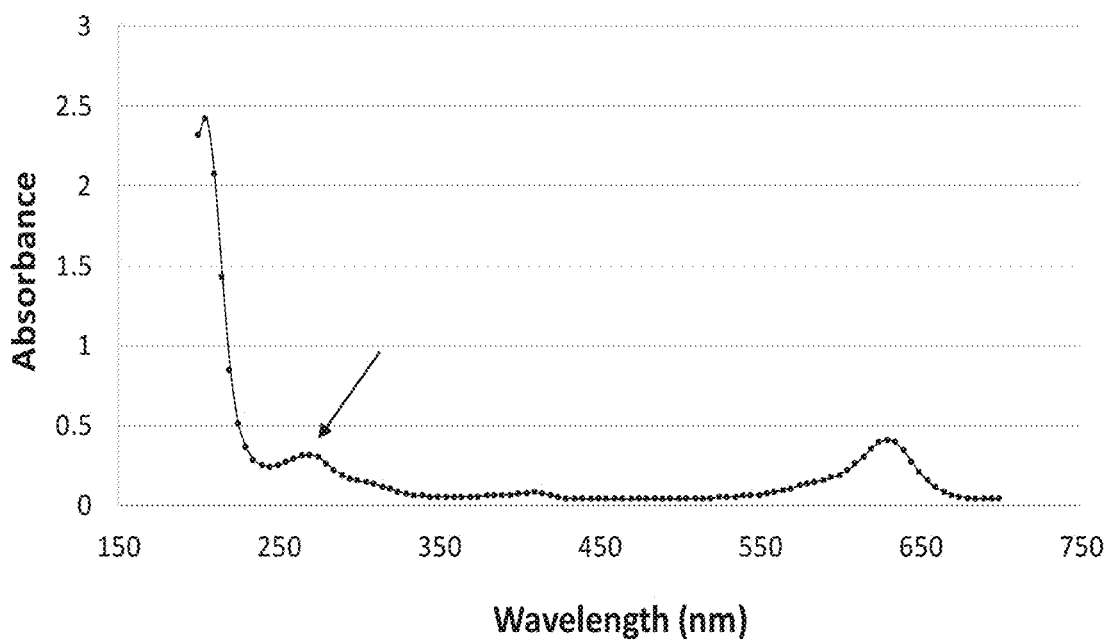
Figure 31E:
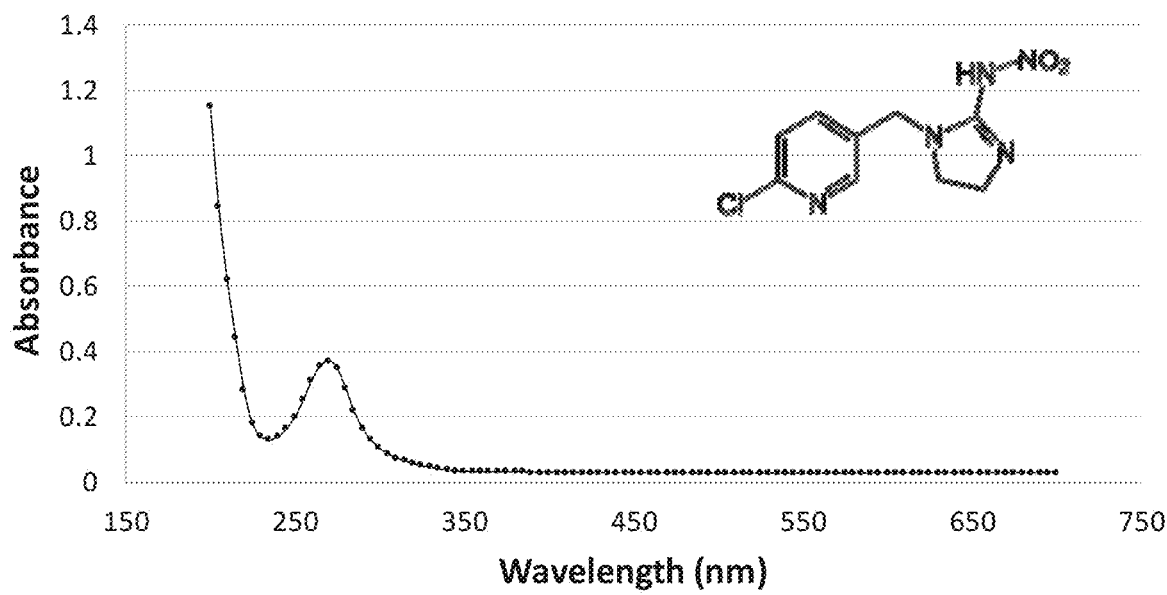
Figure 31F:
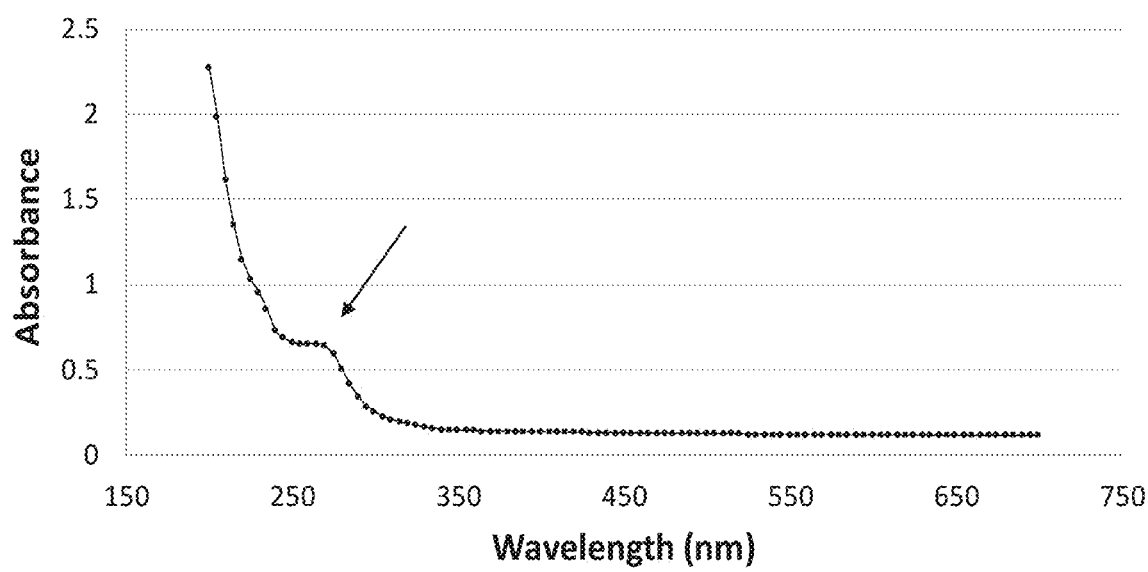

Similarly, FIG. 31C shows spectral data for an imidacloprid solution, which has a pronounced absorbance peak at 275 nm. FIG. 31C shows spectral data for a substantially pure glufosinate solution, and FIG. 31D shows spectral data for a glufosinate solution that is contaminated by trace imidacloprid. As can be seen, the contaminated sample exhibits a minor absorbance peak at about 275 nm, caused by the trace imidacloprid. Similarly, FIG. 31F shows spectral data for a azoxystrobin solution that is contaminated with trace imidacloprid. The contaminated sample of azoxystrobin likewise exhibits a minor absorbance peak at 275 nm. The systems and methods described above can thus be configured to dispatch an alert indicating detection of trace imidacloprid when a minor absorbance peak for trace imidacloprid is exhibited. Detection of other agrochemicals based on unexpected minor absorbance peaks in spectral data is also thought to be possible based on the test data.

Compositions Containing Agrochemicals and Tracer Dyes or Tracer Pigments and Methods for Using Such Compositions Any of the apparatus described herein can be used to detect and/or quantify a pesticide or other agrochemical that has been combined with a tracer dye or a tracer pigment. Tracer dyes and tracer pigments can be combined with pesticides or other agrochemicals in a composition and used as an alternative means to detect and measure the amount of a pesticide in a liquid.

Tables 8 and 9 provide lists of illustrative tracer dyes and pigments suitable for this purpose. The tracer dyes and pigments listed in Tables 8 and 9 absorb in distinct spectral ranges to produce absorbance maxima ($A_{max}$) that differ from the absorbance maxima of the pesticide(s) or other agrochemical(s) in the combined mixture.

TABLE 8

Sample tracer dyes and pigments having an Amax in the UV range, for use with agrochemicals

| Tracer Dye or Pigment Color | Code/Description | $A_{max}$ (nm) | UV/VIS |
| --- | --- | --- | --- |
| Blue | ADA3209* (UV-Visible Fluorescent Blue Organic Pigment) | 408 | UV/VIS |

TABLE 8-continued

Sample tracer dyes and pigments having an λmax in the UV range, for use with agrochemicals

| Tracer Dye or Pigment Color | Code/Description | $\lambda_{max}$ (nm) | UV/VIS |
|---|---|---|---|
| Blue | ADA3216 (UV-Visible Fluorescent Blue Organic Pigment) | 377 | UV |
| Blue | ADA3217 (UV-Visible Fluorescent Green-Blue Organic Pigment) | 404 | UV/VIS |
| Blue | ADA3218 | 365 | UV |
| Blue | ADA3230 | 393 | UV |
| Blue | ADA5205 | 398 | UV |
| Green | ADA6798 (UV-Visible Fluorescent Green Organic Pigment) | 397 | UV |
| Green | ADA9102 (UV-Visible Fluorescent Yellow/Green Organic Pigment) | 250-320 | UV |
| Orange | ADA3204 | 378 | UV |
| Orange/Red | ADA3210 | 390 | UV |
| Red | ADA2041 (UV-Visible Fluorescent Red Organic Pigment) | 342, 408, 470 | UV/VIS |
| Red | ADA3202 (UV-Visible Thermo-Fluorescent Red Organic Pigment) | 390 | UV |
| Red | ADA3215 (UV-Visible Fluorescent Red Pigment) | 390 | UV |
| Red | ADA3232 UV-Visible Fluorescent Organic Pigment) | 365 | UV |
| Red | ADA3233 (UV-Visible Fluorescent Red Pigment) | 382 | UV |
| Red | ADA3245 | 360 | UV |
| Red | ADA4160 | 390 | UV |
| Red & Blue | ADA5762 (UV-Visible Bi-Fluorescent Organic Pigment, UV-A Red/UV-C Blue) | 381, 272 | UV |
| Red | ADA6826 (UV-Visible Thermo-Fluorescent Red Organic Dye) | 390 | UV |
| Red, Yellow-Green | ADA7226 | 381, 250 | UV |
| Red | UV381A** | 381 | UV |
| Red | UV381B | 381 | UV |
| Red | UV382A | 382 | UV |
| Maroon | C101*** (Ruthenium-based dye having the structure: | 546, 403, 338, 307 | UV/VIS |

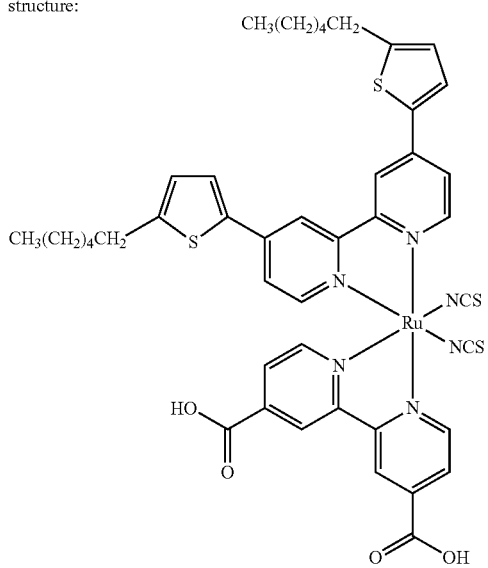

*Dyes and pigments with codes beginning with "ADA" are available from H.W. Sands Corp. (Jupiter, FL).
**Dyes and pigments with codes beginning with "UV" are available from QCR Solutions Corp. (Port St. Lucie, FL).
***The C101 dye is available from Sigma-Aldrich (St. Louis, MO).

TABLE 9

Sample tracer dyes and pigments having an Amax in the visible range, for use with agrochemicals

| Tracer Dye or Pigment Color | Code | Name | Amax (nm) | UV/VIS |
|---|---|---|---|---|
| Yellow-orange | E100* | Curcumin | 425-430 | VIS |
| Yellow-orange | E101* | Riboflavin | 430-435 | VIS |
| Yellow-orange | E101a* | Riboflavin-5'-Phosphate | 430-435 | VIS |
| Yellow | E102* | Tartrazine (triazine azo dye) | 425 | VIS |
| Red Brown | E103 | Alkannin | 490-510 | VIS |
| Green Yellow | E104* | Quinoline Yellow WS | 406 | VIS |
| Yellow | E105 | Fast Yellow AB | 425 | VIS |
| Yellow | E106 | Riboflavin-5'-Sodium Phosphate | 425 | VIS |
| Yellow | E107* | Yellow 2G | 425 | VIS |
| Yellow-Orange | E110*; ** | Sunset Yellow FCF | 490 | VIS |
| Orange | E111 | Orange GGN | 452-460 | VIS |
| Crimson | E120* | Cochineal, Carminic Acid, Carmine | 530-550 | VIS |
| Dark Red | E121* | Citrus Red 2 | 580 | VIS |
| Dark Red | E123* | Amaranth | 555 | VIS |
| Red | E124* | Ponceau 4R | 530 | VIS |
| Red | E127* | Erythrosine | 530 | VIS |
| Red | E128 | Red 2G | 530 | VIS |
| Red | E129* | Allura Red AC | 530 | VIS |
| Blue | E130 | Indanthrene Blue RS | 630 | VIS |
| Dark Blue | E131* | Patent Blue V | 660 | VIS |
| Indigo | E132* | Indigo carmine | 675 | VIS |
| Reddish Blue | E133* | Brilliant Blue FCF | 590-610 | VIS |
| Green | E140* | Chlorophyllins | 440, 680 | VIS |
| Green | E142* | Green S | 400, 650 | VIS |
| Sea Green | E143* | Fast Green FCF | 630 | VIS |
| Brown | E150a* | Plain Caramel | 500 | VIS |
| Brown | E150b* | Caustic Sulphite Caramel | 500 | VIS |
| Brown | E150c* | Ammonia Caramel | 500 | VIS |
| Brown | E150d** | Sulphite Ammonia Caramel | 500 | VIS |
| Brown | E155* | Brown HT | 500 | VIS |
| Yellow-Orange to Brown | E160a* | Alpha-carotene, Beta-carotene, Gamma - carotene | 450 | VIS |
| Orange | E160b*; ** | Annatto, Bixin, Norbixin | 460 | VIS |
| Red | E160c*; ** | Paprika Oleoresin, Capsanthin, Capsorubin | 530 | VIS |
| Bright to Deep Red | E160d*; ** | Lycopene | 550 | VIS |
| Orange Red to Yellow | E160e*; ** | Beta-apo-8'-carotenal | 445 | VIS |
| Yellow-Orange to Brown | E160f* | Ethyl ester of Beta-apo-8-Carotenic Acid | 450, 510-520 | VIS |
| Golden-Yellow to Brownish | E161a | Flavoxanthin | 450 | VIS |
| Orange-Red to Yellow | E161b* | Lutein | 430, 480 | VIS |
| Orange-Red | E161c | Cryoptoxanthin | 490-500 | VIS |
| Orange-Red | E161d | Rubixanthin | 490-500 | VIS |
| Orange | E161e | Violaxanthin | 430, 475 | VIS |
| Purple | E161f | Rhodoxanthin | 580-585 | VIS |
| Violet | E161g*; ** | Canthaxanthin | 580 | VIS |
| Orange-Red | E161h | Zeaxanthin | 430, 480 | VIS |
| Deep Violet | E161i | Citranaxanthin | 520-530 | VIS |
| Red | E161j | Astaxanthin | 520-530 | VIS |
| Red | E162*; ** | Betanin | 520-530 | VIS |
| Orange-Red | E164** | Saffron | 442 | VIS |
| Red | E180* | Rubine, Lithol Rubine BK | 520-530 | VIS |
| Purple | E182 | Orcein | 580 | VIS |
| Orange-Red | — | — | 625 | VIS |
| Blue | VIS404A*** | — | 404 | VIS |

E numbers with (*) are codes for substances that are permitted to be used as food additives for use within the European Union and EFTA. The "E" stands for "Europe" and have met the safety assessment and approval of the European Food Safety Authority.
E numbers with (**) are codes for substances that are permitted to be used as food additives for use within the U.S.
***Available from QCR Solutions Corp. (Port St. Lucie, FL).

A composition is provided. The composition comprises an agrochemical and a tracer dye or a tracer pigment.

The composition can optionally comprise more than one agrochemical, more than one tracer dye, and/or more than one tracer pigment. The composition can optionally comprise one or more tracer dyes and one or more tracer pigments.

A method for detecting the presence of an agrochemical in a liquid is provided. The method comprises obtaining an absorbance spectrum for the liquid. The liquid has contacted equipment previously exposed to a composition comprising the agrochemical and a tracer dye or a tracer pigment. The method further comprises comparing the absorbance spectrum to a reference absorbance spectrum for the tracer dye or the tracer pigment. The reference spectrum for the tracer dye or the tracer pigment having an absorbance maximum ($A_{max}$) at one or more wavelengths. The presence of an $A_{max}$ in the absorbance spectrum for the liquid at the same wavelength or wavelengths indicates that the agrochemical is present in the liquid.

The equipment can comprise agricultural equipment, seed treatment equipment, manufacturing equipment (e.g., pesticide manufacturing equipment, packaging lines, filling lines, chemigation equipment, fertigation equipment, or a combination of any thereof.

The method can further comprise determining the concentration of the agrochemical in the liquid. The concentration of agrochemical in the liquid can be determined by comparing the absorbance at the Amax in the absorbance spectrum for the liquid to a standard curve correlating the absorbance of the tracer dye or the tracer pigment to the concentration of the agrochemical.

At least one of the steps of obtaining the absorbance spectrum and comparing the absorbance spectrum to a reference spectrum can be performed using any of the apparatus described herein, any of the systems described herein, any of the attachments described herein, any of the nozzles described herein, or any of the tanks described herein.

Tracer dyes can also be incorporated into commercial agricultural products and used to distinguish one product from another similar product or an authentic product from an imitation or counterfeit product.

A method for detecting a counterfeit agricultural composition is provided. The method comprises obtaining an absorbance spectrum from a suspected counterfeit agricultural composition and comparing the absorbance spectrum obtained for the suspected counterfeit agricultural composition to a reference absorbance spectrum for a genuine agricultural composition. The genuine agricultural composition comprises an agrochemical and a tracer dye or a tracer pigment. The reference spectrum has an absorbance maximum ($A_{max}$) for the dye or the pigment at one or more wavelengths. The absence of an $A_{max}$ in the absorbance spectrum for the suspected counterfeit agricultural composition at the same wavelength or wavelengths indicates that the suspected counterfeit agricultural composition is a counterfeit composition.

In any of the compositions containing a tracer dye or a tracer pigment, or in any of the methods involving the use of a tracer dye or a tracer pigment, the tracer dye or tracer pigment preferably has one or more absorbance maxima ($A_{max}$) within the ultraviolet (UV) or visible range of the electromagnetic spectrum.

Thus, the tracer dye or tracer pigment can have an absorbance maximum ($A_{max}$) at a wavelength between about 100 nm and about 700 nm.

For example, the tracer dye or tracer pigment can have one or more absorbance maxima in the UV range.

The tracer dye or tracer pigment can have an $A_{max}$ at a wavelength between about 100 nm and about 410 nm.

For example, the tracer dye or tracer pigment can have an $A_{max}$ at a wavelength between about 100 nm and about 400 nm.

The tracer dye or tracer pigment can have an $A_{max}$ at a wavelength between about 100 nm and about 399 nm.

The tracer dye or tracer pigment can have an $A_{max}$ at a wavelength between about 100 nm and about 398 nm.

The tracer dye or tracer pigment can have an $A_{max}$ at a wavelength between about 100 nm and about 395 nm.

The tracer dye or tracer pigment can have an $A_{max}$ at a wavelength between about 250 nm and about 410 nm.

The tracer dye or tracer pigment can have an $A_{max}$ at a wavelength between about 250 nm and about 400 nm.

The tracer dye or tracer pigment can have an $A_{max}$ at a wavelength between about 250 nm and about 399 nm.

The tracer dye or tracer pigment can have an $A_{max}$ at a wavelength between about 250 nm and about 398 nm.

The tracer dye or tracer pigment can have an $A_{max}$ at a wavelength between about 250 nm and about 395 nm.

The tracer dye or tracer pigment can have an $A_{max}$ at a wavelength between about 300 nm and about 410 nm.

The tracer dye or tracer pigment can have an $A_{max}$ at a wavelength between about 300 nm and about 400 nm.

The tracer dye or tracer pigment can have an $A_{max}$ at a wavelength between about 300 nm and about 399 nm.

The tracer dye or tracer pigment can have an $A_{max}$ at a wavelength between about 300 nm and about 398 nm.

The tracer dye or tracer pigment can have an $A_{max}$ at a wavelength between about 300 nm and about 395 nm.

The tracer dye or tracer pigment can have an $A_{max}$ at a wavelength between about 350 nm and about 410 nm.

The tracer dye or tracer pigment can have an $A_{max}$ at a wavelength between about 350 nm and about 400 nm.

The tracer dye or tracer pigment can have an $A_{max}$ at a wavelength between about 350 nm and about 399 nm.

The tracer dye or tracer pigment can have an $A_{max}$ at a wavelength between about 350 nm and about 398 nm.

The tracer dye or tracer pigment can have an $A_{max}$ at a wavelength between about 350 nm and about 395 nm.

The tracer dye or tracer pigment can have an $A_{max}$ at a wavelength between about 250 to about 320 nm.

The tracer dye or the tracer pigment can have an Amax at one or more wavelengths selected from the group consisting of: about 250 nm, about 272 nm, about 307 nm, about 338 nm, about 342 nm, about 360 nm, about 365 nm, about 377 nm, about 378 nm, about 381 nm, about 382 nm, about 390 nm, about 393 nm, about 397 nm, about 398 nm, about 403 nm, about 404 nm, about 408 nm, and combinations of any thereof.

The tracer dye or the tracer pigment can comprise a UV-visible fluorescent blue organic pigment having an Amax at a wavelength of about 408 nm.

The tracer dye or the tracer pigment can comprise a UV-visible fluorescent blue organic pigment having an Amax at a wavelength of about 377 nm.

The tracer dye or the tracer pigment can comprise a UV-visible fluorescent green-blue organic pigment having an Amax at a wavelength of about 404 nm.

The tracer dye or the tracer pigment can comprise a UV-visible fluorescent green organic pigment having an Amax at a wavelength of about 397 nm.

The tracer dye or the tracer pigment can comprise a UV-visible fluorescent yellow/green organic pigment having an Amax at a wavelength of about 250 nm to about 320 nm.

The tracer dye or the tracer pigment can comprise a UV-visible fluorescent red organic pigment having Amax at wavelengths of about 342 nm, about 408 nm, and about 470 nm.

The tracer dye or the tracer pigment can comprise a UV-visible thermo-fluorescent red organic pigment having an Amax at a wavelength of about 390 nm.

The tracer dye or the tracer pigment can comprise a UV-visible fluorescent red pigment having an Amax at a wavelength of about 390 nm.

The tracer dye or the tracer pigment can comprise a UV-visible fluorescent organic pigment having an Amax at a wavelength of about 365 nm.

The tracer dye or the tracer pigment can comprise a UV-visible fluorescent red pigment having an Amax at a wavelength of about 382 nm.

The tracer dye or the tracer pigment can comprise a UV-visible bi-fluorescent organic pigment having Amax at wavelengths of about 272 nm and about 381 nm.

The tracer dye or the tracer pigment can comprise a UV-visible thermo-fluorescent red organic dye having an Amax at a wavelength of about 390 nm.

The tracer dye or the tracer pigment can comprise a ruthenium-based dye having Amax at wavelengths of about 307 nm, about 338 nm, about 403 nm, and about 546 nm.

The tracer dye or the tracer pigment can comprise a combination of two or more of any of the tracer dyes or tracer pigments described herein.

The tracer dye or tracer pigment can have one or more absorbance maxima in the visible range of the electromagnetic spectrum.

The tracer dye or tracer pigment can have an $A_{max}$ at a wavelength between about 400 nm and about 700 nm For example, the tracer dye or the tracer pigment can have an Amax at a wavelength between about 410 nm and about 700 nm.

The tracer dye or the tracer pigment can have an Amax at a wavelength between about 425 nm and about 625 nm.

The tracer dye or the tracer pigment can have an Amax at a wavelength within a range from about 425 to about 430 nm.

The tracer dye or the tracer pigment can have an Amax at a wavelength within a range from about 430 nm to about 435 nm.

The tracer dye or the tracer pigment can have an Amax at a wavelength within a range from about 490 nm to about 510 nm.

The tracer dye or the tracer pigment can have an Amax at a wavelength within a range from about 452 nm to about 460 nm.

The tracer dye or the tracer pigment can have an Amax at a wavelength within a range from about 530 nm to about 550 nm.

The tracer dye or the tracer pigment can have an Amax at a wavelength within a range from about 590 nm to about 610 nm.

The tracer dye or the tracer pigment can have an Amax at a wavelength within a range from about 510 nm to about 520 nm.

The tracer dye or the tracer pigment can have an Amax at a wavelength within a range from about 450 nm to about 500 nm.

The tracer dye or the tracer pigment can have an Amax at a wavelength within a range from about 580 nm to about 585 nm.

The tracer dye or the tracer pigment can have an Amax at a wavelength within a range from about 520 to about 530 nm.

Tracer dye or the tracer pigment can have an Amax at one or more wavelengths selected from the group consisting of: about 400 nm, about 406 nm, about 425 nm, about 430 nm, about 440 nm, about 442 nm, about 445 nm, about 450 nm, about 460 nm, about 470 nm, about 475 nm, about 480 nm, about 490 nm, about 500 nm, about 530 nm, about 546 nm, about 550 nm, about 555 nm, about 580 nm, about 625 nm, about 630 nm, about 650 nm, about 660 nm, about 675 nm, about 680 nm, and combinations of any thereof.

The tracer dye or the tracer pigment can have an Amax at about 425 nm, about 530 nm, or about 625 nm.

The tracer dye or the tracer pigment can comprise curcumin, riboflavin, riboflavin-5'-phosphate, riboflavin-5'-sodium phosphate, tartrazine, alkannin, Quinoline Yellow WS, Fast Yellow AB, Yellow 2G, Sunset Yellow FCF, Orange GGN, cochineal, carminic Acid, carmine, Citrus Red 2, amaranth, Ponceau 4R, erythrosine, Red 2G, Allura Red AC, Indanthrene Blue RS, Patent Blue V, indigo carmine, Brilliant Blue FCF, a chlorophyllin, Green S, Fast Green FCF, a plain caramel, Caustic Sulphite Caramel, Ammonia Caramel, Sulphite Ammonia Caramel, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8-carotenic acid, flavoxanthin, lutein, cryoptoxanthin, rubixanthin, violaxanthin, rhodoxanthin, canthaxanthin, zeaxanthin, citranaxanthin, astaxanthin, betanin, saffron, a rubine dye, orcein, or a combination of any thereof.

Where the tracer dye or tracer pigment comprises a dye or pigment having an $A_{max}$ in the visible range of the electromagnetic spectrum, the dye or the pigment is preferably a dye or a pigment that has been approved as a food additive in Europe and/or the United States. Such dyes and pigments include, but are not limited to curcumin, riboflavin, riboflavin-5'-phosphate, tartrazine, Quinoline Yellow WS, Sunset Yellow FCF, cochineal, carminic Acid, carmine, Citrus Red 2, amaranth, Ponceau 4R, erythrosine, Allura Red AC, Patent Blue V, indigo carmine, Brilliant Blue FCF, a chlorophyllin, Green S, Fast Green FCF, a plain caramel, Caustic Sulphite Caramel, Ammonia Caramel, Sulphite Ammonia Caramel, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8-carotenic acid, lutein, canthaxanthin, betanin, saffron, and rubine dyes. The tracer dye or tracer pigment can comprise any combination of two or more of these dyes or pigments.

For example, the tracer dye or the tracer pigment cam comprise one or more chlorophyllins having Amax at about 440 nm, at about 680 nm, or at both about 440 nm and about 680 nm.

As another example, the tracer dye can comprise a plain caramel having an Amax at about 500 nm.

Where the tracer dye comprises a rubine dye, the rubine dye can comprise Lithol Rubine BK.

The tracer dye or tracer pigment can comprise tartrazine, erythrosine, or a combination thereof.

In any of the compositions or methods, the agrochemical can comprise any of the agrochemicals described herein. For example, the agrochemical can comprise a pesticide, a fertilizer, a plant growth regulator, a biostimulant, or a combination of any thereof.

Where the agrochemical comprises a pesticide, the pesticide can comprise an herbicide, an insecticide, a fungicide, a nematicide, a virucide, an acaricide, a molluscicide, an algicide, a bactericide, or a combination of any thereof.

For example, the pesticide can comprise an herbicide.

Where the pesticide comprises an herbicide, the herbicide can comprise an auxin herbicide (e.g., a phenoxy herbicide, a benzoic acid herbicide, or a combination thereof).

Where the herbicide comprises a phenoxy herbicide, the phenoxy herbicide can comprise 2,4-dichlorophenoxyacetic acid (2,4-D), 2-methyl-4-chlorophenoxyacetic acid (MCPA), 4-(4-chloro-otolyloxy) butyric acid (MCPB), mecoprop, 4-(2,4-dichlorophenoxy)butyric acid (2,4-DB), dichlorprop, dichlorprop-p, mecoprop-p, a salt of any thereof, an ester or any thereof, or a combination of any thereof.

For example, the phenoxy herbicide can comprise 2,4-D.

Where the herbicide comprises a benzoic acid herbicide, the benzoic acid herbicide can comprise dicamba, chloramben, 2,3,6-trichlorobenzoic acid (2,3,6-TBA), a salt of any thereof, an ester of any thereof, or a combination of any thereof.

For example, the benzoic acid herbicide can comprise dicamba.

For example, in any of the methods or compositions, the agrochemical can comprise dicamba and the tracer dye can comprise tartrazine.

As another example, in any of the methods or compositions, the agrochemical can comprise 2,4-D and the tracer dye can comprise erythrosine.

As a further example, in any of the methods or compositions, the agrochemical can comprise dicamba and the tracer dye or the tracer pigment can comprises a dye or pigment having an Amax at about 625 nm.

In any of the methods or compositions, the ratio of the agrochemical to the dye or pigment can be about 10:1 to about 1:100.

EXAMPLE

Spectrophotometric Identification and Measurement of Pesticides Using Tracer Dyes UV-VIS spectra were obtained for formulated dicamba (CLASH™; 56.8% diglycolamine salt of 3,6-dichloro-o-anisic acid) and 2,4-D (WEEDAR® 64; 48.6% 2,4-dichlorophenoxyacetic acid, dimethylamine salt) herbicides provided separately or in combination with tracer dyes used as distinguishing markers for each of the herbicides (FIGS.

32A-32H). Formulated dicamba and 2,4-D herbicides were provided as 1X solutions following the recommended use rates, such that dicamba was at a concentration of 6.0 g/L and 2,4-D was at a concentration of 4.533 g/L. The herbicide-containing solutions were then diluted to a 0.5X concentration (a 0.5X recommended use rate) from the original formulated product, such that the dicamba concentration was 3.0 g/L and the 2,4-D concentration was 2.267 g/L. Additional dilutions were prepared for both of the herbicides as listed in FIGS. 32A and 32B.

Two distinct tracer dyes as described in Table 9 were selected for use with the two herbicides. A yellow tartrazine dye was selected for use in combination with dicamba and a red erythrosine dye was selected for use in combination with 2,4-D. The yellow tartrazine tracer dye was provided in solution at molecular weight of 534.36 grams/mole and diluted by the addition of 1 drop of dye (from a 100 μL pipette tip) to 1 mL of sterile deionized water to form a 1X concentration for the yellow dye. Likewise, the red erythrosine tracer dye was provided in solution at a molecular weight of 879.86 grams/mole and then also diluted by the addition of 1 drop of dye (from a 100 μL pipette tip) to 8 mL of sterile deionized water to form a 1X concentration for the red dye. Further dilutions of each of the tracer dyes were prepared as listed in FIG. 32C (for the yellow dye) and FIG. 32D (for the red dye).

The tracer dyes were combined with the dicamba and 2,4-D herbicides. In particular, starting with the initial 1X solutions of the herbicides and dyes, the formulated dicamba was mixed together with the yellow dye at a ratio of 10:1 (dicamba: yellow dye) and the formulated 2,4-D was mixed together with the red dye at a ratio of 3:1 (2,4-D: red dye). The resulting mixtures of herbicide and dye were designated as 1X solutions and were then subjected to a series of dilutions by adding the appropriate amount of sterile deionized water. These dilutions are listed in FIGS. 32E and 32F, together with the ratios of herbicide:dye in parentheses (dicamba:yellow dye in FIG. 32E and 2,4-D:red dye in FIG. 32F). The herbicide and dye concentrations in the ratios in parentheses in FIGS. 32E and 32F are provided relative to the 1X concentrations of the formulated herbicide and dye solutions alone.

In addition, 1:1 and 2:1 mixtures of the dicamba/yellow dye and 2,4-D/red dye compositions were prepared, starting with the 1X solutions (10:1 dicamba:yellow dye and 3:1 2,4:D:red dye) described above. Dilutions of these 1:1 and 2:1 mixtures were then prepared by adding an appropriate volume of sterile deionized water. The dilutions are shown in FIGS. 32G and 32H. The ratios in FIGS. 32G and 32H are ratios of the dicamba/yellow dye:2-4D/red dye.

Solutions were pipetted (200 μL each) into a UV-STAR® microplate (GREINER BIO-ONE). Spectral traces using a wavelength range 200-700 nm (+/−5 nm) were collected using a BioTek SYNERGY HTX plate reader (BioTek Instruments Inc.). The spectral signatures and maximum absorbance spectra were collected individually for each of the herbicides (dicamba and 2,4-D) each of the tracer dyes (tartrazine dye (yellow) and erythrosine (red)), and for each of the herbicide/dye combinations. Spectra are shown in FIGS. 32A-32H.

Figure 32A:
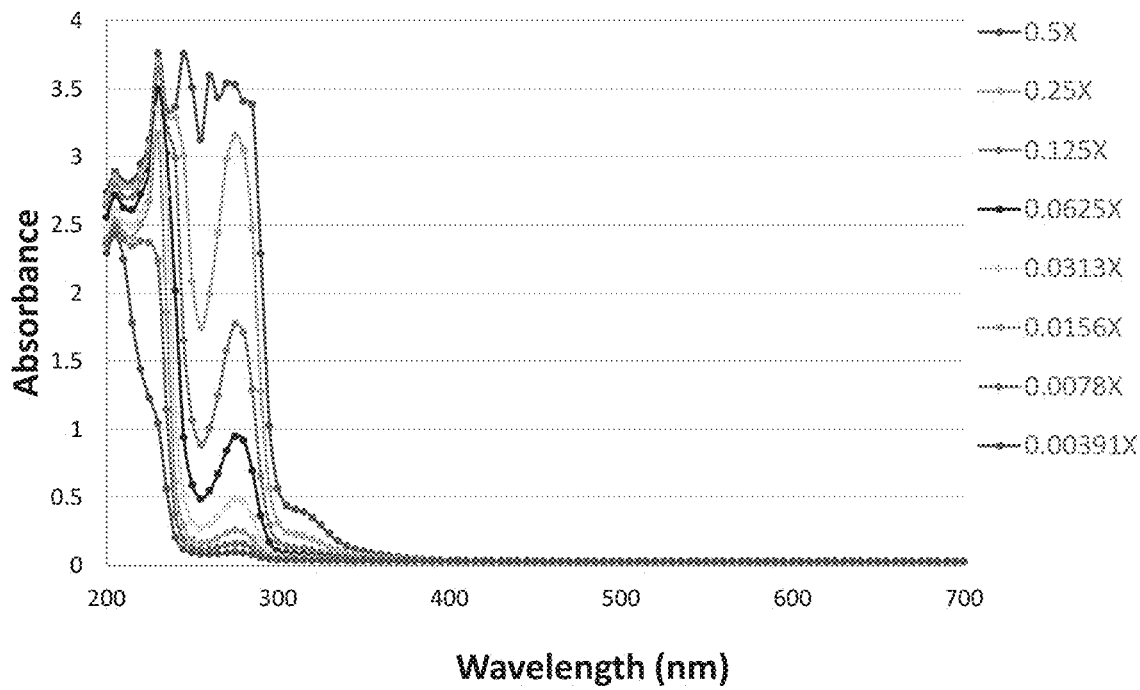
Figure 32B:
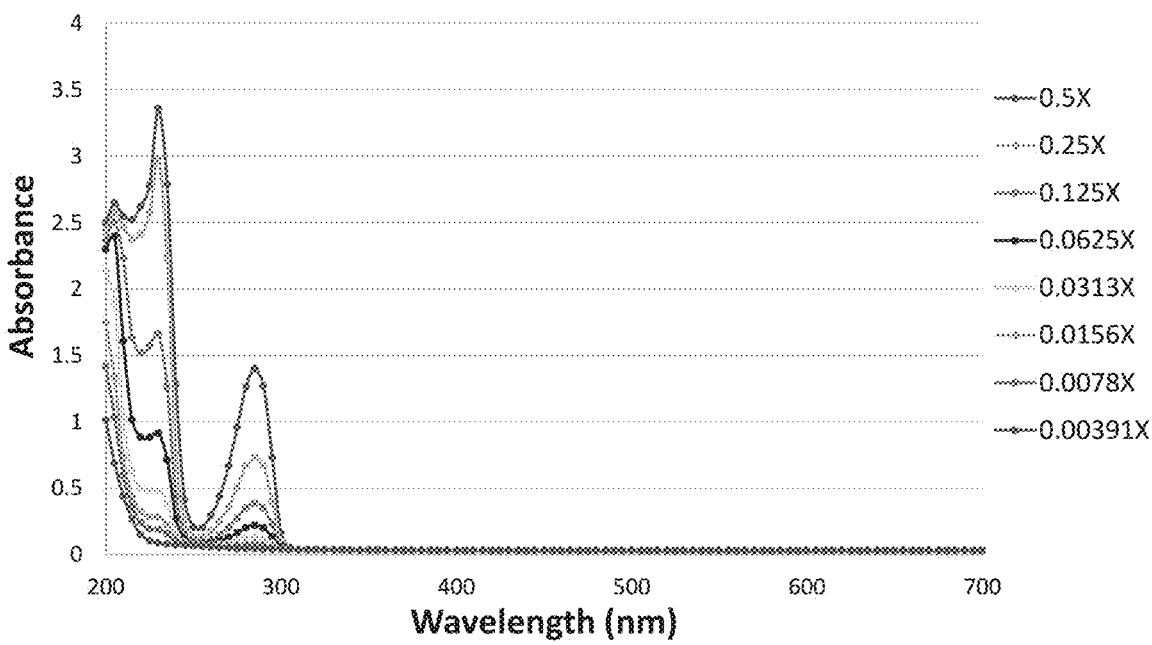
Figure 32C:
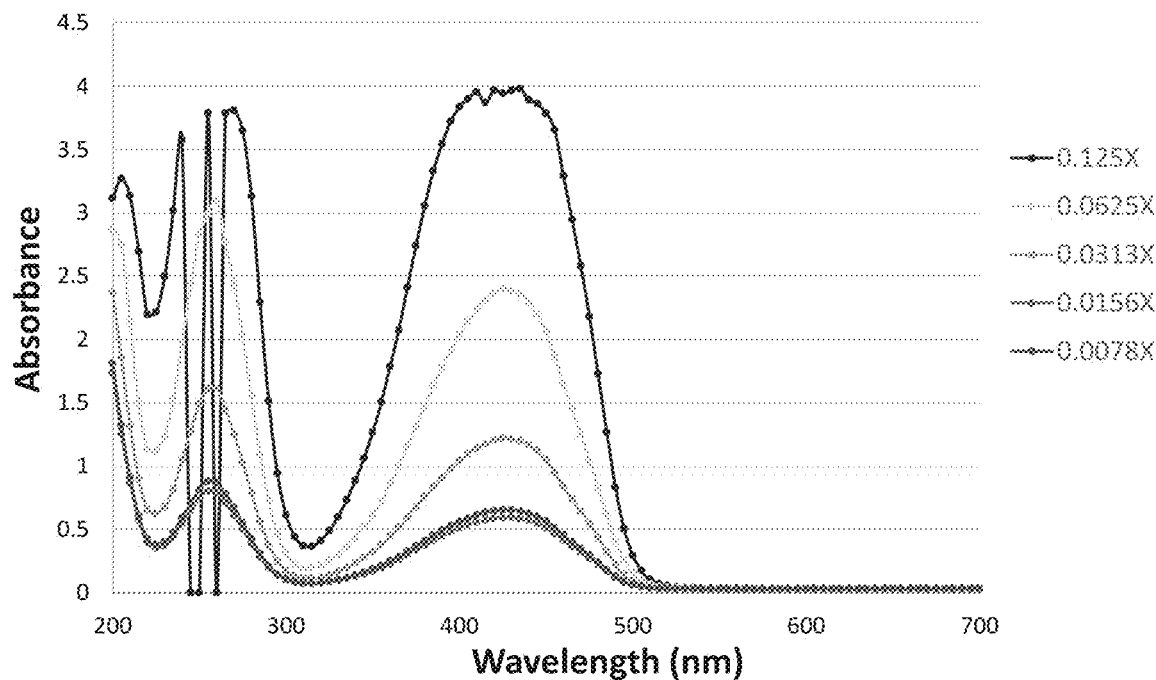
Figure 32D:
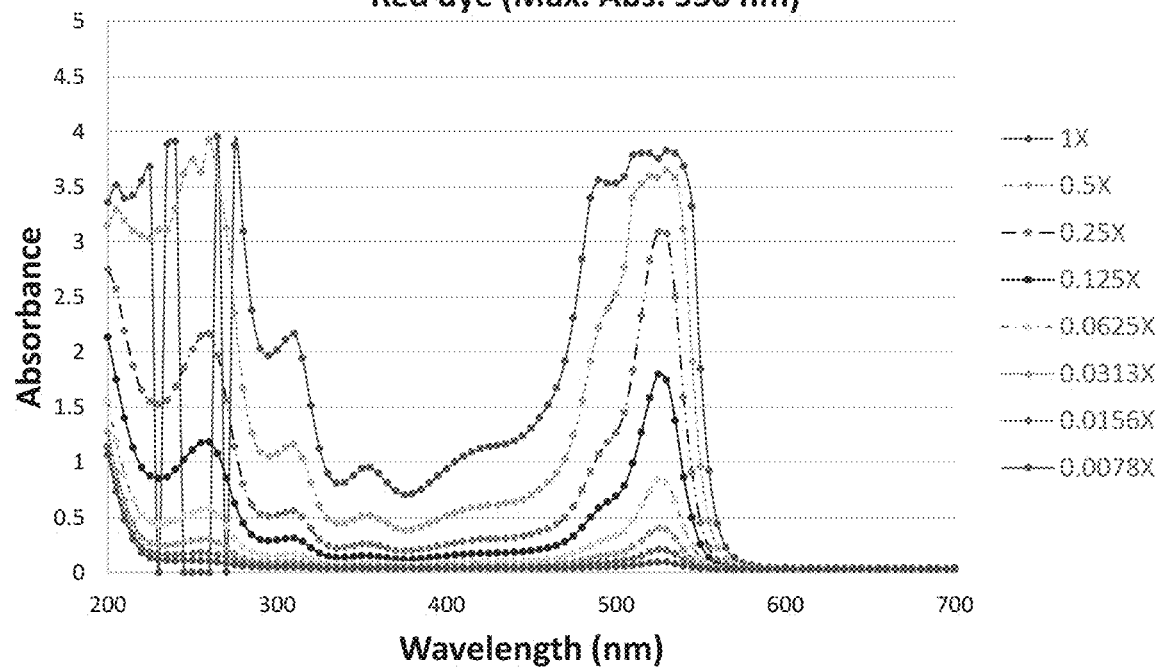
Figure 32E:
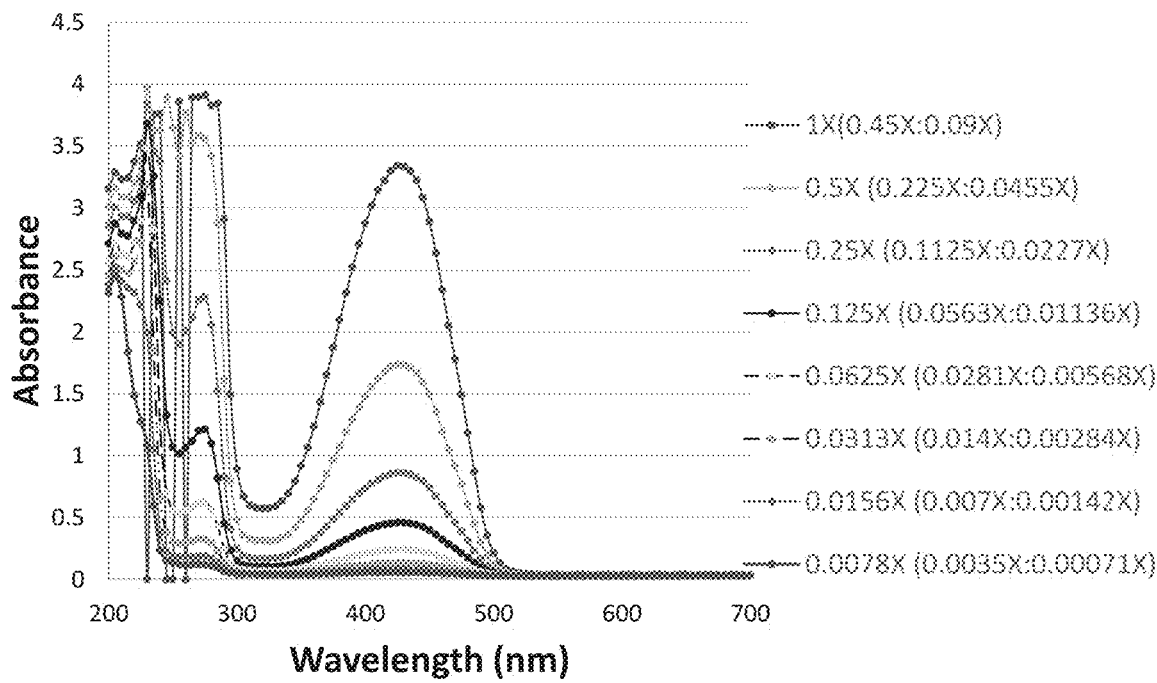
Figure 32F:
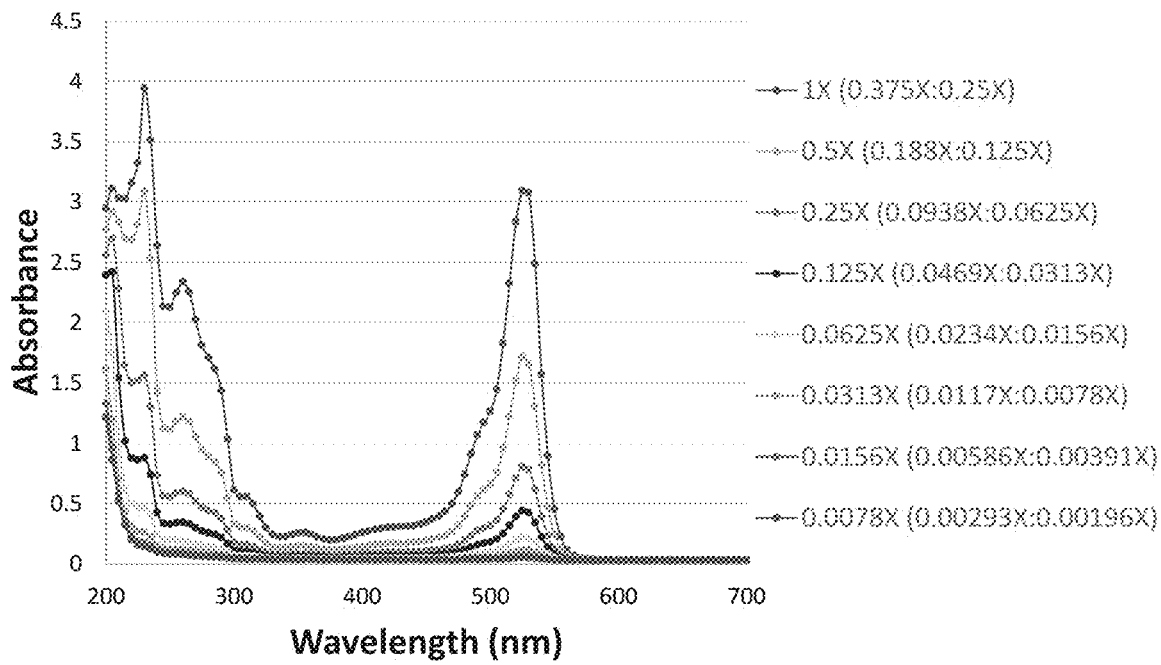
Figure 32G:
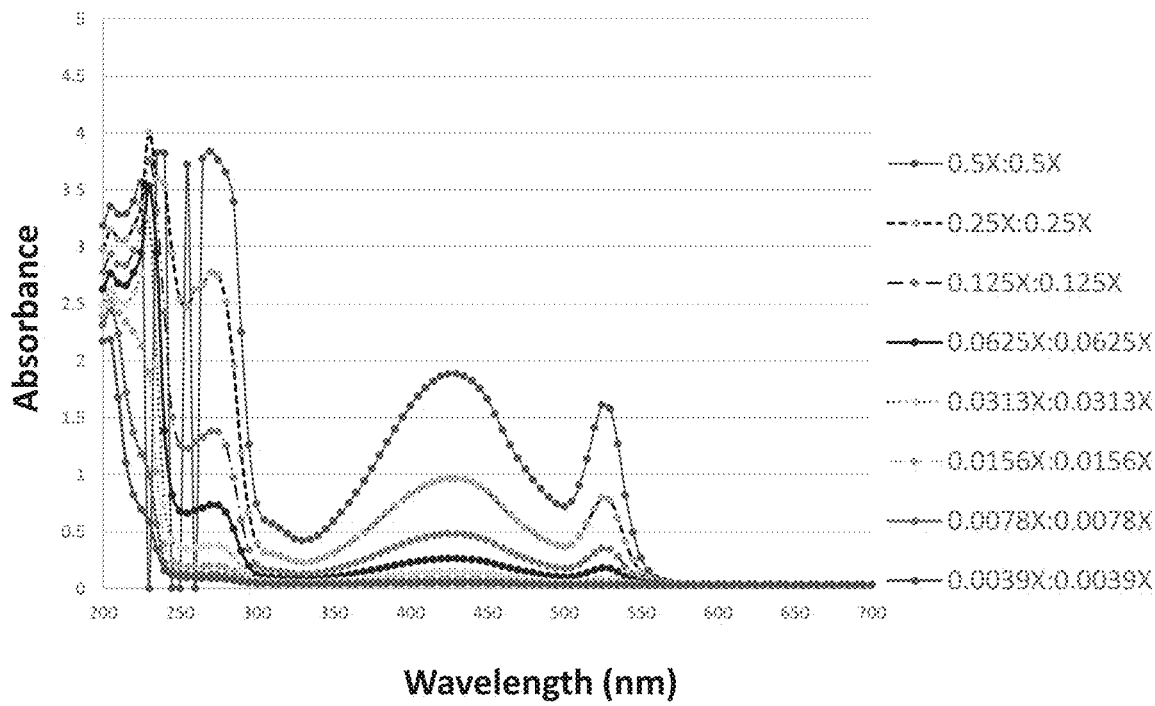
Figure 32H:
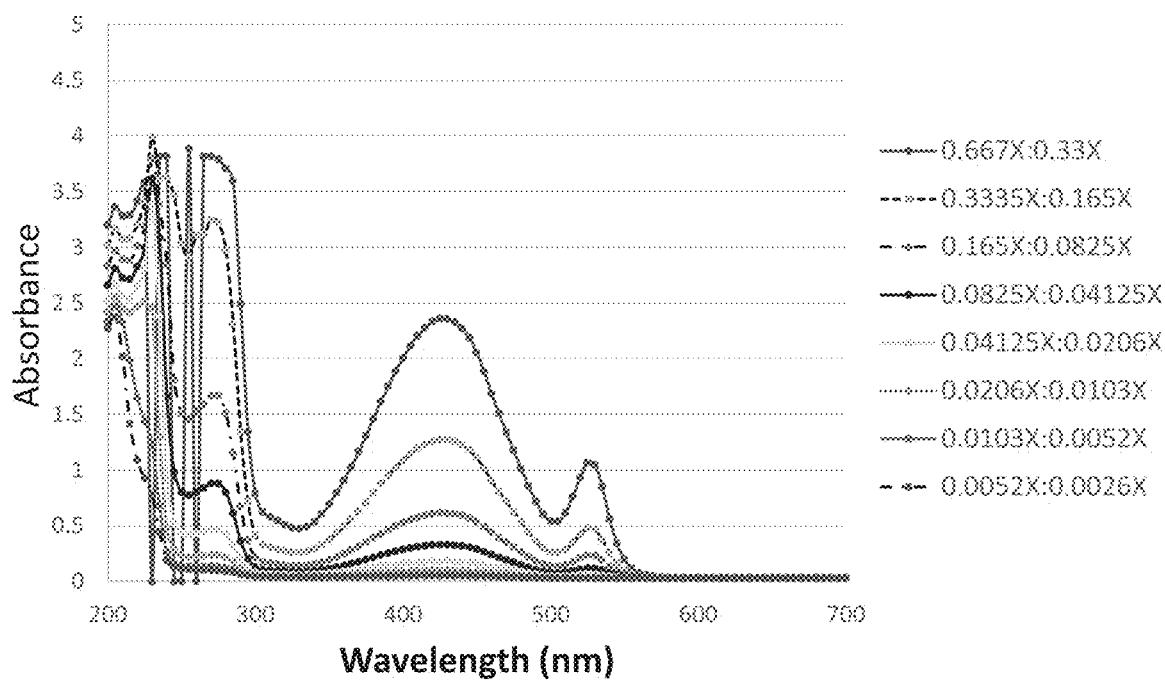

The UV-VIS spectra for the formulated herbicides are shown in FIG. 32A for dicamba (CLASH™) and FIG. 32B for 2,4-D (WEEDAR®64). UV-VIS spectra for the tracer dyes are shown for the tracer dyes in FIG. 32C (yellow tartrazine dye; $A_{max}$=425 nm) and FIG. 32D (red erythrosine dye, $A_{max}$=530 nm). The spectra for the tracer dyes combined with the herbicides are shown in FIG. 32E (yellow dye and formulated dicamba) and FIG. 32F (red dye and formulated 2,4-D. FIGS. 32G and 32H provide spectra for the 1:1 (FIG. 32G) and 2:1 (FIG. 32H) mixtures containing both the dicamba and yellow dye and the 2,4-D and red dye.

Both the yellow and red tracer dyes have distinct absorbance maxima that can be used to identify the dyes separately from one another and separately from the herbicides dicamba or 2,4-D. The tracer dyes can be used to detect and quantify the individual herbicides in a mixture. The yellow and red tracer dyes, provided in combination either with formulated dicamba or 2,4-D individually or as in a mixture with the two herbicides were used to detect and distinguish between the different herbicides in the mixture.

Tracer dyes can also be used to detect dicamba in a product formulated for volatility reduction. Dicamba herbicide (XTENDIMAX® containing 42.8% diglycolamine salt of dicamba (3,6-dichloro-o-anisic acid) with VAPORGRIP® technology) was detected and quantified using a tracer dye (an orange-red dye; $A_{max}$=625 nm) and an apparatus described herein. A formulated dicamba solution (XTENDIMAX® VAPORGRIP®) was added using the recommended use rate after dilution in water to a 100 L spray tank (Optima Croplands). This spray tank that was designed to precisely operate and function as a miniaturized version of a spray tank was connected to the system 11 through tubing placed to recirculate the flow of the herbicide solution from the tank to the apparatus. Spectral traces using the apparatus were collected using a spectrophotometer with UV VIS capabilities that was placed in line with a 1 cm gap stainless steel flow cell that allows for the free movement of liquid through the flow cell using a solarization-resistant fiber optic cable.

Formulated dicamba herbicide (XTENDIMAX® VAPORGRIP®) was detected using a tracer dye that absorbs at an $A_{max}$ of about 625 nm. After dilution in water in the 100 L spray tank, the formulated dicamba was present at the estimated recommended use rate of 12.03 g/L dicamba (1X concentration). A series of dilutions was then prepared by adding an appropriate volume of sterile deionized water to create compositions where the dicamba was present at 6.02 g/L (0.5X), 3.01 g/L (0.25X), or 0.301 g/L (0.025X). The dilutions tested are listed in FIG. 33A.

Spectral traces using a wavelength range 200-800 nm (+/−5 nm) were generated using the apparatus. The UV spectral range of dicamba was compared to that of the tracer dye. The tracer dye absorbs in a UV/VIS spectral range at a different $A_{max}$ wavelength from the dicamba herbicide and the vapor reduction compounds in the XTENDIMAX® VAPORGRIP® formulation and can therefore be effectively used as an alternative measure to quantify the concentration of dicamba.

Figure 33A:
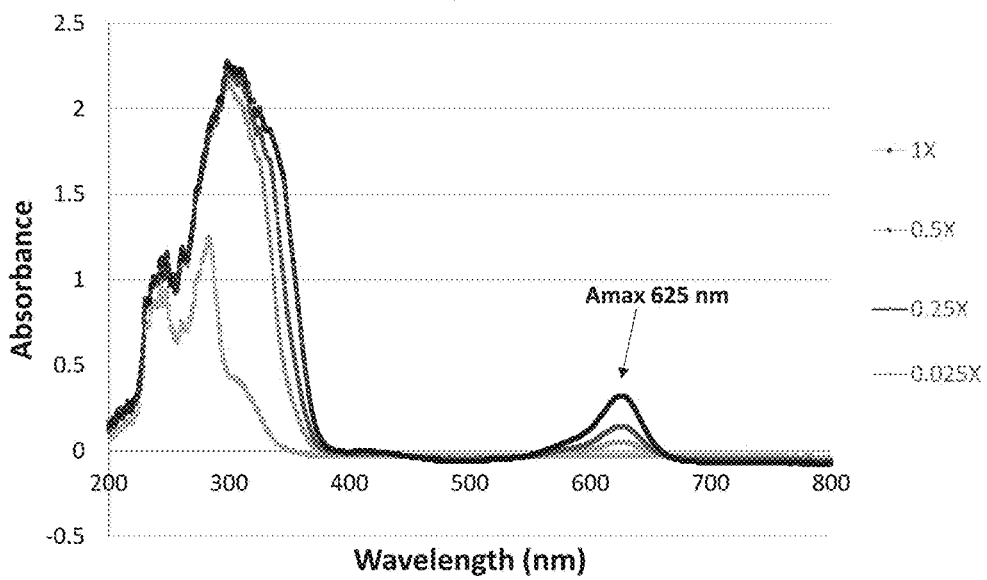

UV/VIS spectra for the formulated dicamba (XTENDIMAX® VAPORGRIP®) mixed with the tracer dye were collected using the apparatus and are shown in FIG. 33A. Spectra for the 1X solution and the series of dilutions are shown and are compared to a 0X (no dicamba) baseline control. The formulated dicamba resulted in two prominent spectral peaks ($A_{max}$ 230 and 280 nm). The tracer dye has an absorbance maximum ($A_{max}$ 625 nm) in a different portion of the UV/VIS spectral range, and thus can be used to detect and quantify the dicamba.

Figure 33B:
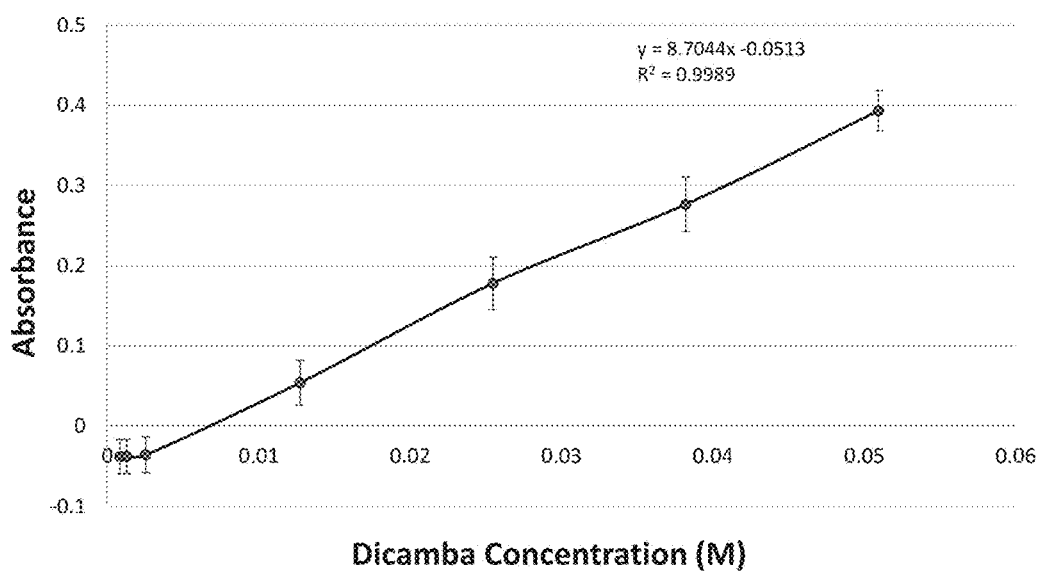

To generate a standard curve for dicamba (XTENDIMAX® VAPORGRIP®), UV/VIS spectra from 200-800 nm were collected using a range of dicamba concentrations in mixtures that included the tracer dye as shown in FIG. 33A. The $A_{max}$ spectral peak (at about 625 nm) for the tracer dye was correlated to the amount of dicamba using the dilutions as described in FIG. 33A to show that the tracer dye can be used as an alternative means to quantify the concentration of dicamba. The standard curve was derived from the correlation of the maximum absorbance wavelength ($A_{max}$ of about 625) for the tracer dye to dicamba concentration (FIG. 33B) that was both linear and highly correlated ($R^2$ value=0.9989). This standard curve was used to accurately determine the concentration of formulated dicamba (XTENDIMAX® VAPORGRIP®) in a sample solution.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the invention are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively, or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives and uses of the aspects of the invention, including what is presently believed to be the best mode of carrying out the aspects of the invention. Additionally, it is to be understood that the aspects of the invention are not limited in application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. It is contemplated that various changes could be made in the above constructions, products, and process without departing from the scope of aspects of the invention. In the preceding specification, various preferred embodiments have been described with reference to the accompanying drawings. It will, however be evident that various modifications and changes may be made thereto, and additional embodiments may be implemented, without departing from the broader scope of the aspects of the invention as set forth in claims that follow. The specification and drawings are accordingly to be regarded in an illustrative rather than restrictive sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description shall be interpreted as illustrative and not in a limiting sense.

What is claimed is:

1. An apparatus for detecting, measuring and quantifying the amount of at least one agrochemical in an environment, the apparatus comprising:
   a light source
   a spectrophotometric device comprising a detector positioned to receive light from the light source after the light has been transmitted through or reflected by said environment, wherein the spectrophotometric device is configured to measure intensity of the received light as a function of wavelength to determine spectral characteristics of the received light; and
   at least one processor configured to measure a concentration of said agrochemical using the spectral characteristics of the received light and perform at least one of the following:
      estimate an agrochemical concentration at a time $t_2$ based on at least one measurement of the concentration of said agrochemical taken at time $t_1$, wherein $t_1$ does not equal $t_2$;
      estimate an agrochemical concentration at a time $t_3$ based on at least two measurements of the concentration of said agrochemical taken at time $t_1$ and time $t_2$, wherein $t_2 > t_1$ and the change in the concentration from time $t_1$ to time $t_2$ represents a reduction of the agrochemical in the environment;
   estimate an agrochemical end-product concentration at a time $t_3$ based on at least two measurements of the concentration of said agrochemical end-product taken at time $t_1$ and time $t_2$, wherein $t_2 > t_1$ and the change in the concentration from time $t_1$ to time $t_2$ represents an accumulation of agrochemical in the environment;
   estimate an agrochemical concentration based on at least two measurements of the agrochemical concentration taken at time $t_1$ and time $t_2$, wherein $t_2 > t_1$ and the change in the concentration from time $t_1$ to time $t_2$ represents an accumulation of the agrochemical in the environment;
   estimate an agrochemical end-product concentration based on at least two measurements of the agrochemical end-product concentration taken at time $t_1$ and time $t_2$, wherein $t_2 > t_1$ and the change in the concentration from time $t_1$ to time $t_2$ represents an reduction of the agrochemical in the environment; and
   combinations thereof.

2. An apparatus as set forth in claim 1 wherein the at least one processor is configured to determine from one of (a) a single absorbance reading and (b) two or more absorbance readings, at least one of the following:
   whether or not there is any detectable levels of agrochemical present; and
   (ii) whether or not a safe zone has been achieved, by using at least one of the following:
   (a) a comparison of the overall absorbance at a set wavelength to a threshold level; and
   (b) a prediction based on a calibration of the single absorbance reading against a non-absorbing background wavelength.

3. An apparatus as set forth in claim 1 further comprising a processor configured to compare the measured concentration of the agrochemical to a desired concentration of an agrochemical and output an indication of a result of the comparison.

4. An apparatus as set forth in claim 1 further comprising:
a structure defining a space for containing a fluid;
at least one window;
wherein the light source and the spectrophotometric device are positioned adjacent the at least one window so the spectrophotometric device can detect light from the light source after the light has interacted with material in said space for containing the fluid.

5. An apparatus as set forth in claim 4 wherein said structure comprises a tank.

6. An apparatus as set forth in claim 5 wherein the light source and spectrophotometric device are built into a wall of the tank.

7. An apparatus as set forth in claim 1 wherein the apparatus comprises a cuvette positioned in a path of light from the light source.

8. An apparatus as set forth in claim 1, wherein the at least one processor is configured to estimate an agrochemical concentration at a time t2 based on at least one measurement of the concentration of said agrochemical taken at time t1, wherein t1 does not equal t2.

9. An apparatus as set forth in claim 1, wherein the at least one processor is configured to estimate an agrochemical concentration at a time t3 based on at least two measurements of the concentration of said agrochemical taken at time t1 and time t2, wherein t2>t1 and the change in the concentration from time t1 to time t2 represents a reduction of the agrochemical in the environment.

10. An apparatus as set forth in claim 1, wherein the at least one processor is configured to estimate an agrochemical end-product concentration at a time t3 based on at least two measurements of the concentration of said agrochemical end-product taken at time t1 and time t2, wherein t2>t1 and the change in the concentration from time t1 to time t2 represents an accumulation of agrochemical in the environment.

11. An apparatus as set forth in claim 1, wherein the at least one processor is configured to estimate an agrochemical concentration based on at least two measurements of the agrochemical concentration taken at time t1 and time t2, wherein t2>t1 and the change in the concentration from time t1 to time t2 represents an accumulation of the agrochemical in the environment.

12. An apparatus as set forth in claim 1, wherein the at least one processor is configured to estimate an agrochemical end-product concentration based on at least two measurements of the agrochemical end-product concentration taken at time t1 and time t2, wherein t2>t1 and the change in the concentration from time t1 to time t2 represents an reduction of the agrochemical in the environment.

13. An apparatus for detecting, measuring and quantifying the amount of at least one agrochemical in an environment, the apparatus comprising:
a light source
a spectrophotometric device comprising a detector positioned to receive light from the light source after the light has been transmitted through or reflected by said environment, wherein the spectrophotometric device is configured to measure intensity of the received light as a function of wavelength to determine spectral characteristics of the received light; and
at least one processor configured to measure a concentration of said agrochemical using the spectral characteristics of the received light and measure an application use rate of the agrochemical using the spectral characteristics of the received light.

14. An apparatus as set forth in claim 13 further comprising:
a structure defining a space for containing a flowing fluid;
a pair of substantially transparent windows;
wherein the light source is configured to direct light through one of the windows and the spectrophotometric device is positioned adjacent the other window and the windows are arranged so the spectrophotometric device can detect light from the light source after the light has passed through the windows and interacted with material in said space for containing the flowing fluid.

15. An apparatus as set forth in claim 14 wherein said structure is selected from the group consisting of a conduit, a pipe, a tubing, a fluid line, a flow cell, a cuvette, a spray boom, a spray nozzle, a nozzle body, a filter body, a spray ball, and an emitter.

16. An apparatus as set forth in claim 14 further comprising a protective casing enclosing at least one of the light source and the spectrophotometric device, wherein the protective casing is at least one of water resistant, shock resistant, heat resistant, chemical resistant, vibration resistant, solvent resistant and dust resistant.

17. An apparatus as set forth in claim 16 wherein the protective casing is at least one of water resistant, shock resistant, heat resistant, chemical resistant, vibration resistant, solvent resistant and dust resistant.

18. An apparatus as set forth in claim 14 wherein the structure comprises a conduit, the conduit having a connector on one end configured for connecting the conduit to an in-line filter or in-line screen.

19. An apparatus as set forth in claim 14 wherein the structure comprises a conduit, the apparatus further comprising a connector on one end of the conduit configured for connecting the conduit to a spray boom.

20. An apparatus as set forth in claim 19 wherein the connector is a first connector, the apparatus further comprising a second connector on the opposite end of the conduit configured to connect the conduit to at least one of a spray nozzle, a nozzle body, a filter body, a spray ball, and an emitter.

21. An apparatus as set forth in claim 14 wherein the structure comprises a spray nozzle having a nozzle body and the windows are installed in the nozzle body generally on opposite sides of the nozzle body.

22. An apparatus as set forth in claim 13 further comprising a mounting system comprising a mount for mounting the light source and spectrophotometric device on a piece of equipment, the mount being constructed to have at least one of the following characteristics: the ability to insulate the mounted component(s) from vibrations; the ability to form a mechanical interface with a corresponding part of the equipment on which the system or a component of the system is to be mounted; resistance to water;
resistance to heat; chemical resistance to one or more agrochemicals; and combinations thereof.

23. An apparatus as set forth in claim 22 wherein the mount comprises a damper configured to insulate at least one of the light source and spectrophotometric device from vibrations.

24. An apparatus as set forth in claim 13 wherein the apparatus comprises an in line flow cell adapted to receive a flow of a solution containing said agrochemical and to direct said flow through light from the light source.

25. An apparatus as set forth in claim 13 wherein the spectrophotometric device is positioned to receive light after the light has interacted with a material in a structure selected from the group consisting of: a tank, a seed treatment apparatus, a sprayer, a spray boom, a container, a nozzle, a nozzle screen, a nozzle filter, a nozzle fitting, a screen, a strainer, a valve, a conduit, and a spray emitted by a sprayer.

26. An apparatus as set forth in claim 13 wherein the spectrophotometric device is configured to measure the concentration of an agrochemical selected from the group consisting of: an herbicide, an insecticide, an insect growth regulator, a biological control agent, a fungicide, a bactericide, a nematicide, an acaricide, a virucide, a fertilizer, and combinations thereof.

27. An apparatus as set forth in claim 13 wherein the at least one processor is configured to identify a substance in the environment based on the spectral characteristics of the received light, wherein the substance is a substance selected from the group consisting of: a pesticide, an herbicide, an insecticide, an insect growth regulator, a biological control agent, a fungicide, a bactericide, a nematicide, an acaricide, a fertilizer, a virucide, a plant growth regulator and combinations thereof.

28. An apparatus as set forth in claim 13 further comprising:
a structure defining a space for containing a flowing fluid;
a pair of substantially transparent windows;
an optical fiber positioned so an end of the optical fiber is adjacent one of the windows;
wherein one of the light source and the spectrophomotric device is positioned adjacent an opposite end of the optical fiber so the optical fiber is positioned to convey light between said one of the light source and spectrophotometric device and the window adjacent the opposite end of the optical fiber, the windows, optical fiber, spectrophotometric device, and light source being arranged so the spectrophotometric device can detect light from the light source after the light has passed through the optical fiber and windows and interacted with any material in said space for containing the flowing fluid.

29. An apparatus as set forth in claim 28 wherein the optical fiber is a solarization resistant optical fiber.

30. An apparatus as set forth in claim 28 wherein the optical fiber is a first optical fiber, the apparatus further comprising a second optical fiber, the second optical fiber being positioned to extend between the other of the spectrophotometric device and the light source and the window that is not adjacent the end of the first optical fiber, the windows, first and second optical fibers, spectrophotometric device, and light source being arranged so the spectrophotometric device can detect light from the light source after the light has passed through the first and second optical fibers and windows and interacted with any material in said space for containing the flowing fluid.

31. An apparatus as set forth in claim 13 further comprising a data exchange interface for outputting information about the concentration of said agrochemical to another device.

32. An apparatus as set forth in claim 13 wherein the spectrophotometric device comprises a plurality of detectors spaced from one another for receiving said light at different locations.

33. An apparatus as set forth in claim 13 wherein the spectrophotometric device comprises a filter adapted to filter a spectral bandwidth from said received light.

34. An apparatus as set forth in claim 13 wherein the at least one processor is configured to compare the measured application use rate of the agrochemical to a desired application use rate for the agrochemical and output an indication of the comparison.

35. An apparatus as set forth in claim 13 wherein the agrochemical for which the application use rate is measured comprises a fertilizer.

36. An apparatus as set forth in claim 13 further comprising a sensor configured to measure a temperature of the environment.

37. An apparatus as set forth in claim 13 further comprising a sensor configured to measure an osmolarity of the environment.

38. An apparatus as set forth in claim 13 further comprising a GPS sensor.

39. An apparatus as set forth in claim 13 further comprising a valve controlled by the at least one processor.

40. An apparatus as set forth in claim 39 wherein the valve is connected to multiple different sources containing multiple different fluids and the at least one processor is configured to selectively actuate the valve to switch which of the multiple different fluids flows through the valve.

41. A method for detecting, measuring and quantifying the amount of at least one agrochemical in an environment, the method comprising:
receiving light from a light source after the light has been transmitted through or reflected by said environment;
measuring intensity of the received light as a function of wavelength to obtain spectral characteristics of the received light;
determining a concentration of said agrochemical using the spectral characteristics of the received light; and
performing at least one of the following steps based on the determined concentration of the agrochemical:
cleaning agricultural equipment defining the environment with a cleaning agent;
ceasing cleaning agricultural equipment defining the environment;
using agricultural equipment defining the environment with another agrochemical;
refraining from using the agricultural equipment defining the environment with another agrochemical;
disposing of rinsate in agricultural equipment defining the environment;
adding cleaning agent to rinsate in agricultural equipment defining the environment;
spraying another agrochemical from agricultural spray equipment defining the environment;
refraining from or ceasing spraying an agrochemical solution having another agrochemical agent in agricultural spray equipment defining the environment;
refraining from treating seeds with a seed treatment comprising another agrochemical agent using seed treatment equipment defining the environment;
treating seeds with a seed treatment comprising another agrochemical agent using seed treatment equipment defining the environment;
generating a dispatch alert indicating that a residue of the agrochemical is present in the environment when the environment is expected to be substantially free of the agrochemical;
adding a detoxifying formulation to a solution in agricultural equipment defining the environment;

generating a dispatch alert indicating that the concentration of the agrochemical in agricultural equipment defining the environment is at a safe zone concentration;

determining compliance with crop loss insurance requirements;

adjusting one of a crop loss insurance premium rate and a crop loss insurance deductible;

advancing a production process for an agrochemical product to a subsequent processing step;

delaying advancing a production process for an agrochemical product to a subsequent processing step;

determining whether to clean a returned drum defining the environment;

cleaning a returned drum defining the environment; and refraining from cleaning a returned drum defining the environment.

42. A method as set forth in claim 41 further comprising using a detector to measure a concentration in the environment of a substance selected from the group consisting of: an adjuvant, a fertilizer, a growth regulator, a micronutrient, a biological control agent, a plant health agent, an inoculant, a surfactant, an osmoprotectant, a safener, a trace molecule, and a hard water solute.

43. A method as set forth in claim 41 wherein the light is received after it is transmitted through or reflected by, a material of said environment that is in a structure associated with agricultural equipment.

44. A method as set forth in claim 41, wherein said performing at least one of the following steps based on the determined agrochemical concentration comprises one of:
cleaning agricultural equipment defining the environment with a cleaning agent; and
ceasing cleaning agricultural equipment defining the environment.

45. A method as set forth in claim 41, wherein said performing at least one of the following steps based on the determined agrochemical concentration comprises using agricultural equipment defining the environment with another agrochemical.

46. A method as set forth in claim 41, wherein said performing at least one of the following steps based on the determined agrochemical concentration comprises refraining from using the agricultural equipment defining the environment with another agrochemical.

47. A method as set forth in claim 41 wherein said performing at least one of the following steps based on the determined agrochemical concentration comprises one of:
disposing of rinsate in agricultural equipment defining the environment; and
adding cleaning agent to rinsate in agricultural equipment defining the environment.

48. A method as set forth in claim 41 wherein said performing at least one of the following steps based on the determined agrochemical concentration comprises spraying another agrochemical from agricultural spray equipment defining the environment.

49. A method as set forth in claim 41 wherein said performing at least one of the following steps based on the determined agrochemical concentration comprises refraining from or ceasing spraying an agrochemical solution having another agrochemical agent in agricultural spray equipment defining the environment.

50. A method as set forth in claim 41 wherein said performing at least one of the following steps based on the determined agrochemical concentration comprises one of:
refraining from treating seeds with a seed treatment comprising another agrochemical agent using seed treatment equipment defining the environment; and
treating seeds with a seed treatment comprising another agrochemical agent using seed treatment equipment defining the environment.

51. A method as set forth in claim 41, wherein said performing at least one of the following steps based on the determined agrochemical concentration comprises one of:
generating a dispatch alert indicating that a residue of the agrochemical is present in the environment when the environment is expected to be substantially free of the agrochemical; and
generating a dispatch alert indicating that the concentration of the agrochemical in agricultural equipment defining the environment is at a safe zone concentration.

52. A method as set forth in claim 41, wherein said performing at least one of the following steps based on the determined agrochemical concentration comprises adding a detoxifying formulation to a solution in agricultural equipment defining the environment.

53. A method as set forth in claim 41, wherein said performing at least one of the following steps based on the determined agrochemical concentration comprises one of:
determining compliance with crop loss insurance requirements; and
adjusting one of a crop loss insurance premium rate and a crop loss insurance deductible.

54. A method as set forth in claim 41, wherein said performing at least one of the following steps based on the determined agrochemical concentration comprises one of:
advancing a production process for an agrochemical product to a subsequent processing step; and
delaying advancing a production process for an agrochemical product to a subsequent processing step.

55. A method as set forth in claim 41, wherein said performing at least one of the following steps based on the determined agrochemical concentration comprises one of:
determining whether to clean a returned drum defining the environment;
cleaning a returned drum defining the environment; and
refraining from cleaning a returned drum defining the environment.

56. A method as set forth in claim 41 wherein the light is received after it is transmitted through or reflected by a material of said environment that is in a structure associated with agricultural equipment.

57. A method as set forth in claim 41 wherein the light is received after it is transmitted through or reflected by a material of said environment that is in a structure associated with seed treatment equipment.

58. A method as set forth in claim 41 wherein the light is received after it is transmitted through or reflected by a material of said environment that is in a structure associated with agrochemical manufacturing equipment.

59. A method for evaluating use of an agrochemical, the method comprising:
providing a fluid that includes the agrochemical;
receiving light from a light source after the light has been transmitted through or reflected by at least a portion of the fluid;
measuring intensity of the received light as a function of wavelength to obtain spectral characteristics of the received light;

determining a concentration of the agrochemical in the fluid using the spectral characteristics of the received light;
dispensing the fluid, wherein the step of receiving light from the light source comprises receiving light that has been transmitted through or reflected by a portion of the fluid that is flowing as the fluid is being dispensed;
determining an application rate of the agrochemical as the fluid is being dispensed;
comparing the determined application rate to a desired application rate for the agrochemical; and
adjusting a flow rate at which the fluid is dispensed based on the comparison between the determined application rate and the desired application rate.

60. A method as set forth in claim 59 wherein the step of dispensing the fluid comprises directing the fluid to flow through a fenestrated structure and the step of receiving light from the light source comprises receiving light that passes through the fenestrated structure.

\* \* \* \* \*